United States Patent
Hatakeyama et al.

(10) Patent No.: US 11,723,263 B2
(45) Date of Patent: *Aug. 8, 2023

(54) ORGANIC ELECTROLUMINESCENT ELEMENT

(71) Applicants: Kwansei Gakuin Educational Foundation, Nishinomiya (JP); SK Materials JNC Co., Ltd., Gyeonggi-do (KR)

(72) Inventors: Takuji Hatakeyama, Hyogo (JP); Akihide Mizutani, Chiba (JP); Toshihiro Koike, Chiba (JP)

(73) Assignees: Kwansei Gakuin Educational Foundation, Hyogo (JP); SK Materials JNC Co., Ltd., Gyeonggi-do (KR)

( * ) Notice: Subject to any disclaimer, the term of this patent is extended or adjusted under 35 U.S.C. 154(b) by 699 days.

This patent is subject to a terminal disclaimer.

(21) Appl. No.: 16/092,856

(22) PCT Filed: Apr. 20, 2017

(86) PCT No.: PCT/JP2017/015871
§ 371 (c)(1),
(2) Date: Oct. 11, 2018

(87) PCT Pub. No.: WO2017/188111
PCT Pub. Date: Nov. 2, 2017

(65) Prior Publication Data
US 2019/0207112 A1    Jul. 4, 2019

(30) Foreign Application Priority Data

Apr. 26, 2016   (JP) ................. 2016-087640

(51) Int. Cl.
*H10K 85/30*      (2023.01)
*C09K 11/06*      (2006.01)
(Continued)

(52) U.S. Cl.
CPC ......... *H10K 85/322* (2023.02); *C07D 209/80* (2013.01); *C07D 209/86* (2013.01);
(Continued)

(58) Field of Classification Search
CPC ............... C07D 209/80; C07D 209/86; C07D 307/77; C07D 307/91; C07D 333/76; C07F 5/02;
(Continued)

(56) References Cited

U.S. PATENT DOCUMENTS 10,689,402 B2 *  6/2020  Hatakeyama ....... H01L 51/0052
2012/0319052 A1  12/2012  Brocke et al.
(Continued)

FOREIGN PATENT DOCUMENTS

JP    2001-172232 A    6/2001
JP    2005-170911 A    6/2005
(Continued)

OTHER PUBLICATIONS

SID, vol. 50, Issue 1, Jun. 2019, pp. 1924-1927. (Year: 2019).*
(Continued)

*Primary Examiner* — Dawn L Garrett
(74) *Attorney, Agent, or Firm* — Foley & Lardner LLP

(57) ABSTRACT

With a light-emission-layer material comprising: a novel polycyclic aromatic compound (1) or a multimer thereof in which a plurality of aromatic rings are linked by a boron atom and a nitrogen atom; and a specific anthracene-based compound (3) that achieves optimum light-emission characteristics in combination with said polycyclic aromatic compound or a multimer thereof, it is possible to provide an organic EL element having optimum light-emission characteristics.

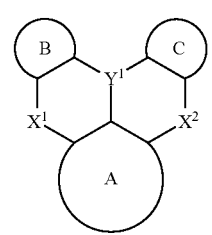

(1)

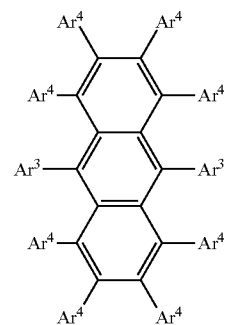

(3)

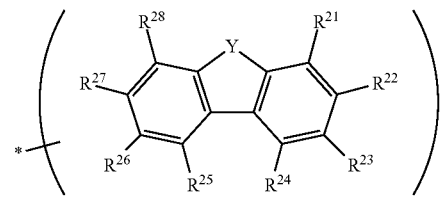

(4)

Ring A to ring C are an aryl ring or the like, $Y^1$ represents B, $X^1$ and $X^2$ represent N—R, R of the N—R is an aryl or the like, and $Ar^3$ and $Ar^4$ are a hydrogen atom, a phenyl, a group represented by formula (4), or the like.

9 Claims, 1 Drawing Sheet

(51) Int. Cl.
| | |
|---|---|
| H10K 50/00 | (2023.01) |
| H10K 50/16 | (2023.01) |
| H10K 85/60 | (2023.01) |
| C07D 209/80 | (2006.01) |
| C07D 209/86 | (2006.01) |
| C07D 307/77 | (2006.01) |
| C07D 307/91 | (2006.01) |
| C07D 333/76 | (2006.01) |
| C07F 5/02 | (2006.01) |
| C09K 11/02 | (2006.01) |
| H10K 50/11 | (2023.01) |
| H10K 50/15 | (2023.01) |
| H10K 50/165 | (2023.01) |
| H10K 50/17 | (2023.01) |

(52) U.S. Cl.
CPC ......... *C07D 307/77* (2013.01); *C07D 307/91* (2013.01); *C07D 333/76* (2013.01); *C07F 5/027* (2013.01); *C09K 11/02* (2013.01); *C09K 11/06* (2013.01); *H10K 50/00* (2023.02); *H10K 50/16* (2023.02); *H10K 85/615* (2023.02); *H10K 85/631* (2023.02); *H10K 85/636* (2023.02); *H10K 85/657* (2023.02); *H10K 85/6572* (2023.02); *H10K 85/6574* (2023.02); *H10K 85/6576* (2023.02); *C07F 5/02* (2013.01); *C09K 2211/1007* (2013.01); *C09K 2211/1014* (2013.01); *C09K 2211/1096* (2013.01); *H10K 50/11* (2023.02); *H10K 50/156* (2023.02); *H10K 50/165* (2023.02); *H10K 50/166* (2023.02); *H10K 50/171* (2023.02)

(58) Field of Classification Search
CPC ......... C07F 5/027; C09K 11/02; C09K 11/06; C09K 2211/1007; C09K 2211/1014; C09K 2211/1096; H01L 27/32; H01L 51/0052; H01L 51/0059; H01L 51/0061; H01L 51/0071; H01L 51/0072; H01L 51/0073; H01L 51/0074; H01L 51/008; H01L 51/50; H01L 51/5012; H01L 51/5064; H01L 51/5076; H01L 51/508; H01L 51/5092; H10K 85/322; H10K 50/00; H10K 50/16; H10K 85/615; H10K 85/631; H10K 85/636; H10K 85/657; H10K 85/6572; H10K 85/6574; H10K 85/6576; H10K 50/11; H10K 50/156; H10K 50/165; H10K 50/166; H10K 50/171; F21Y 2115/15

See application file for complete search history.

(56) References Cited

U.S. PATENT DOCUMENTS

| | | | |
|---|---|---|---|
| 2013/0119365 A1* | 5/2013 | Iwaki | H01L 51/5068 257/40 |
| 2014/0058099 A1 | 2/2014 | Wakamiya et al. | |
| 2015/0236274 A1 | 8/2015 | Hatakeyama et al. | |
| 2015/0325800 A1 | 11/2015 | Ito et al. | |
| 2017/0117469 A1 | 4/2017 | Ito et al. | |
| 2017/0155050 A1* | 6/2017 | Kim | H01L 51/006 |
| 2018/0040821 A1 | 2/2018 | Hatakeyama et al. | |
| 2018/0094000 A1 | 4/2018 | Hatakeyama et al. | |
| 2018/0301629 A1* | 10/2018 | Hatakeyama | C07F 5/027 |
| 2019/0115538 A1* | 4/2019 | Lim | H01L 51/0052 |

FOREIGN PATENT DOCUMENTS

| | | |
|---|---|---|
| KR | 10-2014-0076170 A | 6/2014 |
| WO | WO 2004/061047 A2 | 7/2004 |
| WO | WO 2011/107186 A2 | 9/2011 |
| WO | WO 2012/118164 A1 | 9/2012 |
| WO | WO 2014/141725 A1 | 9/2014 |
| WO | WO 2015/102118 A1 | 7/2015 |
| WO | WO 2016/042781 A1 | 3/2016 |
| WO | WO 2016/143624 A1 | 9/2016 |
| WO | WO 2016/152418 A1 | 9/2016 |
| WO | WO 2016/152544 A2 | 9/2016 |
| WO | WO 2018/203666 A1 * | 11/2018 |

OTHER PUBLICATIONS

Hatakeyama et al., "Ultrapure Blue Thermally Activated Delayed Fluorescence Molecules: Efficient HOMO-LUMO Separation by the Multiple Resonance Effect," Advanced Materials, 2016, 28:2777-2781.

Office Action dated Apr. 21, 2020 in Japanese patent application No. 2018-514545, with machine English translation.

Office Action dated May 7, 2020, in corresponding Chinese patent application No. 201780025438.7, with machine English translation.

\* cited by examiner

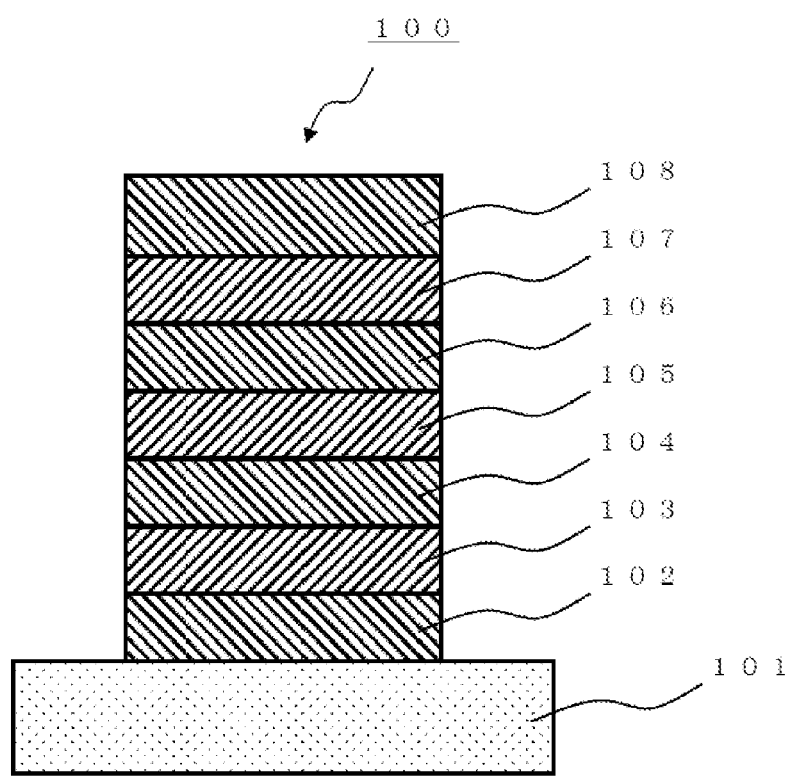

ORGANIC ELECTROLUMINESCENT ELEMENT

CROSS-REFERENCE TO RELATED APPLICATIONS

This application is a National Stage application of PCT/JP2017/015871, filed Apr. 20, 2017, which claims priority from Japanese application JP 2016-087640, filed Apr. 26, 2016.

TECHNICAL FIELD

The present invention relates to an organic electroluminescent element having a light emitting layer containing a polycyclic aromatic compound or a multimer thereof as a dopant material and a specific anthracene-based compound as a host material, and a display apparatus and a lighting apparatus using the same.

BACKGROUND ART

Conventionally, a display apparatus employing a luminescent element that is electroluminescent can be subjected to reduction of power consumption and thickness reduction, and therefore various studies have been conducted thereon. Furthermore, an organic electroluminescent element (hereinafter, referred to as an organic EL element) formed from an organic material has been studied actively because weight reduction or size expansion can be easily achieved. Particularly, active studies have been hitherto conducted on development of an organic material having luminescence characteristics for blue light which is one of the primary colors of light, or the like, and a combination of a plurality of materials having optimum luminescence characteristics, irrespective of whether the organic material is a high molecular weight compound or a low molecular weight compound.

An organic EL element has a structure having a pair of electrodes composed of a positive electrode and a negative electrode, and a single layer or a plurality of layers which are disposed between the pair of electrodes and contain an organic compound. The layer containing an organic compound includes a light emitting layer, a charge transport/injection layer for transporting or injecting charges such as holes or electrons, and the like, and various organic materials suitable for these layers have been developed.

Regarding the materials for light emitting layers, for example, benzofluorene-based compounds and the like have been developed (WO 2004/061047 A). Furthermore, regarding hole transporting materials, for example, triphenylamine-based compounds and the like have been developed (JP 2001-172232 A). Regarding electron transport materials, for example, anthracene-based compounds and the like have been developed (JP 2005-170911 A).

Furthermore, in recent years, materials obtained by improving a triphenylamine derivative have also been reported (WO 2012/118164 A). These materials are characterized in that flatness thereof has been increased by connecting aromatic rings that constitute triphenylamine with reference to N,N'-diphenyl-N,N'-bis(3-methylphenyl)-1,1'-biphenyl-4,4'-diamine (TPD) which has been already put to practical use. In this literature, for example, evaluation of the charge transporting characteristics of a NO-linked system compound (compound 1 of page 63) has been made. However, there is no description on a method for manufacturing materials other than the NO-linked system compound. When elements to be connected are different, the overall electron state of the compound is different. Therefore, the characteristics obtainable from materials other than the NO-linked system compound are not known. Examples of such a compound are also found elsewhere (WO 2011/107186 A). For example, since a compound having a conjugated structure involving high energy of triplet exciton (T1) can emit phosphorescent light having a shorter wavelength, the compound is useful as a material for blue light emitting layer.

CITATION LIST

Patent Literature

Patent Literature 1: WO 2004/061047 A
Patent Literature 2: JP 2001-172232 A
Patent Literature 3: JP 2005-170911 A
Patent Literature 4: WO 2012/118164 A
Patent Literature 5: WO 2011/107186 A

SUMMARY OF INVENTION

Technical Problem

As described above, various materials that are used in organic EL elements have been developed. However, in order to increase a selection range of the material for organic EL elements, it is desired to develop materials formed from compounds different from conventional compounds. In particular, organic EL characteristics obtained from materials other than an NO-linked compound reported in Patent Literature 4 and a method for manufacturing the same are not known, and a compound obtaining optimum luminescence characteristics in combination with materials other than the NO-linked compound is not known.

Solution to Problem

The present inventors conducted intensive studies in order to solve the problems described above. As a result, the present inventors have found a novel polycyclic aromatic compound in which a plurality of aromatic rings are linked with a boron atom and a nitrogen atom, and have succeeded in manufacturing the same. The present inventors have found that an excellent organic EL element is obtained by disposing a light emitting layer containing this polycyclic aromatic compound and a specific anthracene-based compound between a pair of electrodes to constitute an organic EL element, and have completed the present invention.

[1]

An organic electroluminescent element comprising a pair of electrodes composed of a positive electrode and a negative electrode and a light emitting layer disposed between the pair of electrodes, in which the light emitting layer comprises at least one of a polycyclic aromatic compound represented by the following general formula (1) and a polycyclic aromatic compound multimer having a plurality of structures represented by the following general formula (1), and an anthracene-based compound represented by the following general formula (3).

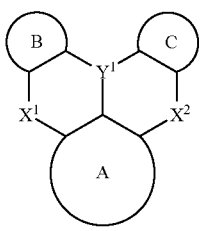

(1)

(In the above formula (1), ring A, ring B and ring C each independently represent an aryl ring or a heteroaryl ring, while at least one hydrogen atom in these rings may be substituted, $Y^1$ represents B, $X^1$ and $X^2$ each independently represent N—R, R of the N—R is an optionally substituted aryl, an optionally substituted heteroaryl or alkyl, R of the N—R may be bonded to the ring A, ring B, and/or ring C with a linking group or a single bond, and at least one hydrogen atom in a compound or a structure represented by formula (1) may be substituted by a halogen atom or a deuterium atom.)

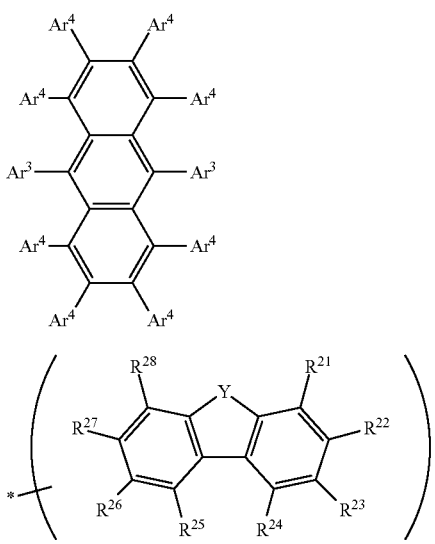

(3)

(4)

(In the above formula (3), $Ar^3$ and $Ar^4$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, provided that a naphthyl group and a naphthyl group fused with one benzene ring are excluded as $Ar^3$, at least one hydrogen atom of a compound represented by formula (3) may be substituted by a deuterium atom, at least one hydrogen atom of a compound represented by formula (3) is substituted by a group represented by the above formula (4), Y represents —O—, —S— or >N—$R^{29}$ in the above formula (4), $R^{21}$ to $R^{28}$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, adjacent groups among $R^{21}$ to $R^{28}$ may be bonded to each other to form a hydrocarbon ring, an aryl ring, or a heteroaryl ring, $R^{29}$ is an optionally substituted aryl or a bonding position with a compound represented by formula (3), and a group represented by formula (4) is substituted by at least one hydrogen atom in a compound represented by formula (3) at *, and is bonded thereto at any position in a structure of formula (4).)

[2]

The organic electroluminescent element described in the above [1], in which in the above formula (1), the ring A, ring B, and ring C each independently represent an aryl ring or a heteroaryl ring, while at least one hydrogen atom in these rings may be substituted by a substituted or unsubstituted aryl, a substituted or unsubstituted heteroaryl, a substituted or unsubstituted diarylamino, a substituted or unsubstituted diheteroarylamino, a substituted or unsubstituted arylheteroarylamino, a substituted or unsubstituted alkyl, a substituted or unsubstituted alkoxy, or a substituted or unsubstituted aryloxy, each of these rings has a 5-membered or 6-membered ring sharing a bond with a fused bicyclic structure at the center of the above formula constructed by $Y^1$, $X^1$, and $X^2$, $Y^1$ represents B, $X^1$ and $X^2$ each independently represent N—R, R of the N—R represents an aryl which may be substituted by an alkyl, a heteroaryl which may be substituted by an alkyl or alkyl, R of the N—R may be bonded to the ring A, ring B, and/or ring C with —O—, —S—, —C(—R)$_2$— or a single bond, R of the —C(—R)$_2$— represents a hydrogen atom or an alkyl, at least one hydrogen atom in a compound or structure represented by formula (1) may be substituted by a halogen atom or a deuterium atom, and in a case of a multimer, the multimer is a dimer or a trimer having two or three structures represented by formula (1).

[3]

The organic electroluminescent element described in the above [1], in which the light emitting layer comprises at least one of a polycyclic aromatic compound represented by the following general formula (2) and a polycyclic aromatic compound multimer having a plurality of structures represented by the following general formula (2), and an anthracene-based compound represented by the following formula (3).

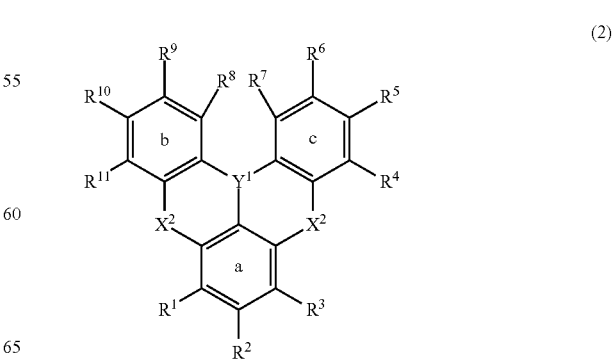

(2)

(In the above formula (2),

R¹, R², R³, R⁴, R⁵, R⁶, R⁷, R⁸, R⁹, R¹⁰, and R¹¹ each independently represent a hydrogen atom, an aryl, a heteroaryl, a diarylamino, a diheteroarylamino, an arylheteroarylamino, an alkyl, an alkoxy, or an aryloxy, while at least one hydrogen atom in these may be substituted by an aryl, a heteroaryl, or an alkyl, adjacent groups among R¹ to R¹¹ may be bonded to each other to form an aryl ring or a heteroaryl ring together with ring a, ring b, or ring c, at least one hydrogen atom in the ring thus formed may be substituted by an aryl, a heteroaryl, a diarylamino, a diheteroarylamino, an arylheteroarylamino, an alkyl, an alkoxy, or an aryloxy, at least one hydrogen atom in these may be substituted by an aryl, a heteroaryl or an alkyl, Y¹ represents B, X¹ and X² each independently represent N—R, R of the N—R represents an aryl having 6 to 12 carbon atoms, a heteroaryl having 2 to 15 carbon atoms, or an alkyl having 1 to 6 carbon atoms, R of the N—R may be bonded to the ring a, ring b and/or ring c with —O—, —S—, —C(—R)₂—, or a single bond, R of the —C(—R)₂— represents an alkyl having 1 to 6 carbon atoms, and at least one hydrogen atom in a compound represented by formula (2) may be substituted by a halogen atom or a deuterium atom.)

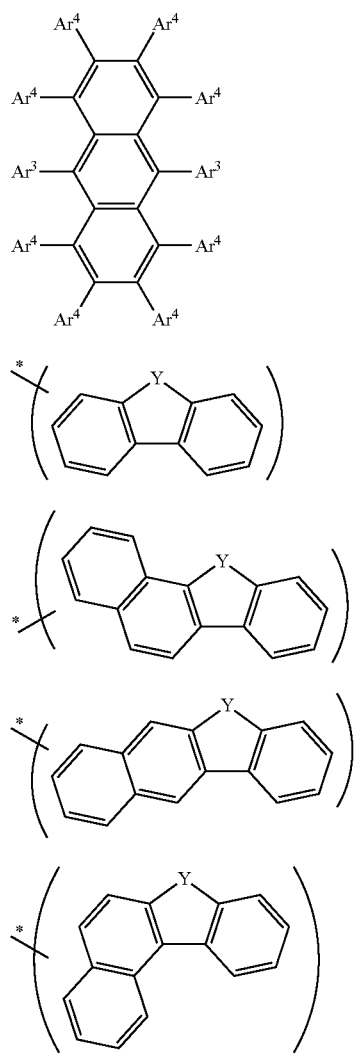

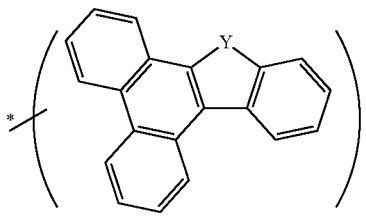

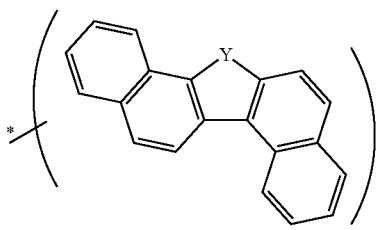

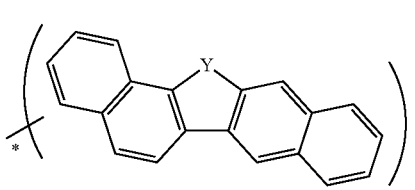

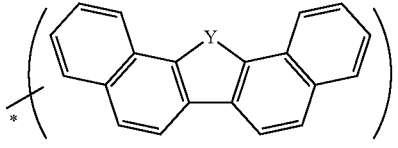

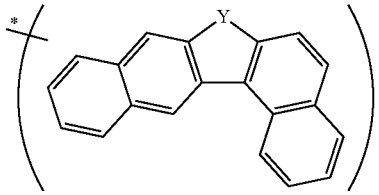

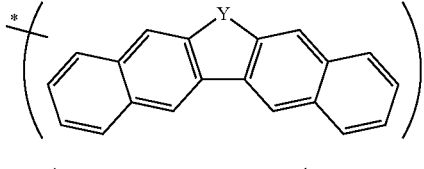

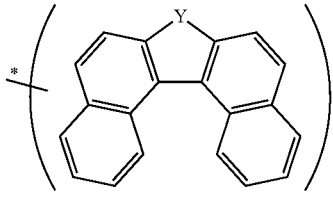

(In the above formula (3),

Ar³ each independently represent a hydrogen atom, an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, provided that a naphthyl group and a naphthyl group fused with one benzene ring are excluded as Ar³ and at least one hydrogen atom in Ar³ is substituted by a group represented by any one of the above formulas (4-1) to (4-11), Ar⁴ each independently represent a hydrogen atom, an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, and at least one hydrogen atom in a compound represented by formula (3) may be substituted by a deuterium atom, in the above formulas (4-1) to (4-11), Y represents —O—, —S— or >N—R²⁹, R²⁹ is an aryl or a bonding position with a compound represented by formula (3), at least one hydrogen atom in groups represented by formulas (4-1) to (4-11) may be substituted by an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, and each of the groups represented by formulas (4-1) to (4-11) is substituted with at least one hydrogen atom in Ar³ at *, and is bonded thereto at any position in structures of formulas (4-1) to (4-11).)

[4]

The organic electroluminescent element described in the above [3], in which in the above formula (2), $R^1$, $R^2$, $R^3$, $R^4$, $R^5$, $R^6$, $R^7$, $R^8$, $R^9$, $R^{10}$, and $R^{11}$ each independently represent a hydrogen atom, an aryl having 6 to 30 carbon atoms, a heteroaryl having 2 to 30 carbon atoms or a diarylamino (the aryl is an aryl having 6 to 12 carbon atoms), adjacent groups among $R^1$ to $R^{11}$ may be bonded to each other to form an aryl having 9 to 16 carbon atoms or a heteroaryl ring having 6 to 15 carbon atoms together with the ring a, ring b, or ring c, at least one hydrogen atom in the ring thus formed may be substituted by an aryl having 6 to 10 carbon atoms, $Y^1$ represents B, $X^1$ and $X^2$ each independently represent N—R, R of the N—R is an aryl having 6 to 10 carbon atoms, at least one hydrogen atom in a compound represented by formula (2) may be substituted by a halogen atom or a deuterium atom, in the above formula (3), Ar³ each independently represent a hydrogen atom, an aryl, a heteroaryl, a diaryl substituted amino, a diheteroaryl substituted amino, or an aryl heteroaryl substituted amino, provided that a naphthyl group and a naphthyl group fused with one benzene ring are excluded as Ar³ and at least one hydrogen atom in Ar³ is substituted by a group represented by any one of the above formulas (4-1) to (4-11), Ar⁴ each independently represent a hydrogen atom, an alkyl, an aryl, a heteroaryl, a trialkylsilyl, a diaryl substituted amino, a diheteroaryl substituted amino, or an aryl heteroaryl substituted amino, and at least one hydrogen atom in a compound represented by formula (3) may be substituted by a deuterium atom.

[5]

The organic electroluminescent element described in the above [1], in which the polycyclic aromatic compound represented by the general formula (1) and the polycyclic aromatic compound multimer having a plurality of structures represented by the general formula (1) are represented by any of the following formulas.

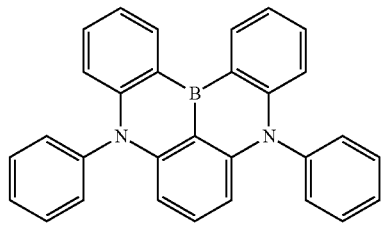

(1-401)

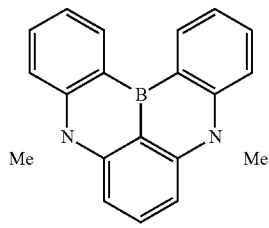

(1-411)

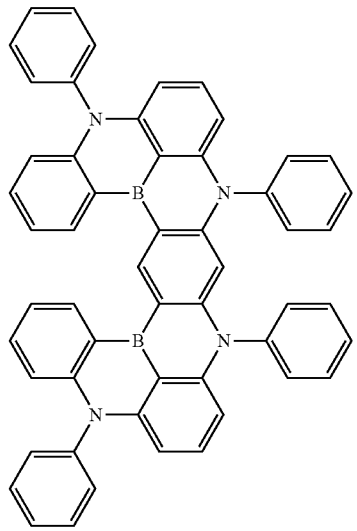

(1-422)

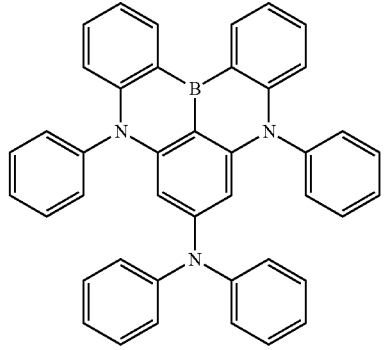

(1-447)

-continued
(1-1152)
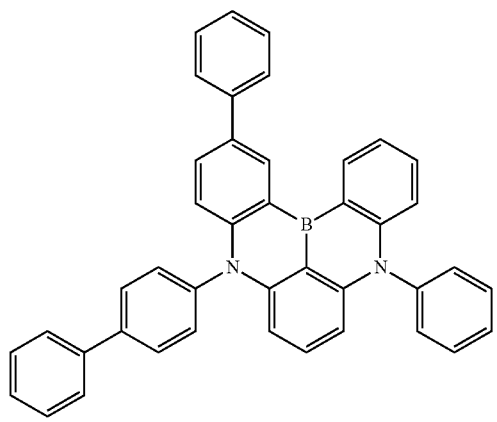
(1-1159)
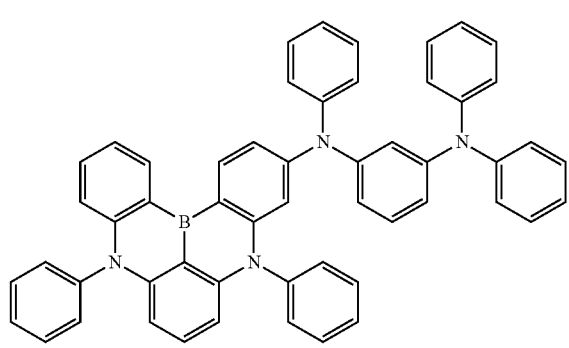
(1-2619)
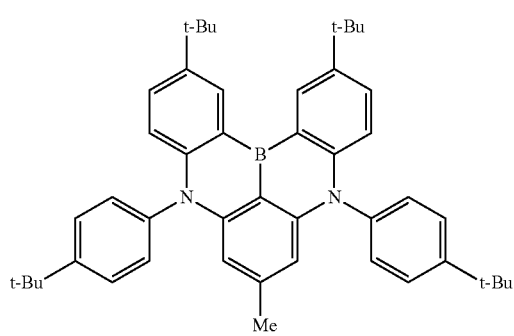
-continued
(1-2620)
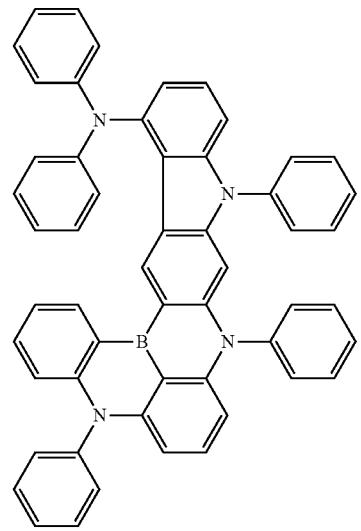
(1-2621)
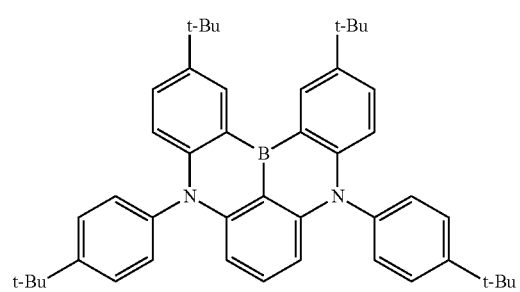
(1-2626)
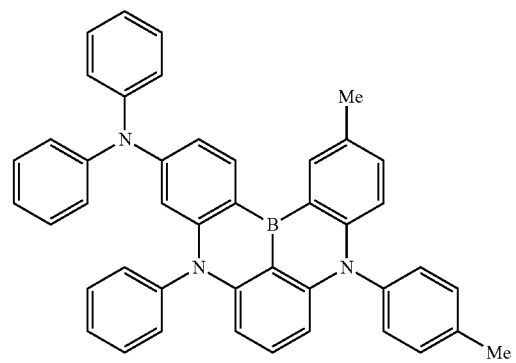
(1-2657)
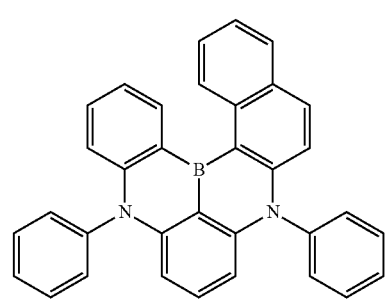

(1-2662)
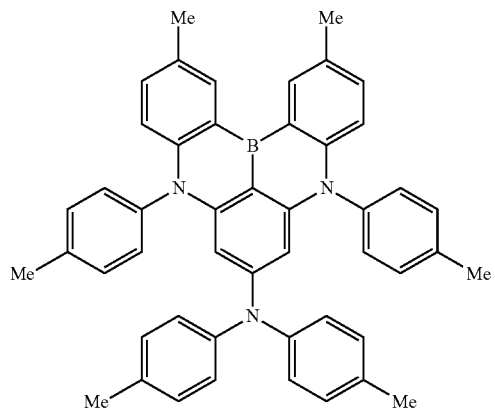
(1-2665)
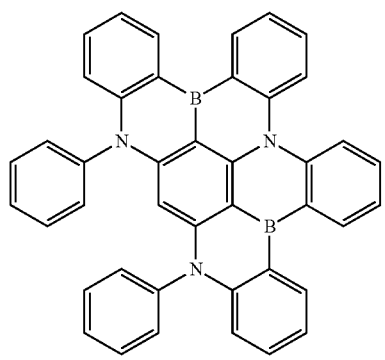
(1-2676)
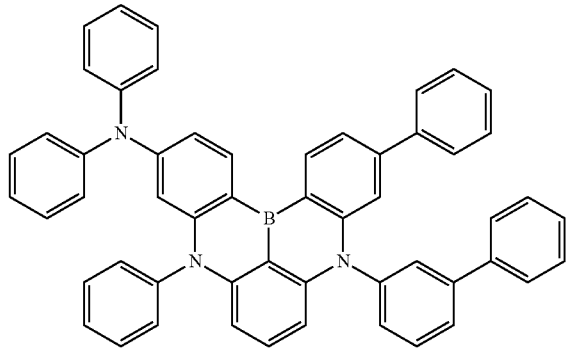
(1-2678)
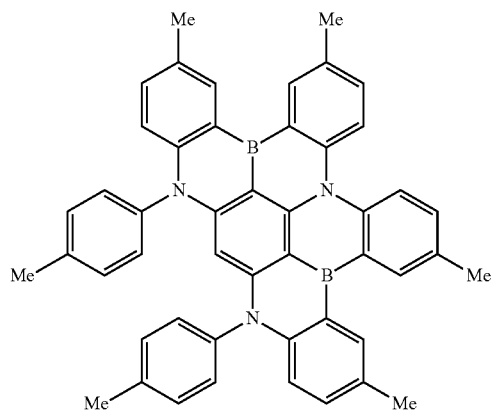
(1-2679)
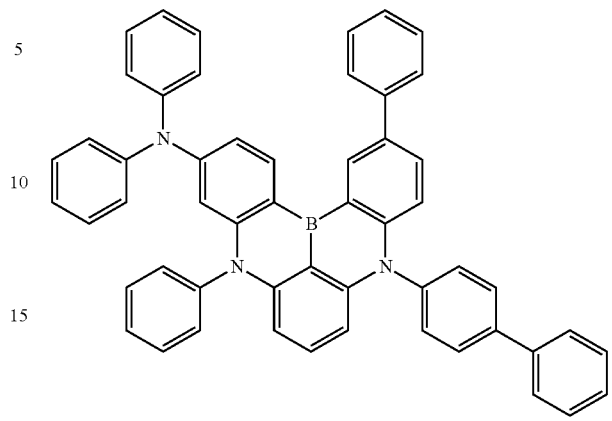
(1-2680)
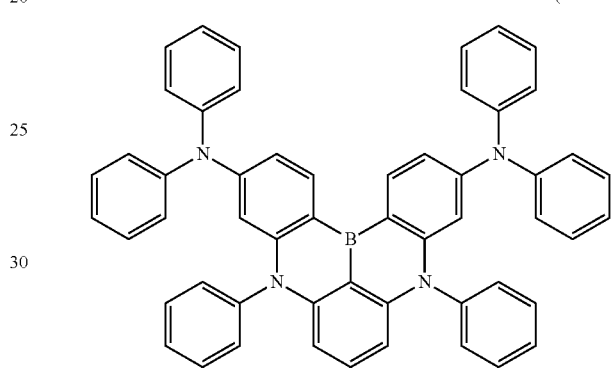
(1-2681)
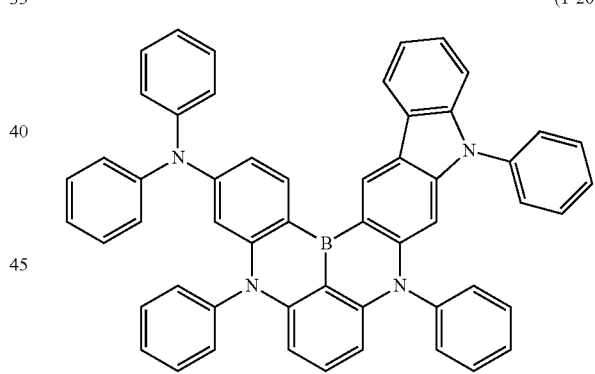
(1-2682)
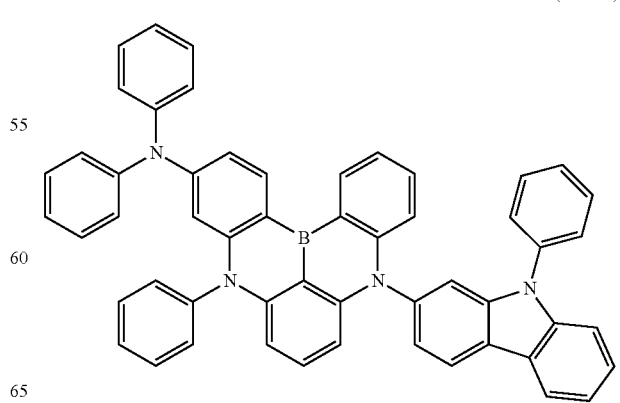

(1-2683)
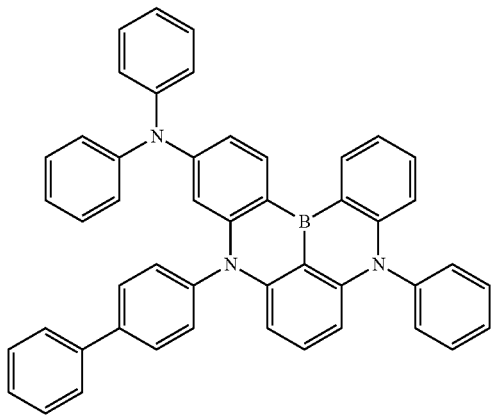
(1-2691)
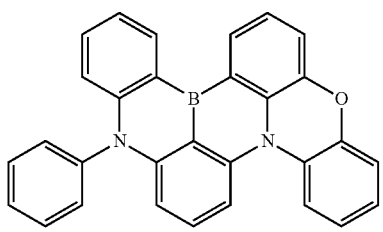
(1-2699)
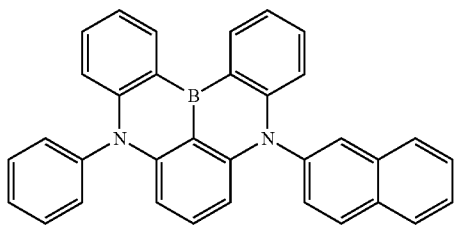
[6]
The organic electroluminescent element described in the above [1], in which the polycyclic aromatic compound represented by the general formula (1) is represented by any of the following formulas.
(1-401-1)
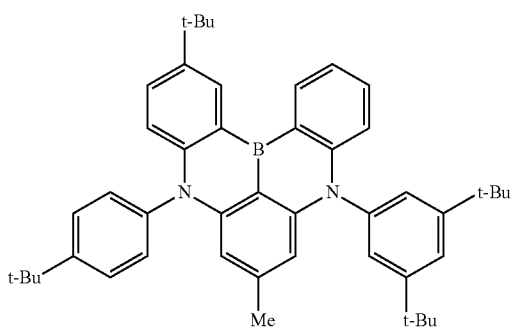
(1-401-2)
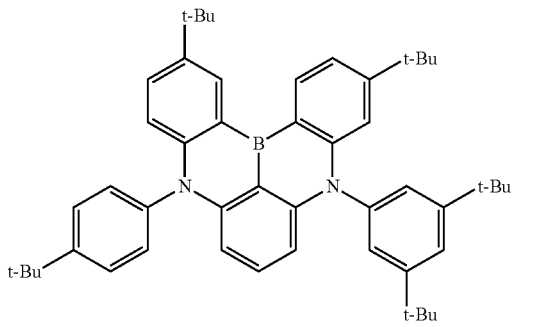
(1-401-3)
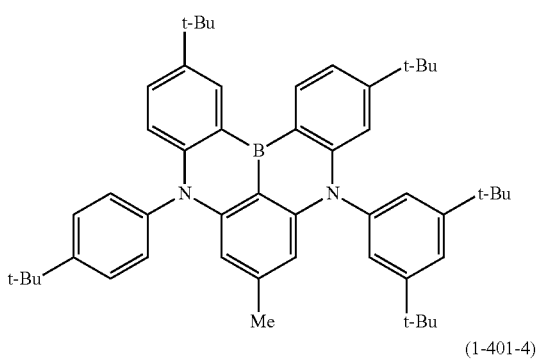
(1-401-4)
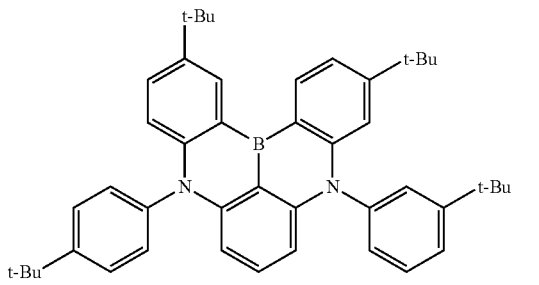
(1-401-5)
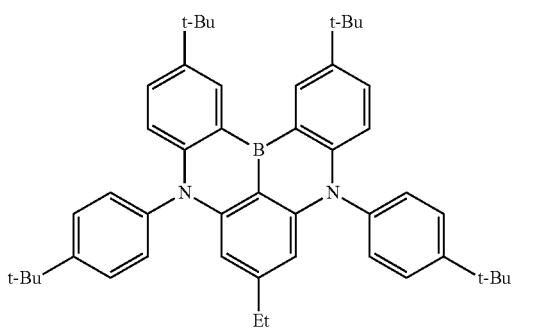
(1-401-6)
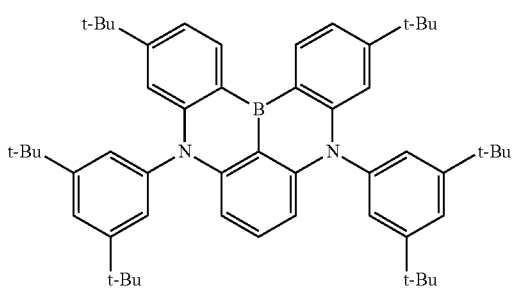

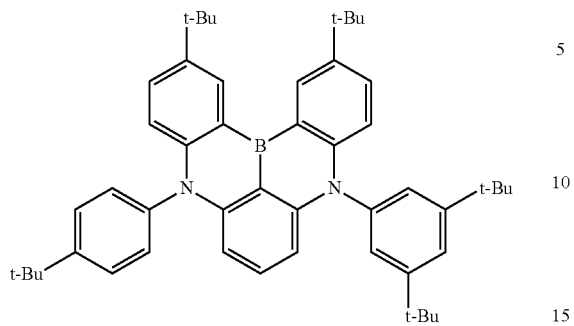
(1-401-7)
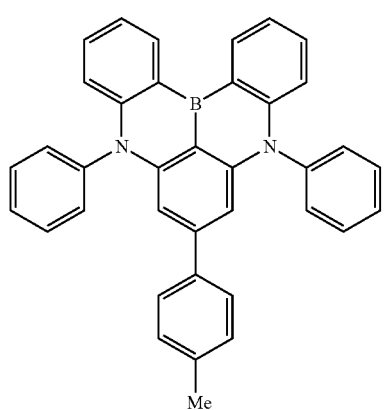
(1-441-1)
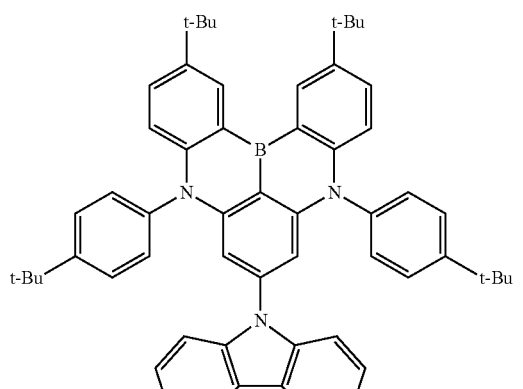
(1-448-1)
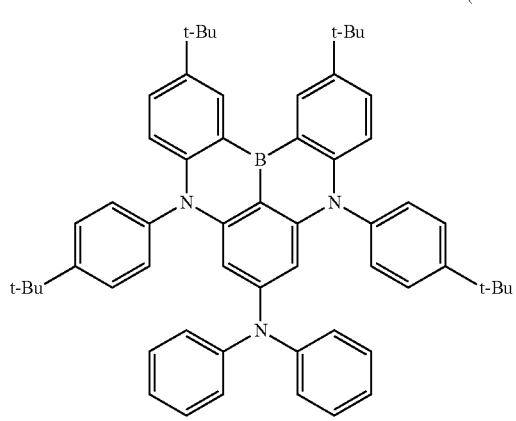
(1-447-1)
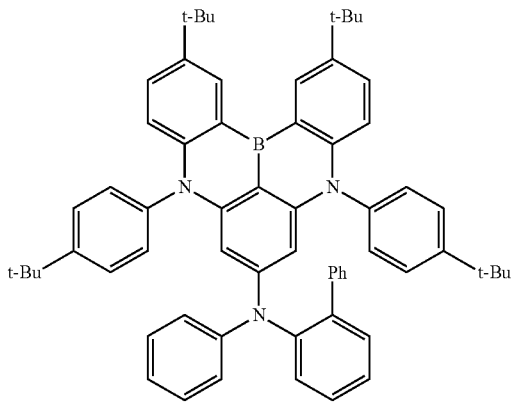
(1-447-2)
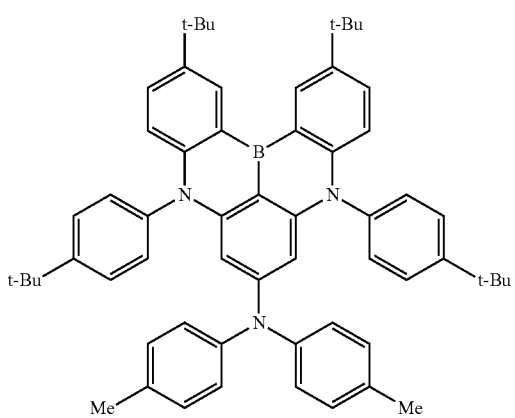
(1-447-3)
(1-449)
[7]
The organic electroluminescent element described in the above [1], in which the compound represented by the general formula (3) is represented by any of the following formulas.

(3-131-N-1)

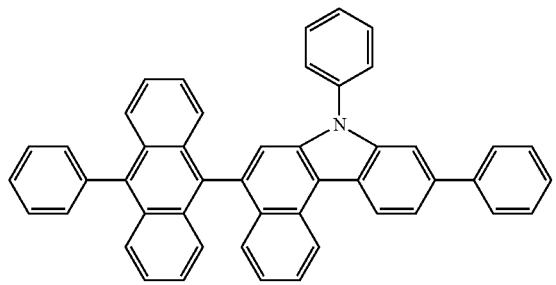

(3-134-O)

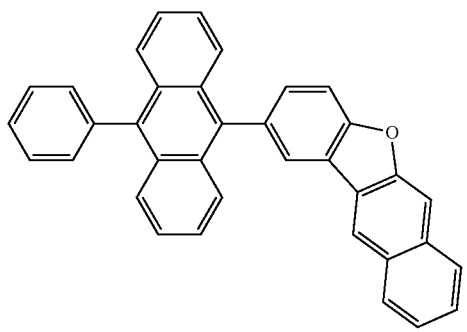

(3-141-O)

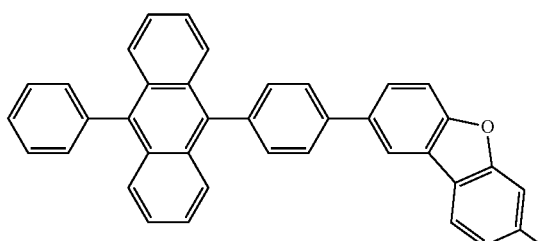

(3-180-O)

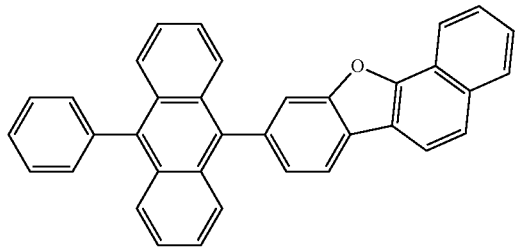

(3-181-O)

(3-181-S)

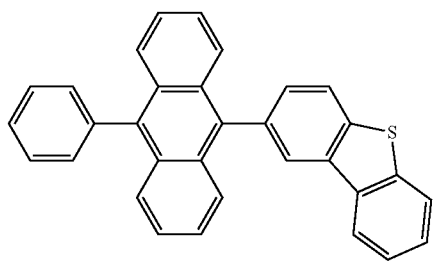

(3-182-N-1)

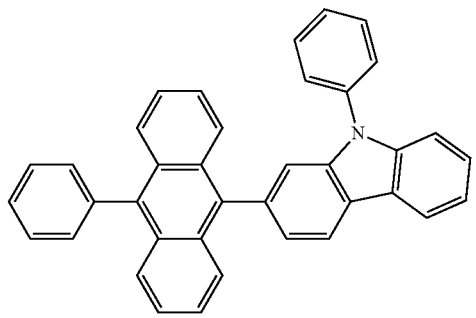

(3-183-N)

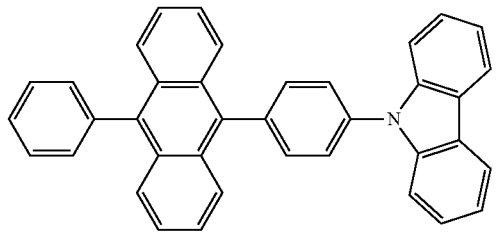

[8]

The organic electroluminescent element described in any one of the above [1] to [7], further comprising an electron transport layer and/or an electron injection layer disposed between the negative electrode and the light emitting layer, in which at least one of the electron transport layer and the electron injection layer comprises at least one selected from the group consisting of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, and a quinolinol-based metal complex.

[9]

The organic electroluminescent element described in the above [8], in which the electron transport layer and/or electron injection layer further comprise/comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

[10]

A display apparatus comprising the organic electroluminescent element described in any one of the above [1] to [9].

[11]
A lighting apparatus comprising the organic electroluminescent element described in any one of the above [1] to [9].

Advantageous Effects of Invention

According to a preferable embodiment of the present invention, it is possible to provide a novel polycyclic aromatic compound and an anthracene-based compound which can obtain optimum light emitting characteristics in combination with the polycyclic aromatic compound, and by manufacturing an organic EL element using a material for a light emitting layer obtained by combining these compounds, it is possible to provide an organic EL element having a low consumption power and an excellent quantum efficiency.

BRIEF DESCRIPTION OF DRAWINGS

The FIGURE is a schematic cross-sectional view illustrating an organic EL element according to the present embodiment.

DESCRIPTION OF EMBODIMENTS

1. Characteristic Light Emitting Layer in Organic EL Element

The present invention relates to an organic EL element including a pair of electrodes composed of a positive electrode and a negative electrode and a light emitting layer disposed between the pair of electrodes, in which the light emitting layer contains at least one of a polycyclic aromatic compound represented by the following general formula (1) and a polycyclic aromatic compound multimer having a plurality of structures represented by the following general formula (1), and an anthracene-based compound represented by the following general formula (3).

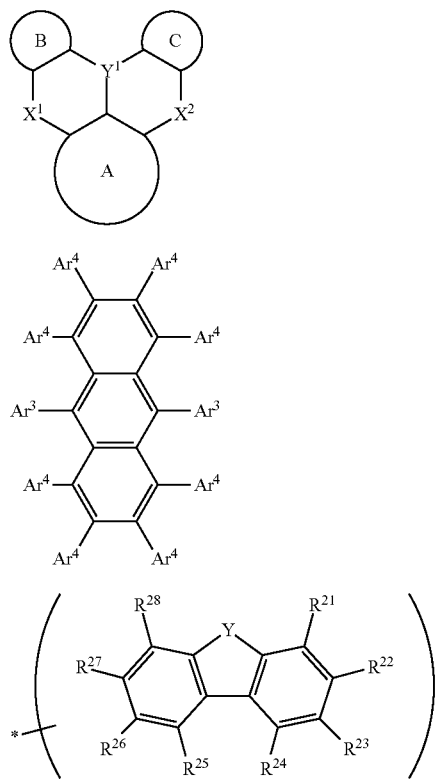

Note that A, B, C, $Y^1$, $X^1$, and $X^2$ in formula (1) are defined in the same manner as described above, and $Ar^3$, $Ar^4$, Y, and $R^{21}$ to $R^{28}$ in formulas (3) and (4) are defined in the same manner as described above.

1-1. Polycyclic Aromatic Compound and Multimer Thereof

Each of a polycyclic aromatic compound represented by general formula (1) and a polycyclic aromatic compound multimer having a plurality of structures represented by general formula (1) basically functions as a dopant. The polycyclic aromatic compound and a multimer thereof are preferably a polycyclic aromatic compound represented by the following general formula (2) or a polycyclic aromatic compound multimer having a plurality of structures represented by the following general formula (2).

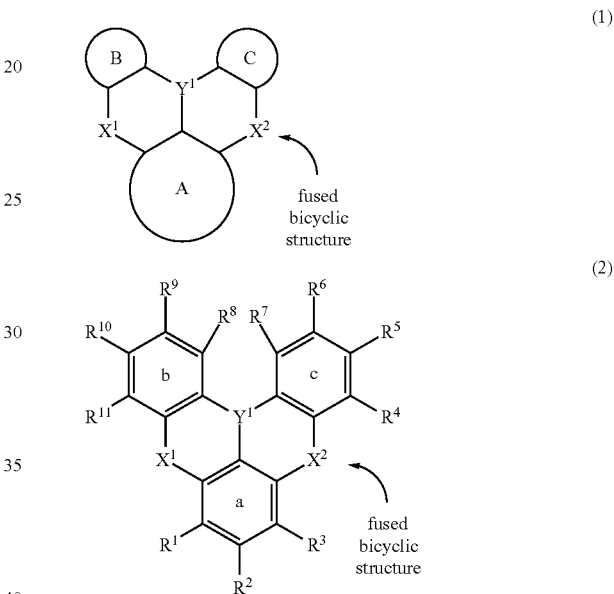

The ring A, ring B and ring C in general formula (1) each independently represent an aryl ring or a heteroaryl ring, and at least one hydrogen atom in these rings may be substituted by a substituent. This substituent is preferably a substituted or unsubstituted aryl, a substituted or unsubstituted heteroaryl, a substituted or unsubstituted diarylamino, a substituted or unsubstituted diheteroarylamino, a substituted or unsubstituted arylheteroarylamino (an amino group having an aryl and a heteroaryl), a substituted or unsubstituted alkyl, a substituted or unsubstituted alkoxy, or a substituted or unsubstituted aryloxy. In a case where these groups have substituents, examples of the substituents include an aryl, a heteroaryl, and an alkyl. Furthermore, the aryl ring or heteroaryl ring preferably has a 5-membered ring or 6-membered ring sharing a bond with a fused bicyclic structure at the center of general formula (1) constituted by $Y^1$, $X^1$, and $X^2$ (hereinafter, this structure is also referred to as "structure D").

Here, the "fused bicyclic structure (structure D)" means a structure in which two saturated hydrocarbon rings that are configured to include $Y^1$, $X^1$ and $X^2$ and indicated at the center of general formula (1) are fused. Furthermore, a "6-membered ring sharing a bond with the fused bicyclic structure" means, for example, ring a (benzene ring (6-membered ring)) fused to the structure D as represented by the above general formula (2). Furthermore, the phrase "aryl ring or heteroaryl ring (which is ring A) has this 6-membered ring" means that the ring A is formed only from this 6-membered ring, or the ring A is formed such that other rings are further fused to this 6-membered ring so as to include this 6-membered ring. In other words, the "aryl ring or heteroaryl ring (which is ring A) having a 6-membered ring" as used herein means that the 6-membered ring that constitutes the entirety or a portion of the ring A is fused to the structure D. The same description applies to the "ring B (ring b)", "ring C (ring c)", and the "5-membered ring".

The ring A (or ring B or ring C) in general formula (1) corresponds to ring a and its substituents $R^1$ to $R^3$ in general formula (2) (or ring b and its substituents $R^4$ to $R^7$, or ring c and its substituents $R^8$ to $R^{11}$). That is, general formula (2) corresponds to a structure in which "rings A to C having 6-membered rings" have been selected as the rings A to C of general formula (1). For this meaning, the rings of general formula (2) are represented by small letters a to c.

In general formula (2), adjacent groups among the substituents $R^1$ to $R^{11}$ of the ring a, ring b, and ring c may be bonded to each other to form an aryl ring or a heteroaryl ring together with the ring a, ring b, or ring c, and at least one hydrogen atom in the ring thus formed may be substituted by an aryl, a heteroaryl, a diarylamino, a diheteroarylamino, an arylheteroarylamino, an alkyl, an alkoxy or an aryloxy, while at least one hydrogen atom in these may be substituted by an aryl, a heteroaryl, or an alkyl. Therefore, in a polycyclic aromatic compound represented by general formula (2), a ring structure constituting the compound changes as represented by the following formulas (2-1) and (2-2) according to a mutual bonding form of substituents in the ring a, ring b or ring c. Ring A', ring B' and ring C' in each formula correspond to the ring A, ring B and ring C in general formula (1), respectively. Note that $R^1$ to $R^{11}$, $Y^1$, $X^1$, and $X^2$ in formulas (2-1) and (2-2) are defined in the same manner as those in formula (2)

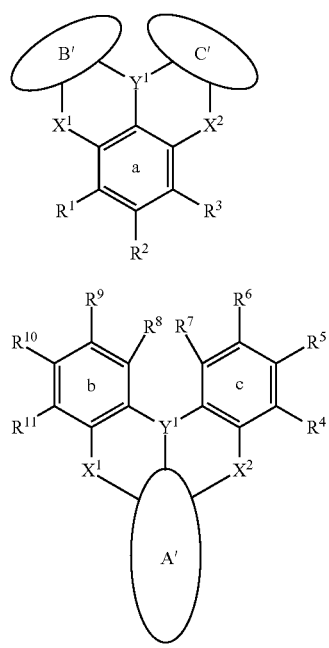

The ring A', ring B' and, ring C' in the above formulas (2-1) and (2-2) each represent, to be described in connection with general formula (2), an aryl ring or a heteroaryl ring formed by bonding adjacent groups among the substituents $R^1$ to $R^{11}$ together with the ring a, ring b, and ring c, respectively (may also be referred to as a fused ring obtained by fusing another ring structure to the ring a, ring b, or ring c). Incidentally, although not indicated in the formula, there is also a compound in which all of the ring a, ring b, and ring c have been changed to the ring A', ring B' and ring C'. Furthermore, as apparent from the above formulas (2-1) and (2-2), for example, $R^8$ of the ring b and $R^7$ of the ring c, $R^{11}$ of the ring b and $R^1$ of the ring a, $R^4$ of the ring c and $R^3$ of the ring a, and the like do not correspond to "adjacent groups", and these groups are not bonded to each other. That is, the term "adjacent groups" means adjacent groups on the same ring.

A compound represented by the above formula (2-1) or (2-2) corresponds to, for example, a compound represented by any one of formulas (1-402) to (1-409) and (1-412) to (1-419) listed as specific compounds that are described below. That is, for example, the compound represented by formula (2-1) or (2-2) is a compound having ring A' (or ring B' or ring C') that is formed by fusing a benzene ring, an indole ring, a pyrrole ring, a benzofuran ring or a benzothiophene ring to a benzene ring which is ring a (or ring b or ring c), and the fused ring A' (or fused ring B' or fused ring C') that has been formed is a naphthalene ring, a carbazole ring, an indole ring, a dibenzofuran ring, or a dibenzothiophene ring.

$Y^1$ in general formulas (1) and (2) represents B.

$X^1$ and $X^2$ in general formula (1) each independently represent N—R, while R of the N—R represents an optionally substituted aryl, or an optionally substituted heteroaryl or an alkyl, and R of the N—R may be bonded to the ring B and/or ring C with a linking group or a single bond. The linking group is preferably —O—, —S— or —C(—R)$_2$—. Incidentally, R of the "—C(—R)$_2$—" represents a hydrogen atom or an alkyl. This description also applies to $X^1$ and $X^2$ in general formula (2).

Here, the provision that "R of the N—R is bonded to the ring A, ring B and/or ring C with a linking group or a single bond" for general formula (1) corresponds to the provision that "R of the N—R is bonded to the ring a, ring b and/or ring c with —O—, —S—, —C(—R)$_2$— or a single bond" for general formula (2).

This provision can be expressed by a compound having a ring structure represented by the following formula (2-3-1), in which $X^1$ or $X^2$ is incorporated into the fused ring B' or C'. That is, for example, the compound is a compound having ring B' (or ring C') formed by fusing another ring to a benzene ring which is ring b (or ring c) in general formula (2) so as to incorporate $X^1$ (or $X^2$). This compound corresponds to, for example, a compound represented by any one of formulas (1-451) to (1-462) or a compound represented by any one of formulas (1-1401) to (1-1460), listed as specific examples that are described below, and the fused ring B' (or fused ring C') that has been formed is, for example, a phenoxazine ring, a phenothiazine ring, or an acridine ring.

The above provision can be expressed by a compound having a ring structure in which $X^1$ and/or $X^2$ are/is incorporated into the fused ring A', represented by the following formula (2-3-2) or (2-3-3). That is, for example, the compound is a compound having ring A' formed by fusing another ring to a benzene ring which is ring a in general formula (2) so as to incorporate $X^1$ (and/or $X^2$). This compound corresponds to, for example, a compound represented by any one of formulas (1-471) to (1-479) listed as specific examples that are described below, and the fused ring A' that has been formed is, for example, a phenoxazine ring, a phenothiazine ring, or an acridine ring. Note that $R^1$ to $R^{11}$, $Y^1$, $X^1$, and $X^2$ in formulas (2-3-1) to (2-3-3) are defined in the same manner as those in formula (2).

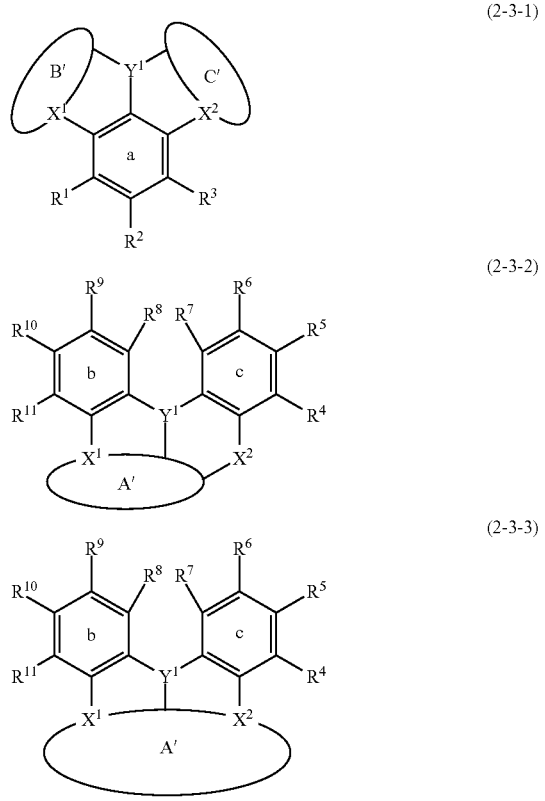

(2-3-1)

(2-3-2)

(2-3-3)

The "aryl ring" as the ring A, ring B or ring C of the general formula (1) is, for example, an aryl ring having 6 to 30 carbon atoms, and the aryl ring is preferably an aryl ring having 6 to 16 carbon atoms, more preferably an aryl ring having 6 to 12 carbon atoms, and particularly preferably an aryl ring having 6 to 10 carbon atoms. Incidentally, this "aryl ring" corresponds to the "aryl ring formed by bonding adjacent groups among $R^1$ to $R^{11}$ together with the ring a, ring b, or ring c" defined by general formula (2). Ring a (or ring b or ring c) is already constituted by a benzene ring having 6 carbon atoms, and therefore the carbon number of 9 in total of a fused ring obtained by fusing a 5-membered ring to this benzene ring becomes a lower limit of the carbon number.

Specific examples of the "aryl ring" include a benzene ring which is a monocyclic system; a biphenyl ring which is a bicyclic system; a naphthalene ring which is a fused bicyclic system; a terphenyl ring (m-terphenyl, o-terphenyl, or p-terphenyl) which is a tricyclic system; an acenaphthylene ring, a fluorene ring, a phenalene ring and a phenanthrene ring which are fused tricyclic systems; a triphenylene ring, a pyrene ring and a naphthacene ring which are fused tetracyclic systems; and a perylene ring and a pentacene ring which are fused pentacyclic systems.

The "heteroaryl ring" as the ring A, ring B or ring C of general formula (1) is, for example, a heteroaryl ring having 2 to 30 carbon atoms, and the heteroaryl ring is preferably a heteroaryl ring having 2 to 25 carbon atoms, more preferably a heteroaryl ring having 2 to 20 carbon atoms, still more preferably a heteroaryl ring having 2 to 15 carbon atoms, and particularly preferably a heteroaryl ring having 2 to 10 carbon atoms. In addition, examples of the "heteroaryl ring" include a heterocyclic ring containing 1 to 5 heteroatoms selected from an oxygen atom, a sulfur atom, and a nitrogen atom in addition to a carbon atom as a ring-constituting atom. Incidentally, this "heteroaryl ring" corresponds to the "heteroaryl ring formed by bonding adjacent groups among the $R^1$ to $R^{11}$ together with the ring a, ring b, or ring c" defined by general formula (2). The ring a (or ring b or ring c) is already constituted by a benzene ring having 6 carbon atoms, and therefore the carbon number of 6 in total of a fused ring obtained by fusing a 5-membered ring to this benzene ring becomes a lower limit of the carbon number.

Specific examples of the "heteroaryl ring" include a pyrrole ring, an oxazole ring, an isoxazole ring, a thiazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzoxazole ring, a benzothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazane ring, an oxadiazole ring, and a thianthrene ring.

At least one hydrogen atom in the above "aryl ring" or "heteroaryl ring" may be substituted by a substituted or unsubstituted "aryl", a substituted or unsubstituted "heteroaryl", a substituted or unsubstituted "diarylamino", a substituted or unsubstituted "diheteroarylamino", a substituted or unsubstituted "arylheteroarylamino", a substituted or unsubstituted "alkyl", a substituted or unsubstituted "alkoxy", or a substituted or unsubstituted "aryloxy", which is a primary substituent. Examples of the aryl of the "aryl", "heteroaryl" and "diarylamino", the heteroaryl of the "diheteroarylamino", the aryl and the heteroaryl of the "arylheteroarylamino", and the aryl of the "aryloxy" as these primary substituents include a monovalent group of the "aryl ring" or "heteroaryl ring" described above.

Furthermore, the "alkyl" as the primary substituent may be either linear or branched, and examples thereof include a linear alkyl having 1 to 24 carbon atoms and a branched alkyl having 3 to 24 carbon atoms. An alkyl having 1 to 18 carbon atoms (branched alkyl having 3 to 18 carbon atoms) is preferable, an alkyl having 1 to 12 carbon atoms (branched alkyl having 3 to 12 carbon atoms) is more preferable, an alkyl having 1 to 6 carbon atoms (branched alkyl having 3 to 6 carbon atoms) is still more preferable, and an alkyl having 1 to 4 carbon atoms (branched alkyl having 3 to 4 carbon atoms) is particularly preferable.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

Furthermore, the "alkoxy" as a primary substituent may be, for example, a linear alkoxy having 1 to 24 carbon atoms or a branched alkoxy having 3 to 24 carbon atoms. The alkoxy is preferably an alkoxy having 1 to 18 carbon atoms (branched alkoxy having 3 to 18 carbon atoms), more preferably an alkoxy having 1 to 12 carbon atoms (branched alkoxy having 3 to 12 carbon atoms), still more preferably an alkoxy having 1 to 6 carbon atoms (branched alkoxy having 3 to 6 carbon atoms), and particularly preferably an alkoxy having 1 to 4 carbon atoms (branched alkoxy having 3 to 4 carbon atoms).

Specific examples of the alkoxy include a methoxy, an ethoxy, a propoxy, an isopropoxy, a butoxy, an isobutoxy, a s-butoxy, a t-butoxy, a pentyloxy, a hexyloxy, a heptyloxy, and an octyloxy.

In the substituted or unsubstituted "aryl", substituted or unsubstituted "heteroaryl", substituted or unsubstituted "diarylamino", substituted or unsubstituted "diheteroarylamino", substituted or unsubstituted "arylheteroarylamino", substituted or unsubstituted "alkyl", substituted or unsubstituted "alkoxy", or substituted or unsubstituted "aryloxy", which is the primary substituent, at least one hydrogen atom may be substituted by a secondary substituent, as described to be substituted or unsubstituted. Examples of this secondary substituent include an aryl, a heteroaryl, and an alkyl, and for the details thereof, reference can be made to the above description on the monovalent group of the "aryl ring" or "heteroaryl ring" and the "alkyl" as the primary substituent. Furthermore, regarding the aryl or heteroaryl as the secondary substituent, an aryl or heteroaryl in which at least one hydrogen atom is substituted by an aryl such as phenyl (specific examples are described above), or an alkyl such as methyl (specific examples are described above), is also included in the aryl or heteroaryl as the secondary substituent. For instance, when the secondary substituent is a carbazolyl group, a carbazolyl group in which at least one hydrogen atom at the 9-position is substituted by an aryl such as phenyl, or an alkyl such as methyl, is also included in the heteroaryl as the secondary substituent.

Examples of the aryl, the heteroaryl, the aryl of the diarylamino, the heteroaryl of the diheteroarylamino, the aryl and the heteroaryl of the arylheteroarylamino, or the aryl of the aryloxy for $R^1$ to $R^{11}$ of general formula (2) include the monovalent groups of the "aryl ring" or "heteroaryl ring" described in general formula (1). Furthermore, regarding the alkyl or alkoxy for $R^1$ to $R^{11}$, reference can be made to the description on the "alkyl" or "alkoxy" as the primary substituent in the above description of general formula (1). In addition, the same also applies to the aryl, heteroaryl or alkyl as the substituents for these groups. Furthermore, the same also applies to the heteroaryl, diarylamino, diheteroarylamino, arylheteroarylamino, alkyl, alkoxy, or aryloxy in a case of forming an aryl ring or a heteroaryl ring by bonding adjacent groups among $R^1$ to $R^{11}$ together with the ring a, ring b or ring c, and the aryl, heteroaryl, or alkyl as a further substituent.

R of the N—R for $X^1$ and $X^2$ of general formula (1) represents an aryl, a heteroaryl, or an alkyl which may be substituted by the secondary substituent described above, and at least one hydrogen atom in the aryl or heteroaryl may be substituted by, for example, an alkyl. Examples of this aryl, heteroaryl or alkyl include those described above. Particularly, an aryl having 6 to 10 carbon atoms (for example, a phenyl or a naphthyl), a heteroaryl having 2 to 15 carbon atoms (for example, carbazolyl), and an alkyl having 1 to 4 carbon atoms (for example, methyl or ethyl) are preferable. This description also applies to $X^1$ and $X^2$ in general formula (2).

R of the "—C(—R)$_2$—" as a linking group for general formula (1) represents a hydrogen atom or an alkyl, and examples of this alkyl include those described above. Particularly, an alkyl having 1 to 4 carbon atoms (for example, methyl or ethyl) is preferable. This description also applies to "—C(—R)$_2$—" as a linking group for general formula (2).

Furthermore, the light emitting layer may contain a polycyclic aromatic compound multimer having a plurality of unit structures each represented by general formula (1), and preferably a polycyclic aromatic compound multimer having a plurality of unit structures each represented by general formula (2). The multimer is preferably a dimer to a hexamer, more preferably a dimer to a trimer, and a particularly preferably a dimer. The multimer may be in a form having a plurality of unit structures described above in one compound, and for example, the multimer may be in a form in which a plurality of unit structures are bonded with a linking group such as a single bond, an alkylene group having 1 to 3 carbon atoms, a phenylene group, or a naphthylene group. In addition, the multimer may be in a form in which a plurality of unit structures are bonded such that any ring contained in the unit structure (ring A, ring B or ring C, or ring a, ring b or ring c) is shared by the plurality of unit structures, or may be in a form in which the unit structures are bonded such that any rings contained in the unit structures (ring A, ring B or ring C, or ring a, ring b or ring c) are fused.

Examples of such a multimer include multimer compounds represented by the following formula (2-4), (2-4-1), (2-4-2), (2-5-1) to (2-5-4), and (2-6). The following formula (2-4) represents a dimer compound, the formula (2-4-1) represents a dimer compound, the formula (2-4-2) represents a trimer compound, the formula (2-5-1) represents a dimer compound, formula (2-5-2) represents a dimer compound, formula (2-5-3) represents a dimer compound, formula (2-5-4) represents a trimer compound, and formula (2-6) represents a dimer compound. A multimer compound represented by the following formula (2-4) corresponds to, for example, a compound represented by formula (1-423) described below. That is, to be described in connection with general formula (2), the multimer compound includes a plurality of unit structures each represented by general formula (2) in one compound so as to share a benzene ring as ring a. Furthermore, a multimer compound represented by the following formula (2-4-1) corresponds to, for example, a compound represented by the following formula (1-2665). That is, to be described in connection with general formula (2), the multimer compound includes two unit structures each represented by general formula (2) in one compound so as to share a benzene ring as ring a. Furthermore, a multimer compound represented by the following formula (2-4-2) corresponds to, for example, a compound represented by the following formula (1-2666). That is, to be described in connection with general formula (2), the multimer compound includes two unit structures each represented by general formula (2) in one compound so as to share a benzene ring as ring a. Furthermore, multimer compounds represented by the following formulas (2-5-1) to (2-5-4) correspond to, for example, compounds represented by the following formulas (1-421), (1-422), (1-424), and (1-425). That is, to be described in connection with general formula (2), the multimer compound includes a plurality of unit structures each represented by general formula (2) in one compound so as to share a benzene ring as ring b (or ring c).

Furthermore, a multimer compound represented by the following formula (2-6) corresponds to, for example, a compound represented by any one of the following formulas (1-431) to (1-435). That is, to be described in connection with general formula (2), for example, the multimer compound includes a plurality of unit structures each represented by general formula (2) in one compound such that a benzene ring as ring b (or ring a or ring c) of a certain unit structure and a benzene ring as ring b (or ring a or ring c) of a certain unit structure are fused. Note that $R^1$ to $R^{11}$, $Y^1$, $X^1$, and $X^2$ in formulas (2-4), (2-4-1), (2-4-2), (2-5-1) to (2-5-4), and (2-6) are defined in the same manner as those in formula (2)

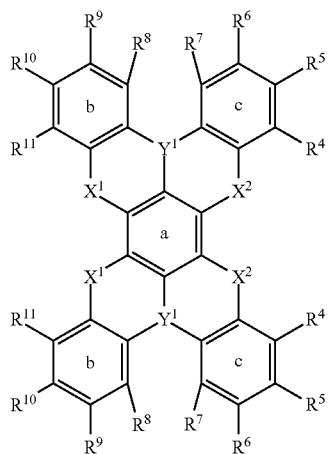

(2-4)

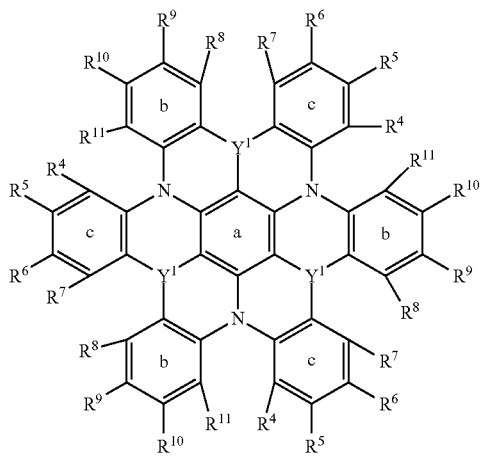

(2-4-2)

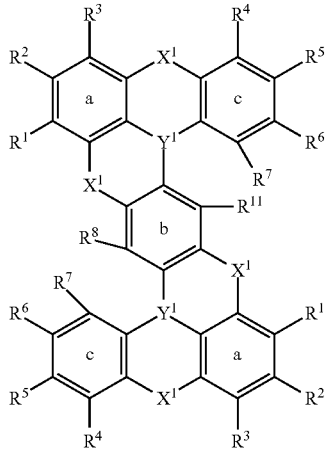

(2-5-1)

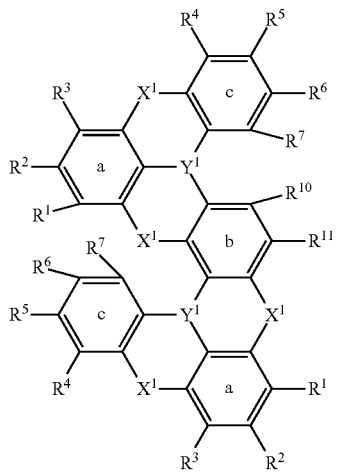

(2-5-2)

-continued

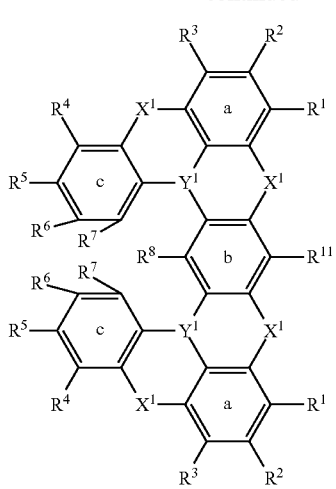
(2-5-3)

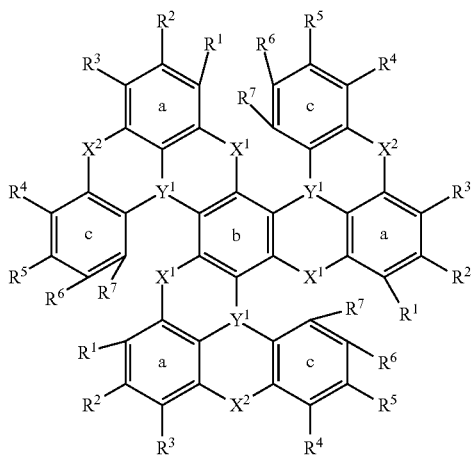
(2-5-4)

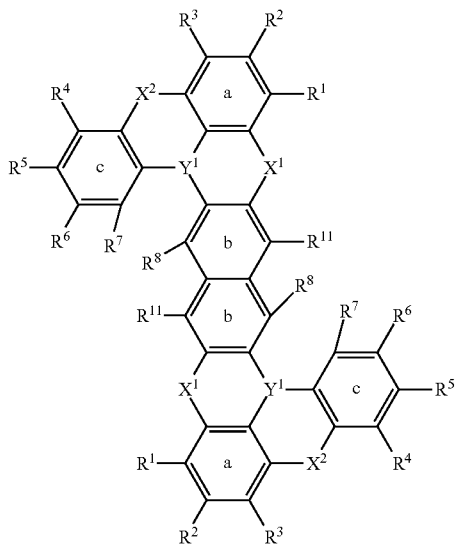
(2-6)

The multimer compound may be a multimer in which a multimer form represented by formula (2-4), (2-4-1) or (2-4-2) and a multimer form represented by any one of formula (2-5-1) to (2-5-4) or (2-6) are combined, may be a multimer in which a multimer form represented by any one of formula (2-5-1) to (2-5-4) and a multimer form represented by formula (2-6) are combined, or may be a multimer in which a multimer form represented by formula (2-4), (2-4-1) or (2-4-2), a multimer form represented by any one of formulas (2-5-1) to (2-5-4), and a multimer form represented by formula (2-6) are combined.

Furthermore, all or a portion of the hydrogen atoms in the chemical structures of the polycyclic aromatic compound represented by general formula (1) or (2) and a multimer thereof may be deuterium atoms.

Furthermore, all or a portion of the hydrogen atoms in the chemical structures of the polycyclic aromatic compound represented by general formula (1) or (2) and a multimer thereof may be halogen atoms. For example, in regard to formula (1), the hydrogen atoms in the ring A, ring B, ring C (ring A to ring C are aryl rings or heteroaryl rings), substituents on the ring A to ring C, and R (=alkyl or aryl) when $X^1$ and $X^2$ each represent N—R, may be substituted by halogen atoms, and among these, a form in which all or a portion of the hydrogen atoms in the aryl or heteroaryl are substituted by halogen atoms may be mentioned. The halogen is fluorine, chlorine, bromine, or iodine, preferably fluorine, chlorine, or bromine, and more preferably chlorine.

More specific examples of the polycyclic aromatic compound and a multimer thereof include compounds represented by the following formulas (1-401) to (1-462), compounds represented by the following formulas (1-1401) to (1-1460), compounds represented by the following formulas (1-471) to (1-479), compounds represented by the following formulas (1-1151) to (1-1159), a compound represented by the following formula (1-2619), and compounds represented by the following formulas (1-2620) to (1-2705).

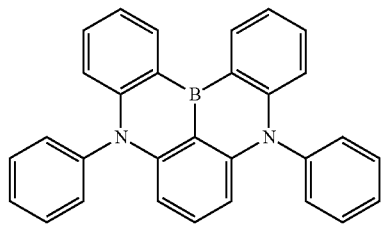
(1-401)

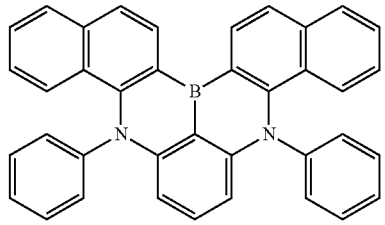
(1-402)

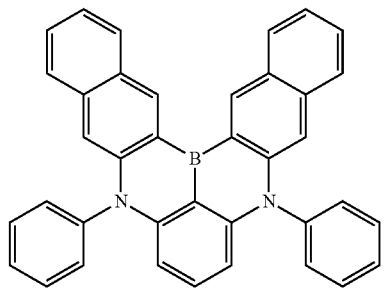
(1-403)

-continued
(1-404)
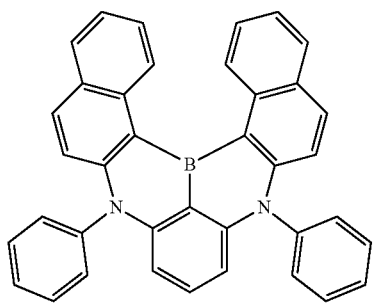
(1-405)
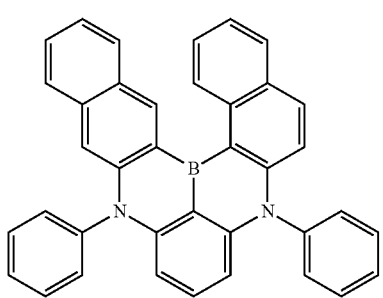
(1-406)
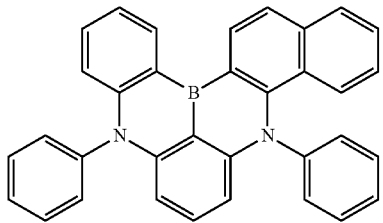
(1-407)
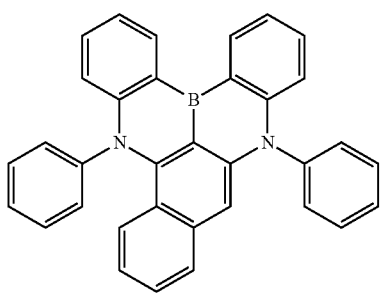
(1-408)
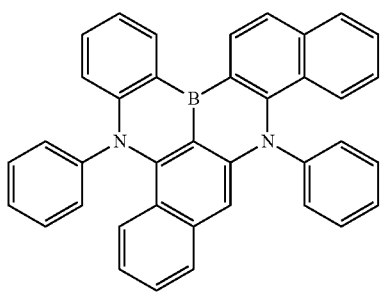
-continued
(1-409)
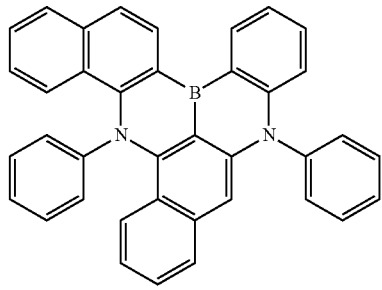
(1-411)
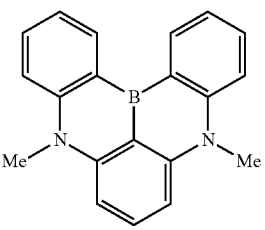
(1-412)
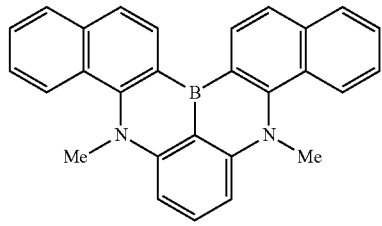
(1-413)
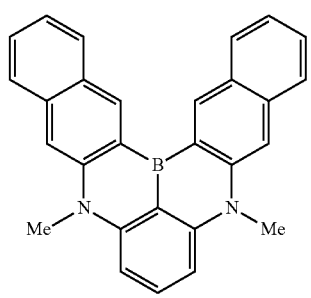
(1-414)
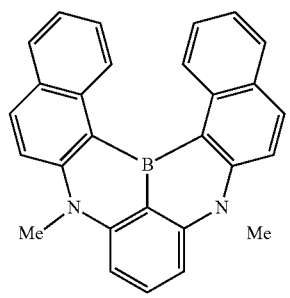
(1-415)
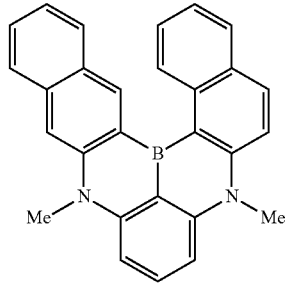

-continued
(1-416)
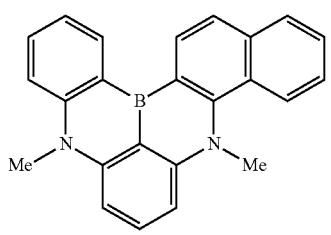
(1-417)
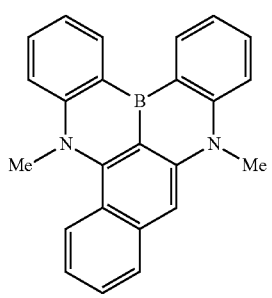
(1-418)
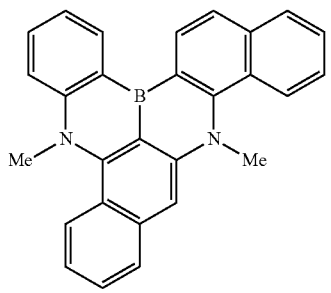
(1-419)
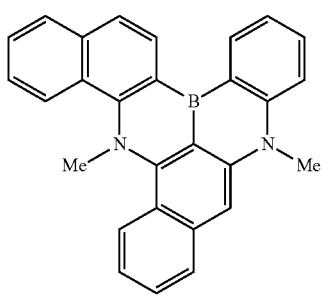
-continued
(1-421)
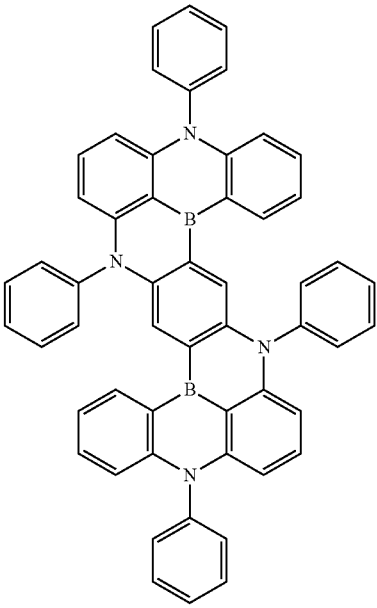
(1-422)
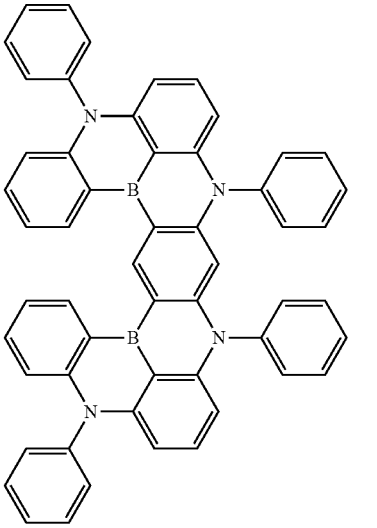
(1-423)
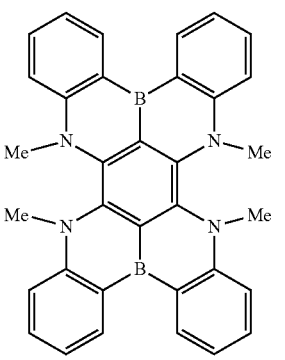

(1-424)
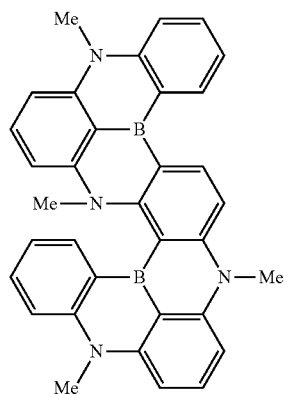
(1-432)
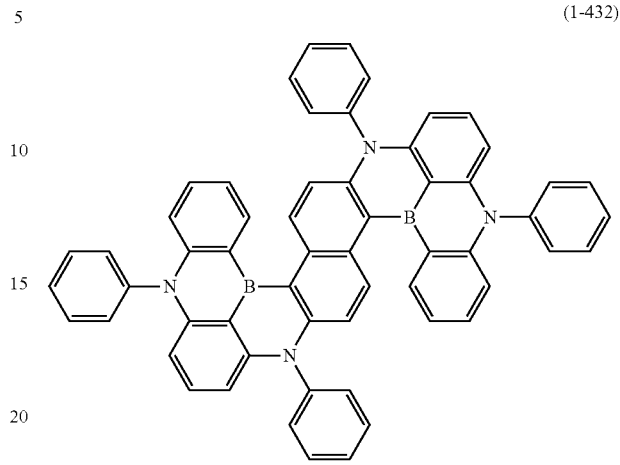
(1-425)
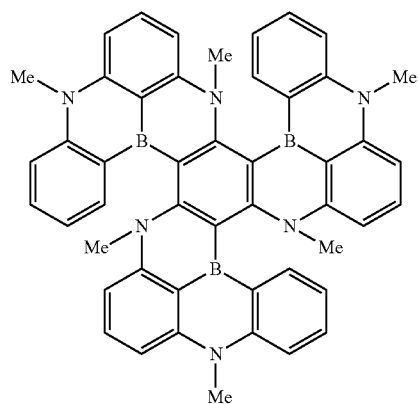
(1-431)
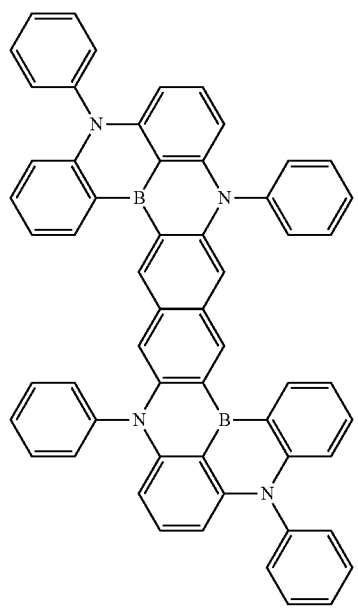
(1-433)
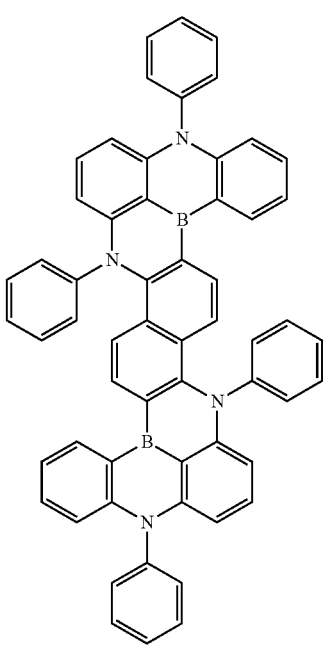

(1-434)
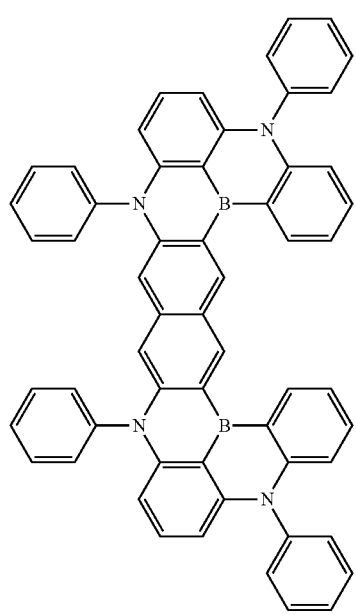
(1-442)
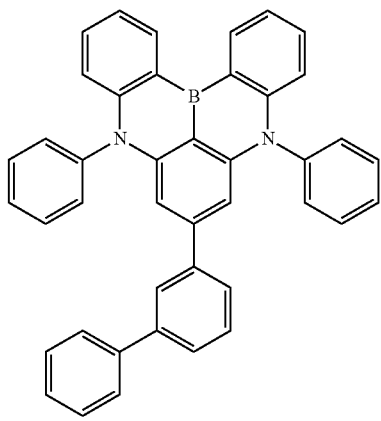
(1-435)
(1-443)
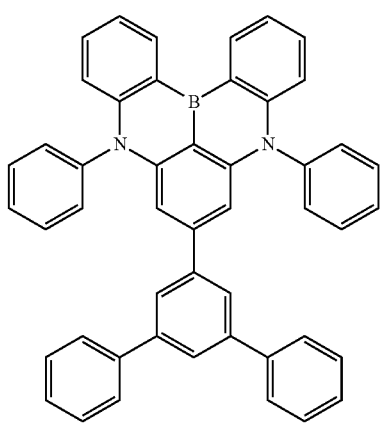
(1-441)
(1-444)
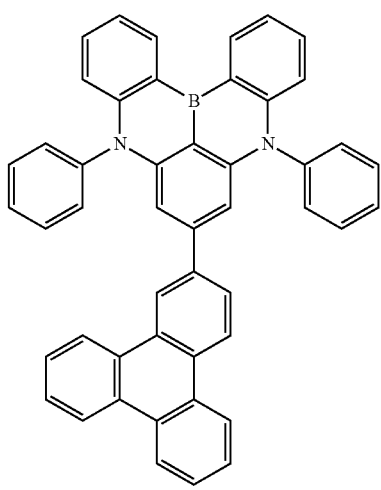

(1-445)
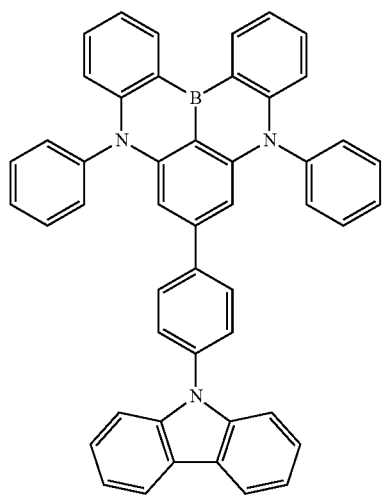
(1-446)
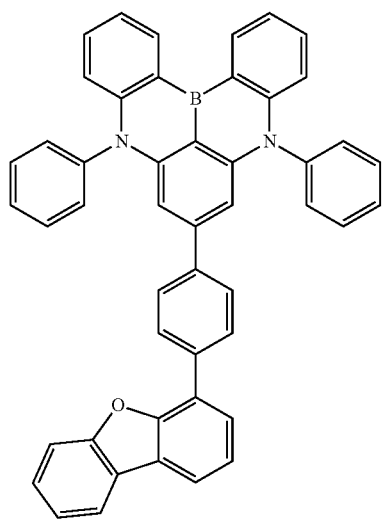
(1-447)
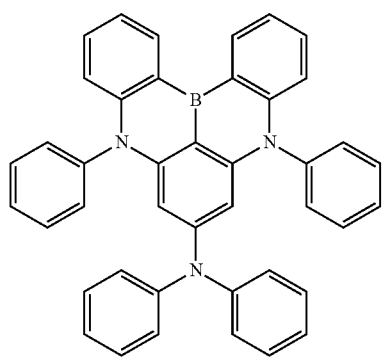
(1-448)
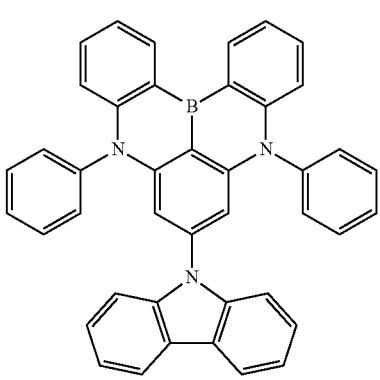
(1-449)
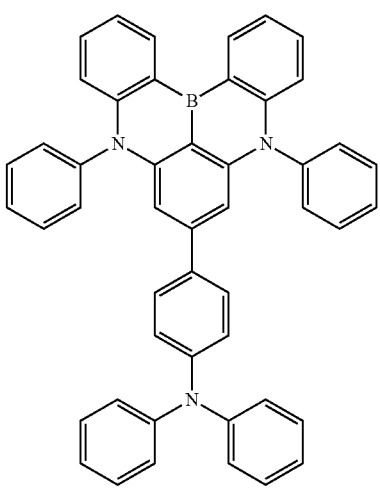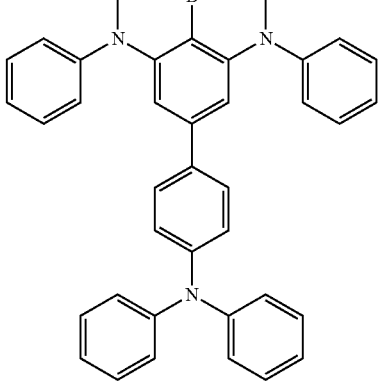
(1-451)
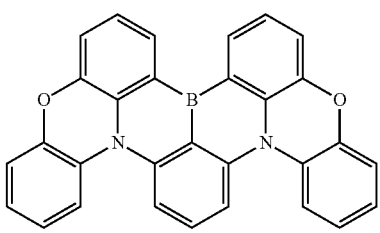
(1-452)
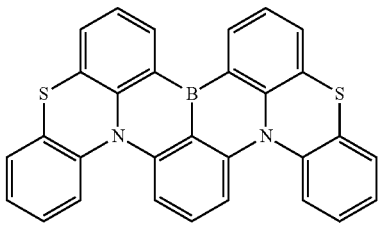
(1-453)
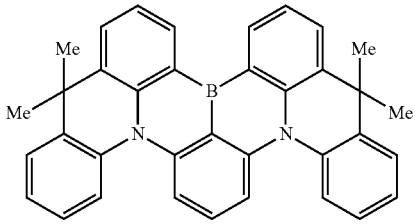

-continued
(1-454)
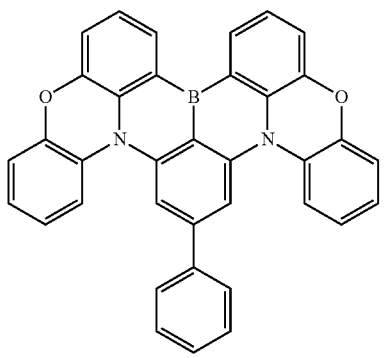
(1-455)
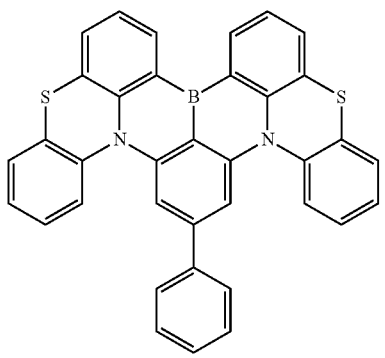
(1-456)
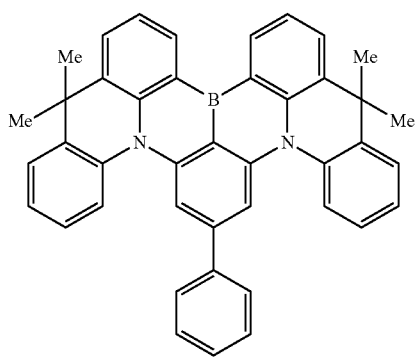
(1-457)
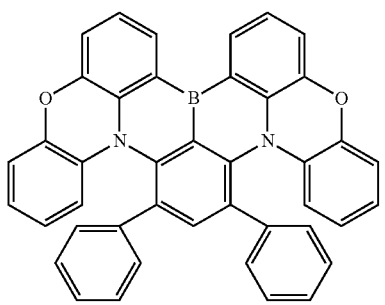
-continued
(1-458)
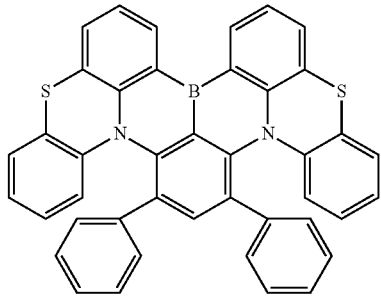
(1-459)
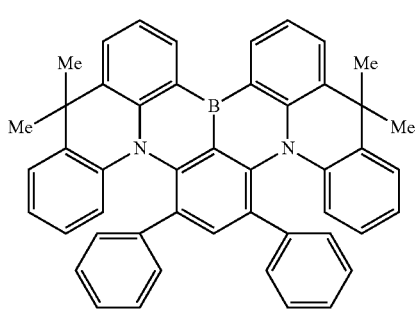
(1-460)
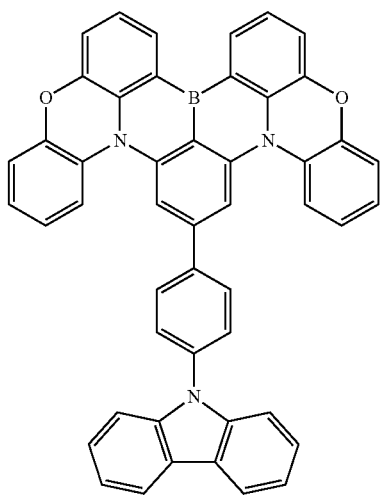
(1-461)
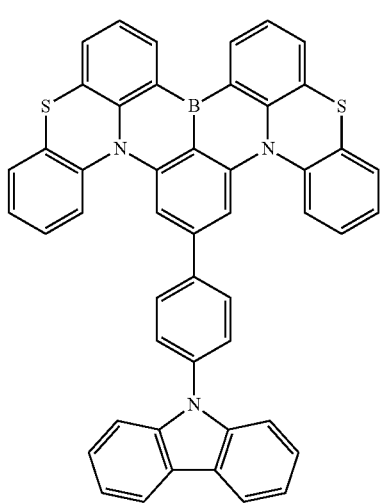

(1-462)
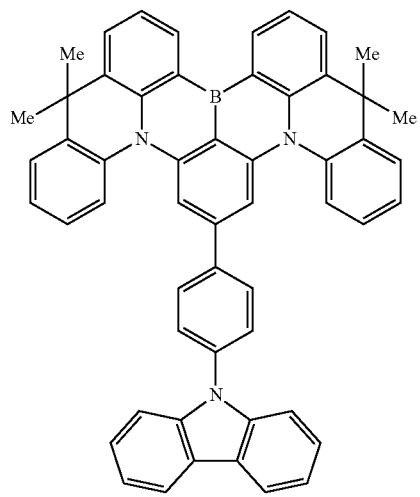
(1-1401)
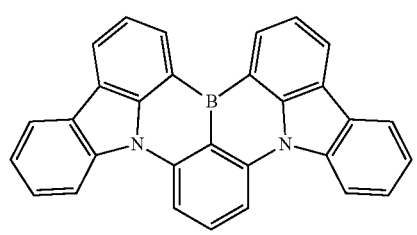
(1-1402)
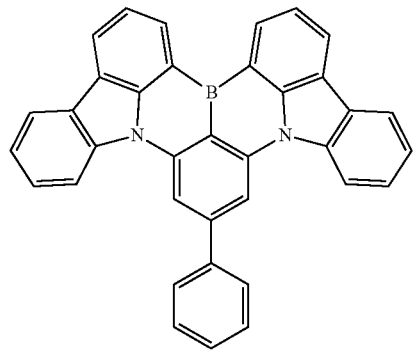
(1-1403)
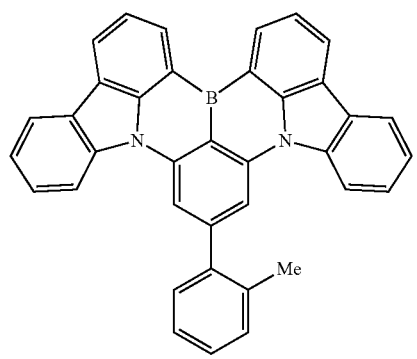
(1-1404)
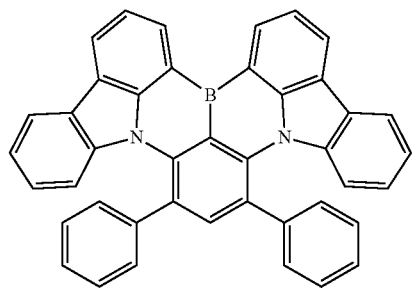
(1-1405)
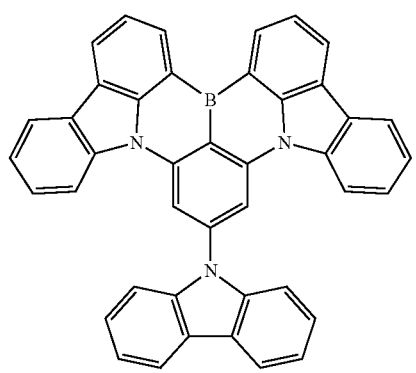
(1-1406)
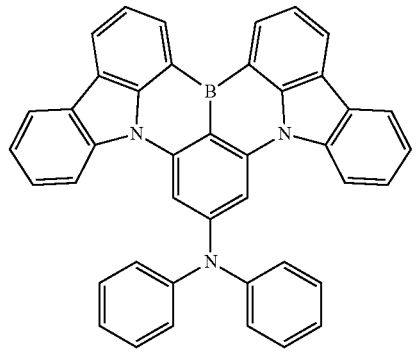
(1-1407)
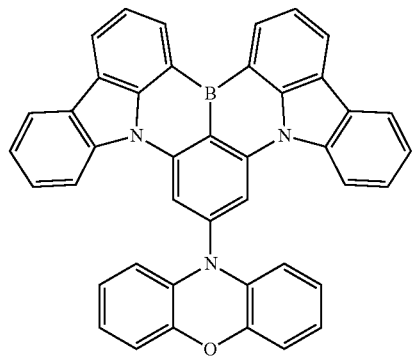

(1-1408)
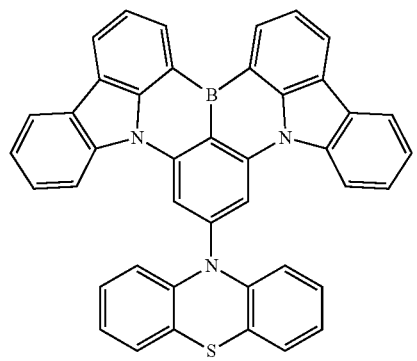
(1-1409)
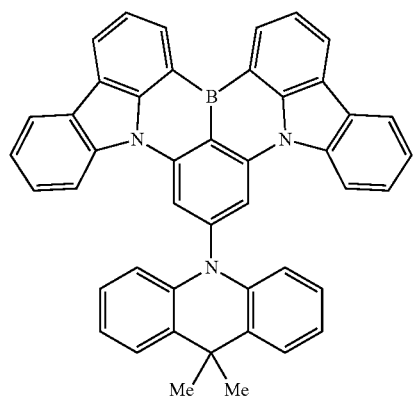
(1-1410)
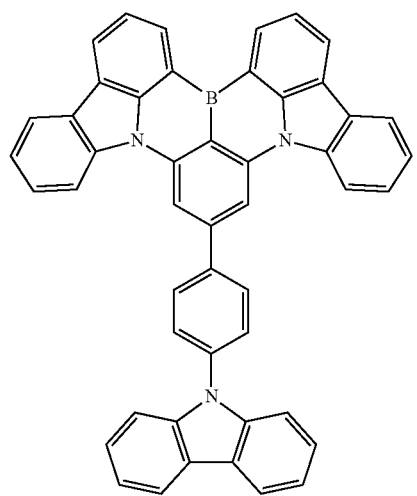
(1-1411)
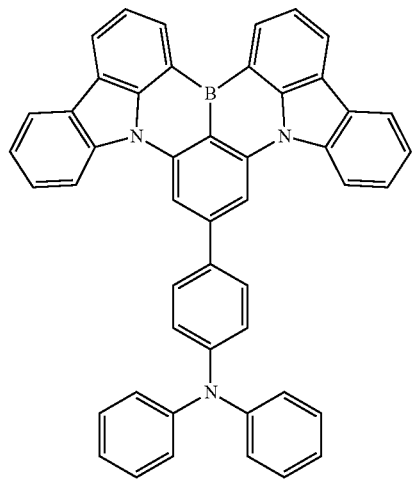
(1-1412)
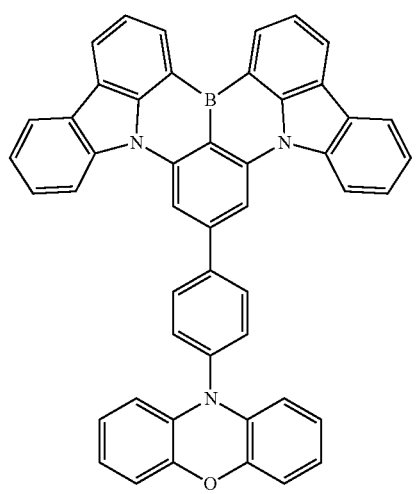
(1-1413)
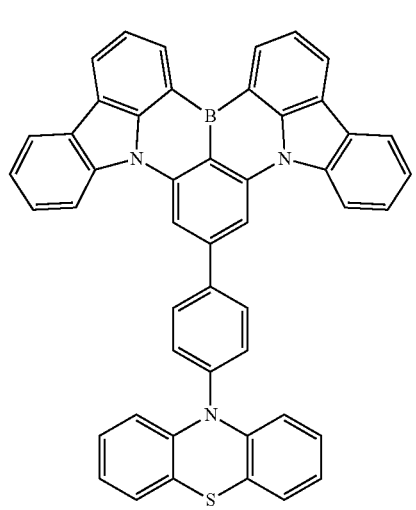

(1-1414)
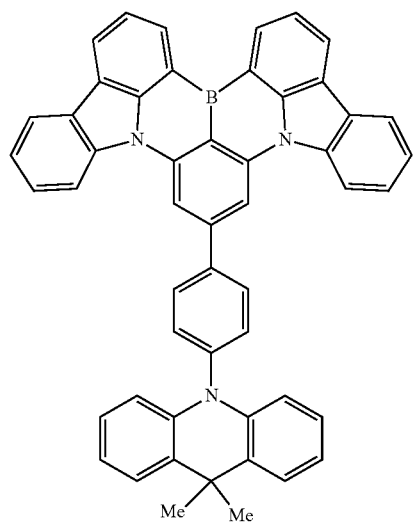
(1-1421)
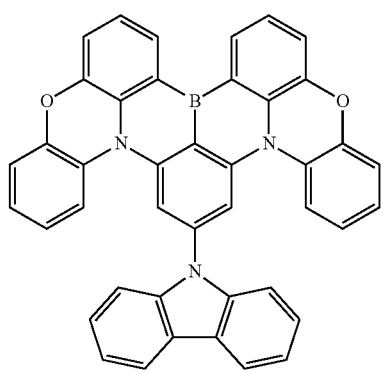
(1-1422)
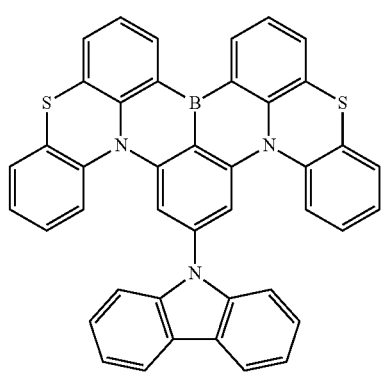
(1-1423)
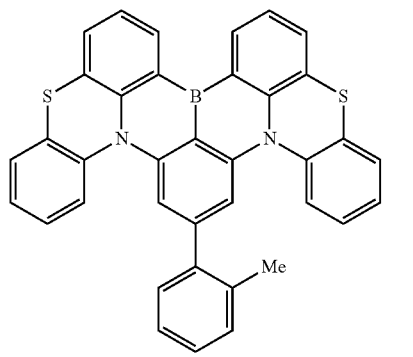
(1-1424)
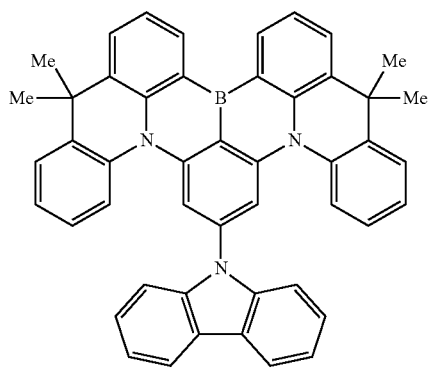
(1-1425)
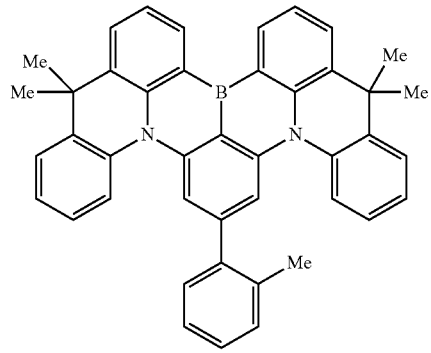
(1-1426)
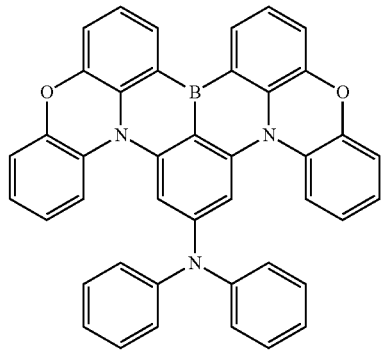
(1-1427)

(1-1428)
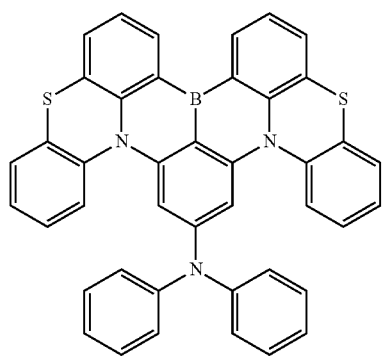
(1-1431)
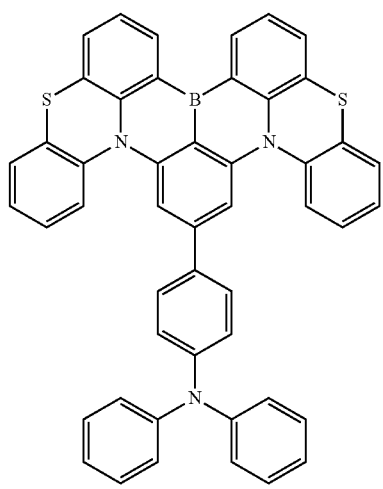
(1-1429)
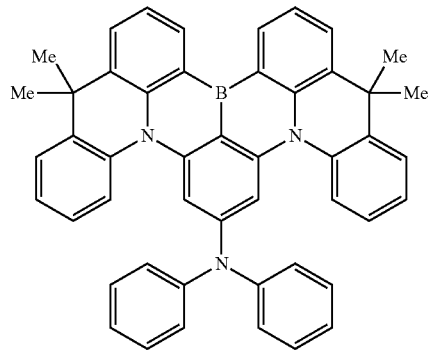
(1-1432)
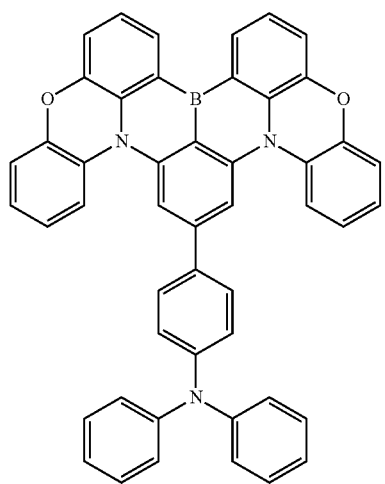
(1-1430)
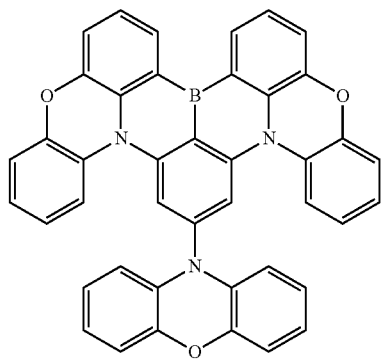
(1-1433)

-continued
(1-1434)
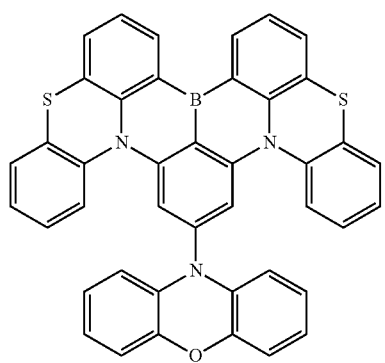
(1-1435)
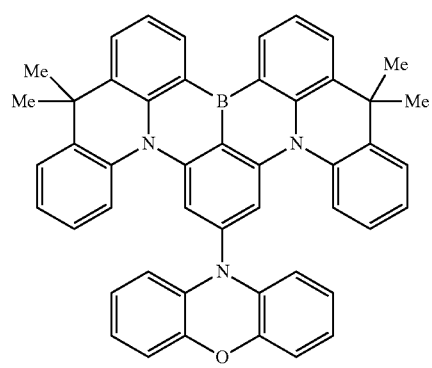
(1-1436)
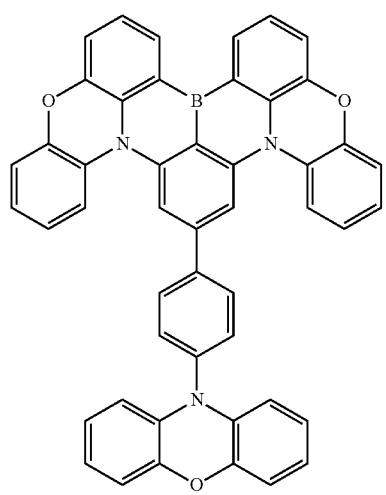
(1-1437)
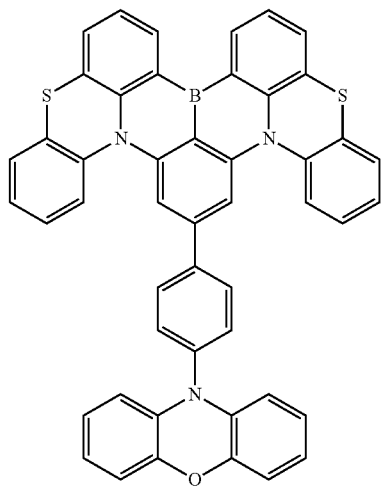
(1-1438)
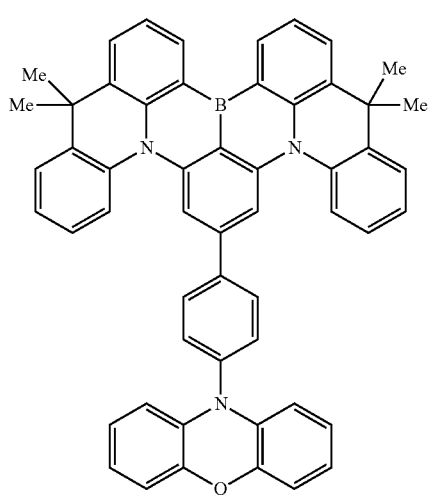
(1-1439)
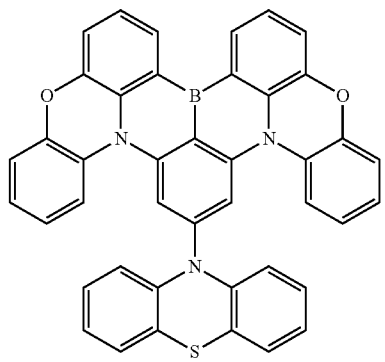

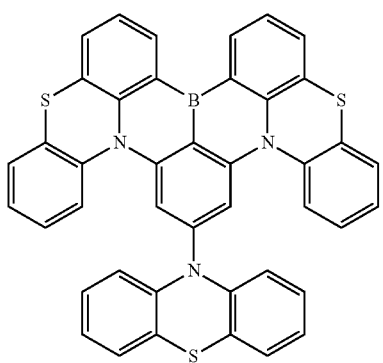
(1-1450)
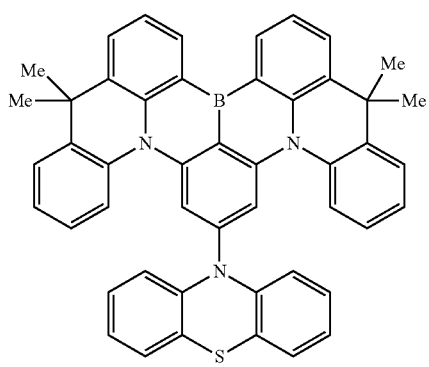
(1-1451)
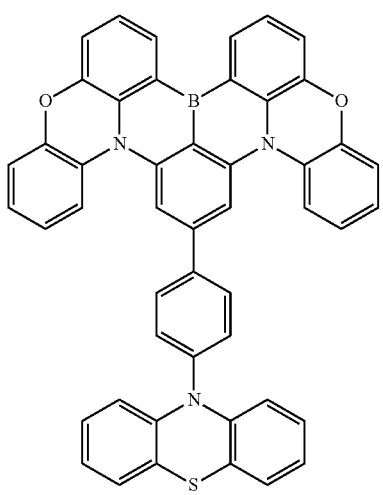
(1-1452)
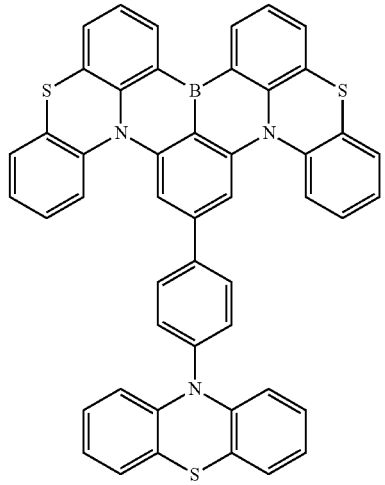
(1-1453)
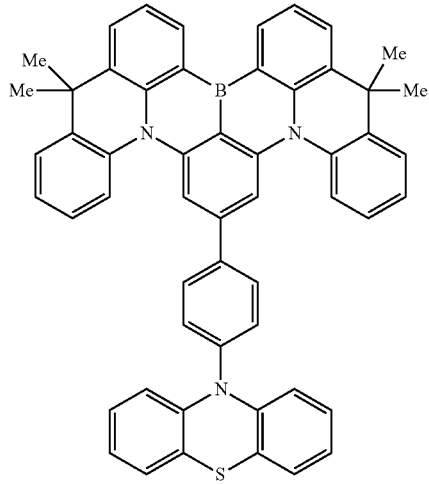
(1-1454)
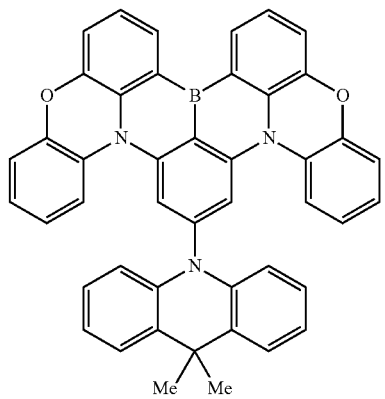
(1-1455)

(1-1456)
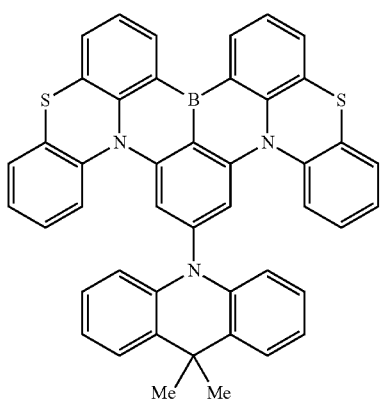
(1-1457)
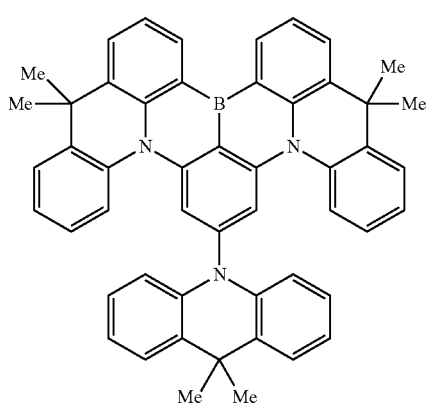
(1-1458)
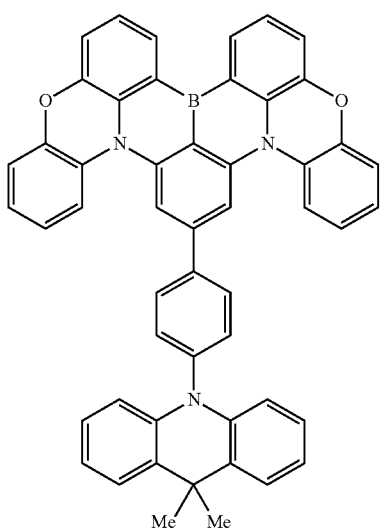
(1-1459)
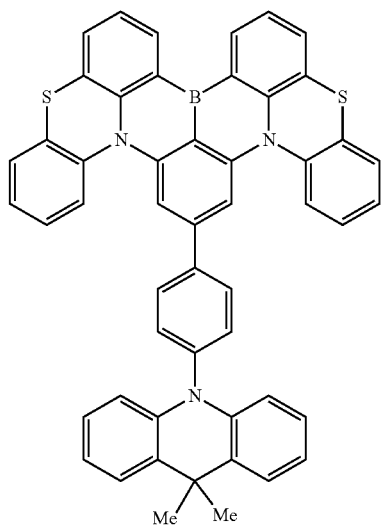
(1-1460)
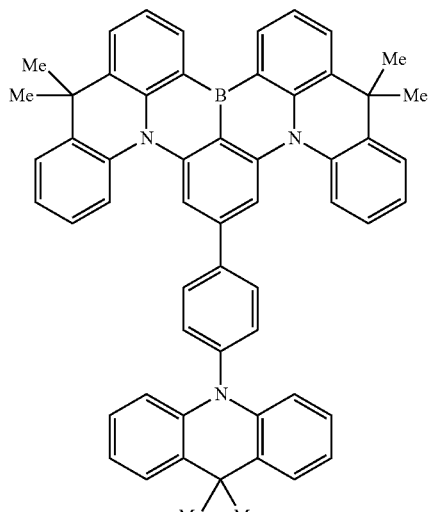
(1-471)
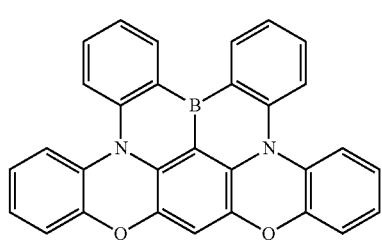
(1-472)
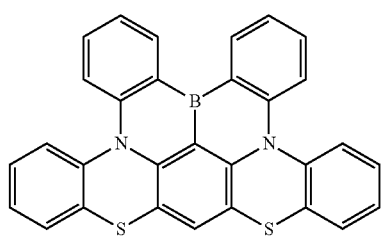

(1-473)
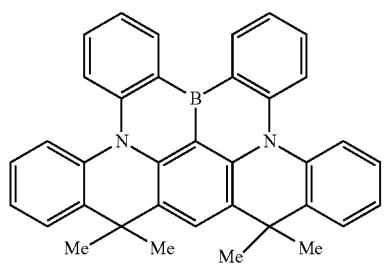
(1-474)
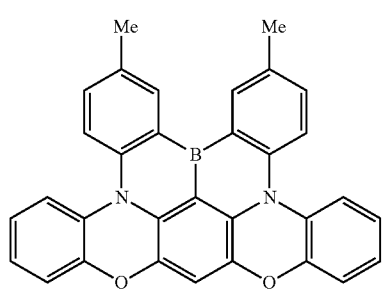
(1-475)
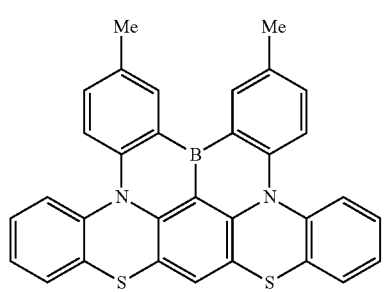
(1-476)
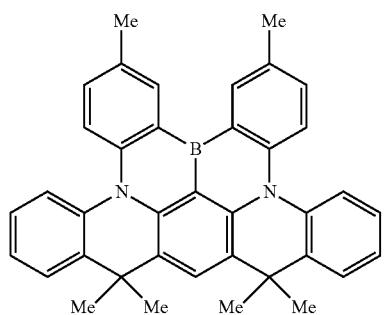
(1-477)
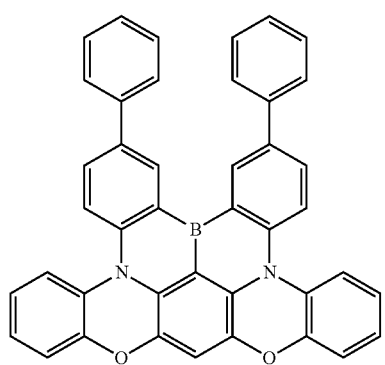
(1-478)
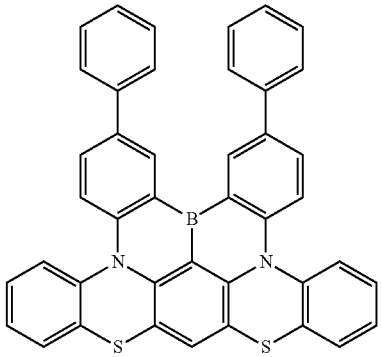
(1-479)
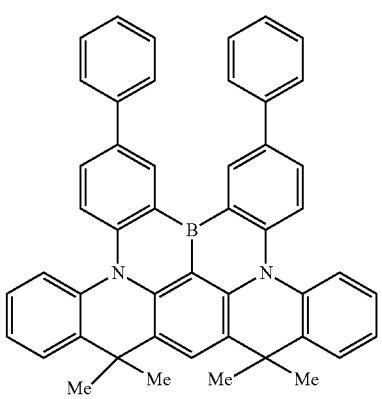
(1-1151)
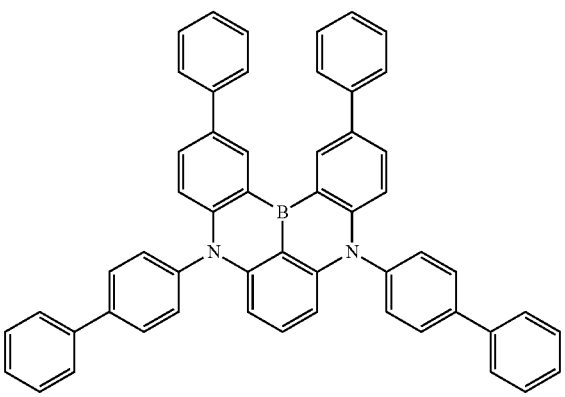
(1-1152)
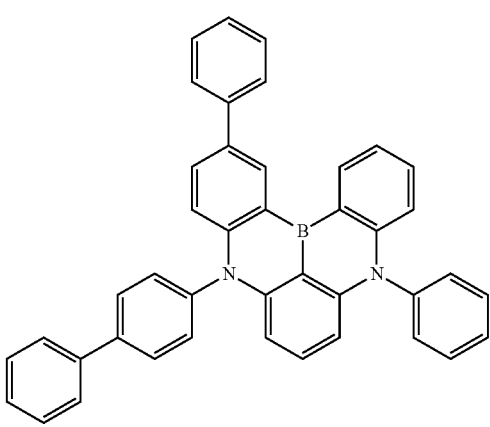

(1-1153) 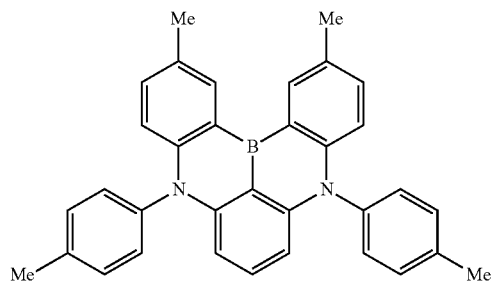
(1-1154) 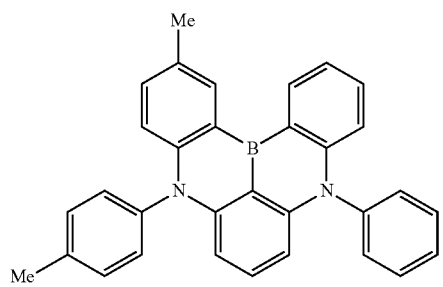
(1-1155) 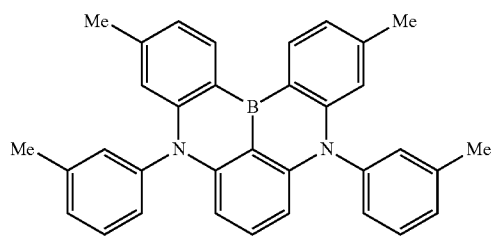
(1-1156) 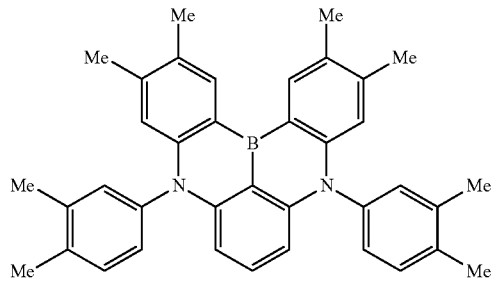
(1-1157) 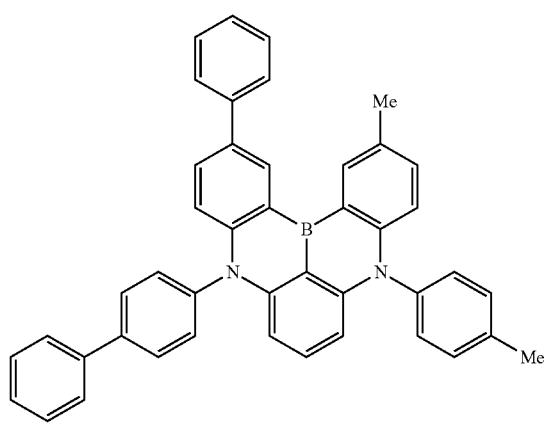
(1-1158) 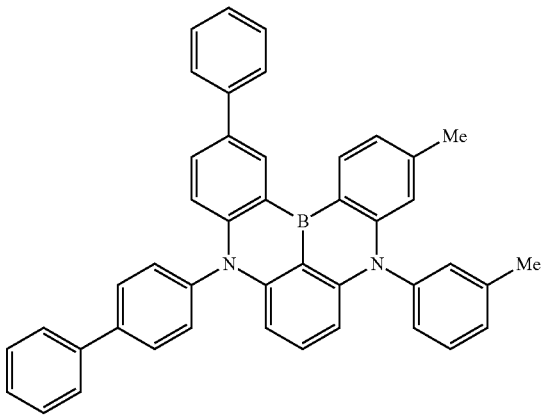
(1-1159) 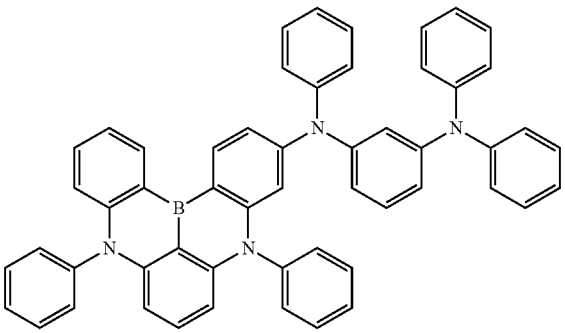
(1-2619) 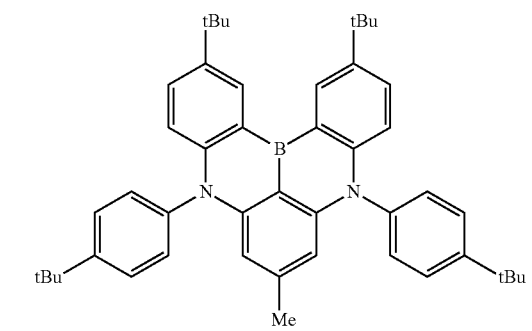
(1-2620) 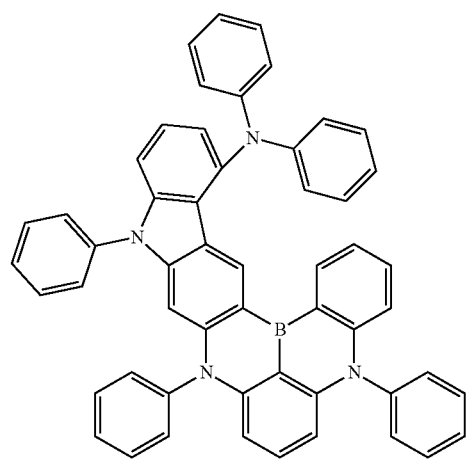

(1-2621)
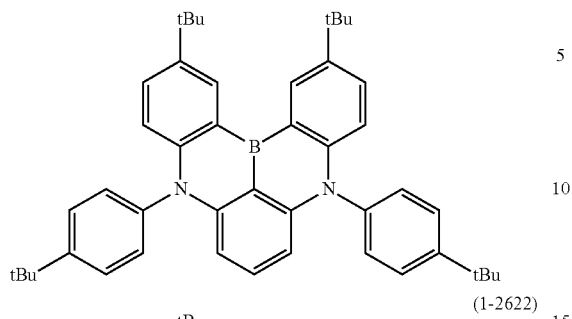
(1-2622)
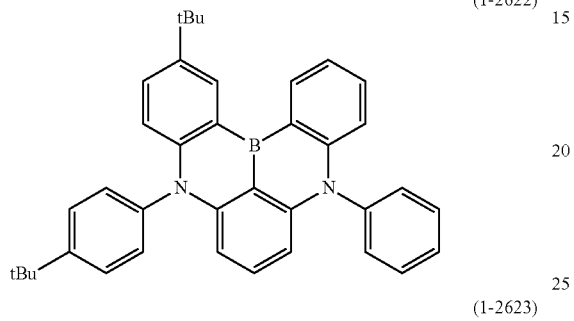
(1-2623)
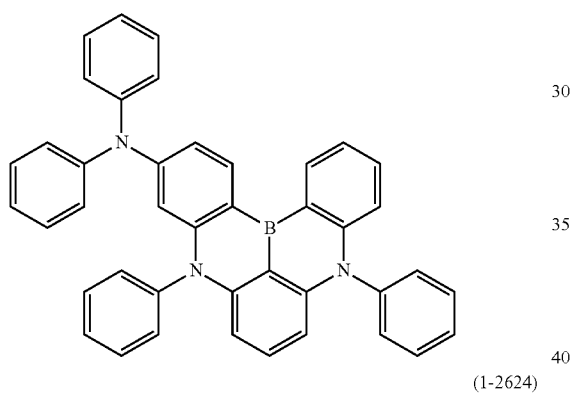
(1-2624)
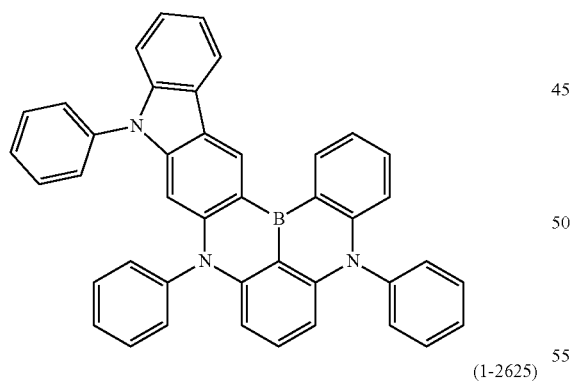
(1-2625)
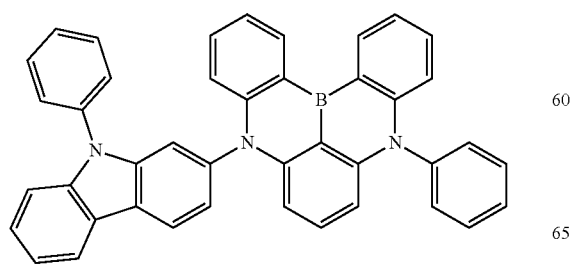
(1-2626)
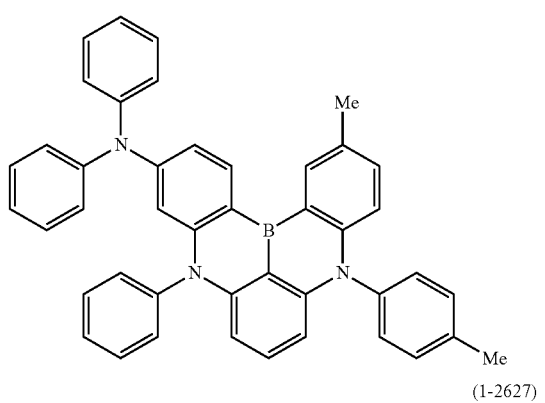
(1-2627)
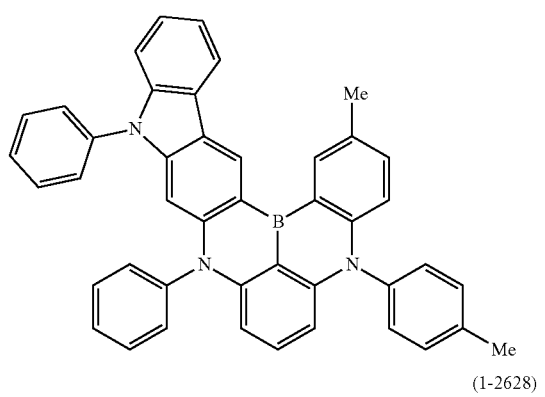
(1-2628)
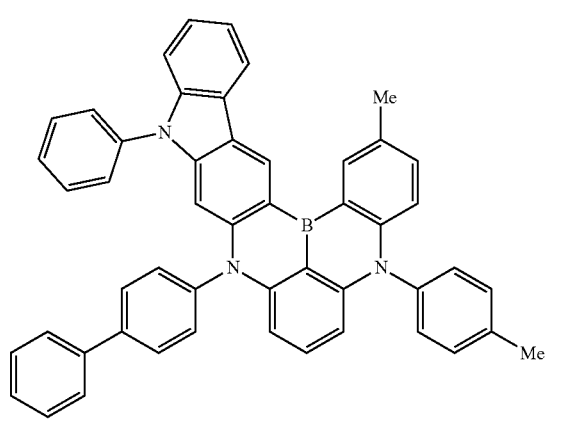
(1-2629)
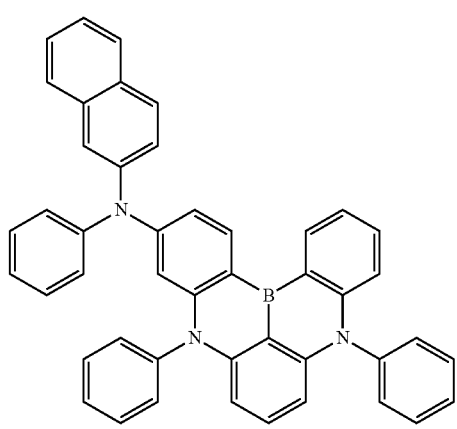

(1-2630)
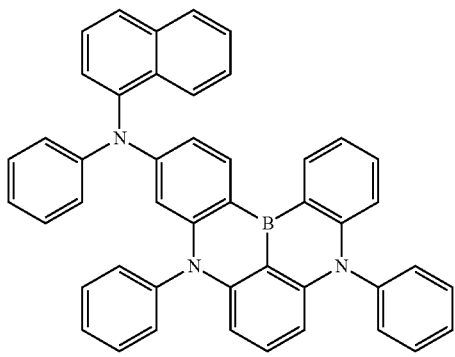
(1-2634)
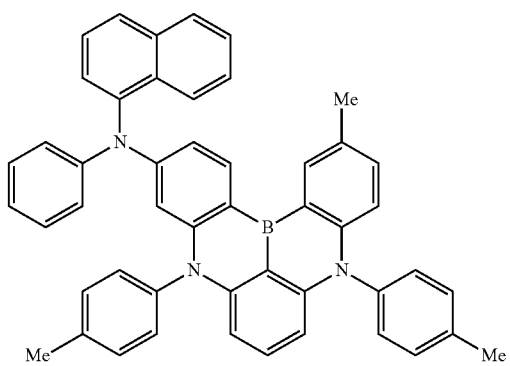
(1-2631)
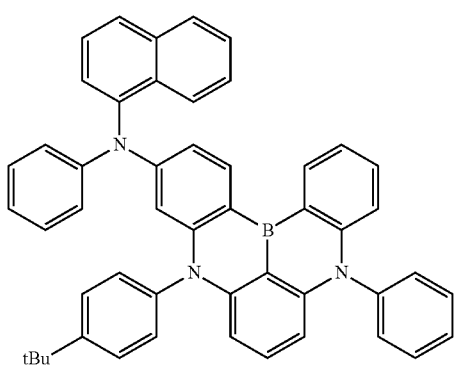
(1-2635)
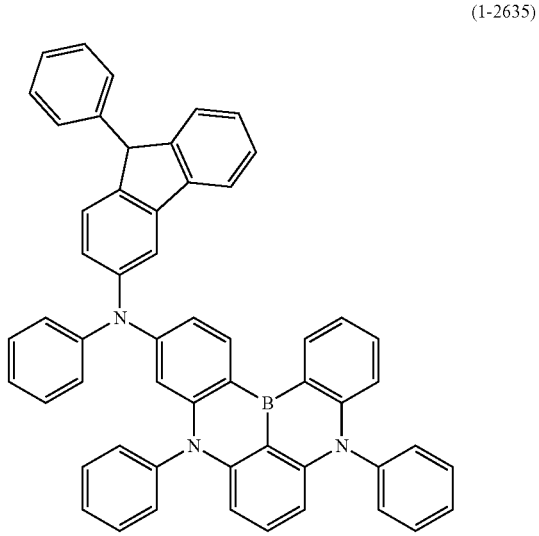
(1-2632)
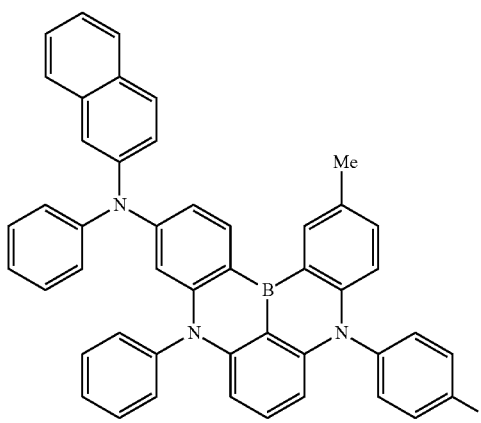
(1-2633)
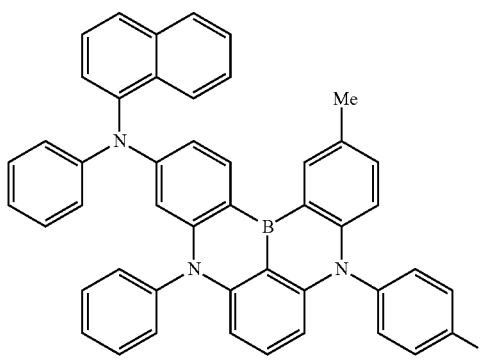
(1-2636)
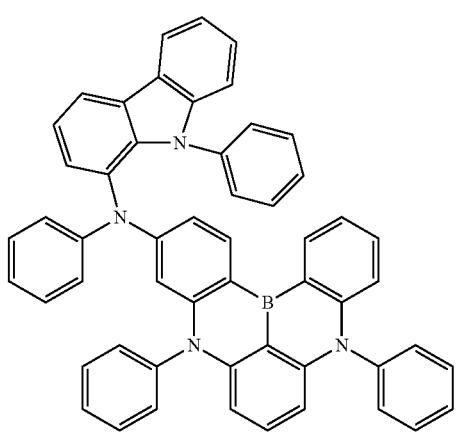

(1-2637)
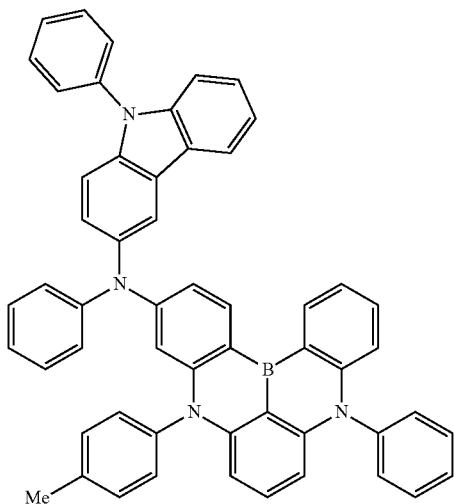
(1-2640)
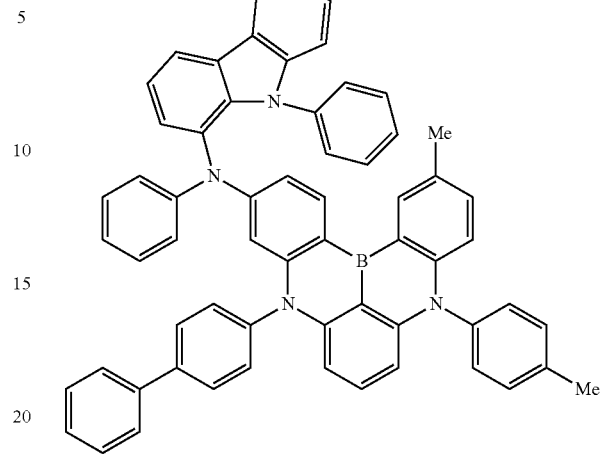
(1-2638)
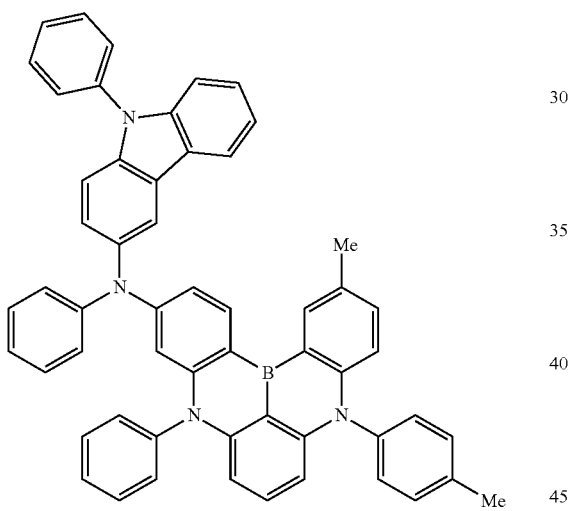
(1-2641)
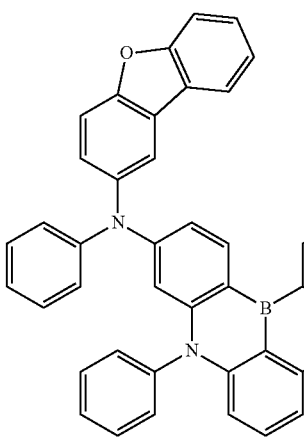
(1-2639)
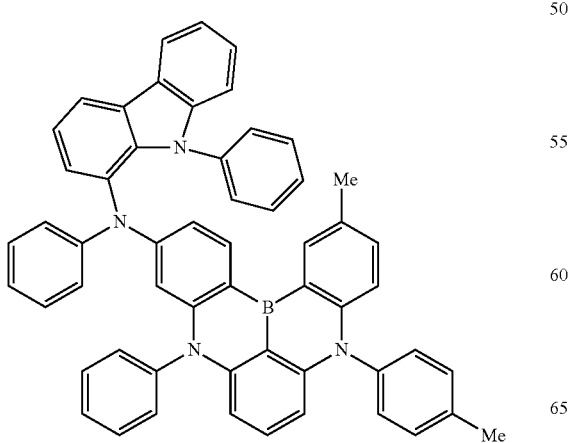
(1-2642)
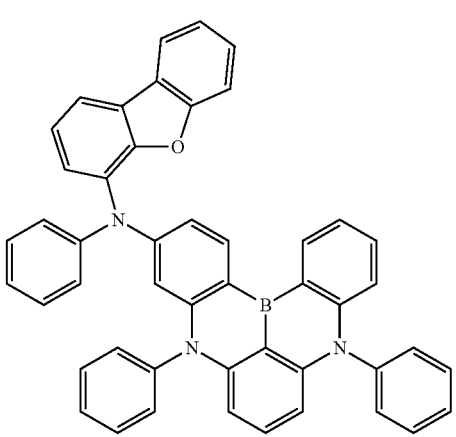

(1-2643)
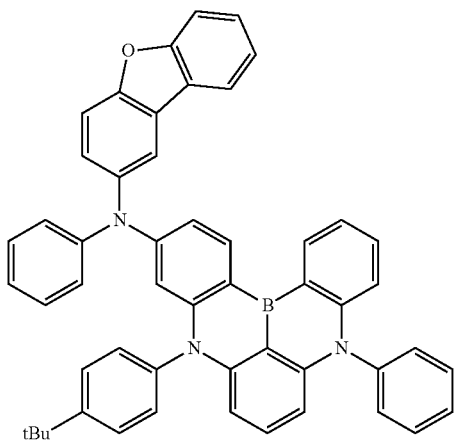
(1-2646)
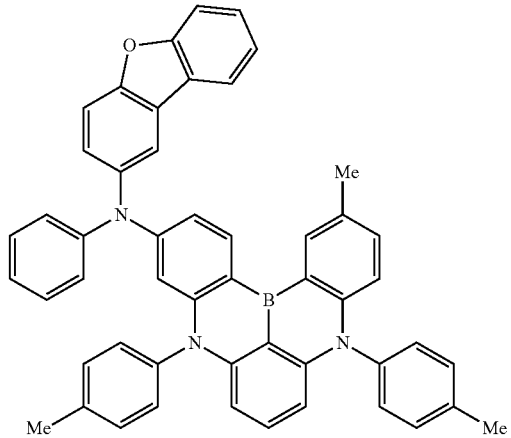
(1-2644)
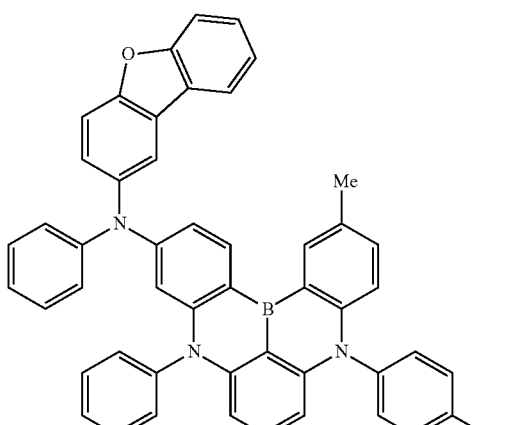
(1-2647)
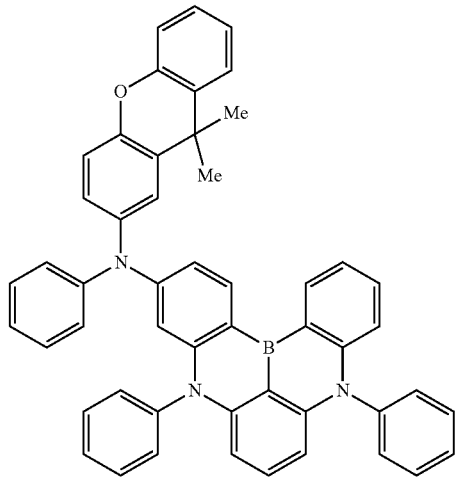
(1-2645)
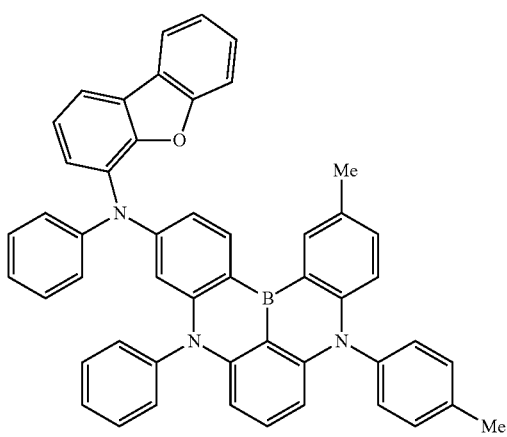
(1-2648)
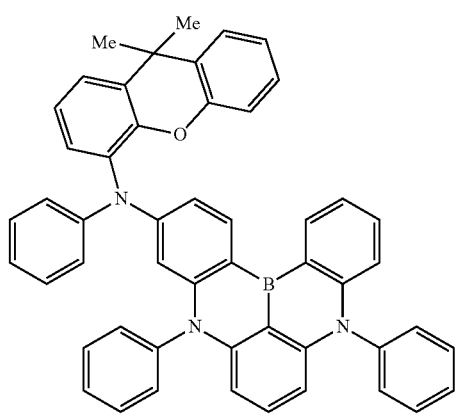

(1-2649)
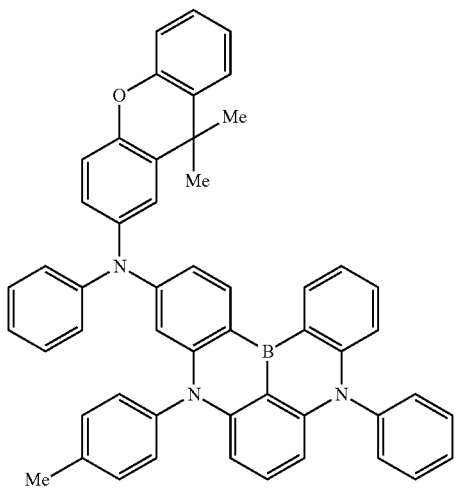
(1-2650)
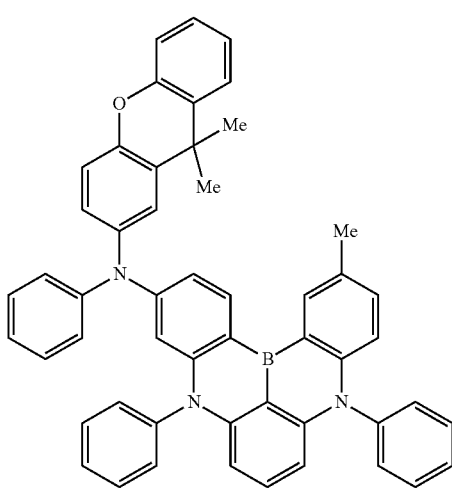
(1-2651)
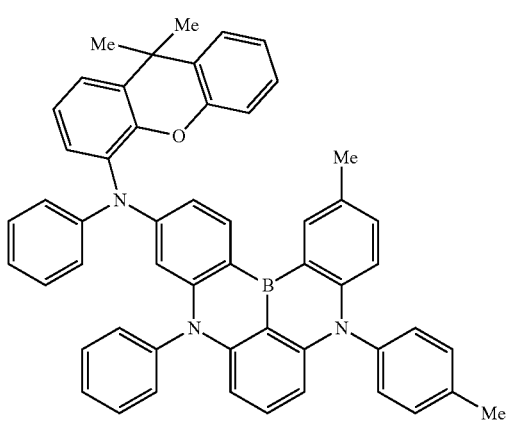
(1-2652)
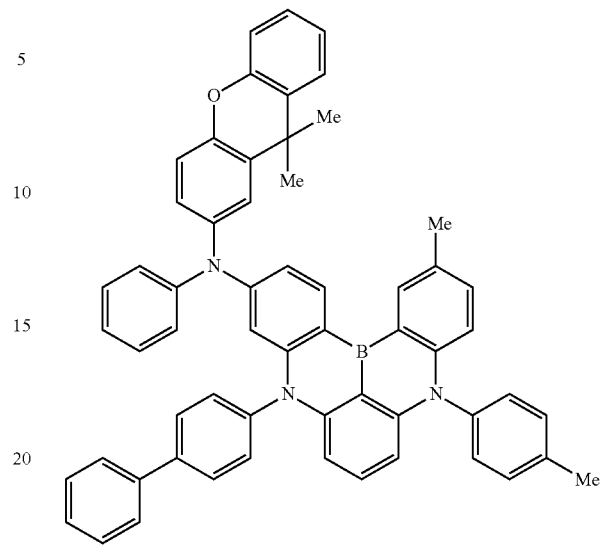
(1-2653)
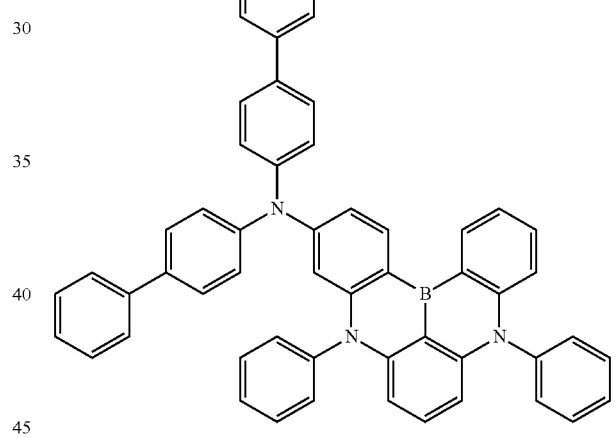
(1-2654)
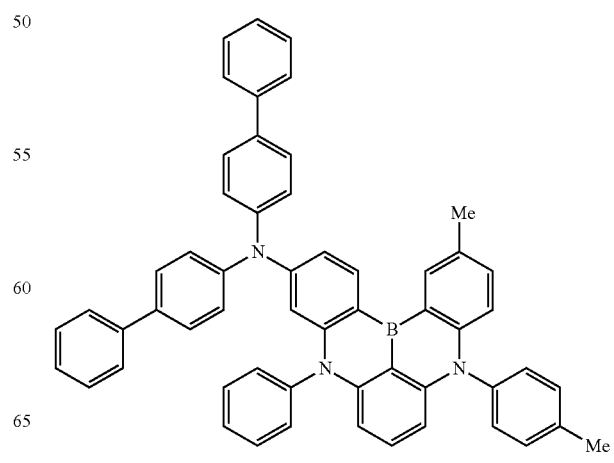

-continued
(1-2655)
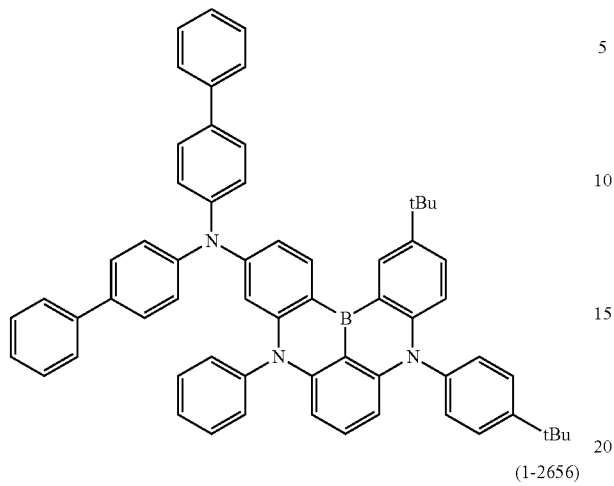
(1-2656)
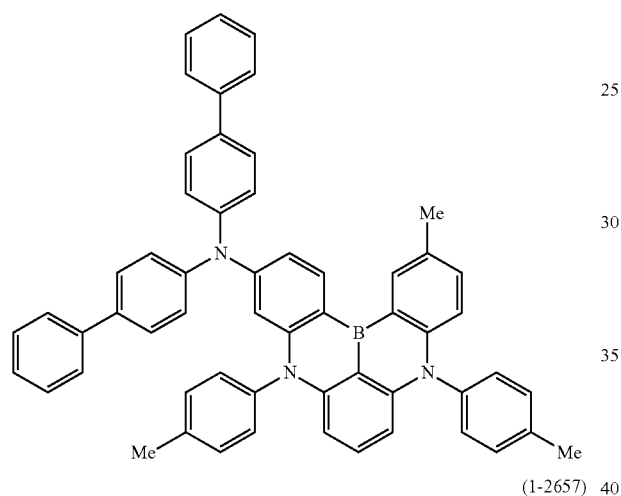
(1-2657)
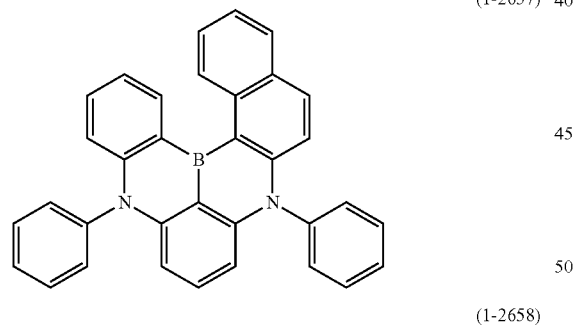
(1-2658)
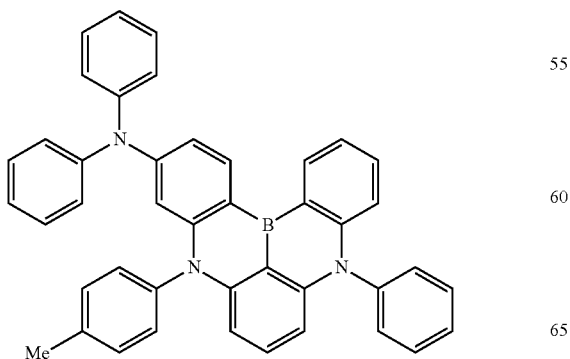
-continued
(1-2659)
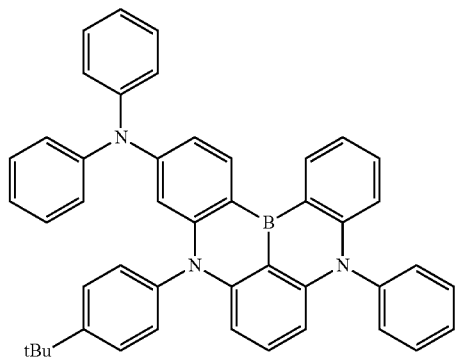
(1-2660)
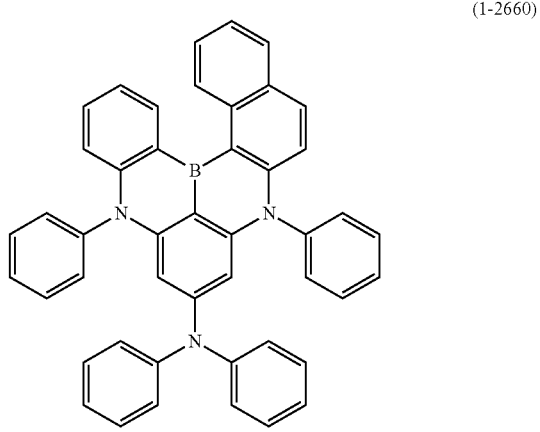
(1-2661)
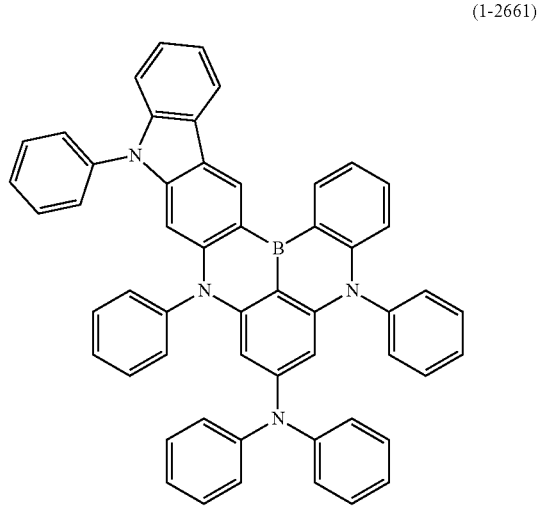

(1-2662)
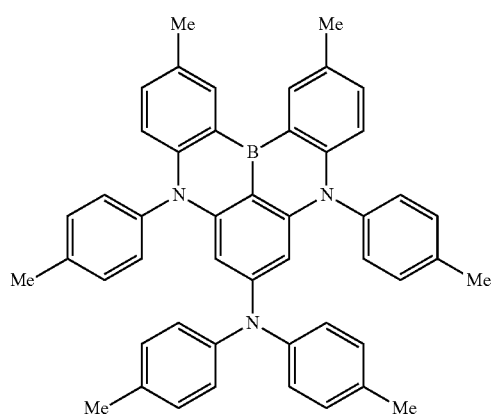
(1-2663)
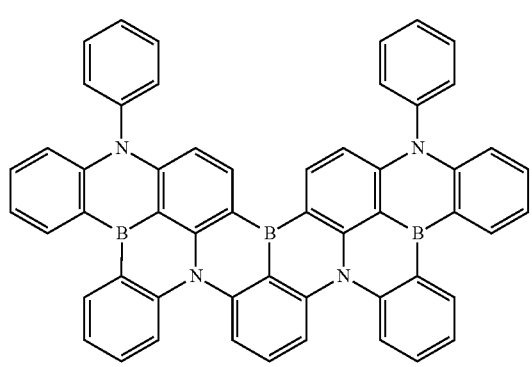
(1-2664)
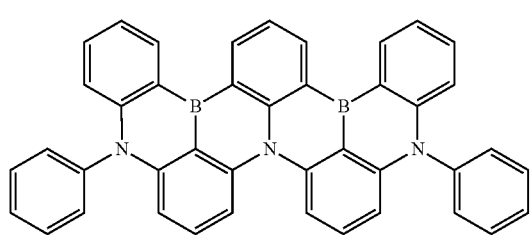
(1-2665)
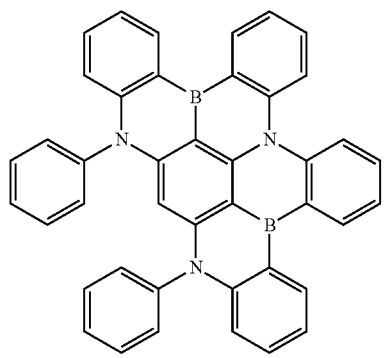
(1-2666)
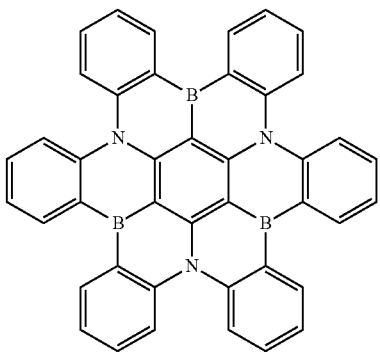
(1-2667)
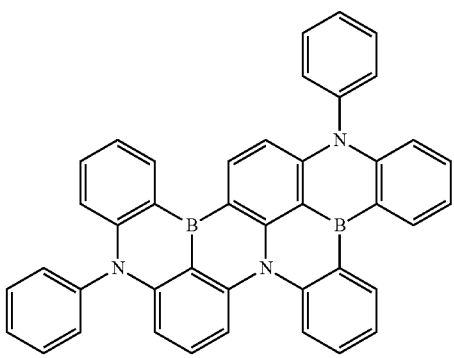
(1-2668)
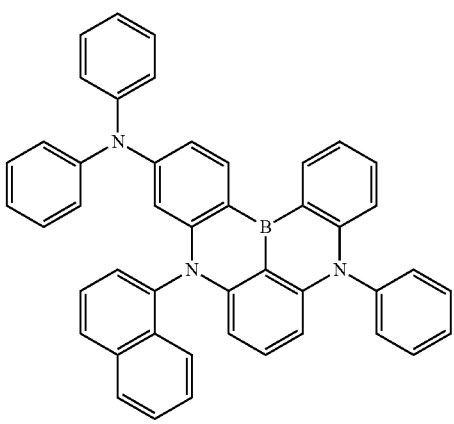
(1-2669)
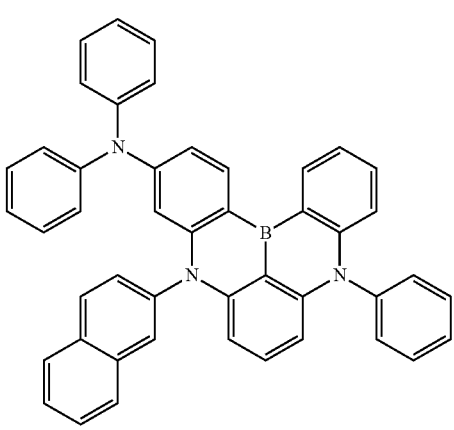

(1-2670)
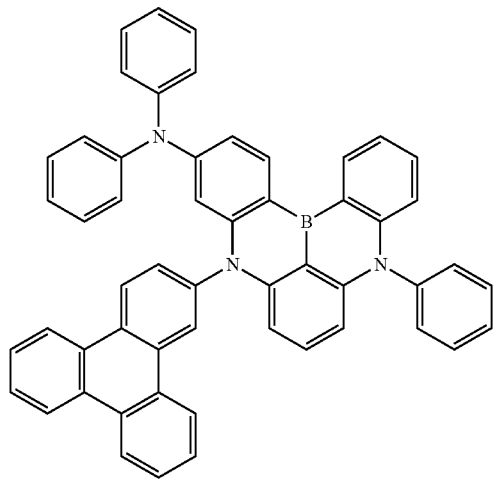
(1-2671)
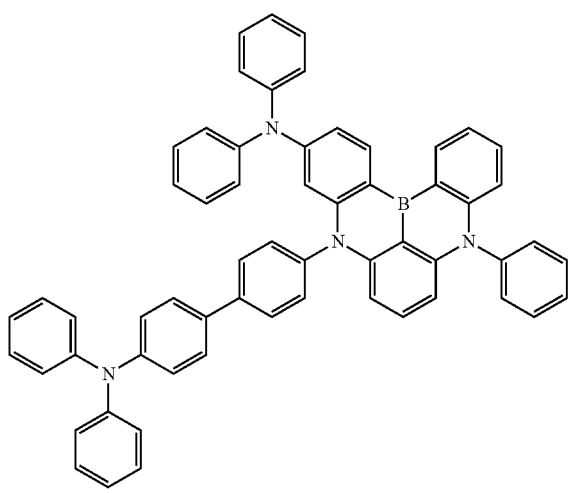
(1-2672)
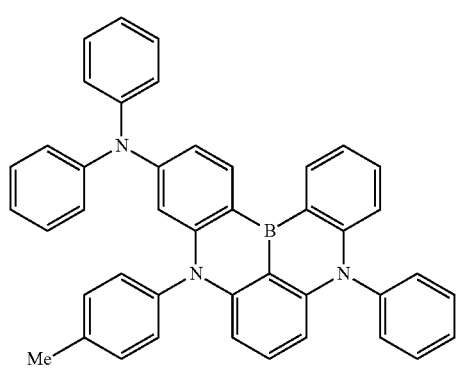
(1-2673)
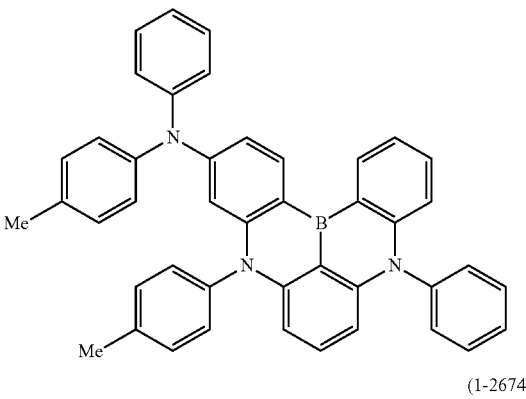
(1-2674)
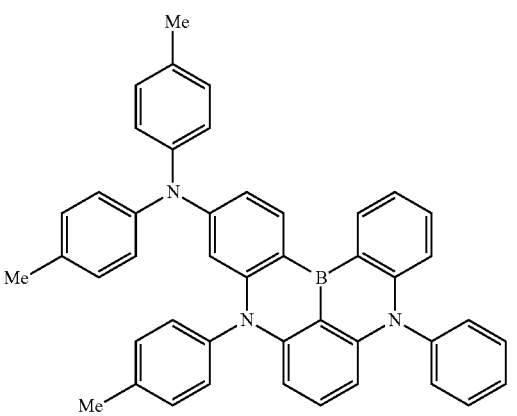
(1-2675)
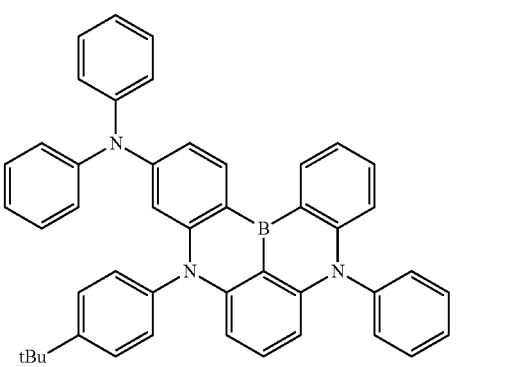
(1-2676)
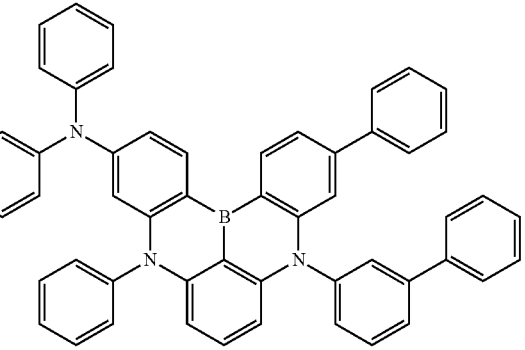

77
-continued
(1-2677)
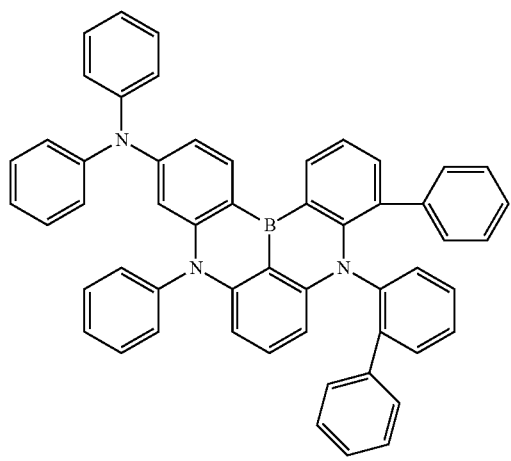
(1-2678)
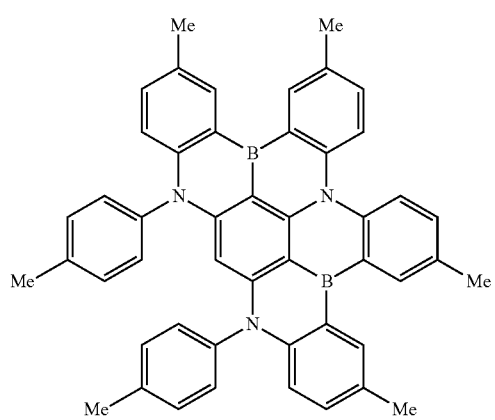
(1-2679)
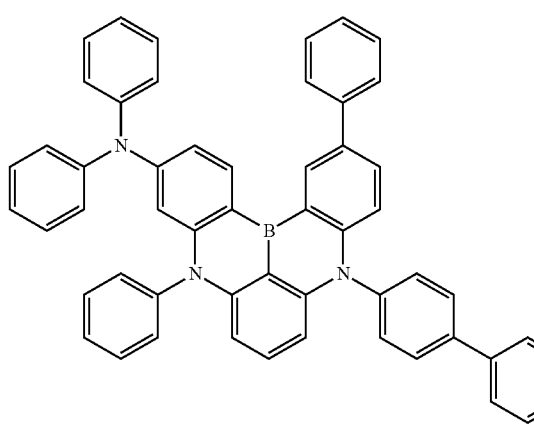
78
-continued
(1-2680)
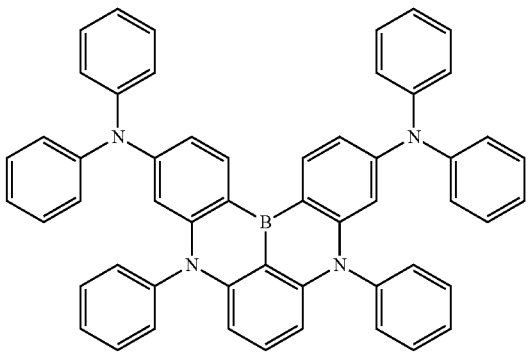
(1-2681)
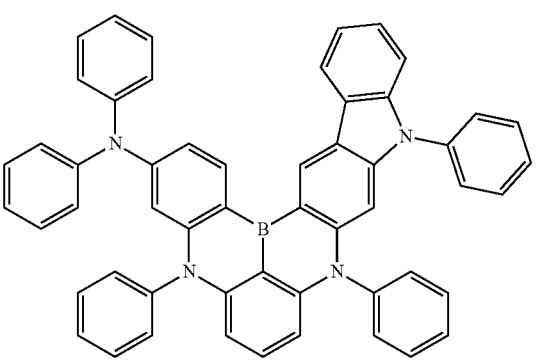
(1-2682)
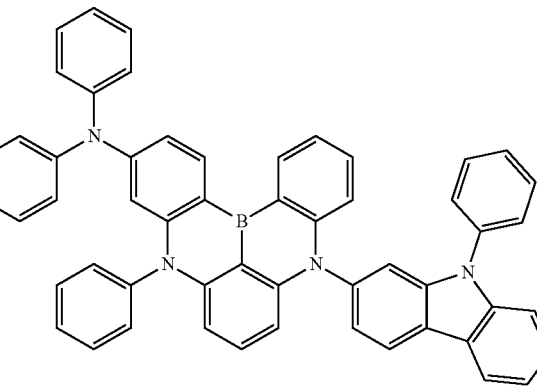
(1-2683)
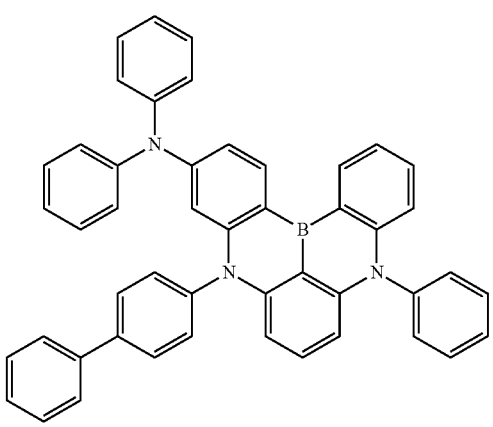

(1-2684)
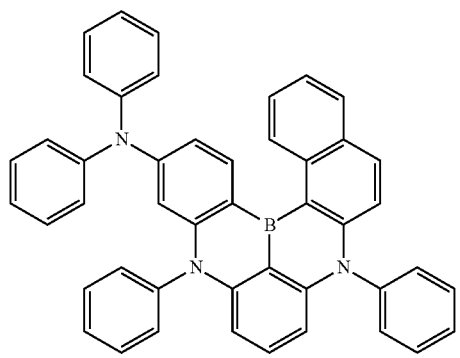
(1-2685)
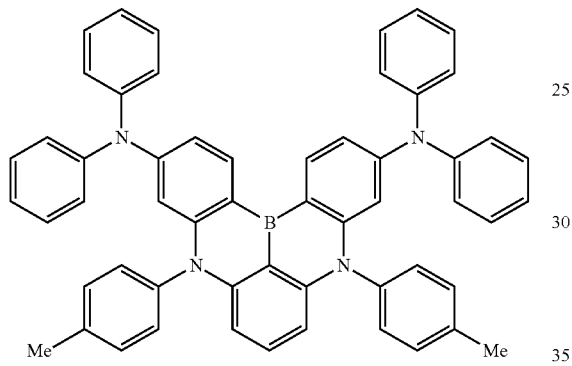
(1-2686)
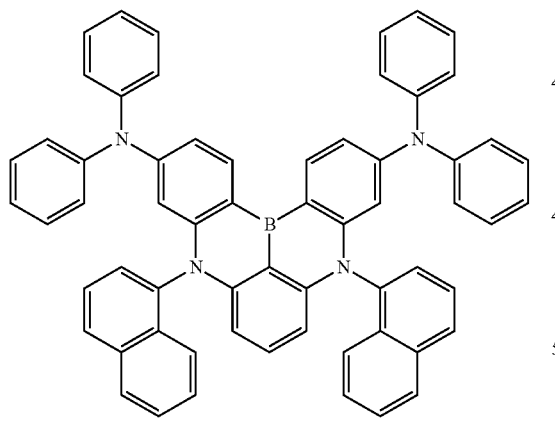
(1-2691)
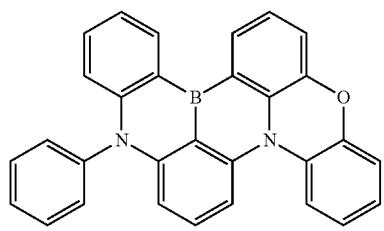
(1-2692)
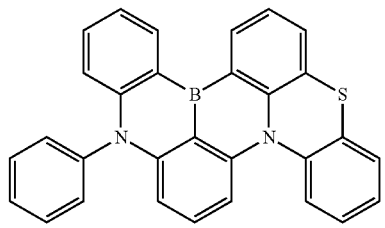
(1-2693)
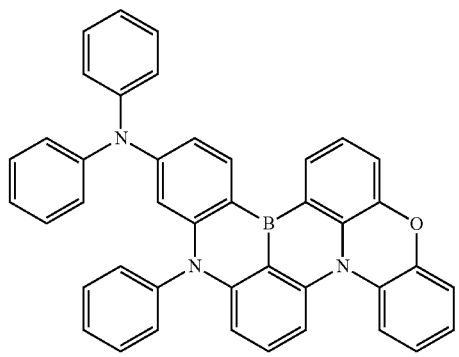
(1-2694)
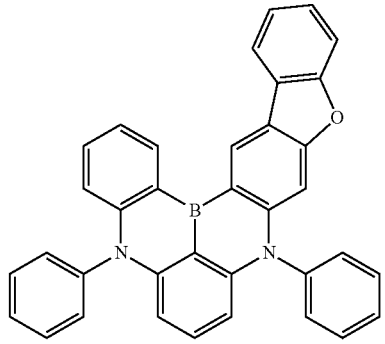
(1-2695)
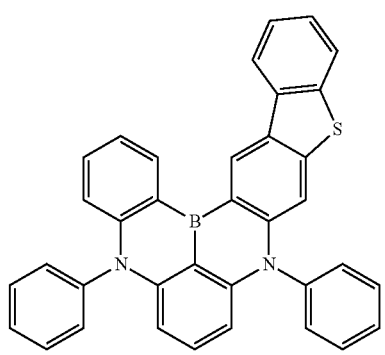

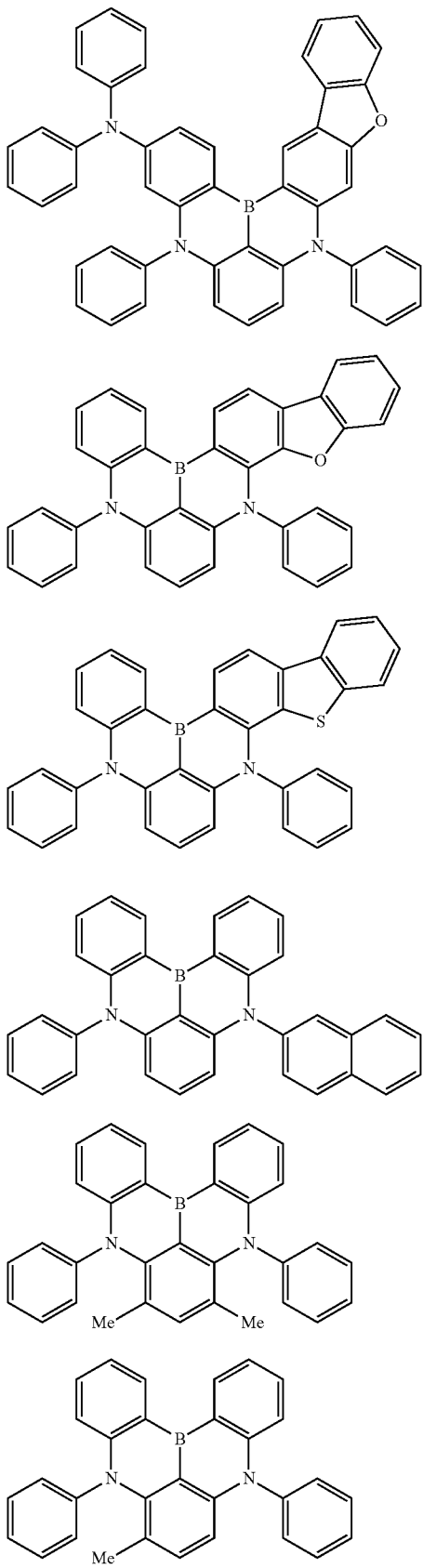
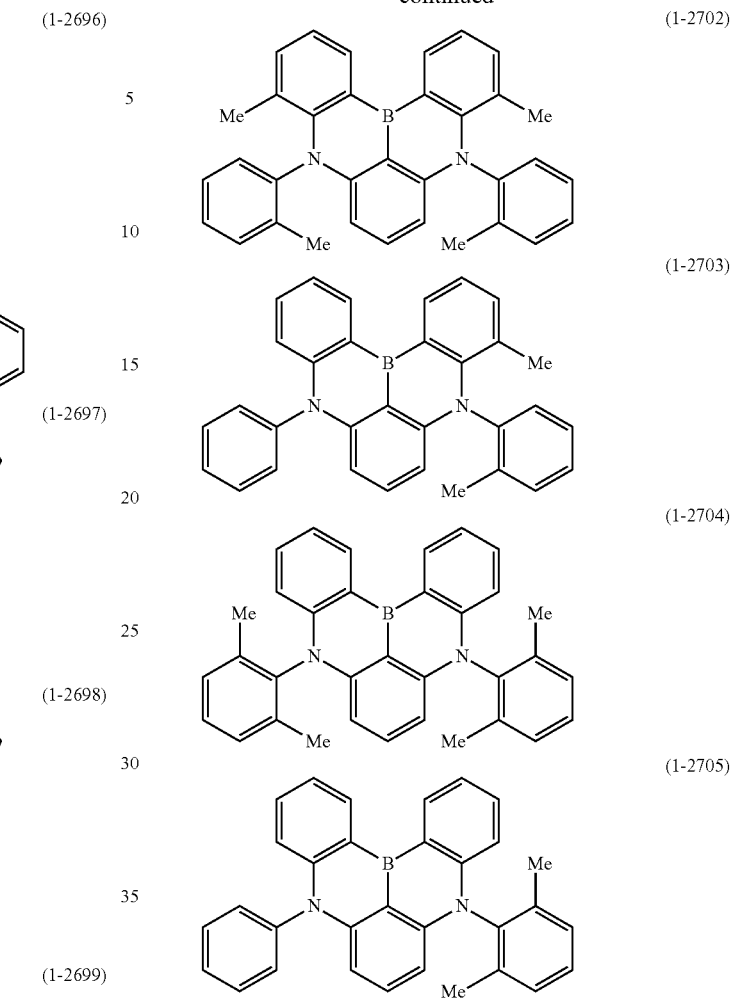

In regard to the polycyclic aromatic compound and a multimer thereof, an increase in the T1 energy (an increase by approximately 0.01 to 0.1 eV) can be expected by introducing a phenyloxy group, a carbazolyl group or a diphenylamino group into the para-position with respect to $Y^1$ in at least one of the ring A, ring B and ring C (ring a, ring b and ring c). Particularly, when a phenyloxy group is introduced into the para-position with respect to B (boron), the HOMO on the benzene rings which are the ring A, ring B and ring C (ring a, ring b and ring c) is more localized to the meta-position with respect to the boron, while the LUMO is localized to the ortho-position and the para-position with respect to the boron. Therefore, particularly, an increase in the T1 energy can be expected.

Specific examples of such a compound include compounds represented by the following formulas (1-4501) to (1-4522).

Note that R in the formulas represents an alkyl, and may be either linear or branched. Examples thereof include a linear alkyl having 1 to 24 carbon atoms and a branched alkyl having 3 to 24 carbon atoms. An alkyl having 1 to 18 carbon atoms (branched alkyl having 3 to 18 carbon atoms) is preferable, an alkyl having 1 to 12 carbon atoms (branched alkyl having 3 to 12 carbon atoms) is more preferable, an alkyl having 1 to 6 carbon atoms (branched alkyl having 3 to 6 carbon atoms) is still more preferable, and an alkyl having 1 to 4 carbon atoms (branched alkyl having 3 to 4 carbon atoms) is particularly preferable. Other examples of R include phenyl.

Furthermore, "PhO—" represents a phenyloxy group, and this phenyl may be substituted by a linear or branched alkyl. For example, the phenyl may be substituted by a linear alkyl having 1 to 24 carbon atoms or a branched alkyl having 3 to 24 carbon atoms, an alkyl having 1 to 18 carbon atoms (a branched alkyl having 3 to 18 carbon atoms), an alkyl having 1 to 12 carbon atoms (a branched alkyl having 3 to 12 carbon atoms), an alkyl having 1 to 6 carbon atoms (a branched alkyl having 3 to 6 carbon atoms), or an alkyl having 1 to 4 carbon atoms (a branched alkyl having 3 or 4 carbon atoms).

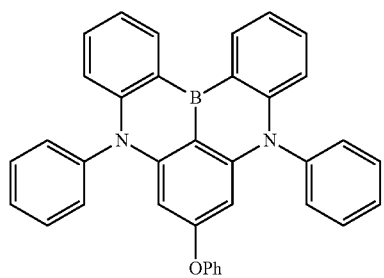
(1-4501)

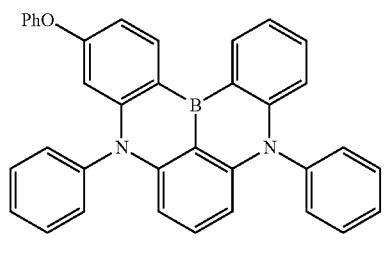
(1-4502)

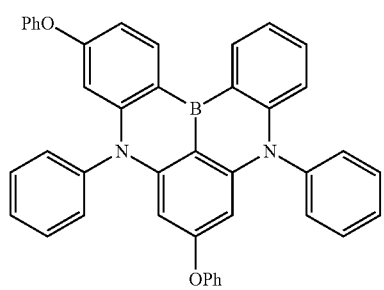
(1-4503)

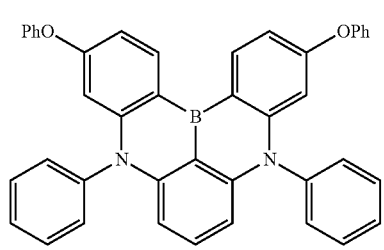
(1-4504)

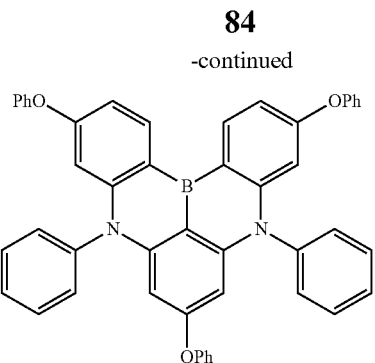
(1-4505)

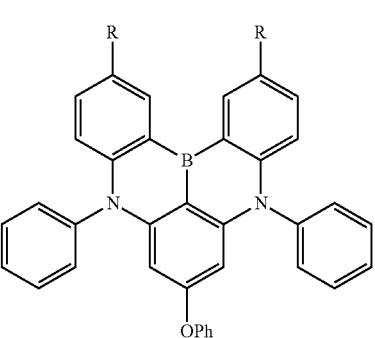
(1-4506)

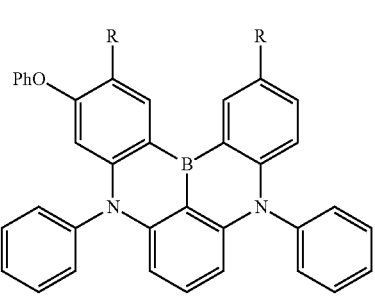
(1-4507)

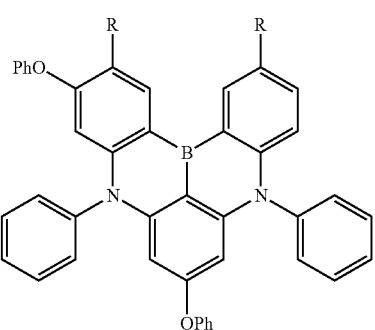
(1-4508)

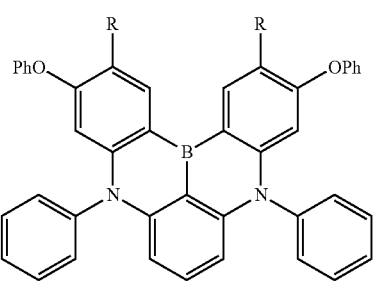
(1-4509)

-continued
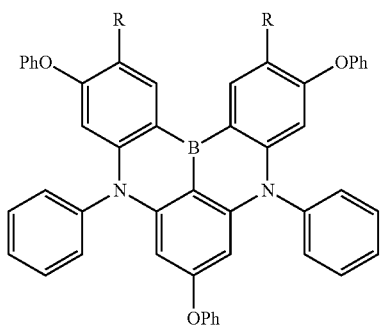
(1-4510)
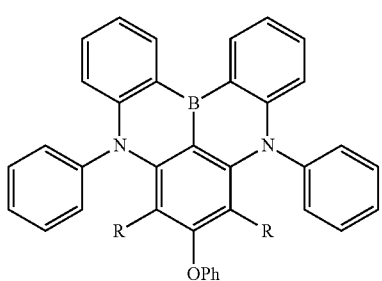
(1-4511)
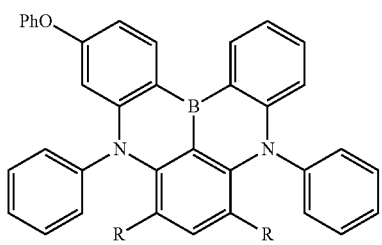
(1-4512)
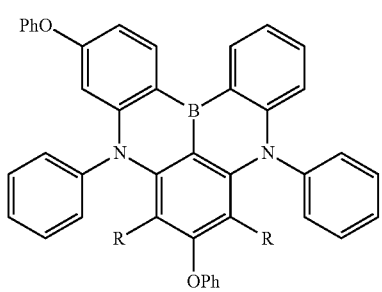
(1-4513)
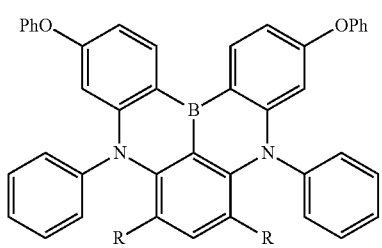
(1-4514)
-continued
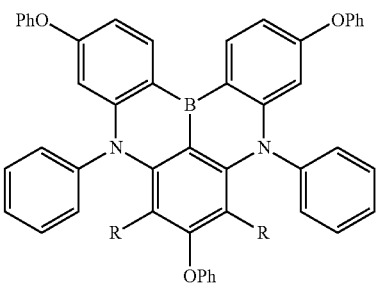
(1-4515)
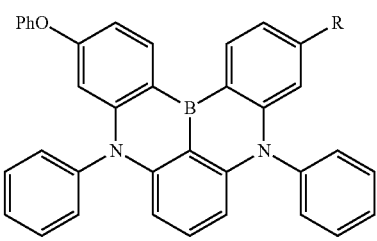
(1-4516)
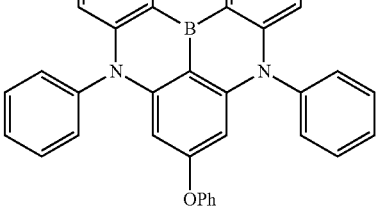
(1-4517)
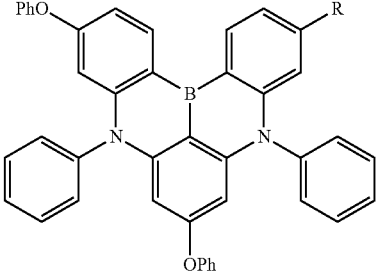
(1-4518)
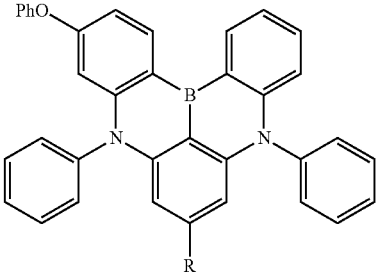
(1-4519)

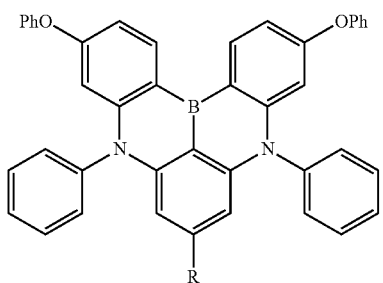
(1-4520)

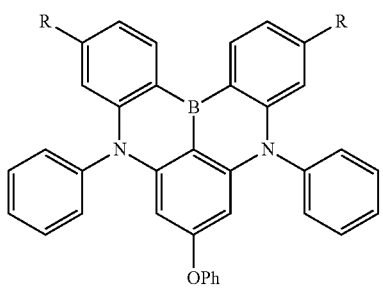
(1-4521)

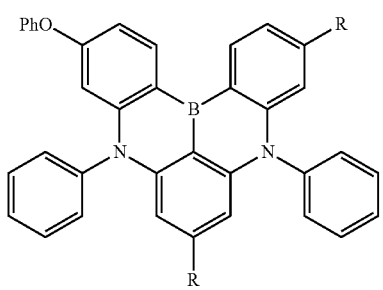
(1-4522)

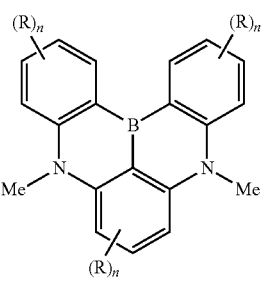
(1-411-R)

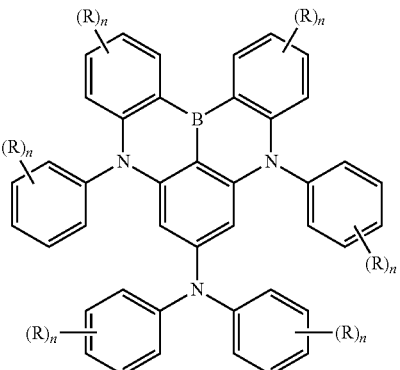
(1-447-R)

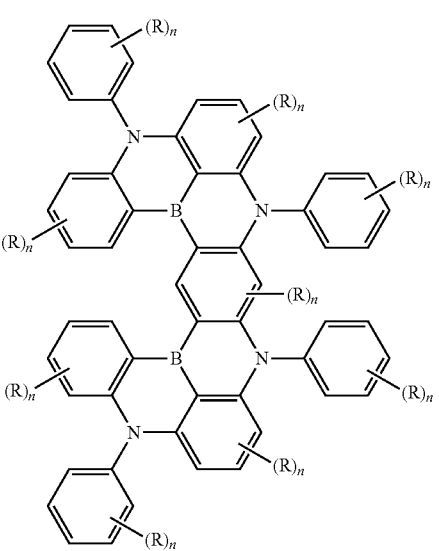
(1-422-R)

Specific examples of the polycyclic aromatic compound and a multimer thereof include the above compounds in which at least one hydrogen atom in one or more aromatic rings in the compound is substituted by one or more alkyls or aryls. More preferable examples thereof include a compound substituted by 1 or 2 of alkyls each having 1 to 12 carbon atoms and aryls each having 6 to 10 carbon atoms.

Specific examples thereof include the following compounds. R's in the following formulas each independently represent an alkyl having 1 to 12 carbon atoms or an aryl having 6 to 10 carbon atoms, and preferably an alkyl or phenyl having 1 to 4 carbon atoms, and n's each independently represent 0 to 2, and preferably 1.

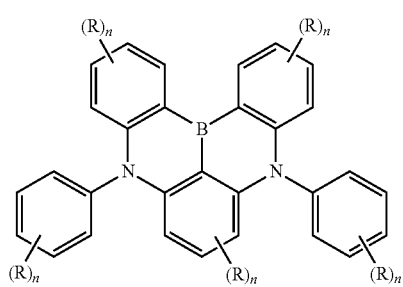
(1-401-R)

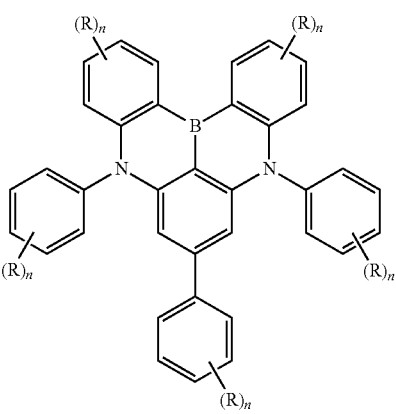
(1-441-R)

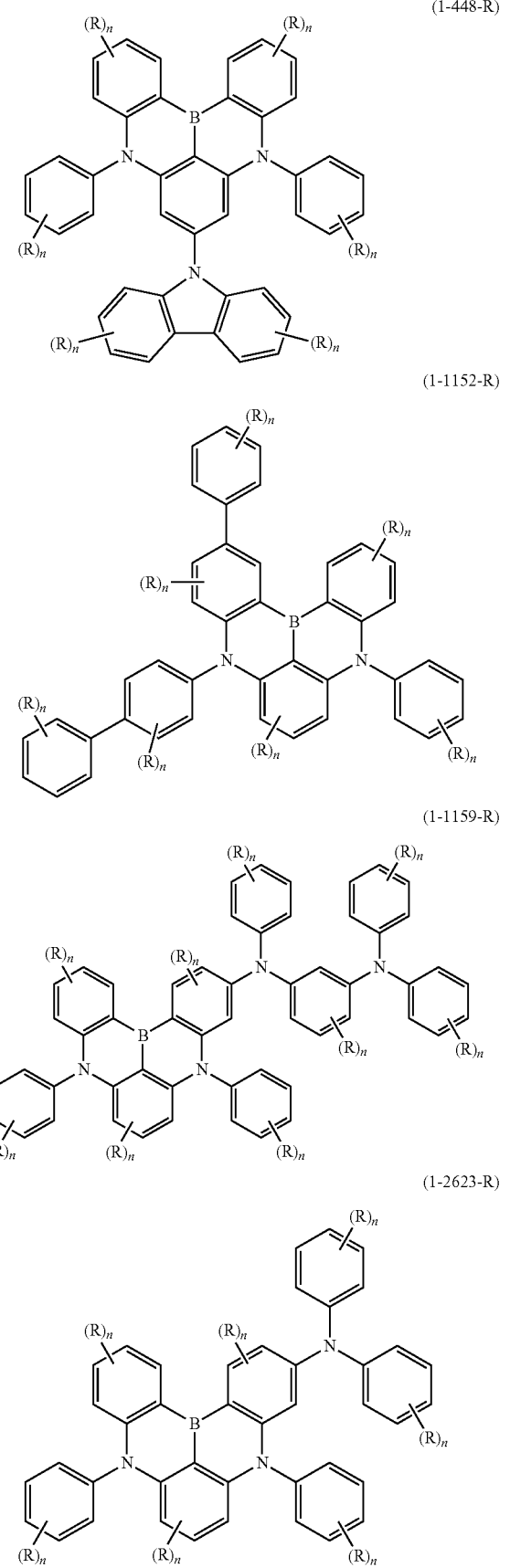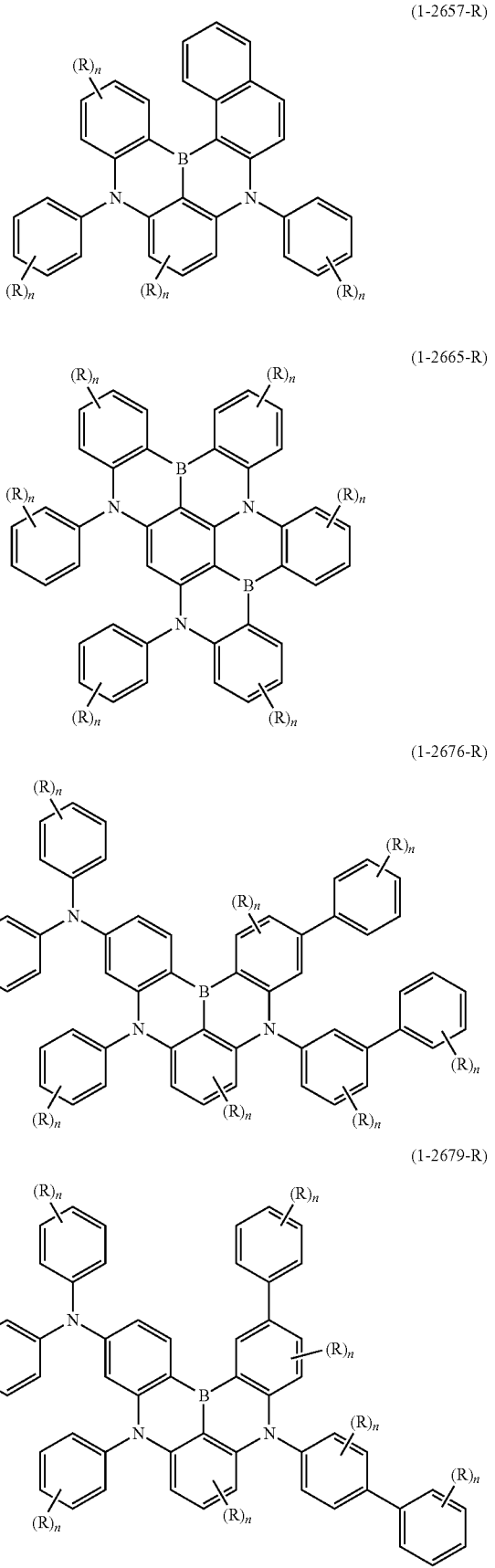

(1-2680-R)

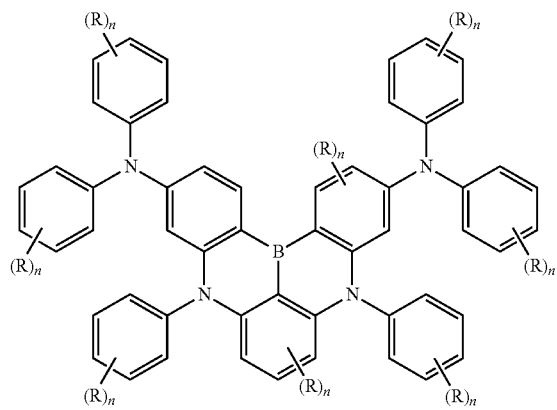

(1-2683-R)

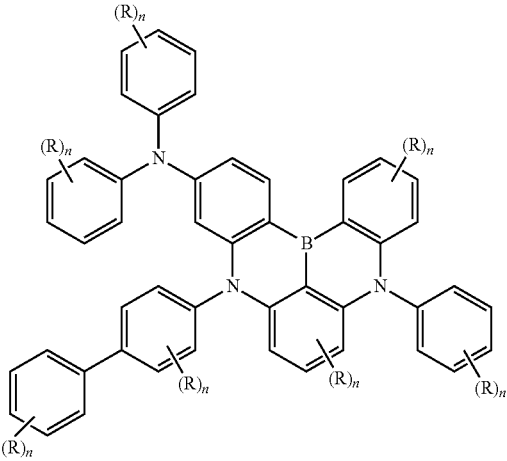

(1-2681-R)

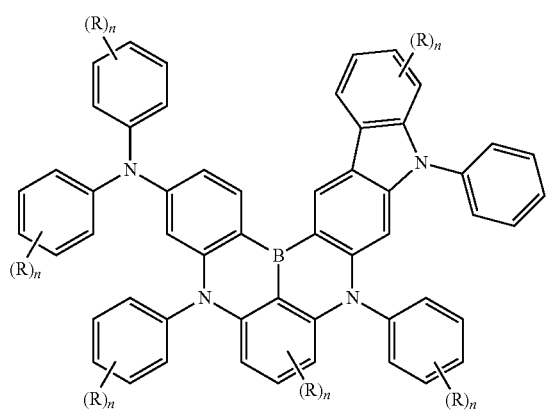

(1-2691-R)

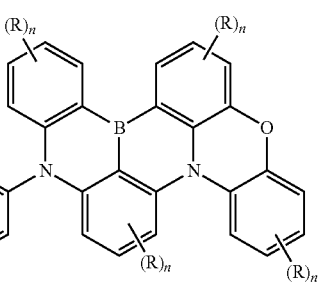

(1-2699-R)

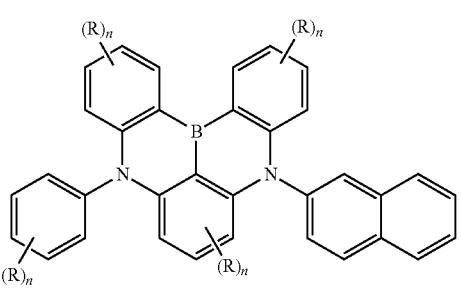

(1-2682-R)

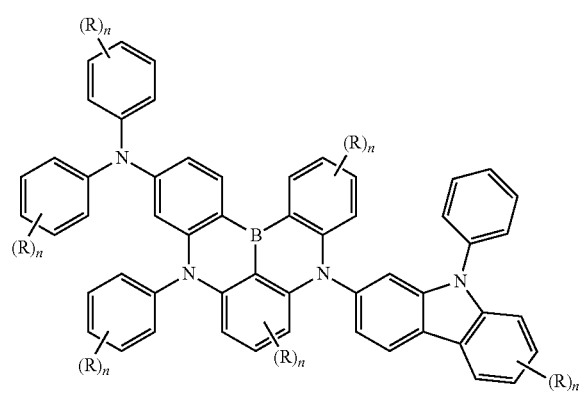

Furthermore, specific examples of the polycyclic aromatic compound and a multimer thereof include a compound in which at least one hydrogen atom in one or more phenyl groups or one phenylene group in the compound is substituted by one or more alkyls each having 1 to 4 carbon atoms, and preferably one or more alkyls each having 1 to 3 carbon atoms (preferably one or more methyl groups). More preferable examples thereof include a compound in which the hydrogen atoms at the ortho-positions of one phenyl group (both of the two sites, preferably any one site) or the hydrogen atoms at the ortho-positions of one phenylene group (all of the four sites at maximum, preferably any one site) are substituted by methyl groups.

By substitution of at least one hydrogen atom at the ortho-position of a phenyl group or a p-phenylene group at a terminal in the compound by a methyl group or the like, adjacent aromatic rings are likely to intersect each other perpendicularly, and conjugation is weakened. As a result, triplet excitation energy ($E_T$) can be increased.

1-2. Method for Manufacturing Polycyclic Aromatic Compound and Multimer Thereof

In regard to the polycyclic aromatic compound represented by general formula (1) or (2) and a multimer thereof, basically, an intermediate is manufactured by first bonding the ring A (ring a), ring B (ring b) and ring C (ring c) with bonding groups (groups containing $X^1$ or $X^2$) (first reaction), and then a final product can be manufactured by bonding the ring A (ring a), ring B (ring b) and ring C (ring c) with bonding groups (groups containing $Y^1$) (second reaction). In the first reaction, a general reaction such as a Buchwald-Hartwig reaction can be utilized in a case of an amination reaction. In the second reaction, a Tandem Hetero-Friedel-Crafts reaction (continuous aromatic electrophilic substitution reaction, the same hereinafter) can be utilized.

As illustrated in the following schemes (1) and (2), the second reaction is a reaction for introducing $Y^1$ (boron) which bonds the ring A (ring a), ring B (ring b) and ring C (ring c). First, a hydrogen atom between $X^1$ and $X^2$ (>N—R) is ortho-metalated with n-butyllithium, sec-butyllithium, t-butyllithium, or the like. Subsequently, boron trichloride, boron tribromide, or the like is added thereto to perform lithium-boron metal exchange, and then a Brønsted base such as N,N-diisopropylethylamine is added thereto to induce a Tandem Bora-Friedel-Crafts reaction. Thus, a desired product can be obtained. In the second reaction, a Lewis acid such as aluminum trichloride may be added in order to accelerate the reaction. Note that $R^1$ to $R^{11}$ and R of N—R in structural formulas in schemes (1) and (2) are defined in the same manner as those in formula (1) or (2).

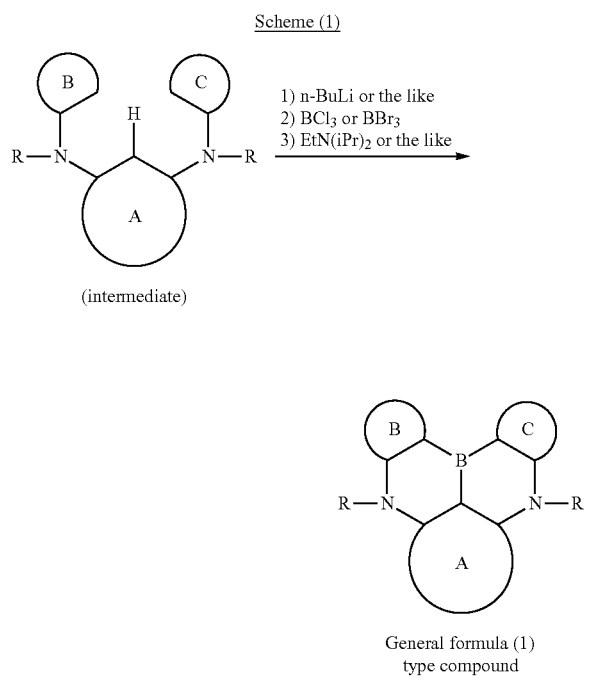

Scheme (1)

(intermediate)

General formula (1) type compound

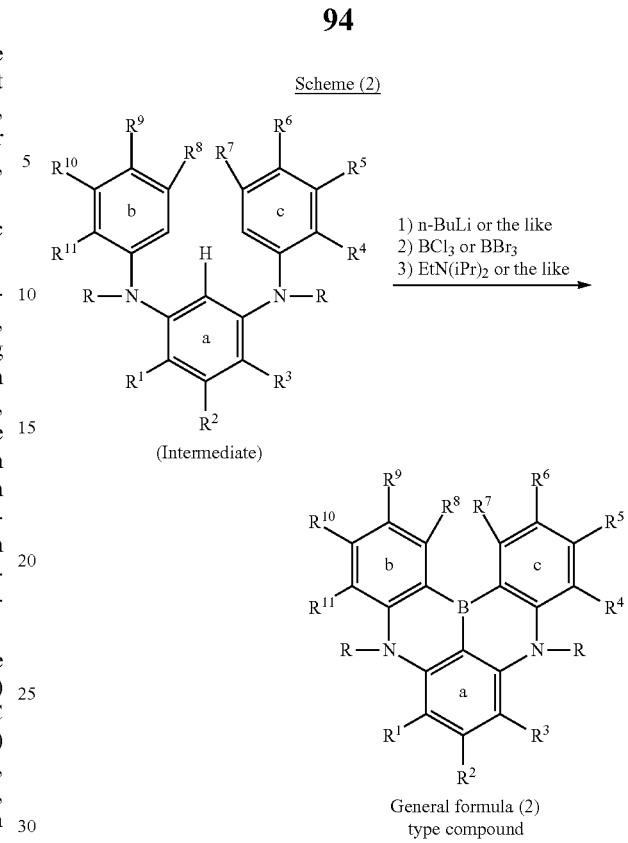

Scheme (2)

(Intermediate)

General formula (2) type compound

Incidentally, the scheme (1) or (2) mainly illustrates a method for manufacturing a polycyclic aromatic compound represented by general formula (1) or (2). However, a multimer thereof can be manufactured using an intermediate having a plurality of ring A's (ring a's), ring B's (ring b's) and ring C's (ring c's). More specifically, the manufacturing method will be described by the following schemes (3) to (5). In this case, a desired product may be obtained by increasing the amount of the reagent used therein such as butyllithium to a double amount or a triple amount. Note that $R^1$ to $R^{11}$ and R of N—R in structural formulas in schemes (3) to (5) are defined in the same manner as those in formula (2).

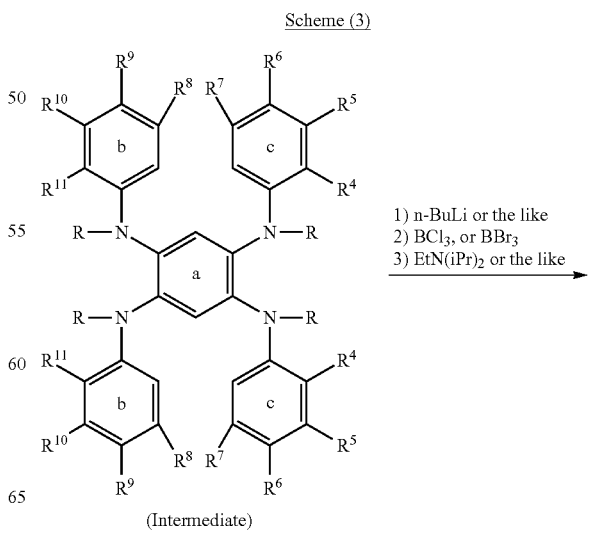

Scheme (3)

(Intermediate)

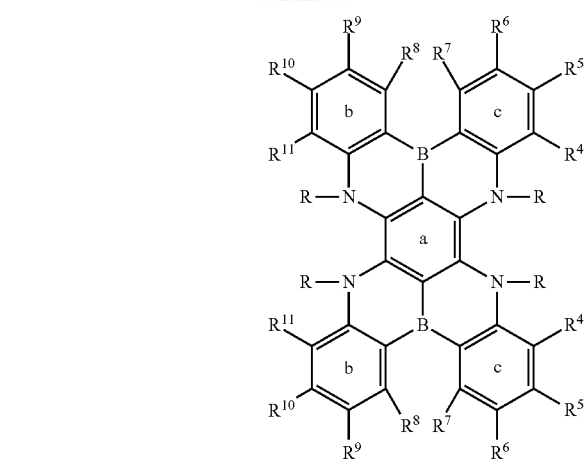

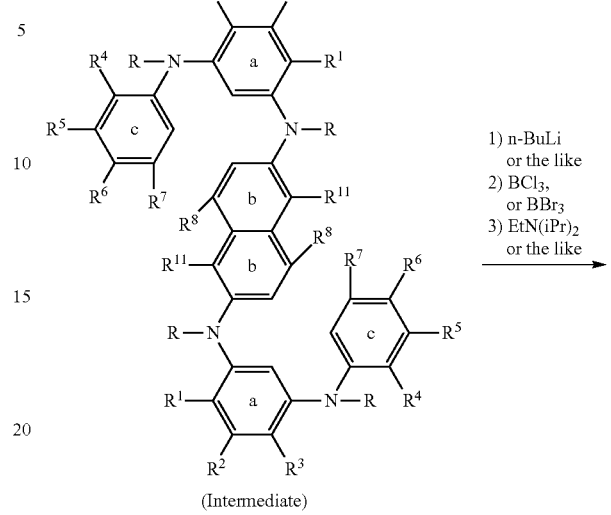

Scheme (4)

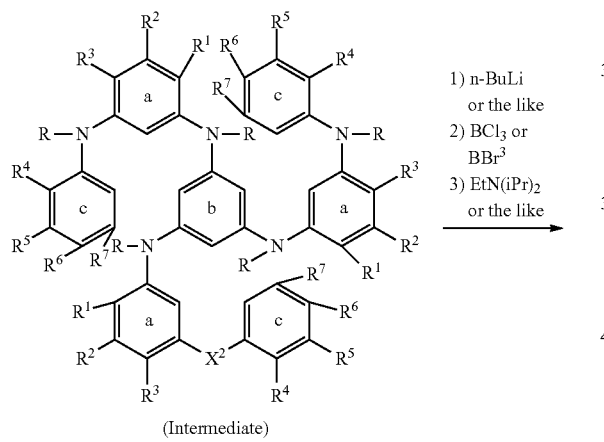

(Intermediate)

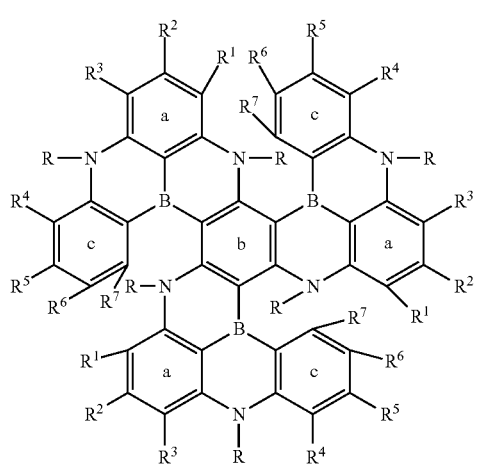

In the above schemes, lithium is introduced into a desired position by ortho-metalation. However, lithium can also be introduced into a desired position by halogen-metal exchange by introducing a bromine atom or the like to a position to which it is wished to introduce lithium, as in the following schemes (6) and (7). Note that $R^1$ to $R^{11}$ and R of N—R in structural formulas in schemes (6) and (7) are defined in the same manner as those in formula (1) or (2).

Scheme (6)

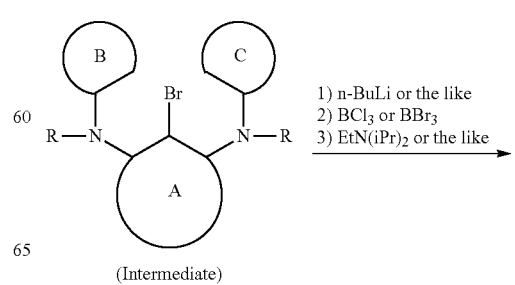

(Intermediate)

-continued

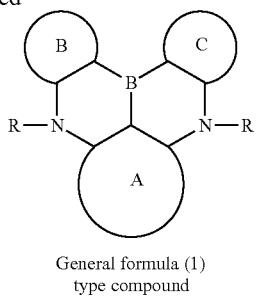

General formula (1) type compound

Furthermore, also in regard to the method for manufacturing a multimer described in scheme (3), a lithium atom can be introduced to a desired position also by halogen-metal exchange by introducing a halogen atom such as a bromine atom or a chlorine atom to a position to which it is wished to introduce a lithium atom, as in the above schemes (6) and (7) (the following schemes (8), (9), and (10)). Note that $R^1$ to $R^{11}$ and R of N—R in structural formulas in schemes (8) to (10) are defined in the same manner as those in formula (2).

Scheme (7)

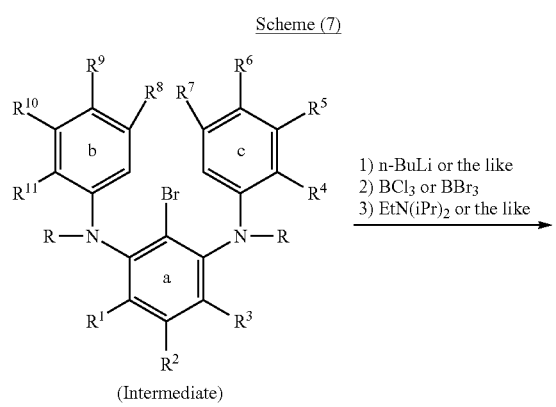

Scheme (8)

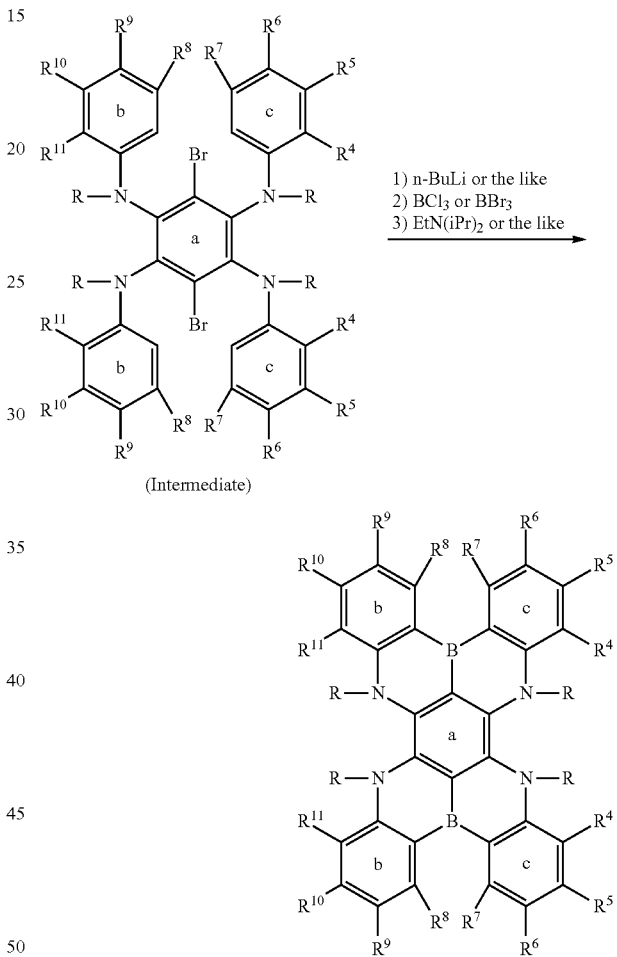

General formula (2) type compound

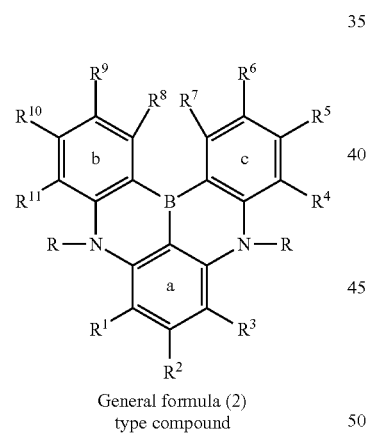

Scheme (9)

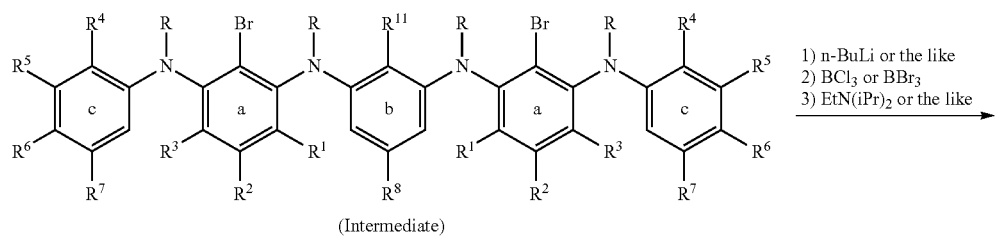

(Intermediate)

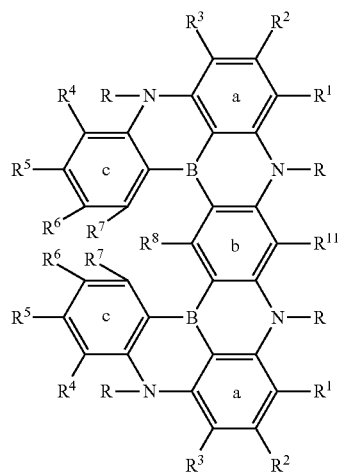

Scheme (10)

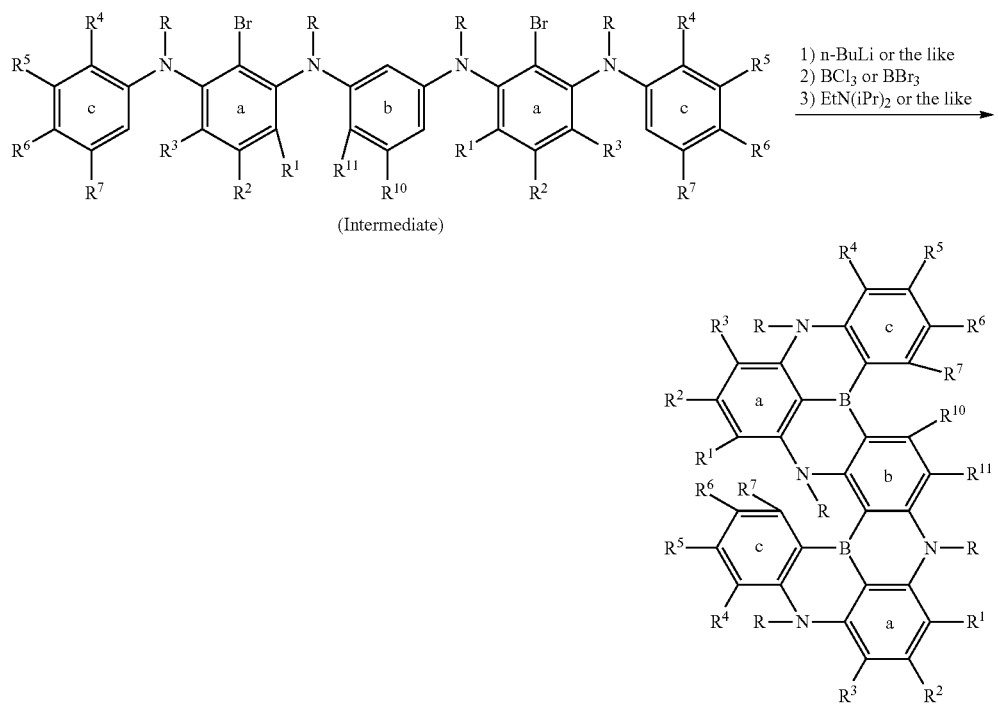

According to this method, a desired product can also be synthesized even in a case in which ortho-metalation cannot be achieved due to the influence of substituents, and therefore the method is useful.

Specific examples of the solvent used in the above reactions include t-butylbenzene and xylene.

By appropriately selecting the above synthesis method and appropriately selecting raw materials to be used, it is possible to synthesize a polycyclic aromatic compound having a substituent at a desired position and a multimer thereof.

Furthermore, in general formula (2), adjacent groups among the substituents $R^1$ to $R^{11}$ of the ring a, ring b and ring c may be bonded to each other to form an aryl ring or a heteroaryl ring together with the ring a, ring b or ring c, and at least one hydrogen atom in the ring thus formed may be substituted by an aryl or a heteroaryl. Therefore, in a polycyclic aromatic compound represented by general formula (2), a ring structure constituting the compound changes as represented by formulas (2-1) and (2-2) of the following schemes (11) and (12) according to a mutual bonding form of substituents in the ring a, ring b, and ring c. These compounds can be synthesized by applying synthesis methods illustrated in the above schemes (1) to (10) to intermediates illustrated in the following schemes (11) and (12). Note that $R^1$ to $R^{11}$, $Y^1$, $X^1$, and $X^2$ in structural formulas in schemes (11) and (12) are defined in the same manner as those in formula (2).

Scheme (11)

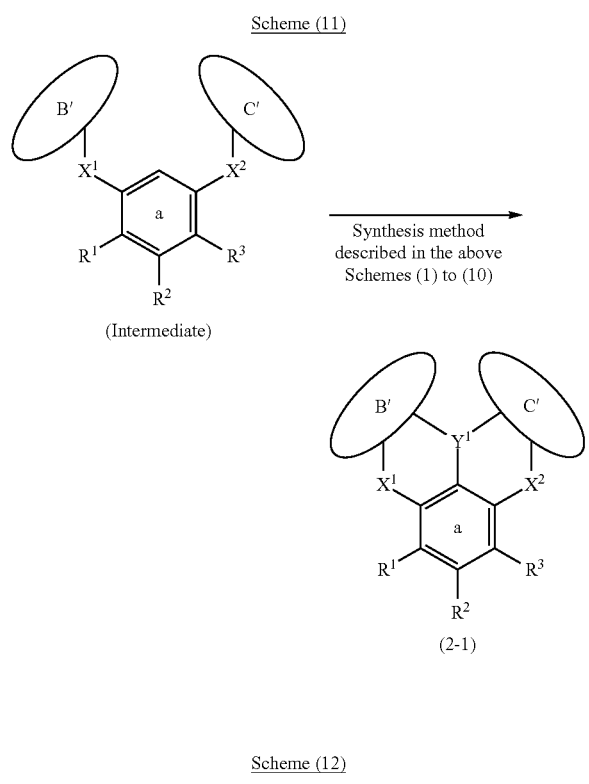

(2-1)

Scheme (12)

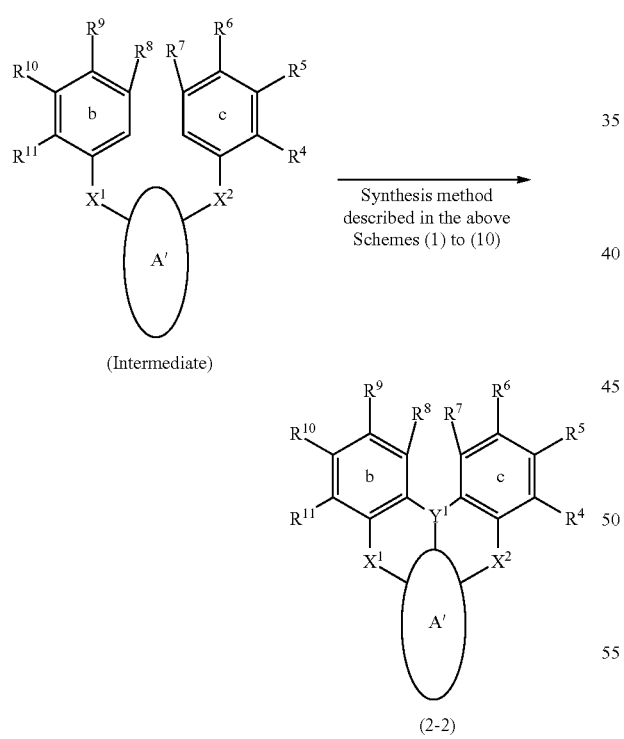

(2-2)

Ring A', ring B' and ring C' in the above formulas (2-1) and (2-2) each represent an aryl ring or a heteroaryl ring formed by bonding adjacent groups among the substituents $R^1$ to $R^{11}$ together with the ring a, ring b, and ring c, respectively (may also be a fused ring obtained by fusing another ring structure to the ring a, ring b, or ring c). Incidentally, although not indicated in the formula, there is also a compound in which all of the ring a, ring b, and ring c have been changed to the ring A', ring B' and ring C'.

Furthermore, the provision that "R of the N—R is bonded to the ring a, ring b, and/or ring c with —O—, —S—, —C(—R)$_2$—, or a single bond" in general formulas (2) can be expressed as a compound having a ring structure represented by formula (2-3-1) of the following scheme (13), in which $X^1$ or $X^2$ is incorporated into the fused ring B' or fused ring C', or a compound having a ring structure represented by formula (2-3-2) or (2-3-3), in which $X^1$ or $X^2$ is incorporated into the fused ring A'. Such a compound can be synthesized by applying the synthesis methods illustrated in the schemes (1) to (10) to the intermediate represented by the following scheme (13). Note that $R^1$ to $R^{11}$, $Y^1$, $X^1$, and $X^2$ in structural formulas in scheme (13) are defined in the same manner as those in formula (2).

Scheme (13)

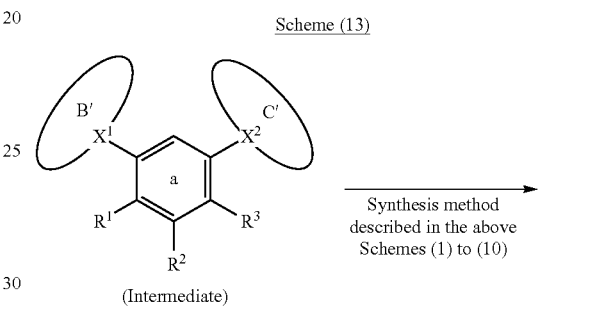

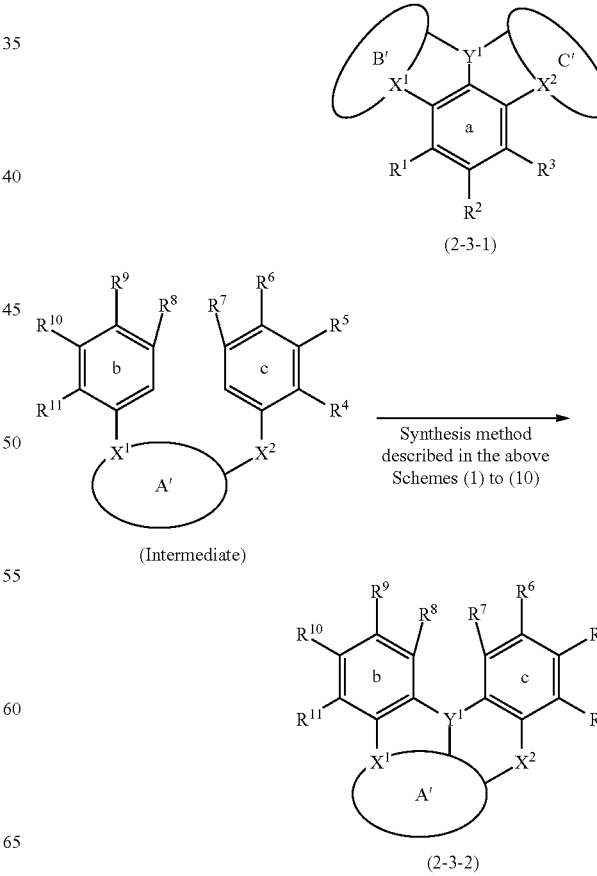

(2-3-2)

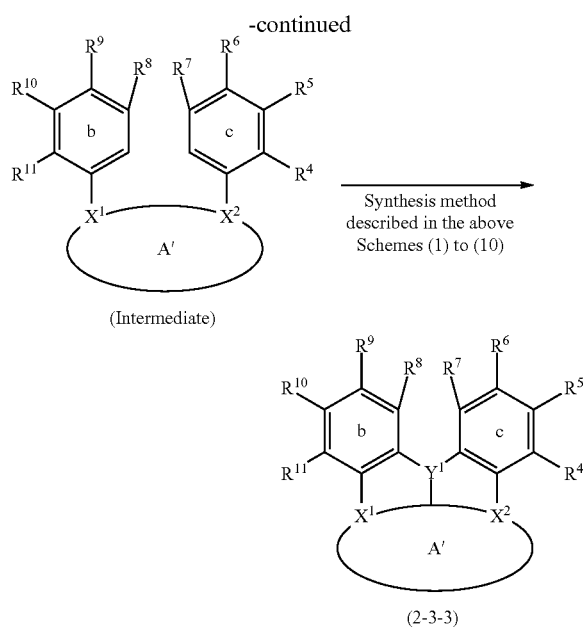

(Intermediate)

(2-3-3)

Furthermore, regarding the synthesis methods of the above schemes (1) to (13), there is shown an example of carrying out the Tandem Hetero-Friedel-Crafts reaction by ortho-metalating a hydrogen atom (or a halogen atom) between $X^1$ and $X^2$ with butyllithium or the like, before boron trichloride, boron tribromide or the like is added. However, the reaction may also be carried out by adding boron trichloride, boron tribromide or the like without conducting ortho-metalation using buthyllithium or the like.

Note that examples of an ortho-metalation reagent used for the above schemes (1) to (13) include an alkyllithium such as methyllithium, n-butyllithium, sec-butyllithium, or t-butyllithium; and an organic alkali compound such as lithium diisopropylamide, lithium tetramethylpiperidide, lithium hexamethyldisilazide, or potassium hexamethyldisilazide.

Incidentally, examples of a metal exchanging reagent for metal-$Y^1$ used for the above schemes (1) to (13) include a halide of $Y^1$ such as trifluoride of $Y^1$, trichloride of $Y^1$, tribromide of $Y^1$, or triiodide of $Y^1$; an aminated halide of $Y^1$ such as $ClPN(NEt_2)_2$; an alkoxylation product of $Y^1$; and an aryloxylation product of $Y^1$.

Incidentally, examples of the Brønsted base used for the above schemes (1) to (13) include N,N-diisopropylethylamine, triethylamine, 2,2,6,6-tetramethylpiperidine, 1,2,2,6,6-pentamethylpiperidine, N,N-dimethylaniline, N,N-dimethyltoluidine, 2,6-lutidine, sodium tetraphenylborate, potassium tetraphenylborate, triphenylborane, tetraphenylsilane, $Ar_4BNa$, $Ar_4BK$, $Ar_3B$, and $Ar_4Si$ (Ar represents an aryl such as phenyl).

Examples of a Lewis acid used for the above schemes (1) to (13) include $AlCl_3$, $AlBr_3$, $AlF_3$, $BF_3 \cdot OEt_2$, $BCl_3$, $BBr_3$, $GaCl_3$, $GaBr_3$, $InCl_3$, $InBr_3$, $In(OTf)_3$, $SnCl_4$, $SnBr_4$, $AgOTf$, $ScCl_3$, $Sc(OTf)_3$, $ZnCl_2$, $ZnBr_2$, $Zn(OTf)_2$, $MgCl_2$, $MgBr_2$, $Mg(OTf)_2$, $LiOTf$, $NaOTf$, $KOTf$, $Me_3SiOTf$, $Cu(OTf)_2$, $CuCl_2$, $YCl_3$, $Y(OTf)_3$, $TiCl_4$, $TiBr_4$, $ZrCl_4$, $ZrBr_4$, $FeCl_3$, $FeBr_3$, $COCl_3$, and $COBr_3$.

In the above schemes (1) to (13), a Brønsted base or a Lewis acid may be used in order to accelerate the Tandem Hetero Friedel-Crafts reaction. However, in a case where a halide of $Y^1$ such as trifluoride of $Y^1$, trichloride of $Y^1$, tribromide of $Y^1$, or triiodide of $Y^1$ is used, an acid such as hydrogen fluoride, hydrogen chloride, hydrogen bromide, or hydrogen iodide is generated along with progress of an aromatic electrophilic substitution reaction. Therefore, it is effective to use a Brønsted base that captures an acid. On the other hand, in a case where an aminated halide of $Y^1$ or an alkoxylation product of $Y^1$ is used, an amine or an alcohol is generated along with progress of the aromatic electrophilic substitution reaction. Therefore, in many cases, it is not necessary to use a Brønsted base. However, leaving ability of an amino group or an alkoxy group is low, and therefore it is effective to use a Lewis acid that promotes leaving of these groups.

A polycyclic aromatic compound or a multimer thereof also includes compounds in which at least a portion of hydrogen atoms are substituted by deuterium atoms or substituted by halogen atoms such as fluorine atoms or chlorine atoms. However, these compounds can be synthesized as described above using raw materials that are deuterated, fluorinated or chlorinated at desired sites.

1-3. Anthracene-Based Compound

Basically, an anthracene-based compound represented by general formula (3) functions as a host.

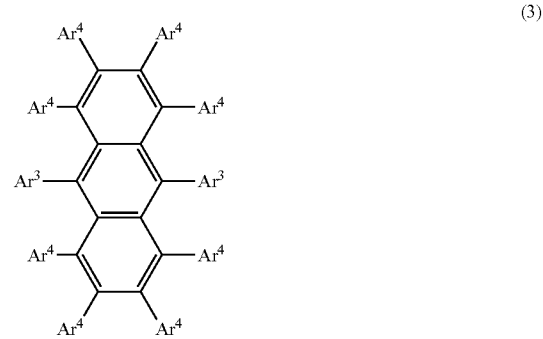

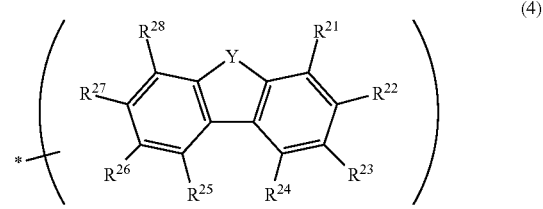

In general formula (3), $Ar^3$ and $Ar^4$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, provided that a naphthyl group and a naphthyl group fused with one benzene ring are excluded as $Ar^3$.

At least one hydrogen atom in a chemical structure of an anthracene-based compound represented by general formula (3) is substituted with a group represented by the above formula (4). At least one hydrogen atom in the compound represented by formula (3) is substituted by the group represented by formula (4) at *.

In the above formula (4), Y represents —O—, —S—, or >N—$R^{29}$, $R^{21}$ to $R^{28}$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, adjacent groups among $R^{21}$ to $R^{28}$ may be bonded to each other to form a hydrocarbon ring, an aryl ring, or a heteroaryl ring, and $R^{29}$ is an optionally substituted aryl or a bonding position with a compound represented by formula (3).

The "alkyl" as the "optionally substituted alkyl" in $Ar^3$ and $Ar^4$ in the above formula (3) and $R^{21}$ to $R^{28}$ in the above formula (4) may be either linear or branched, and examples thereof include a linear alkyl having 1 to 24 carbon atoms and a branched alkyl having 3 to 24 carbon atoms. An alkyl having 1 to 18 carbon atoms (branched alkyl having 3 to 18 carbon atoms) is preferable, an alkyl having 1 to 12 carbon atoms (branched alkyl having 3 to 12 carbon atoms) is more preferable, an alkyl having 1 to 6 carbon atoms (branched alkyl having 3 to 6 carbon atoms) is still more preferable, and an alkyl having 1 to 4 carbon atoms (branched alkyl having 3 to 4 carbon atoms) is particularly preferable.

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

Examples of the "aryl" as the "optionally substituted aryl" in $Ar^3$ and $Ar^4$ in the above formula (3) and $R^{21}$ to $R^{28}$ in the above formula (4) include an aryl having 6 to 30 carbon atoms. An aryl having 6 to 16 carbon atoms is preferable, an aryl having 6 to 12 carbon atoms is more preferable, and an aryl having 6 to 10 carbon atoms is particularly preferable. However, a naphthyl group and a naphthyl group fused with one benzene ring are excluded as $Ar^3$.

Specific examples of the "aryl" include phenyl which is a monocyclic system; biphenylyl which is a bicyclic system; naphthyl which is a fused bicyclic system; terphenylyl (m-terphenylyl, o-terphenylyl, or p-terphenylyl) which is a tricyclic system; acenaphthylenyl, fluorenyl, phenalenyl, and phenanthrenyl which are fused tricyclic systems; triphenylenyl, pyrenyl, and naphthacenyl which are fused tetracyclic systems; and perylenyl and pentacenyl which are fused pentacyclic systems. However, a naphthyl group and a naphthyl group fused with one benzene ring are excluded as $Ar^3$.

Examples of the "heteroaryl" as the "optionally substituted heteroaryl" in $Ar^3$ and $Ar^4$ in the above formula (3) and $R^{21}$ to $R^{28}$ in the above formula (4) include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the heteroaryl include a heterocyclic ring containing 1 to 5 heteroatoms, selected from an oxygen atom, a sulfur atom, and a nitrogen atom in addition to a carbon atom as a ring-constituting atom.

Specific examples of the "heteroaryl" include a pyrrolyl, an oxazolyl, an isoxazolyl, a thiazolyl, an isothiazolyl, an imidazolyl, an oxadiazolyl, a thiadiazolyl, a triazolyl, a tetrazolyl, a pyrazolyl, a pyridyl, a pyrimidinyl, a pyridazinyl, a pyrazinyl, a triazinyl, an indolyl, an isoindolyl, a 1H-indazolyl, a benzoimidazolyl, a benzoxazolyl, a benzothiazolyl, a 1H-benzotriazolyl, a quinolyl, an isoquinolyl, a cinnolyl, a quinazolyl, a quinoxalinyl, a phthalazinyl, a naphthyridinyl, a purinyl, a pteridinyl, a carbazolyl, an acridinyl, a phenoxathiinyl, a phenoxazinyl, a phenothiazinyl, a phenazinyl, an indolizinyl, a furyl, a benzofuranyl, an isobenzofuranyl, a dibenzofuranyl, a thienyl, a benzo[b]thienyl, a dibenzothienyl, a furazanyl, an oxadiazolyl, a thianthrenyl, a naphthobenzofuranyl, and a naphthobenzothienyl.

Examples of the "alkoxy" as the "optionally substituted alkoxy" in $Ar^3$ and $Ar^4$ in the above formula (3) and $R^{21}$ to $R^{28}$ in the above formula (4) include a linear alkoxy having 1 to 24 carbon atoms and a branched alkoxy having 3 to 24 carbon atoms. An alkoxy having 1 to 18 carbon atoms (branched alkoxy having 3 to 18 carbon atoms) is preferable, an alkoxy having 1 to 12 carbon atoms (branched alkoxy having 3 to 12 carbon atoms) is more preferable, an alkoxy having 1 to 6 carbon atoms (branched alkoxy having 3 to 6 carbon atoms) is still more preferable, and an alkoxy having 1 to 4 carbon atoms (branched alkoxy having 3 to 4 carbon atoms) is particularly preferable.

Specific examples of the "alkoxy" include a methoxy, an ethoxy, a propoxy, an isopropoxy, a butoxy, an isobutoxy, a s-butoxy, a t-butoxy, a pentyloxy, a hexyloxy, a heptyloxy, and an octyloxy.

Examples of the "aryloxy" as the "optionally substituted aryloxy" in $Ar^3$ and $Ar^4$ in the above formula (3) and $R^{21}$ to $R^{28}$ in the above formula (4) include a group in which a hydrogen atom of an —OH group is substituted by an aryl. For this aryl, those described as the above "aryl" in $Ar^3$, $Ar^4$ and $R^{21}$ to $R^{28}$ can be cited.

Examples of the "arylthio" as the "optionally substituted arylthio" in $Ar^3$ and $Ar^4$ in the above formula (3) and $R^{21}$ to $R^{28}$ in the above formula (4) include a group in which a hydrogen atom of an —SH group is substituted by an aryl. For this aryl, those described as the above "aryl" in $Ar^3$, $Ar^4$ and $R^{21}$ to $R^{28}$ can be cited.

Examples of the "trialkylsilyl" in $Ar^3$ and $Ar^4$ in the above formula (3) and $R^{21}$ to $R^{28}$ in the above formula (4) include a group in which three hydrogen atoms in a silyl group are each independently substituted by an alkyl. For this alkyl, those described as the above "alkyl" in $Ar^3$, $Ar^4$ and $R^{21}$ to $R^{28}$ can be cited. A preferable alkyl for substitution is an alkyl having 1 to 4 carbon atoms, and specific examples thereof include methyl, ethyl, propyl, i-propyl, butyl, sec-butyl, t-butyl, and cyclobutyl.

Specific examples of the "trialkylsilyl" include a trimethylsilyl, a triethylsilyl, a tripropylsilyl, a tri-i-propylsilyl, a tributylsilyl, a tri sec-butylsilyl, a tri-t-butylsilyl, an ethyl dimethylsilyl, a propyldimethylsilyl, an i-propyldimethylsilyl, a butyldimethylsilyl, a sec-butyldimethylsilyl, a t-butyldimethylsilyl, a methyldiethylsilyl, a propyldiethylsilyl, an i-propyldiethylsilyl, a butyldiethylsilyl, a sec-butyl diethylsilyl, a t-butyldiethylsilyl, a methyldipropylsilyl, an ethyldipropylsilyl, a butyldipropylsilyl, a sec-butyldipropylsilyl, a t-butyldipropylsilyl, a methyl di-i-propylsilyl, an ethyl di-i-propylsilyl, a butyl di-i-propylsilyl, a sec-butyl di-i-propylsilyl, and a t-butyl di-i-propylsilyl.

Examples of the "substituted amino" as the "optionally substituted amino" in $Ar^3$ and $Ar^4$ in the above formula (3) and $R^{21}$ to $R^{28}$ in the above formula (4) include an amino group in which two hydrogen atoms are substituted by an aryl or a heteroaryl. A group in which two hydrogen atoms are substituted by aryls is a diaryl-substituted amino, a group in which two hydrogen atoms are substituted by heteroaryls is a diheteroaryl-substituted amino, and group in which two hydrogen atom are substituted by an aryl and a heteroaryl is an arylheteroaryl-substituted amino. For the aryl and heteroaryl, those described as the above "aryl" and "heteroaryl" in $Ar^3$, $Ar^4$ and $R^{21}$ to $R^{28}$ can be cited.

Specific examples of the "substituted amino" include diphenylamino, dinaphthylamino, phenylnaphthylamino, dipyridylamino, phenylpyridylamino, and naphthylpyridylamino.

Examples of the "halogen atom" in $Ar^3$ and $Ar^4$ in the above formula (3) and $R^{21}$ to $R^{28}$ in the above formula (4) include a fluorine atom, a chlorine atom, a bromine atom, and an iodine atom.

Some of the groups described as $Ar^3$, $Ar^4$ and $R^{21}$ to $R^{28}$ may be substituted as described above, and examples of the substituent in this case include an alkyl, an aryl, and a heteroaryl. For the alkyl, aryl, or heteroaryl, those described as the above "alkyl", "aryl" or "heteroaryl" in $Ar^3$, $Ar^4$ and $R^{21}$ to $R^{28}$ can be cited. Incidentally, a naphthyl group and a naphthyl group fused with one benzene ring are excluded as $Ar^3$, but the naphthyl group and the naphthyl group fused with one benzene ring are not excluded as an aryl serving as a substituent of $Ar^3$.

$R^{29}$ in ">N—$R^{29}$" as Y is an optionally substituted aryl. For the aryl, those described as the above "aryl" in $Ar^3$, $Ar^4$ and $R^{21}$ to $R^{28}$ can be cited. As the substituent, those described as the substituent for $Ar^3$, $Ar^4$ and $R^{21}$ to $R^{28}$ can be cited. Further $R^{29}$ can be a bonding position with a compound represented by formula (3).

Adjacent groups among $R^{21}$ to $R^{28}$ may be bonded to each other to form a hydrocarbon ring, an aryl ring, or a heteroaryl ring. Examples of a case of not forming a ring include a group represented by the following formula (4-1). Examples of a case of forming a ring include groups represented by the following formulas (4-2) to (4-11). Note that at least one hydrogen atom in a group represented by any one of formulas (4-1) to (4-11) may be substituted by an alkyl, an aryl, a heteroaryl, an alkoxy, an aryloxy, an arylthio, a trialkylsilyl, a diaryl-substituted amino, a diheteroaryl-substituted amino, an arylheteroaryl-substituted amino, a halogen atom, a hydroxy, or a cyano. For these, those described as the above groups in $Ar^3$, $Ar^4$ and $R^{21}$ to $R^{28}$ can be cited.

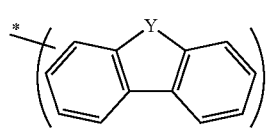

(4-1)

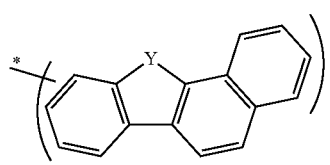

(4-2)

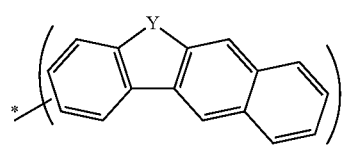

(4-3)

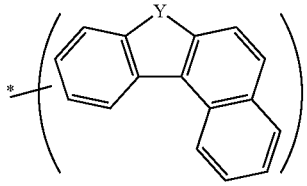

(4-4)

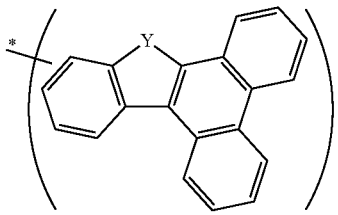

(4-5)

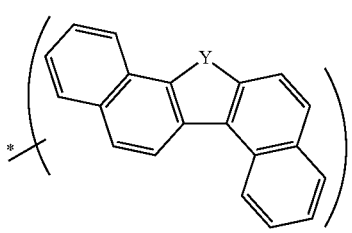

(4-6)

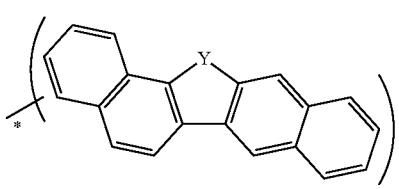

(4-7)

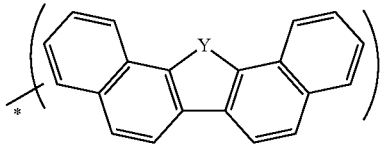

(4-8)

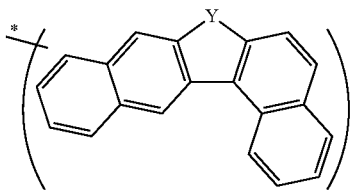

(4-9)

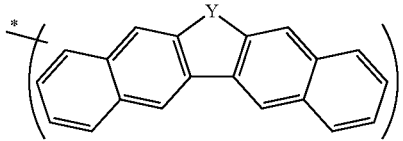

(4-10)

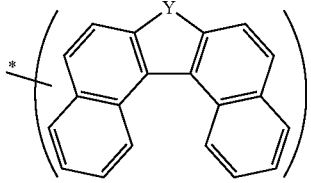

(4-11)

Examples of the ring formed by bonding adjacent groups to each other include a cyclohexane ring in a case of a hydrocarbon ring. Examples of the aryl ring and heteroaryl ring include ring structures described in the above "aryl" and "heteroaryl" in $Ar^3$, $Ar^4$ and $R^{21}$ to $R^{28}$, and these rings are formed so as to be fused with one or two benzene rings in the above formula (4-1).

Examples of the group represented by formula (4) include a group represented by any one of the above formulas (4-1) to (4-11). A group represented by any one of the above formulas (4-1) to (4-4) is preferable, a group represented by any one of the above formulas (4-1), (4-3), and (4-4) is more preferable, and a group represented by the above formula (4-1) is still more preferable.

The group represented by formula (4) is substituted at * in formula (4) by at least one hydrogen atom of the compound represented by formula (3) as described above. However, as a substitution position in the compound of formula (3), preferably, the group represented by formula (4) is directly bonded to the 9-position and/or 10-position of the anthracene ring of formula (3) (corresponding to a case where the group represented by formula (4) is substituted by a hydrogen atom when $Ar^3$ is the hydrogen atom), or the group represented by formula (4) is bonded thereto via $Ar^3$ (corresponding to a case where at least one hydrogen atom in $Ar^3$ is substituted by a group represented by formula (4) when $Ar^3$ is other than a hydrogen atom).

A position at which at least one hydrogen atom in a compound represented by formula (3) is substituted by the group represented by formula (4) in the structure of the group represented by formula (4) may be any position in the structure formula (4). For example, bonding can be made at any one of the two benzene rings in the structure of formula (4), at any ring formed by bonding adjacent groups among $R^{21}$ to $R^{28}$ in the structure of formula (4), or at any position in $R^{29}$ in ">N—$R^{29}$" as Y in the structure of formula (4).

Examples of the group represented by formula (4) include the following groups. Y and * in the formula have the same definitions as above.

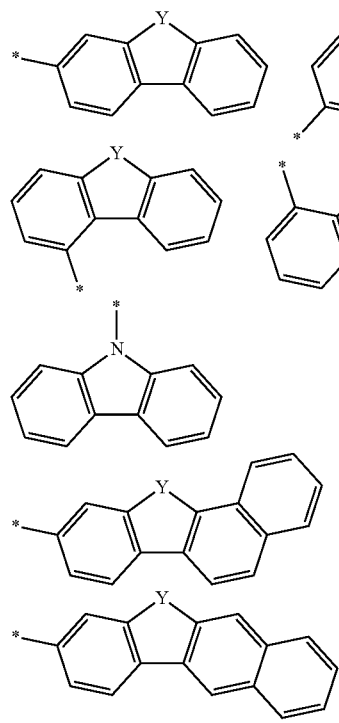

-continued

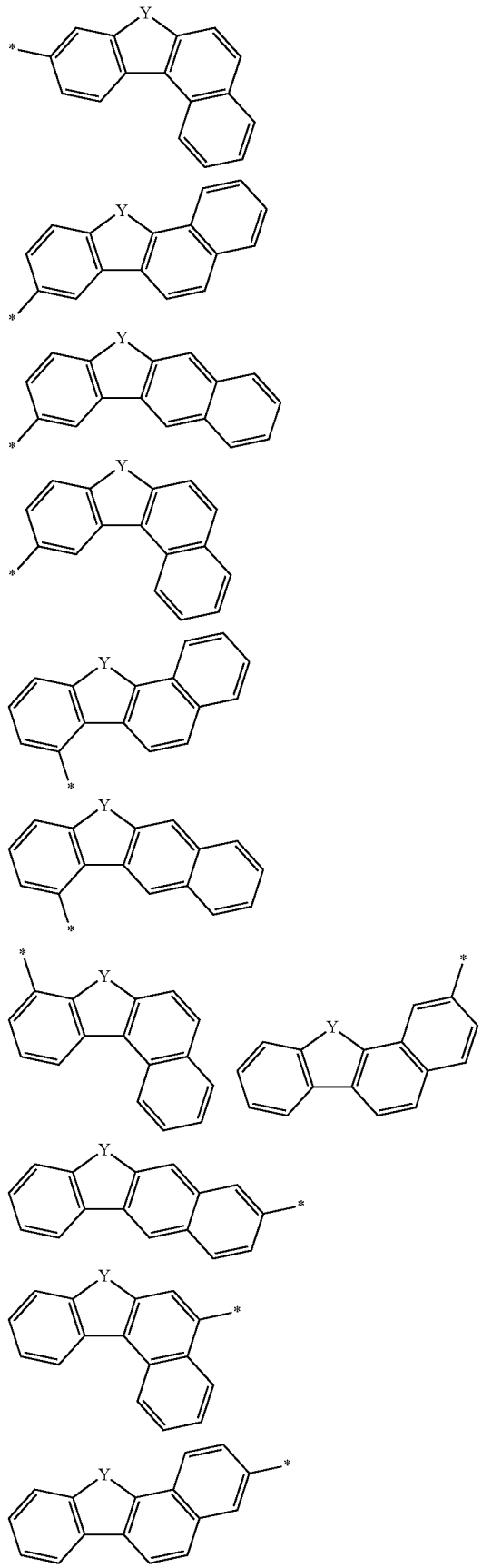

111
-continued
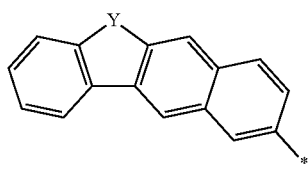
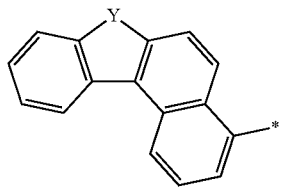
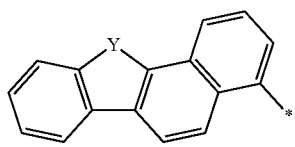
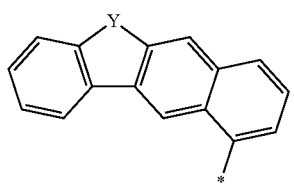
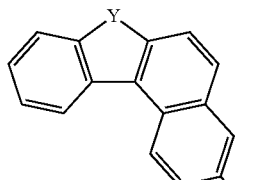
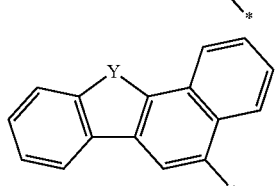
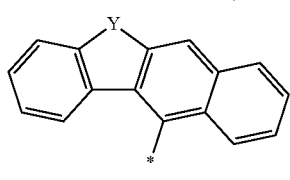
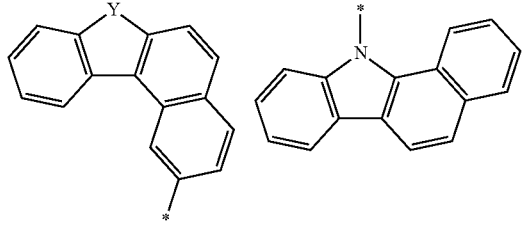
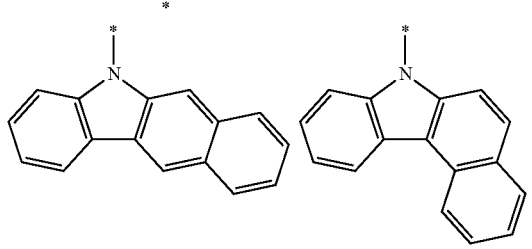
112
-continued
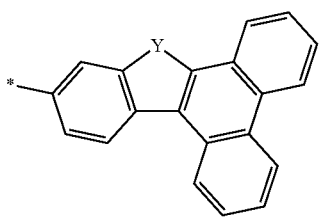
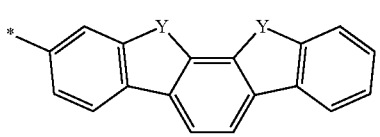
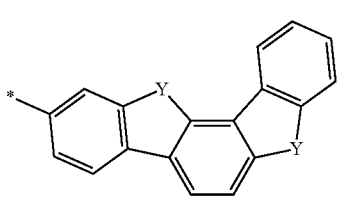
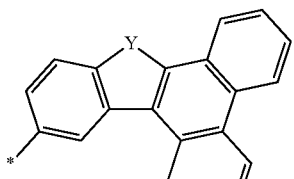
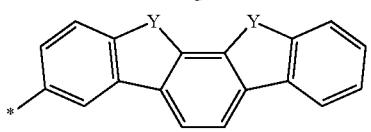
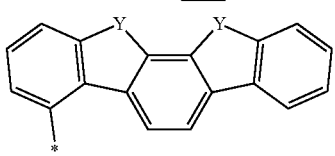
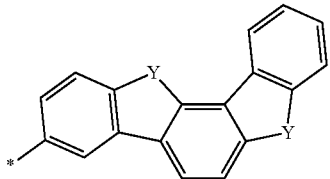
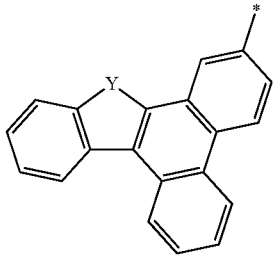
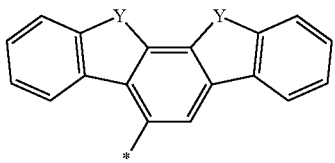

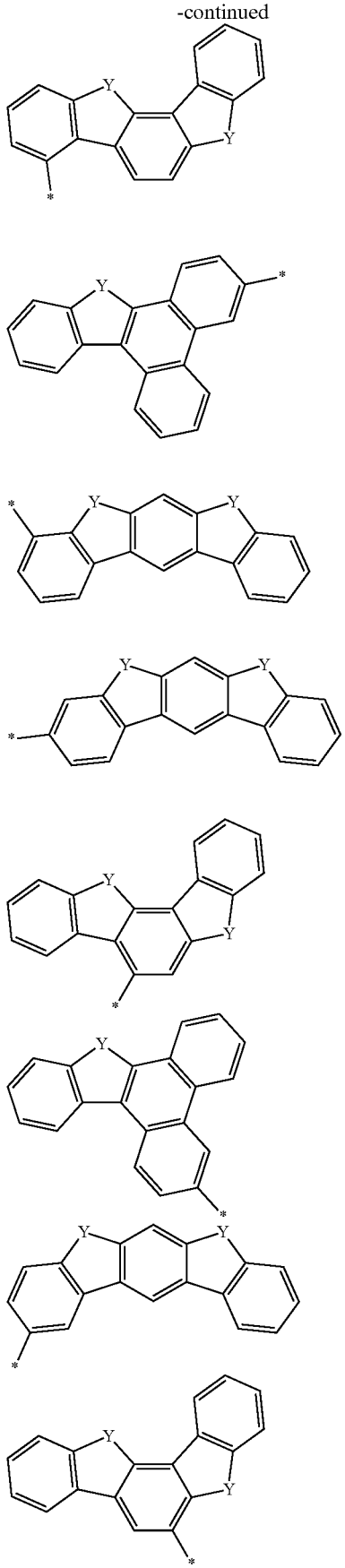
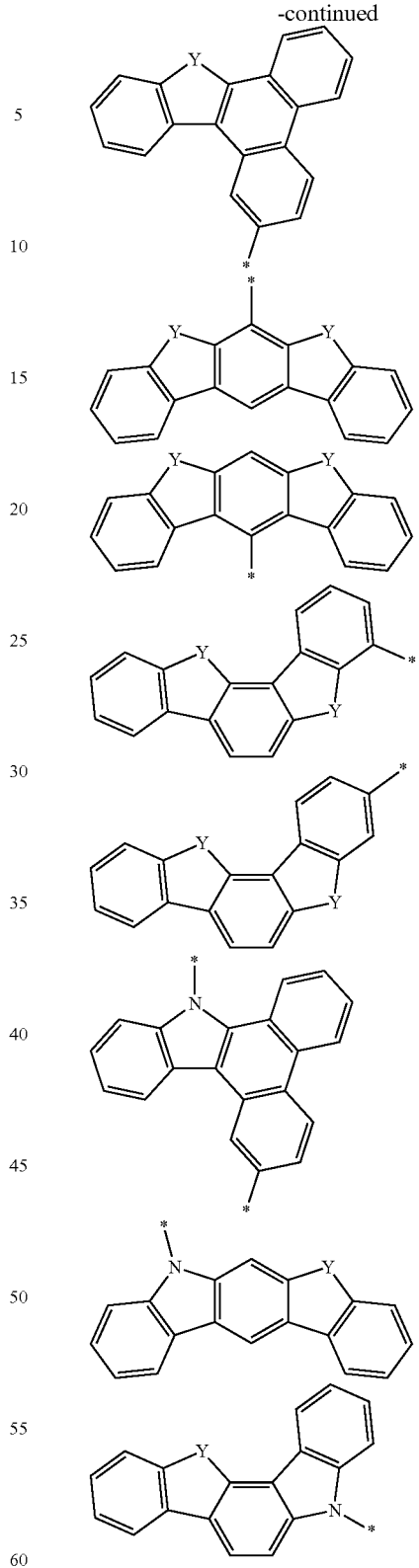
Furthermore, all or a portion of the hydrogen atoms in the chemical structure of an anthracene-based compound represented by general formula (3) may be deuterium atoms.
Specific examples of the anthracene-based compound include compounds represented by the following formulas (3-101) to (3-127). Note that the group represented by formula (4) is omitted in these compounds. However, at least one hydrogen atom in these compounds is substituted by the group represented by formula (4).
(3-101)
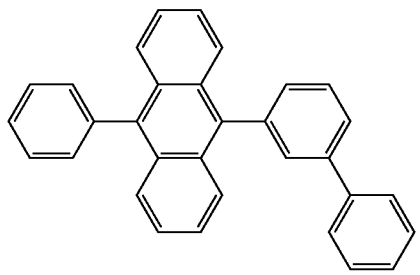
(3-102)
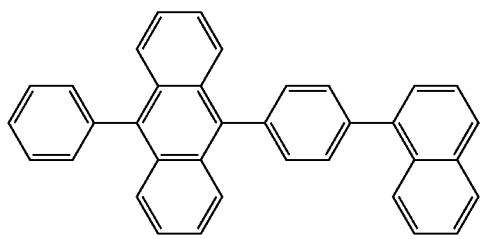
(3-103)
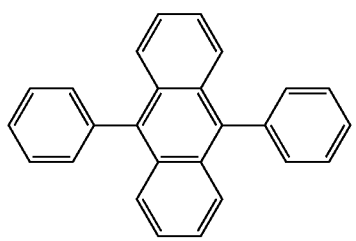
(3-104)
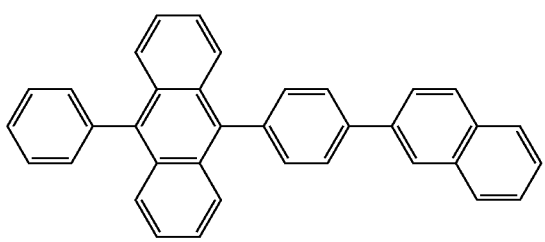
(3-105)
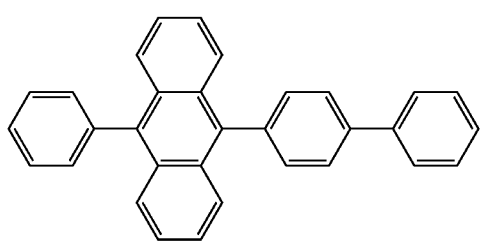
(3-106)
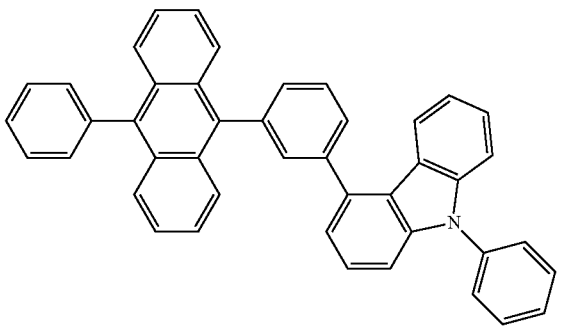
(3-107)
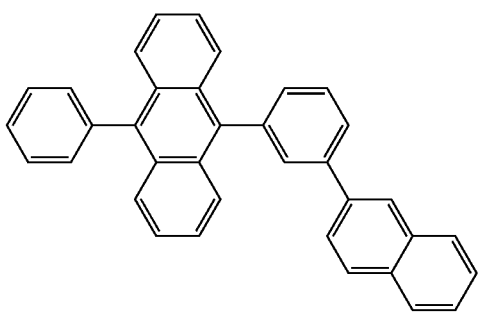
(3-108)
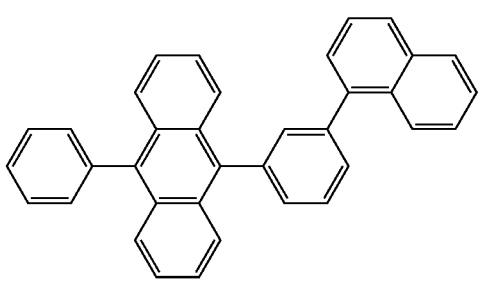
(3-111)
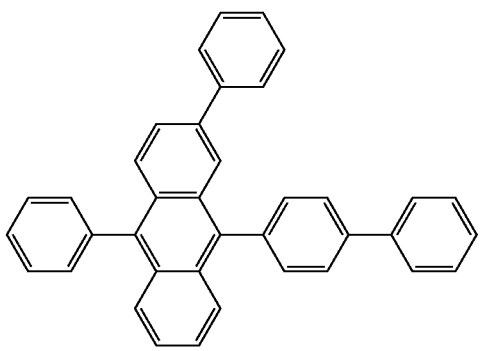

(3-112)
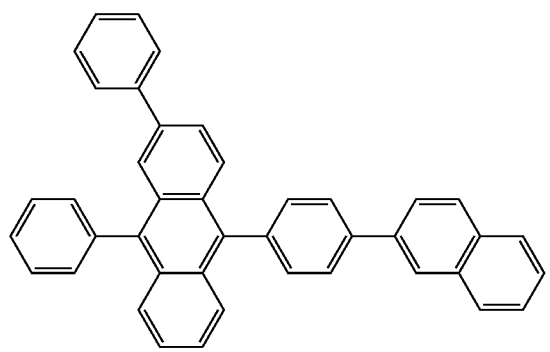
(3-116)
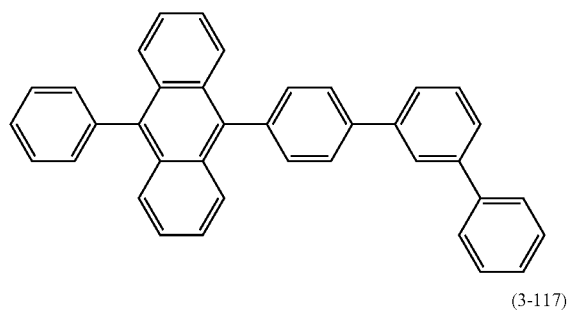
(3-113)
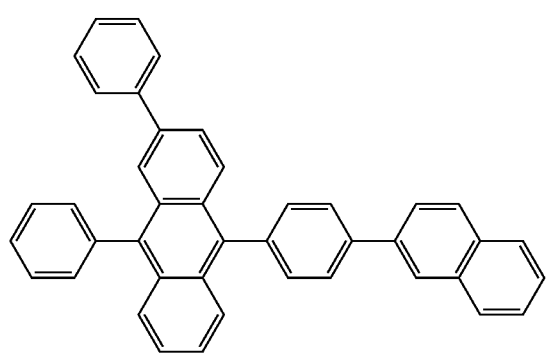
(3-117)
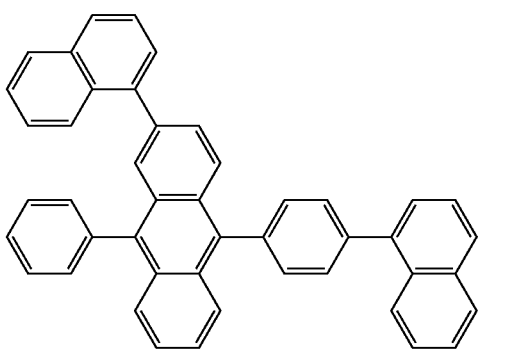
(3-114)
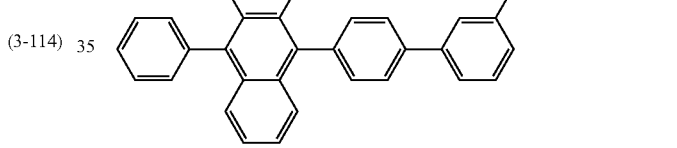
(3-118)
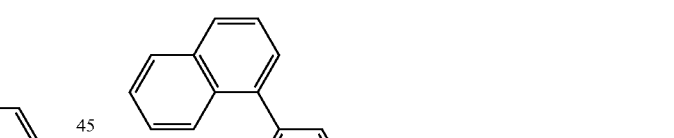
(3-115)
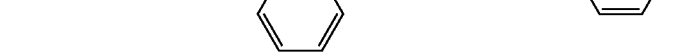
(3-119)
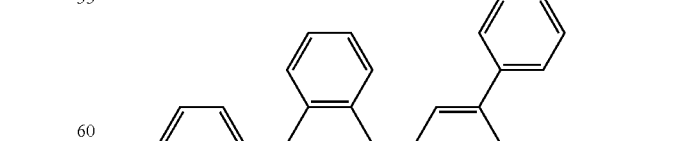
(3-121)
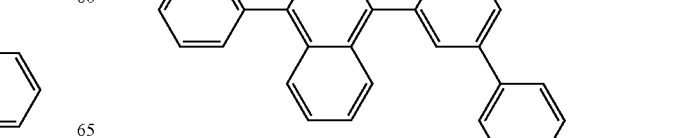

(3-122)

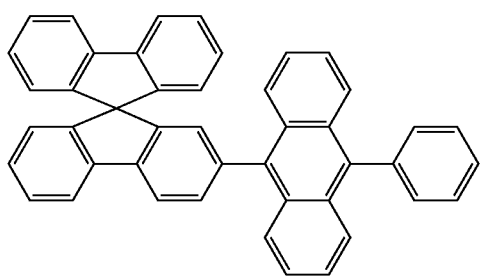

(3-127)

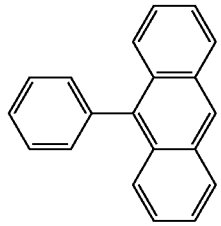

Further, other specific examples of the anthracene-based compound include compounds represented by the following formulas (3-131-Y) to (3-179-Y), compounds represented by the following formulas (3-180-Y) to (3-182-Y), and a compound represented by the following formula (3-183-N). Y in the formulas may be any one of —O—, —S—, and >N—$R^{29}$ ($R^{29}$ is as defined above), and $R^{29}$ is, for example, a phenyl group. Regarding a formula number, for example, when Y is O, formula (3-131-Y) is expressed by formula (3-131-O), when Y is —S—, formula (3-131-Y) is expressed by formula (3-131-S), and when Y is >N—$R^{29}$, formula (3-131-Y) is expressed by formula (3-131-N).

(3-123)

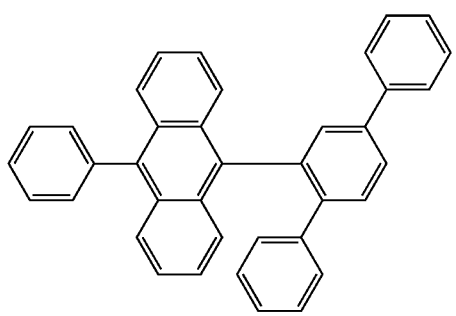

(1-124)

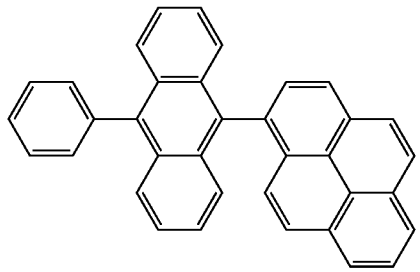

(3-131-Y)

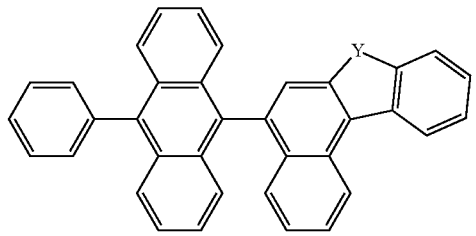

(3-125)

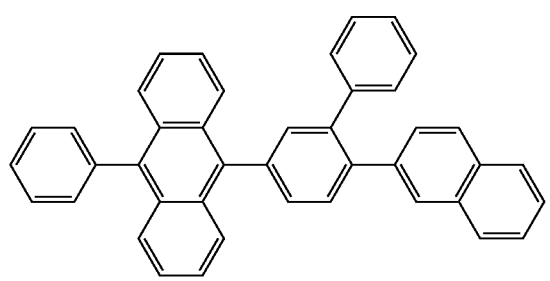

(3-132-Y)

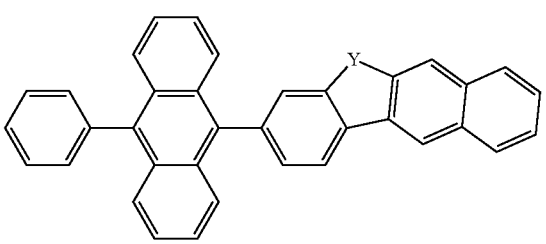

(3-126)

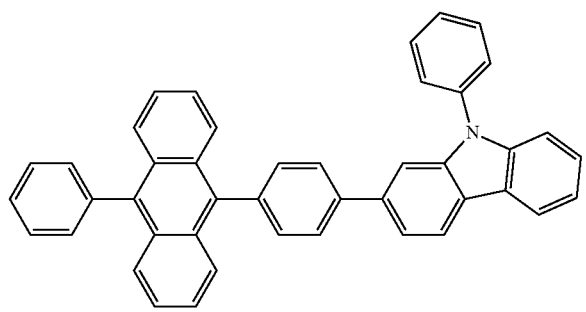

(3-133-Y)

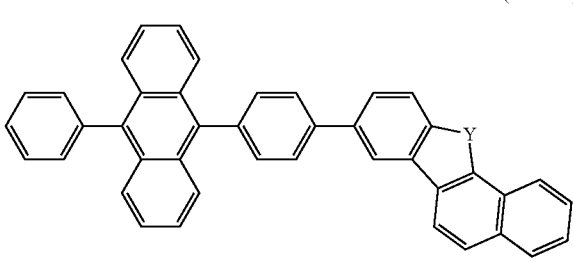

(3-134-Y)
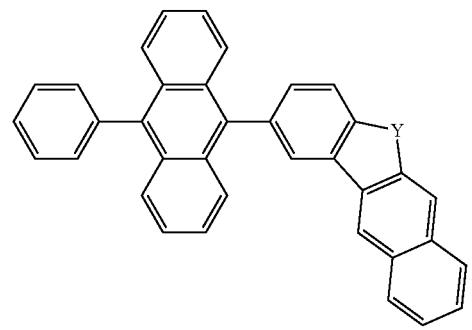
(3-138-Y)
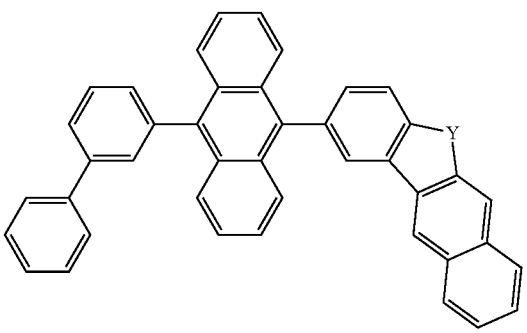
(3-135-Y)
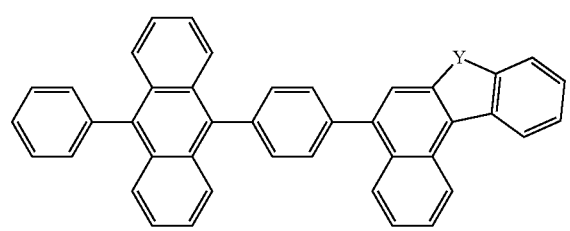
(3-139-Y)
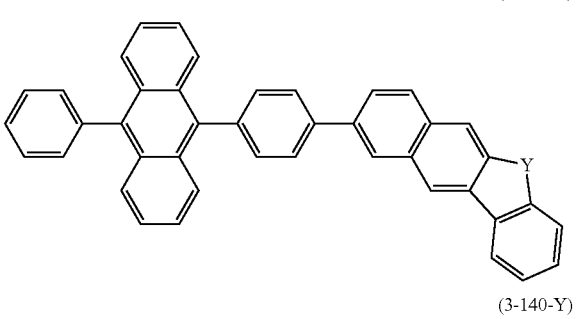
(3-136-Y)
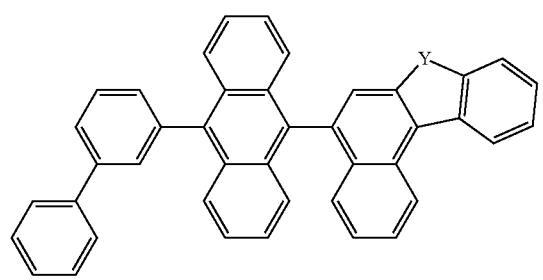
(3-140-Y)
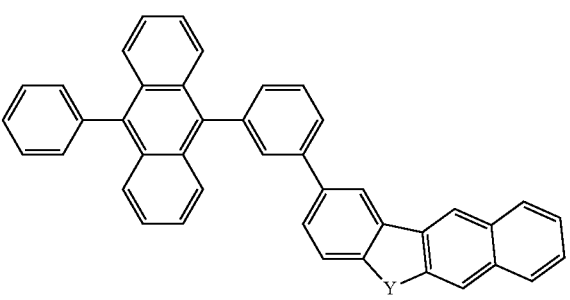
(3-137-Y)
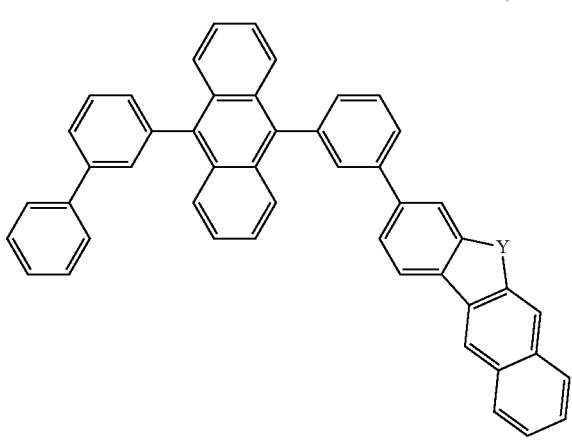
(3-141-Y)
(3-142-Y)
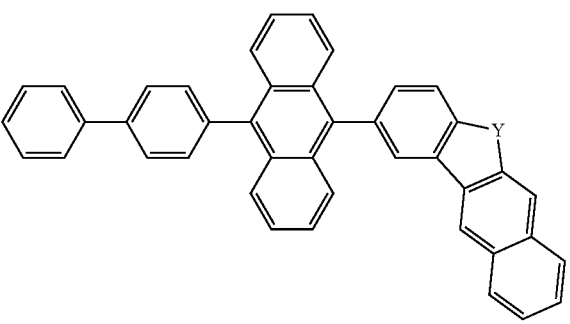

(3-143-Y)
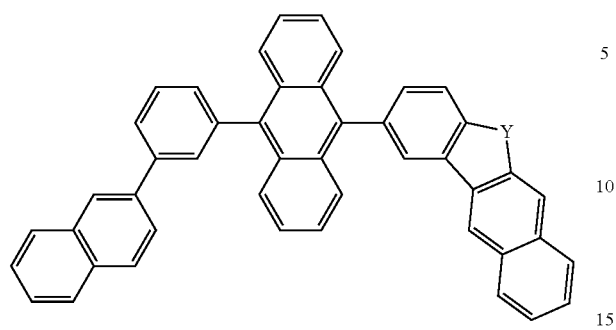
(3-144-Y)
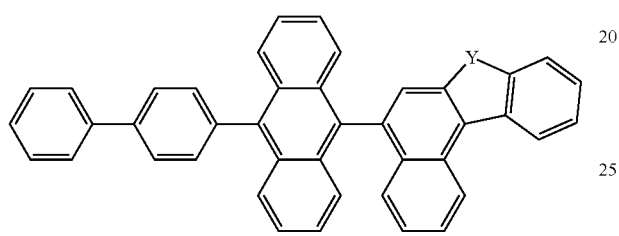
(3-145-Y)
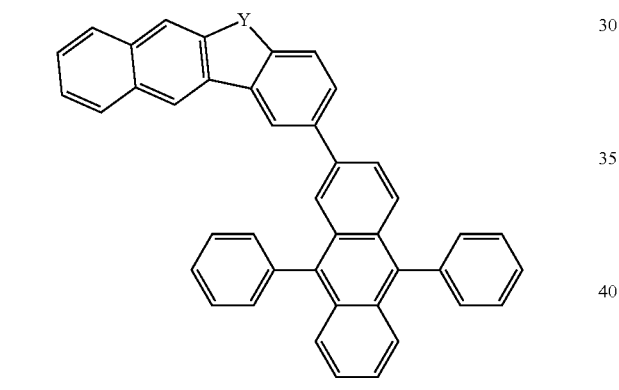
(3-146-Y)
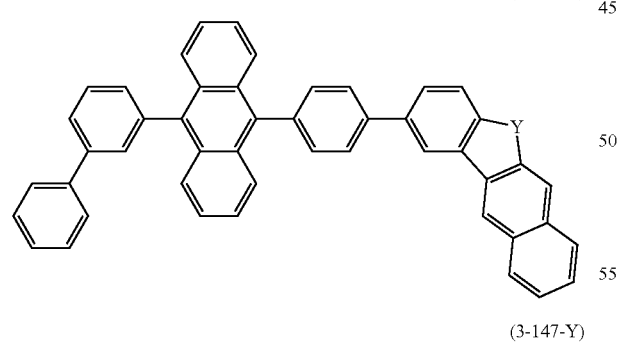
(3-147-Y)
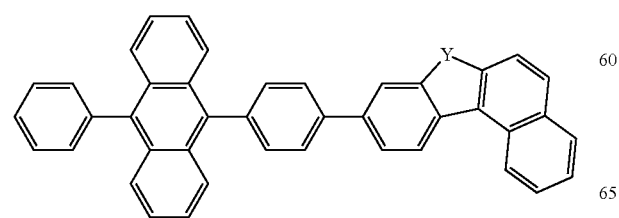
(3-148-Y)
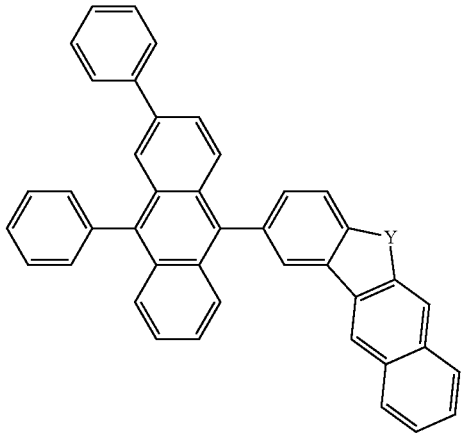
(3-149-Y)
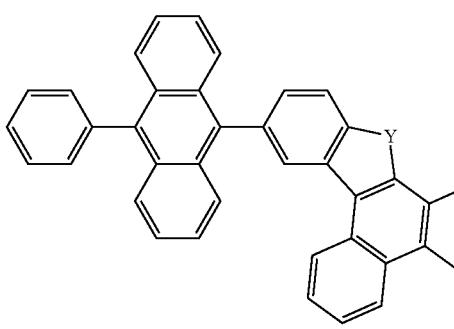
(3-150-Y)
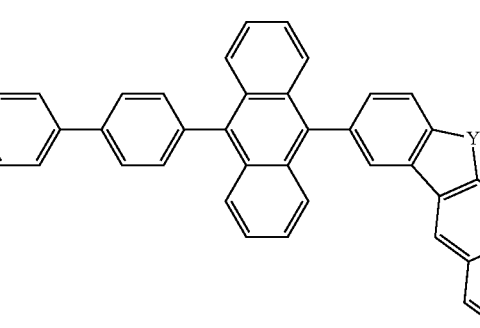
(3-151-Y)
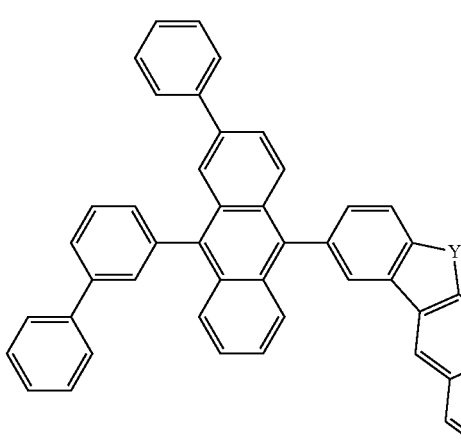

-continued
(3-152-Y)
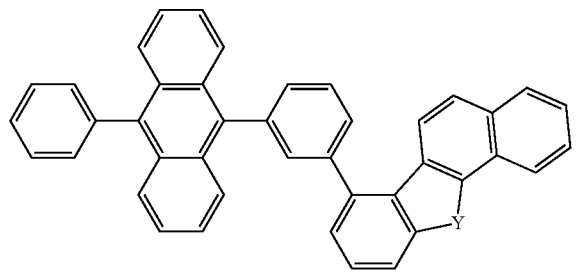
(3-153-Y)
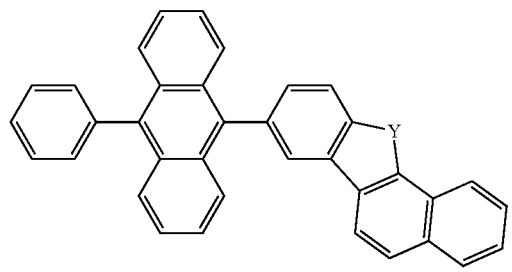
(3-154-Y)
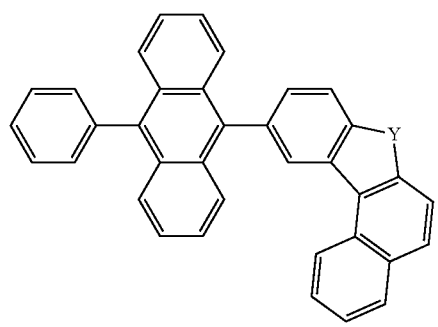
(3-155-Y)
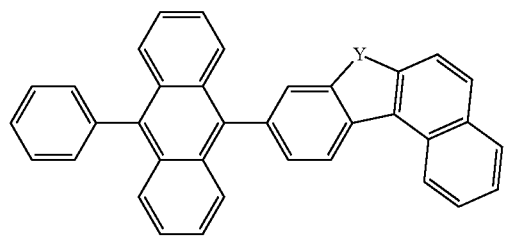
(3-156-Y)
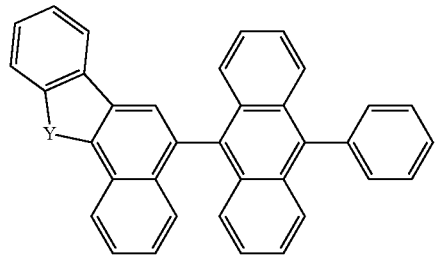
-continued
(3-157-Y)
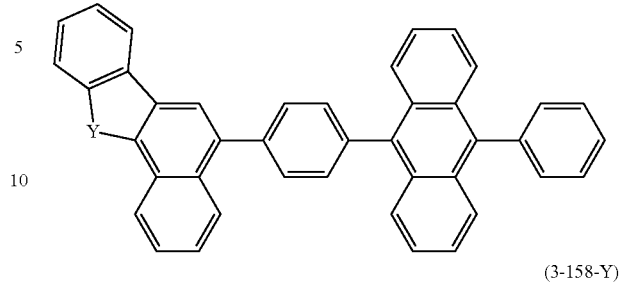
(3-158-Y)
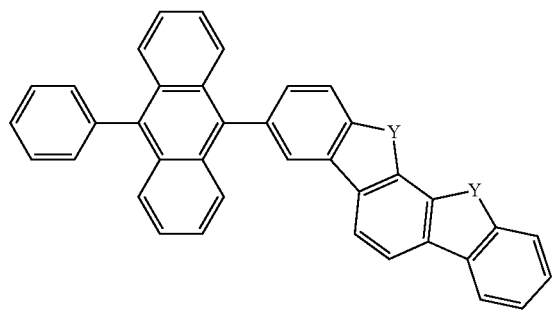
(3-159-Y)
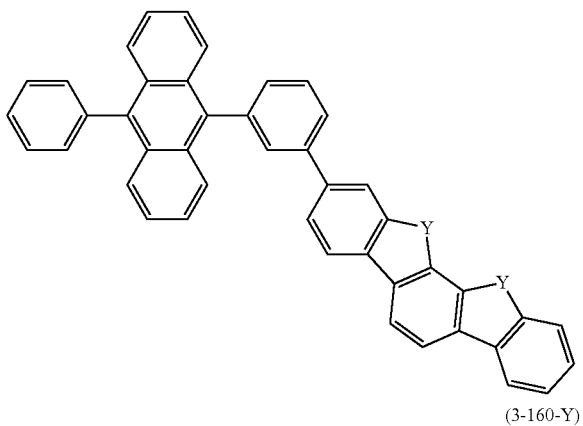
(3-160-Y)
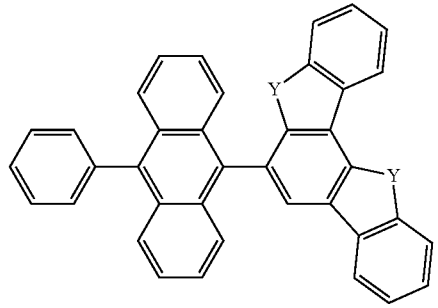
(3-161-Y)
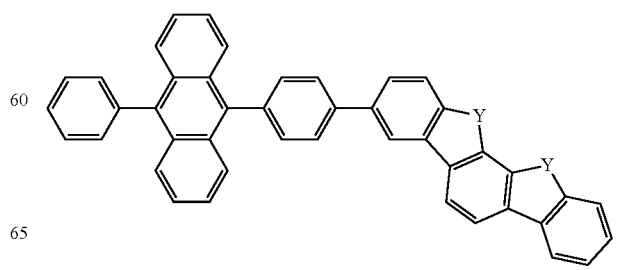

-continued
(3-162-Y)
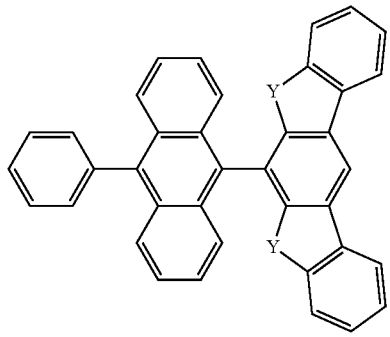
(3-163-Y)
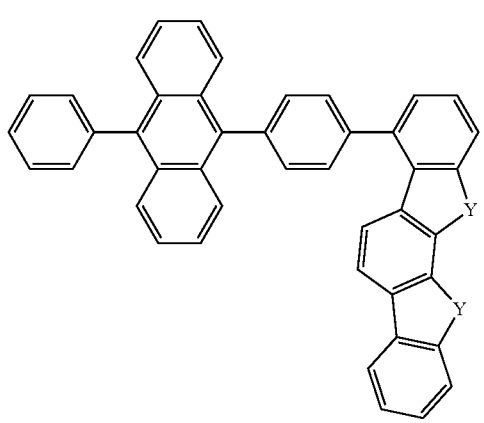
(3-164-Y)
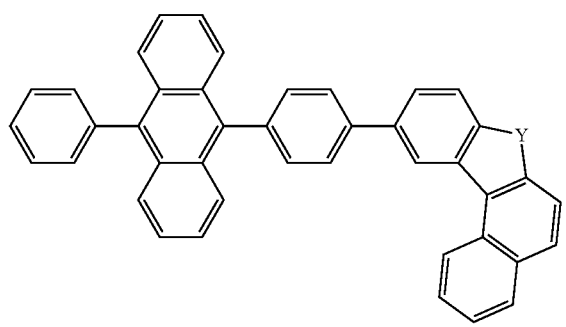
(3-165-Y)
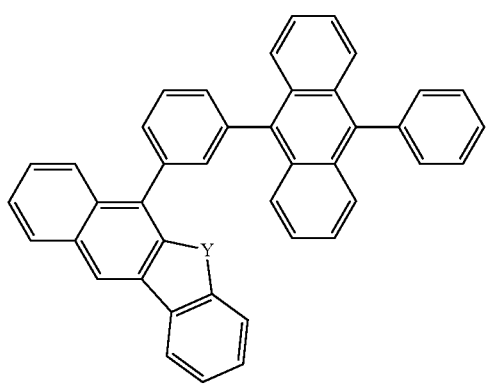
-continued
(3-166-Y)
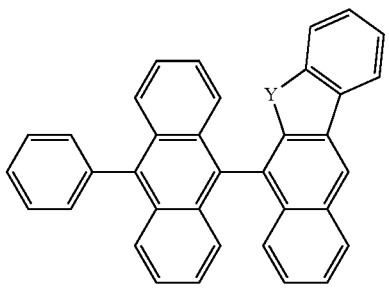
(3-167-Y)
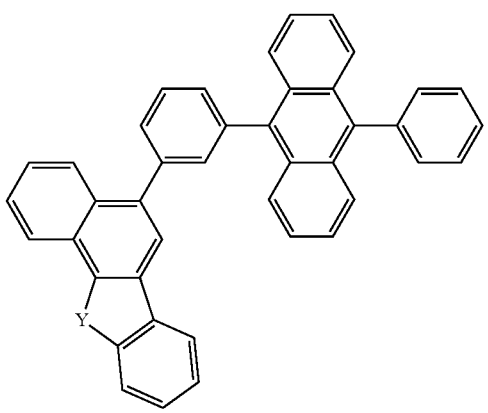
(3-168-Y)
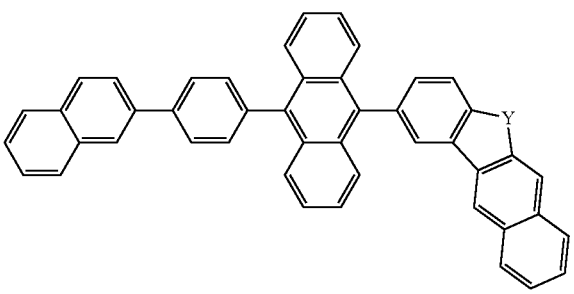
(3-169-Y)
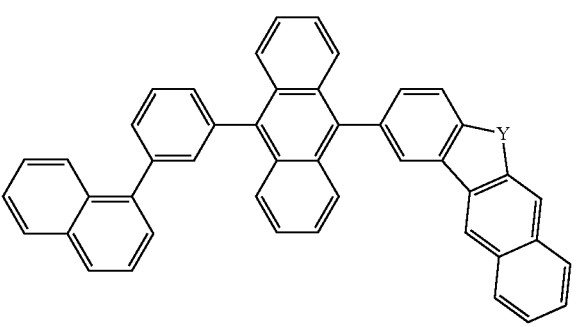

-continued
(3-170-Y)
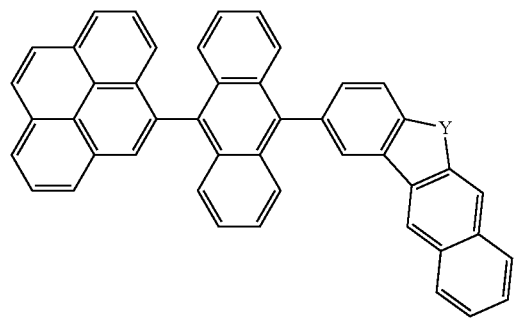
(3-171-Y)
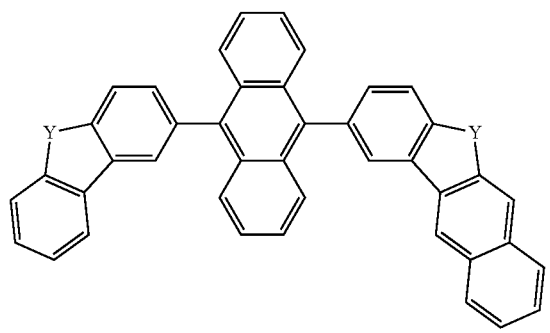
(3-172-Y)
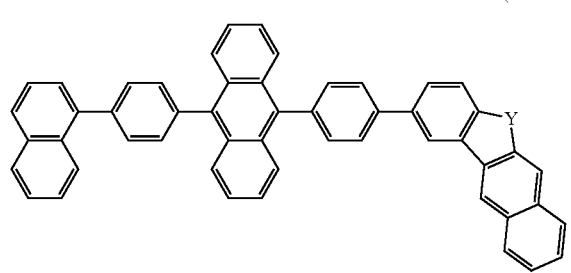
(3-173-Y)
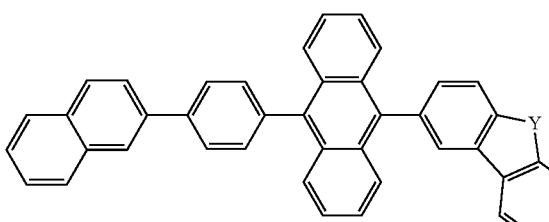
(3-174-Y)
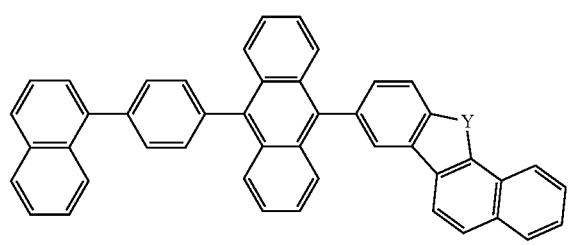
-continued
(3-175-Y)
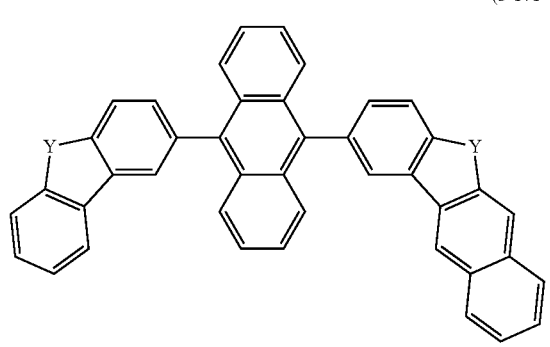
(3-176-Y)
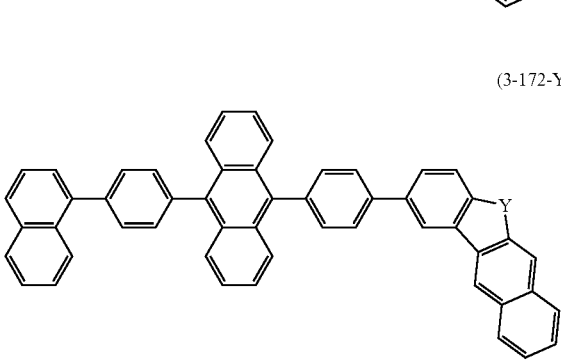
(3-177-Y)
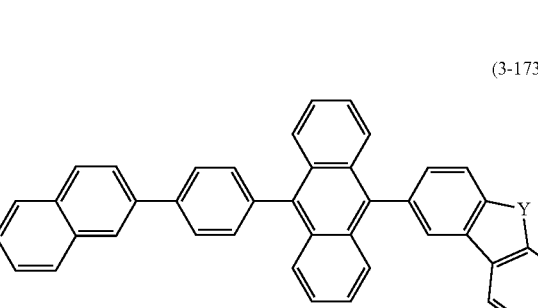
(3-178-Y)
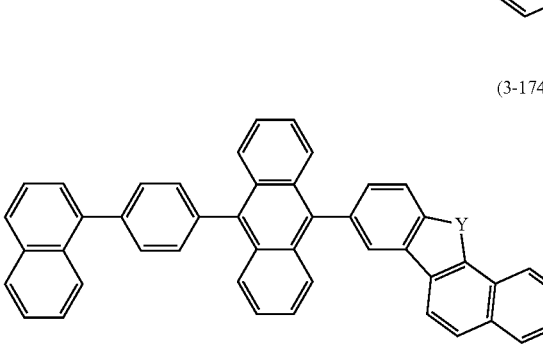
(3-179-Y)
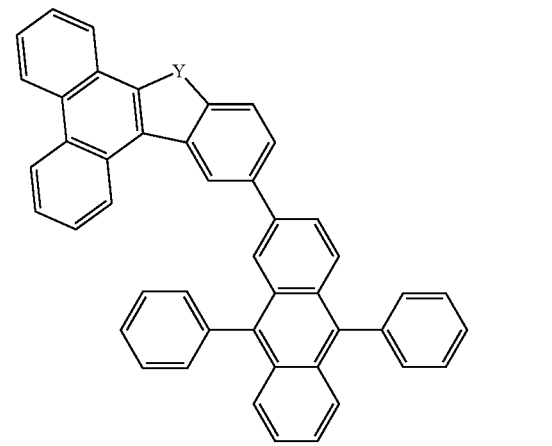

-continued

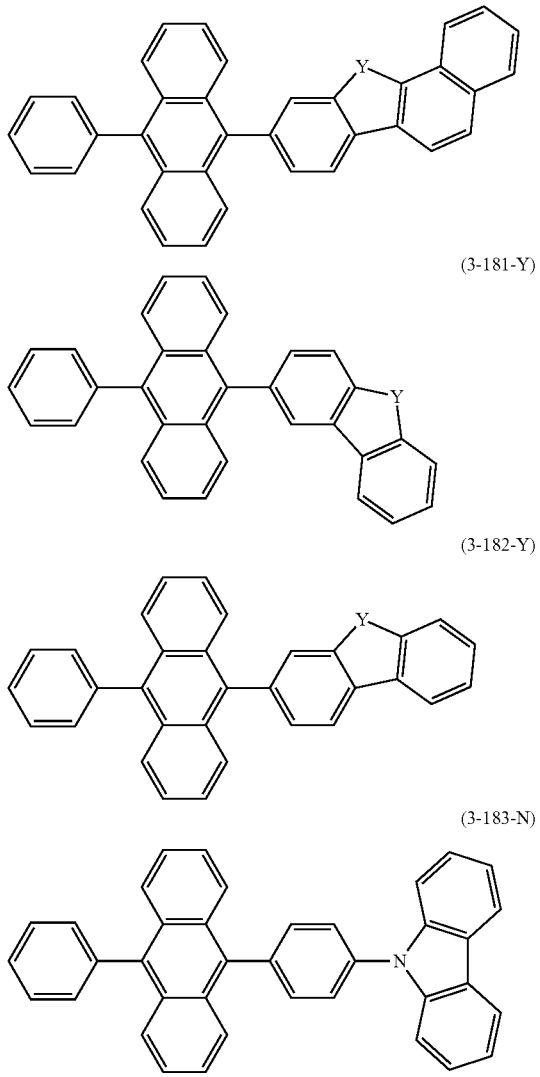

(3-180-Y)

(3-181-Y)

(3-182-Y)

(3-183-N)

1-4. Method for Manufacturing Anthracene-Based Compound

The anthracene-based compound represented by formula (3) can be manufactured by using a reactive compound of anthracene substituted by $Ar^3$ and $Ar^4$, a reactive compound having a structure represented by formula (4), and the like as starting raw materials and applying Suzuki coupling, Negishi coupling, or another well-known coupling reaction. Examples of a reactive group of these reactive compounds include a halogen atom and boronic acid. As a specific manufacturing method, for example, the synthesis method in paragraphs [0089] to [0175] of WO 2014/141725 A can be referred to.

2. Organic Electroluminescent Element

Hereinafter, an organic EL element according to the present embodiment will be described in detail based on the drawings. The FIGURE is a schematic cross-sectional view illustrating the organic EL element according to the present embodiment.

<Structure of Organic Electroluminescent Element>

An organic EL element 100 illustrated in the FIGURE includes a substrate 101, a positive electrode 102 provided on the substrate 101, a hole injection layer 103 provided on the positive electrode 102, a hole transport layer 104 provided on the hole injection layer 103, a light emitting layer 105 provided on the hole transport layer 104, an electron transport layer 106 provided on the light emitting layer 105, an electron injection layer 107 provided on the electron transport layer 106, and a negative electrode 108 provided on the electron injection layer 107.

Incidentally, the organic EL element 100 may be configured, by reversing the manufacturing order, to include, for example, the substrate 101, the negative electrode 108 provided on the substrate 101, the electron injection layer 107 provided on the negative electrode 108, the electron transport layer 106 provided on the electron injection layer 107, the light emitting layer 105 provided on the electron transport layer 106, the hole transport layer 104 provided on the light emitting layer 105, the hole injection layer 103 provided on the hole transport layer 104, and the positive electrode 102 provided on the hole injection layer 103.

Not all of the above layers are essential. The configuration includes the positive electrode 102, the light emitting layer 105, and the negative electrode 108 as a minimum constituent unit, while the hole injection layer 103, the hole transport layer 104, the electron transport layer 106, and the electron injection layer 107 are optionally provided. Each of the above layers may be formed of a single layer or a plurality of layers.

A form of layers constituting the organic EL element may be, in addition to the above structure form of "substrate/positive electrode/hole injection layer/hole transport layer/light emitting layer/electron transport layer/electron injection layer/negative electrode", a structure form of "substrate/positive electrode/hole transport layer/light emitting layer/electron transport layer/electron injection layer/negative electrode", "substrate/positive electrode/hole injection layer/light emitting layer/electron transport layer/electron injection layer/negative electrode", "substrate/positive electrode/hole injection layer/hole transport layer/light emitting layer/electron injection layer/negative electrode", "substrate/positive electrode/hole injection layer/hole transport layer/light emitting layer/electron transport layer/negative electrode", "substrate/positive electrode/light emitting layer/electron transport layer/electron injection layer/negative electrode", "substrate/positive electrode/hole transport layer/light emitting layer/electron injection layer/negative electrode", "substrate/positive electrode/hole transport layer/light emitting layer/electron transport layer/negative electrode", "substrate/positive electrode/hole injection layer/light emitting layer/electron injection layer/negative electrode", "substrate/positive electrode/hole injection layer/light emitting layer/electron transport layer/negative electrode", "substrate/positive electrode/light emitting layer/electron transport layer/negative electrode", or "substrate/positive electrode/light emitting layer/electron injection layer/negative electrode".

<Substrate in Organic Electroluminescent Element>

The substrate 101 serves as a support of the organic EL element 100, and usually, quartz, glass, metals, plastics, and the like are used. The substrate 101 is formed into a plate shape, a film shape, or a sheet shape according to a purpose, and for example, a glass plate, a metal plate, a metal foil, a plastic film, and a plastic sheet are used. Among these examples, a glass plate and a plate made of a transparent synthetic resin such as polyester, polymethacrylate, polycarbonate, or polysulfone are preferable. For a glass substrate, soda lime glass, alkali-free glass, and the like are used. The thickness is only required to be a thickness sufficient for maintaining mechanical strength. Therefore, the thickness is only required to be 0.2 mm or more, for example. The upper limit value of the thickness is, for example, 2 mm or less, and preferably 1 mm or less. Regarding a material of glass, glass having fewer ions eluted from the glass is desirable, and therefore alkali-free glass is preferable. However, soda lime glass which has been subjected to barrier coating with $SiO_2$ or the like is also commercially available, and therefore this soda lime glass can be used. Furthermore, the substrate 101 may be provided with a gas barrier film such as a dense silicon oxide film on at least one surface in order to increase a gas barrier property. Particularly in a case of using a plate, a film, or a sheet made of a synthetic resin having a low gas barrier property as the substrate 101, a gas barrier film is preferably provided.

<Positive Electrode in Organic Electroluminescent Element>

The positive electrode 102 plays a role of injecting a hole into the light emitting layer 105. Incidentally, in a case where the hole injection layer 103 and/or the hole transport layer 104 are/is provided between the positive electrode 102 and the light emitting layer 105, a hole is injected into the light emitting layer 105 through these layers.

Examples of a material to form the positive electrode 102 include an inorganic compound and an organic compound. Examples of the inorganic compound include a metal (aluminum, gold, silver, nickel, palladium, chromium, and the like), a metal oxide (indium oxide, tin oxide, indium-tin oxide (ITO), indium-zinc oxide (IZO), and the like), a metal halide (copper iodide and the like), copper sulfide, carbon black, ITO glass, and Nesa glass. Examples of the organic compound include an electrically conductive polymer such as polythiophene such as poly(3-methylthiophene), polypyrrole, or polyaniline. In addition to these compounds, a material can be appropriately selected for use from materials used as a positive electrode of an organic EL element.

A resistance of a transparent electrode is not limited as long as a sufficient current can be supplied to light emission of a luminescent element. However, low resistance is desirable from a viewpoint of consumption power of the luminescent element. For example, an ITO substrate having a resistance of $300\Omega/\square$ or less functions as an element electrode. However, a substrate having a resistance of about $10\Omega/\square$ can be also supplied at present, and therefore it is particularly desirable to use a low resistance product having a resistance of, for example, 100 to $5\Omega/\square$, preferably 50 to $5\Omega/\square$. The thickness of an ITO can be arbitrarily selected according to a resistance value, but an ITO having a thickness of 50 to 300 nm is often used.

<Hole Injection Layer and Hole Transport Layer in Organic Electroluminescent Element>

The hole injection layer 103 plays a role of efficiently injecting a hole that migrates from the positive electrode 102 into the light emitting layer 105 or the hole transport layer 104. The hole transport layer 104 plays a role of efficiently transporting a hole injected from the positive electrode 102 or a hole injected from the positive electrode 102 through the hole injection layer 103 to the light emitting layer 105. The hole injection layer 103 and the hole transport layer 104 are each formed by laminating and mixing one or more kinds of hole injection/transport materials, or by a mixture of hole injection/transport materials and a polymer binder. Furthermore, a layer may be formed by adding an inorganic salt such as iron(III) chloride to the hole injection/transport materials.

A hole injecting/transporting substance needs to efficiently inject/transport a hole from a positive electrode between electrodes to which an electric field is applied, and preferably has high hole injection efficiency and transports an injected hole efficiently. For this purpose, a substance which has low ionization potential, large hole mobility, and excellent stability, and in which impurities that serve as traps are not easily generated at the time of manufacturing and at the time of use, is preferable.

As a material to form the hole injection layer 103 and the hole transport layer 104, any compound can be selected for use among compounds that have been conventionally used as charge transporting materials for holes, p-type semiconductors, and known compounds used in a hole injection layer and a hole transport layer of an organic EL element. Specific examples thereof include a heterocyclic compound including a carbazole derivative (N-phenylcarbazole, polyvinylcarbazole, and the like), a biscarbazole derivative such as bis(N-arylcarbazole) or bis(N-alkylcarbazole), a triarylamine derivative (a polymer having an aromatic tertiary amino in a main chain or a side chain, 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-dphenyl-1,1'-diamine, $N^4,N^{4'}$-diphenyl-$N^4,N^{4'}$-bis(9-phenyl-9H-carbazol-3-yl)-[1,1'-biphenyl]-4,4'-diamine, $N^4,N^4,N^{4'},N^{4'}$-tetra[1,1'-biphenyl]-4-yl)-[1,1'-biphenyl]-4,4'-diamine, a triphenylamine derivative such as 4,4',4''-tris(3-methylphenyl(phenyl) amino)triphenylamine, a starburst amine derivative, and the like), a stilbene derivative, a phthalocyanine derivative (non-metal, copper phthalocyanine, and the like), a pyrazoline derivative, a hydrazone-based compound, a benzofuran derivative, a thiophene derivative, an oxadiazole derivative, a quinoxaline derivative (for example, 1,4,5,8,9,12-hexaazatriphenylene-2,3,6,7,10,11-hexacarbonitrile, and the like), and a porphyrin derivative, and a polysilane. Among the polymer-based materials, a polycarbonate, a styrene derivative, a polyvinylcarbazole, a polysilane, and the like having the above monomers in side chains are preferable. However, there is no particular limitation as long as a compound can form a thin film needed for manufacturing a luminescent element, can inject a hole from a positive electrode, and can transport a hole.

Furthermore, it is also known that electroconductivity of an organic semiconductor is strongly affected by doping into the organic semiconductor. Such an organic semiconductor matrix substance is formed of a compound having a good electron-donating property, or a compound having a good electron-accepting property. For doping with an electron-donating substance, a strong electron acceptor such as tetracyanoquinonedimethane (TCNQ) or 2,3,5,6-tetrafluorotetracyano-1,4-benzoquinonedimethane (F4TCNQ) is known (see, for example, "M. Pfeiffer, A. Beyer, T. Fritz, K. Leo, Appl. Phys. Lett., 73(22), 3202-3204 (1998)" and "J. Blochwitz, M. Pheiffer, T. Fritz, K. Leo, Appl. Phys. Lett., 73(6), 729-731 (1998)"). These compounds generate a so-called hole by an electron transfer process in an electron-donating type base substance (hole transporting substance). Electroconductivity of the base substance depends on the number and mobility of the holes fairly significantly. Known examples of a matrix substance having a hole transporting characteristic include a benzidine derivative (TPD and the like), a starburst amine derivative (TDATA and the like), and a specific metal phthalocyanine (particularly, zinc phthalocyanine (ZnPc) and the like) (JP 2005-167175 A).

<Light Emitting Layer in Organic Electroluminescent Element>

The light emitting layer 105 emits light by recombining a hole injected from the positive electrode 102 and an electron injected from the negative electrode 108 between electrodes to which an electric field is applied. A material to form the light emitting layer 105 is only required to be a compound which is excited by recombination between a hole and an electron and emits light (luminescent compound), and is preferably a compound which can form a stable thin film shape, and exhibits strong light emission (fluorescence) efficiency in a solid state. In the present invention, as a material for a light emitting layer, at least one of a polycyclic aromatic compound represented by the above general formula (1) and a polycyclic aromatic compound multimer having a plurality of structures represented by the above general formula (1) as a dopant material, and an anthracene-based compound represented by the above general formula (3) as a host material can be used.

The light emitting layer may be formed of a single layer or a plurality of layers, and each layer is formed of a material for a light emitting layer (a host material and a dopant material). Each of the host material and the dopant material may be formed of a single kind, or a combination of a plurality of kinds. The dopant material may be included in the host material wholly or partially. Regarding a doping method, doping can be performed by a co-deposition method with a host material, or alternatively, a dopant material may be mixed in advance with a host material, and then vapor deposition may be carried out simultaneously.

The amount of use of the host material depends on the kind of the host material, and may be determined according to a characteristic of the host material. The reference of the amount of use of the host material is preferably from 50 to 99.999% by weight, more preferably from 80 to 99.95% by weight, and still more preferably from 90 to 99.9% by weight with respect to the total amount of a material for a light emitting layer.

The amount of use of the dopant material depends on the kind of the dopant material, and may be determined according to a characteristic of the dopant material. The reference of the amount of use of the dopant is preferably from 0.001 to 50% by weight, more preferably from 0.05 to 20% by weight, and still more preferably from 0.1 to 10% by weight with respect to the total amount of a material for a light emitting layer. The amount of use within the above range is preferable, for example, from a viewpoint of being able to prevent a concentration quenching phenomenon.

Examples of a host material that can be used in combination with an anthracene-based compound represented by the above general formula (3) include a fused ring derivative of another anthracene, pyrene, or the like conventionally known as a luminous body, a bisstyryl derivative such as a bisstyrylanthracene derivative or a distyrylbenzene derivative, a tetraphenylbutadiene derivative, a cyclopentadiene derivative, a fluorene derivative, and a benzofluorene derivative.

<Electron Injection Layer and Electron Transport Layer in Organic Electroluminescent Element>

The electron injection layer 107 plays a role of efficiently injecting an electron migrating from the negative electrode 108 into the light emitting layer 105 or the electron transport layer 106. The electron transport layer 106 plays a role of efficiently transporting an electron injected from the negative electrode 108, or an electron injected from the negative electrode 108 through the electron injection layer 107 to the light emitting layer 105. The electron transport layer 106 and the electron injection layer 107 are each formed by laminating and mixing one or more kinds of electron transport/injection materials, or by a mixture of an electron transport/injection material and a polymeric binder.

An electron injection/transport layer is a layer that manages injection of an electron from a negative electrode and transport of an electron, and is preferably a layer that has high electron injection efficiency and can efficiently transport an injected electron. For this purpose, a substance which has high electron affinity, large electron mobility, and excellent stability, and in which impurities that serve as traps are not easily generated at the time of manufacturing and at the time of use, is preferable. However, when a transport balance between a hole and an electron is considered, in a case where the electron injection/transport layer mainly plays a role of efficiently preventing a hole coming from a positive electrode from flowing toward a negative electrode side without being recombined, even if electron transporting ability is not so high, an effect of enhancing light emission efficiency is equal to that of a material having high electron transporting ability. Therefore, the electron injection/transport layer according to the present embodiment may also include a function of a layer that can efficiently prevent migration of a hole.

A material (electron transport material) for forming the electron transport layer 106 or the electron injection layer 107 can be arbitrarily selected for use from compounds conventionally used as electron transfer compounds in a photoconductive material, and known compounds that are used in an electron injection layer and an electron transport layer of an organic EL element.

A material used in an electron transport layer or an electron injection layer preferably includes at least one selected from a compound formed of an aromatic ring or a heteroaromatic ring including one or more kinds of atoms selected from carbon, hydrogen, oxygen, sulfur, silicon, and phosphorus atoms, a pyrrole derivative and a fused ring derivative thereof, and a metal complex having an electron-accepting nitrogen atom. Specific examples of the material include a fused ring-based aromatic ring derivative of naphthalene, anthracene, or the like, a styryl-based aromatic ring derivative represented by 4,4'-bis(diphenylethenyl)biphenyl, a perinone derivative, a coumarin derivative, a naphthalimide derivative, a quinone derivative such as anthraquinone or diphenoquinone, a phosphorus oxide derivative, a carbazole derivative, and an indole derivative. Examples of the metal complex having an electron-accepting nitrogen atom include a hydroxyazole complex such as a hydroxyphenyloxazole complex, an azomethine complex, a tropolone metal complex, a flavonol metal complex, and a benzoquinoline metal complex. These materials are used singly, but may also be used in a mixture with other materials.

Furthermore, specific examples of other electron transfer compounds include a pyridine derivative, a naphthalene derivative, an anthracene derivative, a phenanthroline derivative, a perinone derivative, a coumarin derivative, a naphthalimide derivative, an anthraquinone derivative, a diphenoquinone derivative, a diphenylquinone derivative, a perylene derivative, an oxadiazole derivative (1,3-bis[(4-t-butylphenyl)-1,3,4-oxadiazolyl]phenylene and the like), a thiophene derivative, a triazole derivative (N-naphthyl-2,5-diphenyl-1,3,4-triazole and the like), a thiadiazole derivative, a metal complex of an oxine derivative, a quinolinol-based metal complex, a quinoxaline derivative, a polymer of a quinoxaline derivative, a benzazole compound, a gallium complex, a pyrazole derivative, a perfluorinated phenylene derivative, a triazine derivative, a pyrazine derivative, a benzoquinoline derivative (2,2'-bis(benzo[h]quinolin-2-yl)-9,9'-spirobifluorene and the like), an imidazopyridine derivative, a borane derivative, a benzimidazole derivative (tris(N-phenylbenzimidazol-2-yl)benzene and the like), a benzoxazole derivative, a benzothiazole derivative, a quinoline derivative, an oligopyridine derivative such as terpyridine, a bipyridine derivative, a terpyridine derivative (1,3-bis(4'-(2,2':6'2''-terpyridinyl))benzene and the like), a naphthyridine derivative (bis(1-naphthyl)-4-(1,8-naphthyridin-2-yl)phenylphosphine oxide and the like), an aldazine derivative, a carbazole derivative, an indole derivative, a phosphorus oxide derivative, and a bisstyryl derivative.

Furthermore, a metal complex having an electron-accepting nitrogen atom can also be used, and examples thereof include a quinolinol-based metal complex, a hydroxyazole complex such as a hydroxyphenyloxazole complex, an azomethine complex, a tropolone-metal complex, a flavonol-metal complex, and a benzoquinoline-metal complex.

The materials described above are used singly, but may also be used in a mixture with other materials.

Among the above materials, a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, a quinolinol-based metal complex are preferable.

<Borane Derivative>

The borane derivative is, for example, a compound represented by the following general formula (ETM-1), and specifically disclosed in JP 2007-27587 A.

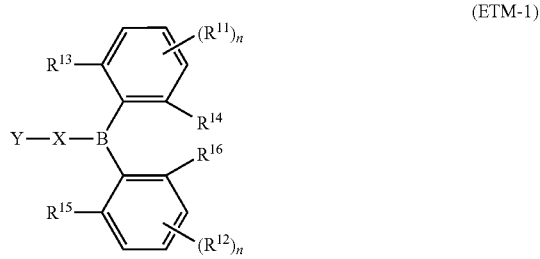

(ETM-1)

In the above formula (ETM-1), $R^{11}$ and $R^{12}$ each independently represent at least one of a hydrogen atom, an alkyl, an optionally substituted aryl, a substituted silyl, an optionally substituted nitrogen-containing heterocyclic ring, and a cyano, $R^{13}$ to $R^{16}$ each independently represent an optionally substituted alkyl or an optionally substituted aryl, X represents an optionally substituted arylene, Y represents an optionally substituted aryl having 16 or fewer carbon atoms, a substituted boryl, or an optionally substituted carbazolyl, and n's each independently represent an integer of 0 to 3. Examples of a substituent in a case of being "optionally substituted" or "substituted" include an aryl, a heteroaryl, and an alkyl.

Among compounds represented by the above general formula (ETM-1), a compound represented by the following general formula (ETM-1-1) and a compound represented by the following general formula (ETM-1-2) are preferable.

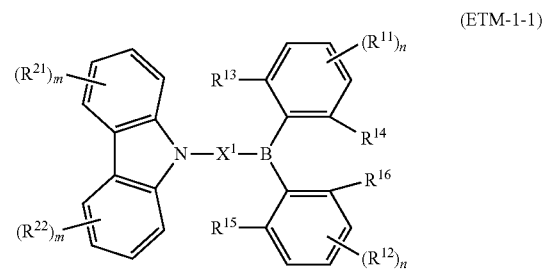

(ETM-1-1)

In formula (ETM-1-1), $R^{11}$ and $R^{12}$ each independently represent at least one of a hydrogen atom, an alkyl, an optionally substituted aryl, a substituted silyl, an optionally substituted nitrogen-containing heterocyclic ring, and a cyano, $R^{13}$ to $R^{16}$ each independently represent an optionally substituted alkyl or an optionally substituted aryl, $R^{21}$ and $R^{22}$ each independently represent at least one of a hydrogen atom, an alkyl, an optionally substituted aryl, a substituted silyl, an optionally substituted nitrogen-containing heterocyclic ring, and a cyano, $X^1$ represents an optionally substituted arylene having 20 or fewer carbon atoms, n's each independently represent an integer of 0 to 3, and m's each independently represent an integer of 0 to 4. Examples of a substituent in a case of being "optionally substituted" or "substituted" include an aryl, a heteroaryl, and an alkyl.

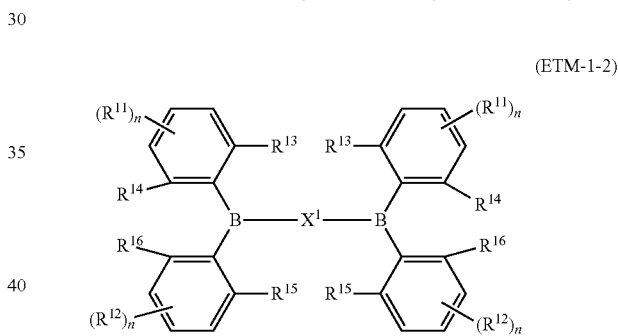

(ETM-1-2)

In formula (ETM-1-2), $R^{11}$ and $R^{12}$ each independently represent at least one of a hydrogen atom, an alkyl, an optionally substituted aryl, a substituted silyl, an optionally substituted nitrogen-containing heterocyclic ring, and a cyano, $R^{13}$ to $R^{16}$ each independently represent an optionally substituted alkyl or an optionally substituted aryl, $X^1$ represents an optionally substituted arylene having 20 or fewer carbon atoms, and n's each independently represent an integer of 0 to 3. Examples of a substituent in a case of being "optionally substituted" or "substituted" include an aryl, a heteroaryl, and an alkyl.

Specific examples of $X^1$ include divalent groups represented by the following formulas (X-1) to (X-9).

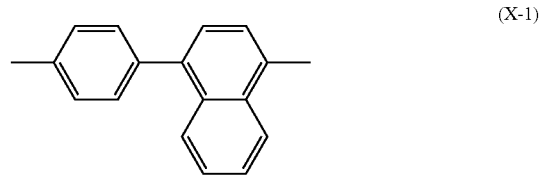

(X-1)

-continued (X-2)

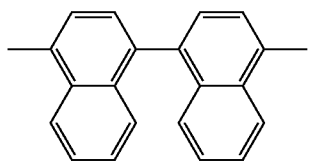

(X-3)

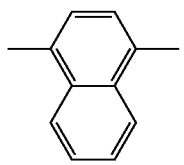

(X-4)

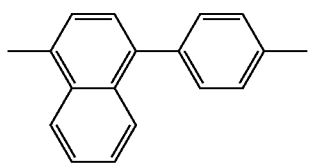

(X-5)

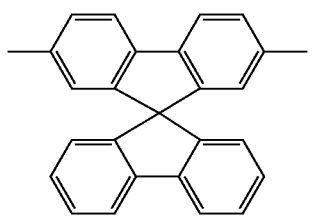

(X-6)

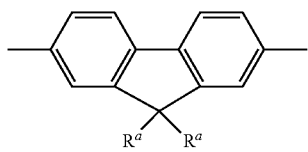

(X-7)

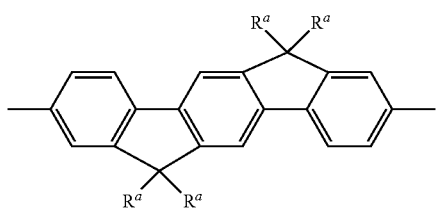

(X-8)

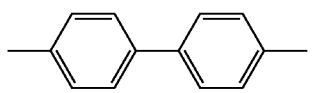

(X-9)

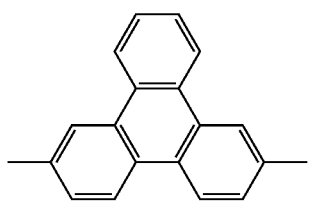

(In each formula, $R^a$'s each independently represent an alkyl group or an optionally substituted phenyl group.)

Specific examples of this borane derivative include the followings.

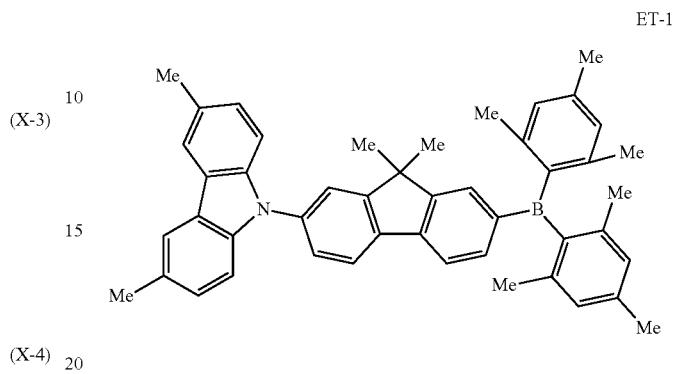

ET-1

This borane derivative can be manufactured using known raw materials and known synthesis methods.

<Pyridine Derivative>

A pyridine derivative is, for example, a compound represented by the following formula (ETM-2), and preferably a compound represented by formula (ETM-2-1) or (ETM-2-2).

$$\varnothing\text{-(Pyridine-based substituent)}_n$$ (ETM-2)

(ETM-2-1)

(ETM-2-2)

φ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4.

In the above formula (ETM-2-1), $R^{11}$ to $R^{18}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms).

In the above formula (ETM-2-2), $R^{11}$ and $R^{12}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms), and $R^{11}$ and $R^{12}$ may be bonded to each other to form a ring.

In each formula, the "pyridine-based substituent" is any one of the following formulas (Py-1) to (Py-15), and the pyridine-based substituents may be each independently substituted by an alkyl having 1 to 4 carbon atoms. The pyridine-based substituent may be bonded to φ, an anthracene ring, or a fluorene ring in each formula via a phenylene group or a naphthylene group.

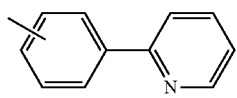
(Py-1)

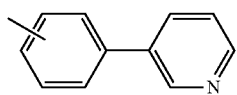
(Py-2)

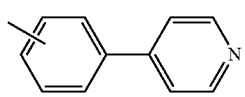
(Py-3)

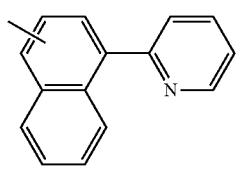
(Py-4)

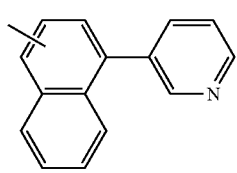
(Py-5)

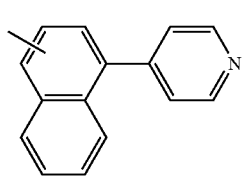
(Py-6)

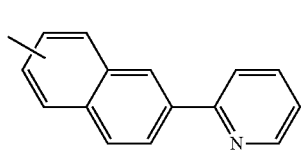
(Py-7)

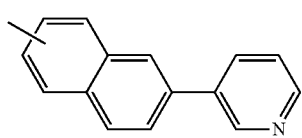
(Py-8)

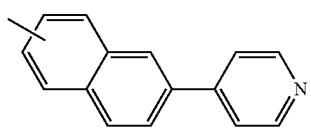
(Py-9)

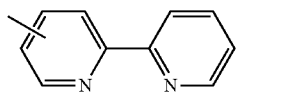
(Py-10)

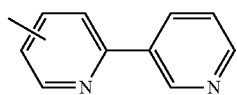
(Py-11)

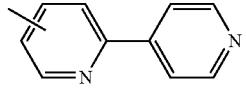
(Py-12)

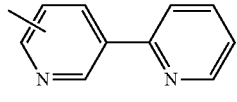
(Py-13)

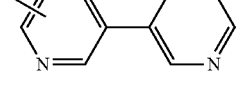
(Py-14)

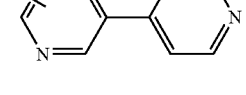
(Py-15)

The pyridine-based substituent is any one of the above-formulas (Py-1) to (Py-15). However, among these formulas, the pyridine-based substituent is preferably any one of the following formulas (Py-21) to (Py-44).

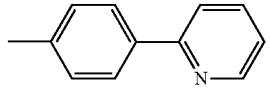
(Py-21)

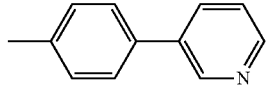
(Py-22)

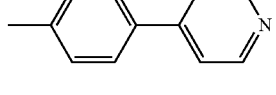
(Py-23)

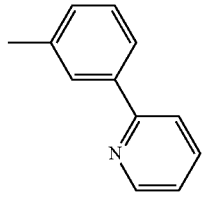
(Py-24)

(Py-25)

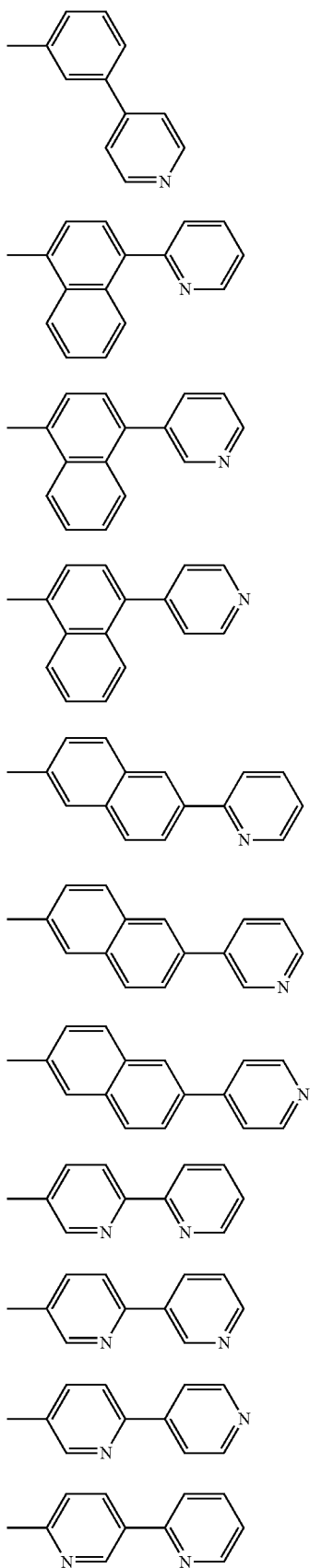
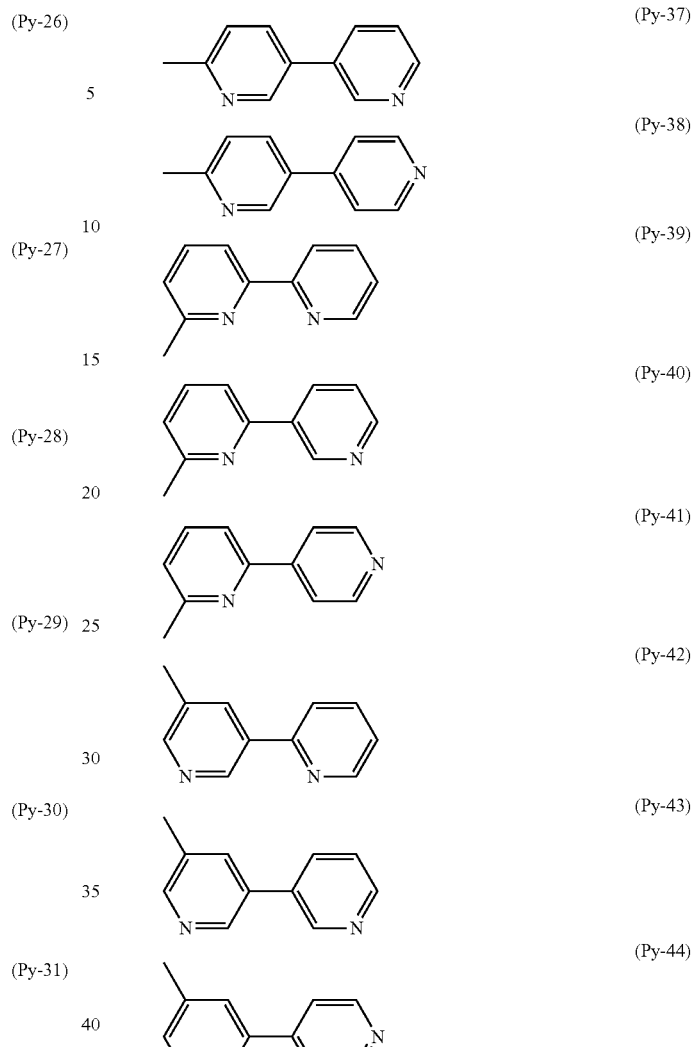

At least one hydrogen atom in each pyridine derivative may be substituted by a deuterium atom. One of the two "pyridine-based substituents" in the above formulas (ETM-2-1) and (ETM-2-2) may be substituted by an aryl.

The "alkyl" in $R^{11}$ to $R^{18}$ may be either linear or branched, and examples thereof include a linear alkyl having 1 to 24 carbon atoms and a branched alkyl having 3 to 24 carbon atoms. A preferable "alkyl" is an alkyl having 1 to 18 carbon atoms (branched alkyl having 3 to 18 carbon atoms). A more preferable "alkyl" is an alkyl having 1 to 12 carbons (branched alkyl having 3 to 12 carbons). A still more preferable "alkyl" is an alkyl having 1 to 6 carbon atoms (branched alkyl having 3 to 6 carbon atoms). A particularly preferable "alkyl" is an alkyl having 1 to 4 carbon atoms (branched alkyl having 3 to 4 carbon atoms).

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

As the alkyl having 1 to 4 carbon atoms by which the pyridine-based substituent is substituted, the above description of the alkyl can be cited.

Examples of the "cycloalkyl" in $R^{11}$ to $R^{18}$ include a cycloalkyl having 3 to 12 carbon atoms. A preferable "cycloalkyl" is a cycloalkyl having 3 to 10 carbons. A more preferable "cycloalkyl" is a cycloalkyl having 3 to 8 carbon atoms. A still more preferable "cycloalkyl" is a cycloalkyl having 3 to 6 carbon atoms.

Specific examples of the "cycloalkyl" include a cyclopropyl, a cyclobutyl, a cyclopentyl, a cyclohexyl, a methylcyclopentyl, a cycloheptyl, a methylcyclohexyl, a cyclooctyl, and a dimethylcyclohexyl.

As the "aryl" in $R^{11}$ to $R^{18}$, a preferable aryl is an aryl having 6 to 30 carbon atoms, a more preferable aryl is an aryl having 6 to 18 carbon atoms, a still more preferable aryl is an aryl having 6 to 14 carbon atoms, and a particularly preferable aryl is an aryl having 6 to 12 carbon atoms.

Specific examples of the "aryl having 6 to 30 carbon atoms" include phenyl which is a monocyclic aryl; (1-,2-)naphthyl which is a fused bicyclic aryl; acenaphthylene-(1-, 3-,4-,5-)yl, a fluorene-(1-,2-,3-,4-,9-)yl, phenalene-(1-, 2-)yl, and (1-,2-,3-,4-,9-)phenanthryl which are fused tricyclic aryls; triphenylene-(1-, 2-)yl, pyrene-(1-,2-, 4-)yl, and naphthacene-(1-, 2-, 5-)yl which are fused tetracyclic aryls; and perylene-(1-,2-,3-)yl and pentacene-(1-, 2-, 5-, 6-)yl which are fused pentacyclic aryls.

Preferable examples of the "aryl having 6 to 30 carbon atoms" include a phenyl, a naphthyl, a phenanthryl, a chrysenyl, and a triphenylenyl. More preferable examples thereof include a phenyl, a 1-naphthyl, a 2-naphthyl, and a phenanthryl. Particularly preferable examples thereof include a phenyl, a 1-naphthyl, and a 2-naphthyl.

$R^{11}$ and $R^{12}$ in the above formula (ETM-2-2) may be bonded to each other to form a ring. As a result, cyclobutane, cyclopentane, cyclopentene, cyclopentadiene, cyclohexane, fluorene, indene, or the like may be spiro-bonded to a 5-membered ring of a fluorene skeleton.

Specific examples of this pyridine derivative include the followings.

ET-2

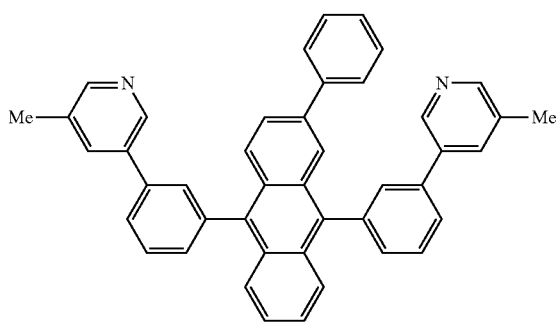

ET-3

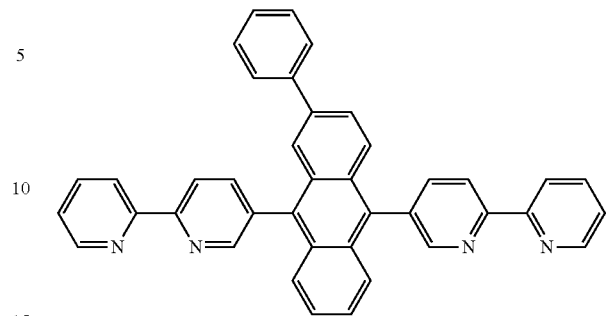

ET-6

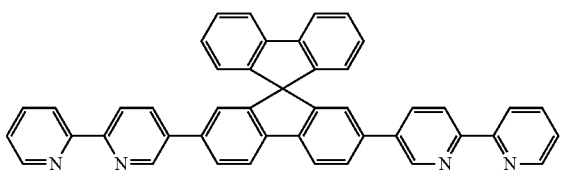

ET-7

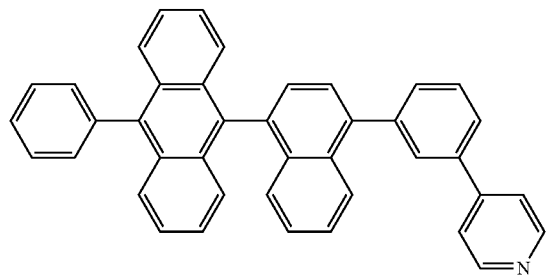

This pyridine derivative can be manufactured using known raw materials and known synthesis methods.

<Fluoranthene Derivative>

The fluoranthene derivative is, for example, a compound represented by the following general formula (ETM-3), and specifically disclosed in WO 2010/134352 A.

(ETM-3)

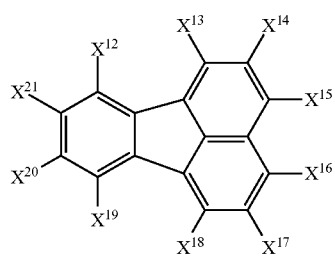

In the above formula (ETM-3), $X^{12}$ to $X^{21}$ each represent a hydrogen atom, a halogen atom, a linear, branched or cyclic alkyl, a linear, branched or cyclic alkoxy, a substituted or unsubstituted aryl, or a substituted or unsubstituted heteroaryl. Examples of a substituent in a case of being substituted include an aryl, a heteroaryl, and an alkyl.

Specific examples of this fluoranthene derivative include the followings.

(ETM-3-1)

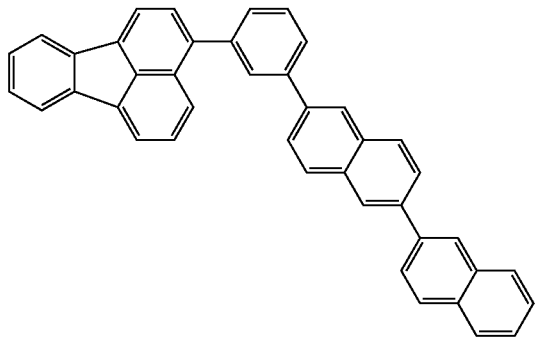

(ETM-3-2)

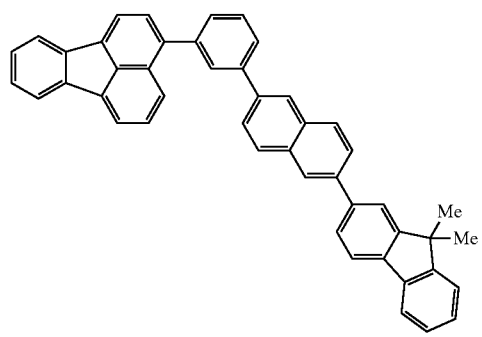

(ETM-3-3)

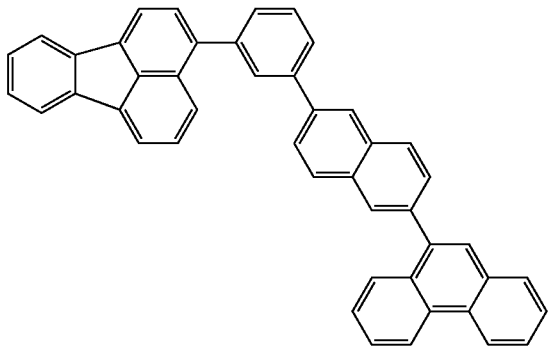

<BO-Based Derivative>

The BO-based derivative is, for example, a polycyclic aromatic compound represented by the following formula (ETM-4) or a polycyclic aromatic compound multimer having a plurality of structures represented by the following formula (ETM-4).

(ETM-4)

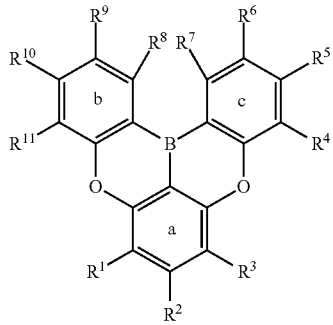

$R^1$ to $R^{11}$ each independently represent a hydrogen atom, an aryl, a heteroaryl, a diarylamino, a diheteroarylamino, an arylheteroarylamino, an alkyl, an alkoxy, or an aryloxy, while at least one hydrogen atom in these may be substituted by an aryl, a heteroaryl, or an alkyl.

Adjacent groups among $R^1$ to $R^{11}$ may be bonded to each other to form an aryl ring or a heteroaryl ring together with the ring a, ring b, or ring c, and at least one hydrogen atom in the ring thus formed may be substituted by an aryl, a heteroaryl, a diarylamino, a diheteroarylamino, an arylheteroarylamino, an alkyl, an alkoxy, or an aryloxy, while at least one hydrogen atom in these may be substituted by an aryl, a heteroaryl, or an alkyl.

At least one hydrogen atom in a compound or structure represented by formula (ETM-4) may be substituted by a halogen atom or a deuterium atom.

For description of a substituent in formula (ETM-4), a form of ring formation, and a multimer formed by combining a plurality of structures of formula (ETM-4), the description of a polycyclic aromatic compound represented by the above general formula (1) or (2) and a multimer thereof can be cited.

Specific examples of this BO-based derivative include the followings.

ET-5

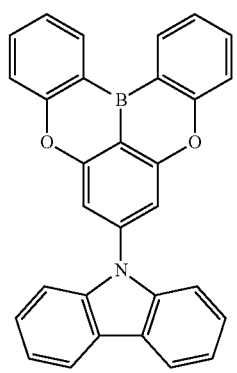

This BO-based derivative can be manufactured using known raw materials and known synthesis methods.

<Anthracene Derivative>

One of the anthracene derivatives is, for example, a compound represented by the following formula (ETM-5-1).

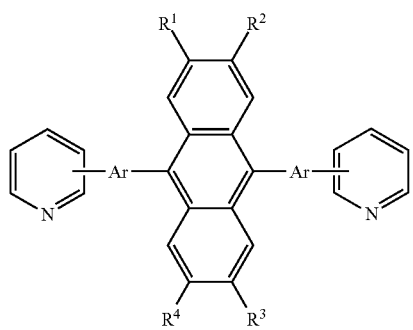

(ETM-5-1)

Ar's each independently represent a divalent benzene or naphthalene, $R^1$ to $R^4$ each independently represent a hydrogen atom, an alkyl having 1 to 6 carbon atoms, a cycloalkyl having 3 to 6 carbon atoms, or an aryl having 6 to 20 carbon atoms.

Ar's can be each independently selected from a divalent benzene and naphthalene appropriately. Two Ar's may be different from or the same as each other, but are preferably the same from a viewpoint of easiness of synthesis of an anthracene derivative. Ar is bonded to pyridine to form "a moiety formed of Ar and pyridine". For example, this moiety is bonded to anthracene as a group represented by any one of the following formulas (Py-1) to (Py-12).

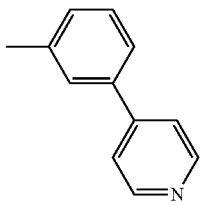
(Py-1)

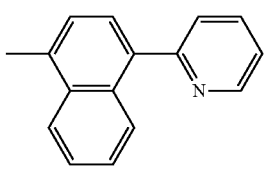
(Py-2)

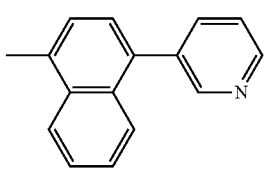
(Py-3)

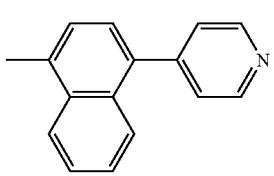
(Py-4)

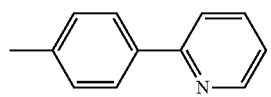
(Py-5)

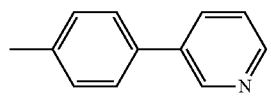
(Py-6)

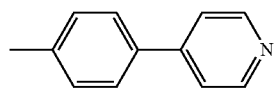
(Py-7)

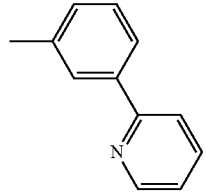
(Py-8)

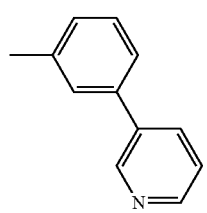
(Py-9)

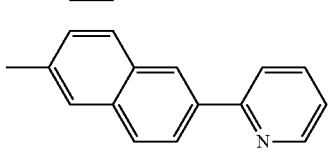
(Py-10)

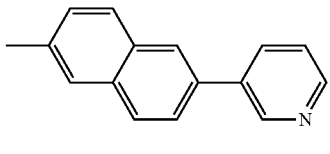
(Py-11)

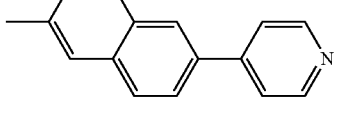
(Py-12)

Among these groups, a group represented by any one of the above formulas (Py-1) to (Py-9) is preferable, and a group represented by any one of the above formulas (Py-1) to (Py-6) is more preferable. Two "moieties formed of Ar and pyridine" bonded to anthracene may have the same structure as or different structures from each other, but preferably have the same structure from a viewpoint of easiness of synthesis of an anthracene derivative. However, two "moieties formed of Ar and pyridine" preferably have the same structure or different structures from a viewpoint of element characteristics.

The alkyl having 1 to 6 carbon atoms in $R^1$ to $R^4$ may be either linear or branched. That is, the alkyl having 1 to 6 carbon atoms is a linear alkyl having 1 to 6 carbon atoms or a branched alkyl having 3 to 6 carbon atoms. More preferably, the alkyl having 1 to 6 carbon atoms is an alkyl having 1 to 4 carbon atoms (branched alkyl having 3 to 4 carbon atoms). Specific examples thereof include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, and 2-ethylbutyl. Methyl, ethyl, n-propyl, isopropyl, n-butyl, isobutyl, s-butyl, and t-butyl are preferable. Methyl, ethyl, and a t-butyl are more preferable.

Specific examples of the cycloalkyl having 3 to 6 carbon atoms in $R^1$ to $R^4$ include a cyclopropyl, a cyclobutyl, a cyclopentyl, a cyclohexyl, a methylcyclopentyl, a cycloheptyl, a methylcyclohexyl, a cyclooctyl, and a dimethylcyclohexyl.

For the aryl having 6 to 20 carbon atoms in $R^1$ to $R^4$, an aryl having 6 to 16 carbon atoms is preferable, an aryl having 6 to 12 carbon atoms is more preferable, and an aryl having 6 to 10 carbon atoms is particularly preferable.

Specific examples of the "aryl having 6 to 20 carbon atoms" include phenyl, (o-, m-, p-) tolyl, (2,3-, 2,4-, 2,5-, 2,6-, 3,4-, 3,5-) xylyl, mesityl (2,4,6-trimethylphenyl), and (o-, m-, p-)cumenyl which are monocyclic aryls; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; anthracene-(1-, 2-, 9-)yl, acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; triphenylene-(1-, 2-)yl, pyrene-(1-, 2-, 4-)yl, and tetracene-(1-, 2-, 5-)yl which are fused tetracyclic aryls; and perylene-(1-, 2-, 3-)yl which is a fused pentacyclic aryl.

The "aryl having 6 to 20 carbon atoms" is preferably a phenyl, a biphenylyl, a terphenylyl, or a naphthyl, more preferably a phenyl, a biphenylyl, a 1-naphthyl, a 2-naphthyl, or an m-terphenyl-5'-yl, still more preferably a phenyl, a biphenylyl, a 1-naphthyl, or a 2-naphthyl, and most preferably a phenyl.

One of the anthracene derivatives is, for example, a compound represented by the following formula (ETM-5-2).

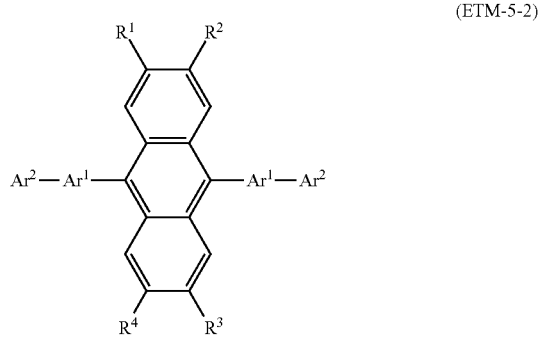

(ETM-5-2)

$Ar^1$'s each independently represent a single bond, a divalent benzene, naphthalene, anthracene, fluorene, or phenalene.

$Ar^2$'s each independently represent an aryl having 6 to 20 carbon atoms. The same description as the "aryl having 6 to 20 carbon atoms" in the above formula (ETM-5-1) can be cited. An aryl having 6 to 16 carbon atoms is preferable, an aryl having 6 to 12 carbon atoms is more preferable, and an aryl having 6 to 10 carbon atoms is particularly preferable. Specific examples thereof include a phenyl, a biphenylyl, a naphthyl, a terphenylyl, an anthracenyl, an acenaphthylenyl, a fluorenyl, a phenalenyl, a phenanthryl, a triphenylenyl, a pyrenyl, a tetracenyl, and a perylenyl.

$R^1$ to $R^4$ each independently represent a hydrogen atom, an alkyl having 1 to 6 carbon atoms, a cycloalkyl having 3 to 6 carbon atoms, or an aryl having 6 to 20 carbon atoms. The same description as in the above formula (ETM-5-1) can be cited.

Specific examples of these anthracene derivatives include the followings.

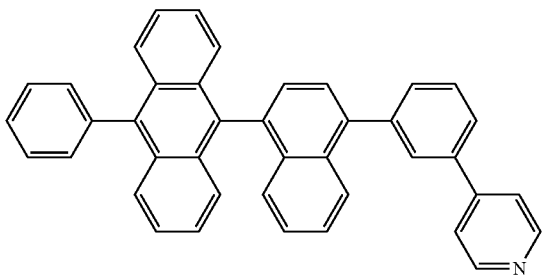

ET-7

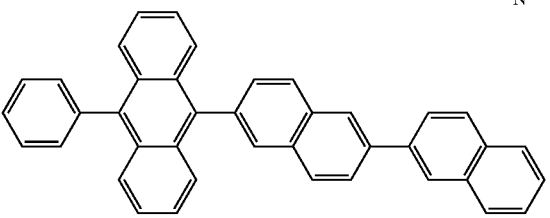

These anthracene derivatives can be manufactured using known raw materials and known synthesis methods.

<Benzofluorene Derivative>

The benzofluorene derivative is, for example, a compound represented by the following formula (ETM-6).

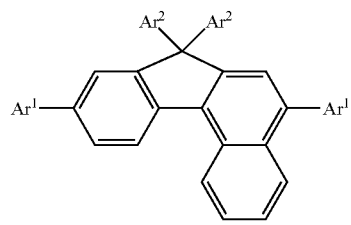

(ETM-6)

$Ar^1$'s each independently represent an aryl having 6 to 20 carbon atoms. The same description as the "aryl having 6 to 20 carbon atoms" in the above formula (ETM-5-1) can be cited. An aryl having 6 to 16 carbon atoms is preferable, an aryl having 6 to 12 carbon atoms is more preferable, and an aryl having 6 to 10 carbon atoms is particularly preferable. Specific examples thereof include a phenyl, a biphenylyl, a naphthyl, a terphenylyl, an anthracenyl, an acenaphthylenyl, a fluorenyl, a phenalenyl, a phenanthryl, a triphenylenyl, a pyrenyl, a tetracenyl, and a perylenyl.

$Ar^2$'s each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms), and two $Ar^2$'s may be bonded to each other to form a ring.

The "alkyl" in $Ar^2$ may be either linear or branched, and examples thereof include a linear alkyl having 1 to 24 carbon atoms and a branched alkyl having 3 to 24 carbon atoms. A preferable "alkyl" is an alkyl having 1 to 18 carbon atoms (branched alkyl having 3 to 18 carbon atoms). A more preferable "alkyl" is an alkyl having 1 to 12 carbons (branched alkyl having 3 to 12 carbons). A still more preferable "alkyl" is an alkyl having 1 to 6 carbon atoms (branched alkyl having 3 to 6 carbon atoms). A particularly preferable "alkyl" is an alkyl having 1 to 4 carbon atoms (branched alkyl having 3 to 4 carbon atoms). Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, and 1-methylhexyl.

Examples of the "cycloalkyl" in $Ar^2$ include a cycloalkyl having 3 to 12 carbon atoms. A preferable "cycloalkyl" is a cycloalkyl having 3 to 10 carbons. A more preferable "cycloalkyl" is a cycloalkyl having 3 to 8 carbon atoms. A still more preferable "cycloalkyl" is a cycloalkyl having 3 to 6 carbon atoms. Specific examples of the "cycloalkyl" include cyclopropyl, cyclobutyl, cyclopentyl, cyclohexyl, methylcyclopentyl, cycloheptyl, methylcyclohexyl, cyclooctyl, and dimethylcyclohexyl.

As the "aryl" in $Ar^2$, a preferable aryl is an aryl having 6 to 30 carbon atoms, a more preferable aryl is an aryl having 6 to 18 carbon atoms, a still more preferable aryl is an aryl having 6 to 14 carbon atoms, and a particularly preferable aryl is an aryl having 6 to 12 carbon atoms.

Specific examples of the "aryl having 6 to 30 carbon atoms" include phenyl, naphthyl, acenaphthylenyl, fluorenyl, phenalenyl, phenanthryl, triphenylenyl, pyrenyl, naphthacenyl, perylenyl, and pentacenyl.

Two $Ar^2$'s may be bonded to each other to form a ring. As a result, cyclobutane, cyclopentane, cyclopentene, cyclopentadiene, cyclohexane, fluorene, indene, or the like may be spiro-bonded to a 5-membered ring of a fluorene skeleton.

Specific examples of this benzofluorene derivative include the followings.

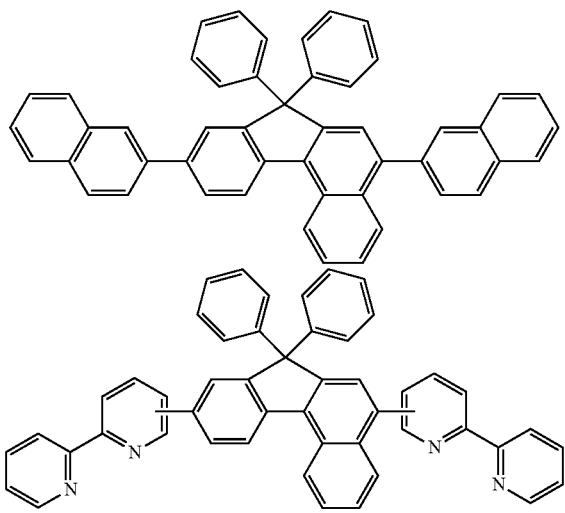

This benzofluorene derivative can be manufactured using known raw materials and known synthesis methods.

<Phosphine Oxide Derivative>

The phosphine oxide derivative is, for example, a compound represented by the following formula (ETM-7-1) Details are also described in WO 2013/079217 A.

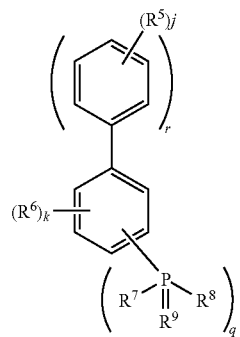

(ETM-7-1)

$R^5$ represents a substituted or unsubstituted alkyl having 1 to 20 carbon atoms, an aryl having 6 to 20 carbon atoms, or a heteroaryl having 5 to 20 carbon atoms, $R^6$ represents CN, a substituted or unsubstituted alkyl having 1 to 20 carbons, a heteroalkyl having 1 to 20 carbons, an aryl having 6 to 20 carbons, a heteroaryl having 5 to 20 carbons, an alkoxy having 1 to 20 carbons, or an aryloxy having 6 to 20 carbon atoms, $R^7$ and $R^8$ each independently represent a substituted or unsubstituted aryl having 6 to 20 carbon atoms or a heteroaryl having 5 to 20 carbon atoms, $R^9$ represents an oxygen atom or a sulfur atom, j represents 0 or 1, k represents 0 or 1, r represents an integer of 0 to 4, and q represents an integer of 1 to 3.

Examples of a substituent in a case of being substituted include an aryl, a heteroaryl, and an alkyl.

The phosphine oxide derivative may be, for example, a compound represented by the following formula (ETM-7-2).

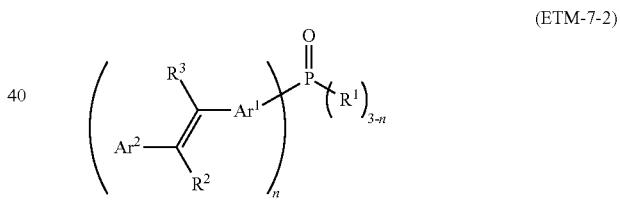

(ETM-7-2)

$R^1$ to $R^3$ may be the same as or different from each other and are selected from a hydrogen atom, an alkyl group, a cycloalkyl group, an aralkyl group, an alkenyl group, a cycloalkenyl group, an alkynyl group, an alkoxy group, an alkylthio group, an aryl ether group, an aryl thioether group, an aryl group, a heterocyclic group, a halogen atom, a cyano group, an aldehyde group, a carbonyl group, a carboxyl group, an amino group, a nitro group, a silyl group, and a fused ring formed with an adjacent substituent.

$Ar^1$'s may be the same as or different from each other, and represents an arylene group or a heteroarylene group. $Ar^2$'s may be the same as or different from each other, and represents an aryl group or a heteroaryl group. However, at least one of $Ar^1$ and $Ar^2$ has a substituent or forms a fused ring with an adjacent substituent. n represents an integer of 0 to 3. When n is 0, no unsaturated structure portion is present. When n is 3, $R^1$ is not present.

Among these substituents, the alkyl group represents a saturated aliphatic hydrocarbon group such as a methyl group, an ethyl group, a propyl group, or a butyl group. This saturated aliphatic hydrocarbon group may be unsubstituted or substituted. The substituent in a case of being substituted is not particularly limited, and examples thereof include an alkyl group, an aryl group, and a heterocyclic group, and this point is also common to the following description. The number of carbon atoms in the alkyl group is not particularly limited, but is usually in a range of 1 to 20 from a viewpoint of availability and cost.

The cycloalkyl group represents a saturated alicyclic hydrocarbon group such as a cyclopropyl, a cyclohexyl, a norbornyl, or an adamantyl. This saturated alicyclic hydrocarbon group may be unsubstituted or substituted. The carbon number of the alkyl group moiety is not particularly limited, but is usually in a range of 3 to 20.

Furthermore, the aralkyl group represents an aromatic hydrocarbon group via an aliphatic hydrocarbon, such as a benzyl group or a phenylethyl group. Both the aliphatic hydrocarbon and the aromatic hydrocarbon may be unsubstituted or substituted. The carbon number of the aliphatic moiety is not particularly limited, but is usually in a range of 1 to 20.

The alkenyl group represents an unsaturated aliphatic hydrocarbon group containing a double bond, such as a vinyl group, an allyl group, or a butadienyl group. This unsaturated aliphatic hydrocarbon group may be unsubstituted or substituted. The carbon number of the alkenyl group is not particularly limited, but is usually in a range of 2 to 20.

The cycloalkenyl group represents an unsaturated alicyclic hydrocarbon group containing a double bond, such as a cyclopentenyl group, a cyclopentadienyl group, or a cyclohexene group. This unsaturated alicyclic hydrocarbon group may be unsubstituted or substituted.

The alkynyl group represents an unsaturated aliphatic hydrocarbon group containing a triple bond, such as an acetylenyl group. This unsaturated aliphatic hydrocarbon group may be unsubstituted or substituted. The carbon number of the alkynyl group is not particularly limited, but is usually in a range of 2 to 20.

The alkoxy group represents an aliphatic hydrocarbon group via an ether bond, such as a methoxy group. The aliphatic hydrocarbon group may be unsubstituted or substituted. The carbon number of the alkoxy group is not particularly limited, but is usually in a range of 1 to 20.

The alkylthio group is a group in which an oxygen atom of an ether bond of an alkoxy group is substituted by a sulfur atom.

The aryl ether group represents an aromatic hydrocarbon group via an ether bond, such as a phenoxy group. The aromatic hydrocarbon group may be unsubstituted or substituted. The carbon number of the aryl ether group is not particularly limited, but is usually in a range of 6 to 40.

The aryl thioether group is a group in which an oxygen atom of an ether bond of an aryl ether group is substituted by a sulfur atom.

Furthermore, the aryl group represents an aromatic hydrocarbon group such as a phenyl group, a naphthyl group, a biphenyl group, a phenanthryl group, a terphenyl group, or a pyrenyl group. The aryl group may be unsubstituted or substituted. The carbon number of the aryl group is not particularly limited, but is usually in a range of 6 to 40.

Furthermore, the heterocyclic group represents a cyclic structural group having an atom other than a carbon atom, such as a furanyl group, a thiophenyl group, an oxazolyl group, a pyridyl group, a quinolinyl group, or a carbazolyl group. This cyclic structural group may be unsubstituted or substituted. The carbon number of the heterocyclic group is not particularly limited, but is usually in a range of 2 to 30.

Halogen refers to fluorine, chlorine, bromine, and iodine.

The aldehyde group, the carbonyl group, and the amino group can include those substituted by an aliphatic hydrocarbon, an alicyclic hydrocarbon, an aromatic hydrocarbon, a heterocyclic ring, or the like.

Furthermore, the aliphatic hydrocarbon, the alicyclic hydrocarbon, the aromatic hydrocarbon, and the heterocyclic ring may be unsubstituted or substituted.

The silyl group represents, for example, a silicon compound group such as a trimethylsilyl group. This silicon compound group may be unsubstituted or substituted. The number of carbon atoms of the silyl group is not particularly limited, but is usually in a range of 3 to 20. The number of silicon atoms is usually 1 to 6.

The fused ring formed with an adjacent substituent is, for example, a conjugated or unconjugated fused ring formed between $Ar^1$ and $R^2$, $Ar^1$ and $R^3$, $Ar^2$ and $R^2$, $Ar^2$ and $R^3$, $R^2$ and $R^3$, or $Ar^1$ and $Ar^2$. Here, when n is 1, two $R^1$'s may form a conjugated or nonconjugated fused ring. These fused rings may contain a nitrogen atom, an oxygen atom, or a sulfur atom in the ring structure, or may be fused with another ring.

Specific examples of this phosphine oxide derivative include the followings.

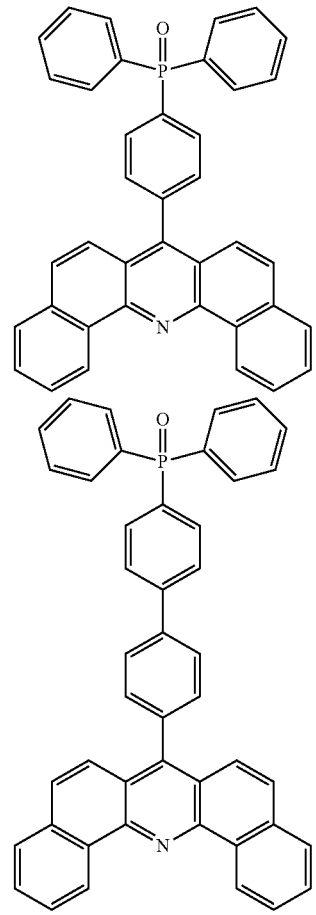

This phosphine oxide derivative can be manufactured using known raw materials and known synthesis methods.

<Pyrimidine Derivative>

The pyrimidine derivative is, for example, a compound represented by the following formula (ETM-8), and preferably a compound represented by the following formula (ETM-8-1). Details are also described in WO 2011/021689 A.

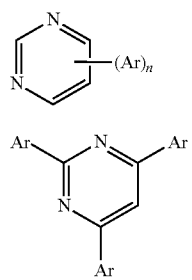

(ETM-8)

(ETM-8-1)

Ar's each independently represent an optionally substituted aryl or an optionally substituted heteroaryl. n represents an integer of 1 to 4, preferably an integer of 1 to 3, and more preferably 2 or 3.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

Specific examples of this pyrimidine derivative include the followings.

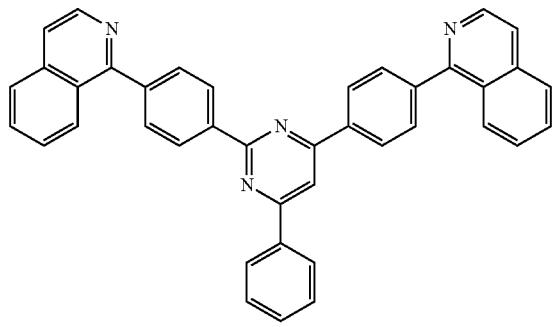 [SMILES: c1ccc(-c2cc(-c3ccc(-c4nccc5ccccc45)cc3)nc(-c3ccc(-c4nccc5ccccc45)cc3)n2)cc1]

This pyrimidine derivative can be manufactured using known raw materials and known synthesis methods.

<Carbazole Derivative>

The carbazole derivative is, for example, a compound represented by the following formula (ETM-9), or a multimer obtained by bonding a plurality of the compounds with a single bond or the like. Details are described in US 2014/0197386 A.

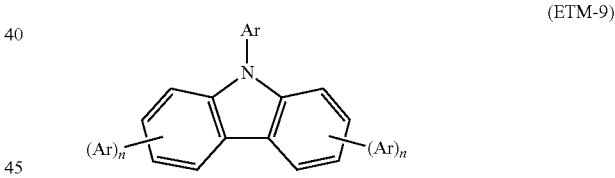

(ETM-9)

Ar's each independently represent an optionally substituted aryl or an optionally substituted heteroaryl. n independently represents an integer of 0 to 4, preferably an integer of 0 to 3, and more preferably 0 or 1.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

The carbazole derivative may be a multimer obtained by bonding a plurality of compounds represented by the above formula (ETM-9) with a single bond or the like. In this case, the compounds may be bonded with an aryl ring (preferably, a polyvalent benzene ring, naphthalene ring, anthracene ring, fluorene ring, benzofluorene ring, phenalene ring, phenanthrene ring or triphenylene ring) in addition to a single bond.

Specific examples of this carbazole derivative include the followings.

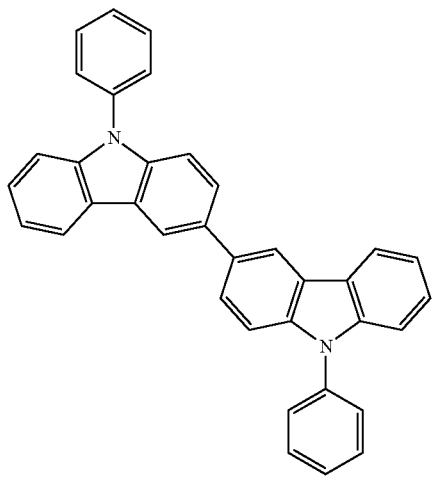

-continued

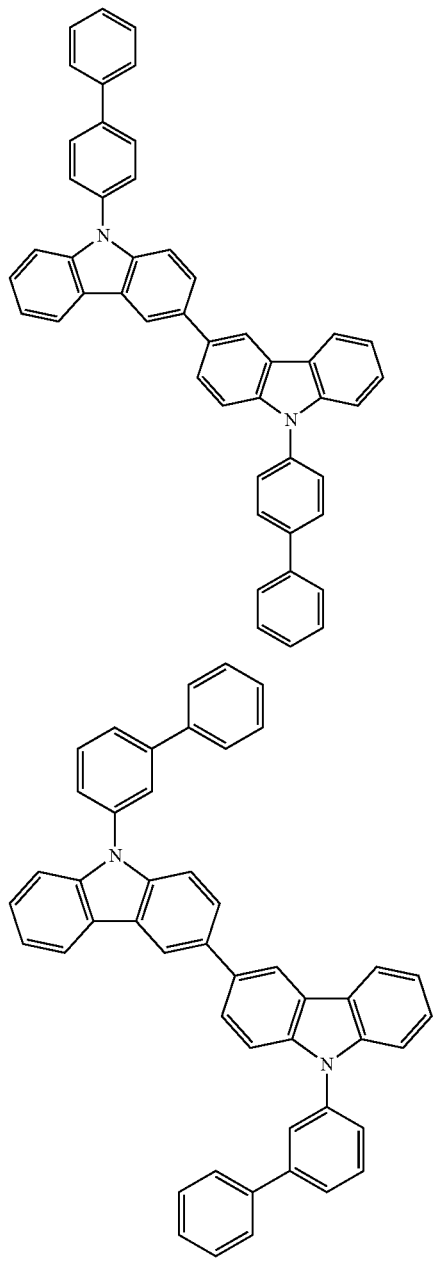

This carbazole derivative can be manufactured using known raw materials and known synthesis methods.

<Triazine Derivative>

The triazine derivative is, for example, a compound represented by the following formula (ETM-10), and preferably a compound represented by the following formula (ETM-10-1). Details are described in US 2011/0156013 A.

(ETM-10)

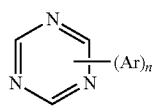

-continued

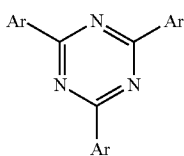
(ETM-10-1)

Ar's each independently represent an optionally substituted aryl or an optionally substituted heteroaryl. n represents an integer of 1 to 3, preferably 2 or 3.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, LH-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

Specific examples of this triazine derivative include the followings.

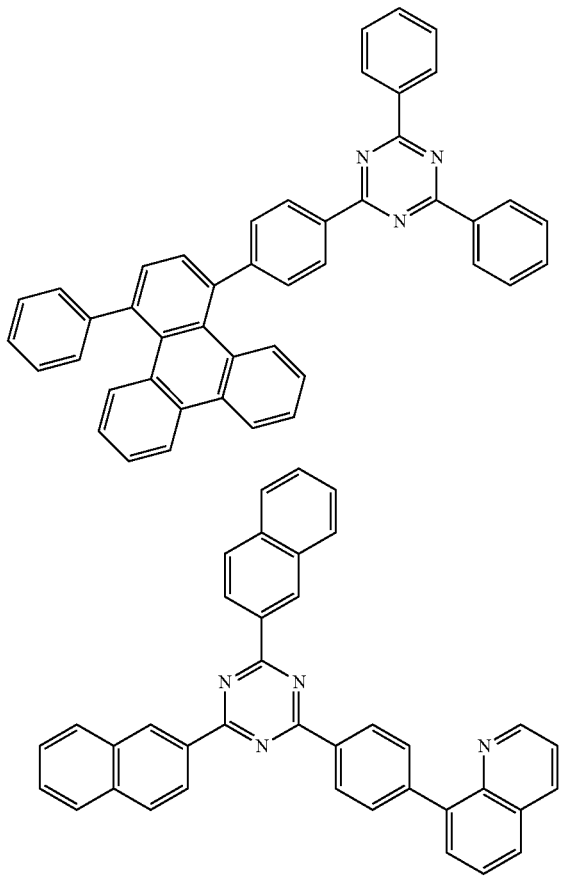

This triazine derivative can be manufactured using known raw materials and known synthesis methods.

<Benzimidazole Derivative>

The benzimidazole derivative is, for example, a compound represented by the following formula (ETM-11).

φ-(Benzimidazole-based substituent)n      (ETM-11)

φ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4. A "benzimidazole-based substituent" is a substituent in which the pyridyl group in the "pyridine-based substituent" in the formulas (ETM-2), (ETM-2-1), and (ETM-2-2) is substituted by a benzimidazole group, and at least one hydrogen atom in the benzimidazole derivative may be substituted by a deuterium atom.

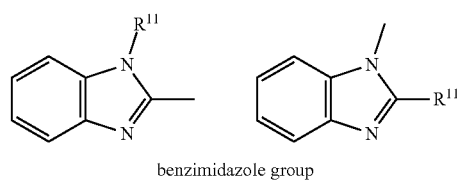

benzimidazole group $R^{11}$ in the above benzimidazole represents a hydrogen atom, an alkyl having 1 to 24 carbon atoms, a cycloalkyl having 3 to 12 carbon atoms, or an aryl having 6 to 30 carbon atoms. The description of $R^{11}$ in the above formulas (ETM-2-1), and (ETM-2-2) can be cited.

Furthermore, φ is preferably an anthracene ring or a fluorene ring. For the structure in this case, the structure of the above formula (ETM-2-1) or (ETM-2-2) can be cited. For $R^1$ to $R^{18}$ in each formula, those described in the above formula (ETM-2-1) or (ETM-2-2) can be cited. In the above formula (ETM-2-1) or (ETM-2-2), a form in which two pyridine-based substituents are bonded has been described. However, when these substituents are substituted by benzimidazole-based substituents, both the pyridine-based substituents may be substituted by benzimidazole-based substituents (that is, n=2), or one of the pyridine-based substituents may be substituted by a benzimidazole-based substituent and the other pyridine-based substituent may be substituted by any one of $R^{11}$ to $R^{18}$ (that is, n=1). Furthermore, for example, at least one of $R^{11}$ to $R^{18}$ in the above formula (ETM-2-1) may be substituted by a benzimidazole-based substituent and the "pyridine-based substituent" may be substituted by any one of $R^{11}$ to $R^{18}$.

Specific examples of this benzimidazole derivative include 1-phenyl-2-(4-(10-phenylanthracen-9-yl)phenyl)-1H-benzo[d]imidazole, 2-(4-(10-(naphthalen-2-yl)anthracen-9-yl)phenyl)-1-phenyl-1H-benzo[d]imidazole, 2-(3-(10-(naphthalen-2-yl)anthracen-9-yl)phenyl)-1-phenyl-1H-benzo[d]imidazole, 5-(10-(naphthlen-2-yl)anthracen-9-yl)-1,2-diphenyl-1H-benzo[d]imidazole, 1-(4-(10-(naphthalen-2-yl)anthracen-9-yl)phenyl)-2-phenyl-1H-benzo[d]imidazole, 2-(4-(9,10-di(naphthalen-2-yl)anthracen-2-yl)phenyl)-1-phenyl-1H-benzo[d]imidazole, 1-(4-(9,10-di(naphthalen-2-yl)anthracen-2-yl)phenyl)-2-phenyl-1H-benzo[d]imidazole, and 5-(9,10-di(naphthalen-2-yl)anthracen-2-yl)-1,2-diphenyl-1H-benzo[d]imidazole.

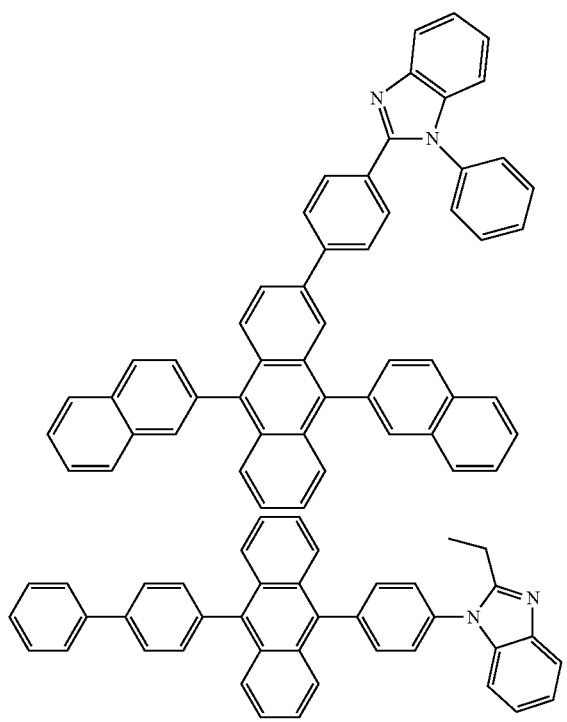

This benzimidazole derivative can be manufactured using known raw materials and known synthesis methods.

<Phenanthroline Derivative>

The phenanthroline derivative is, for example, a compound represented by the following formula (ETM-12) or (ETM-12-1). Details are described in WO 2006/021982 A.

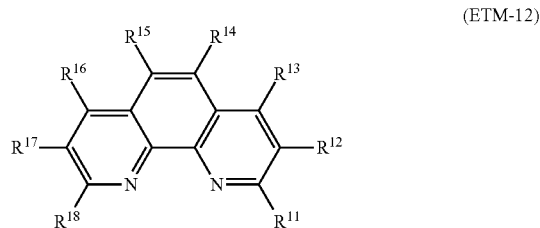

(ETM-12)

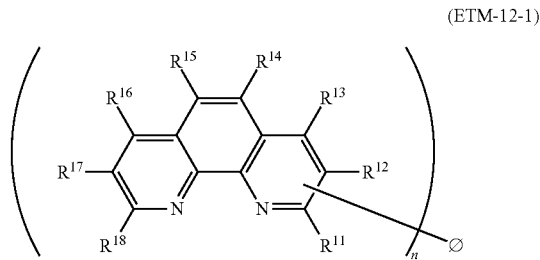

(ETM-12-1)

φ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4.

In each formula, $R^{11}$ to $R^{18}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms). In the above formula (ETM-12-1), any one of $R^{11}$ to $R^{18}$ is bonded to φ which is an aryl ring.

At least one hydrogen atom in each phenanthroline derivative may be substituted by a deuterium atom.

For the alkyl, cycloalkyl, and aryl in $R^{11}$ to $R^{18}$, the description of $R^{11}$ to $R^{18}$ in the above formula (ETM-2) can be cited. In addition to the above, examples of the p include those having the following structural formulas. Note that R's in the following structural formulas each independently represent a hydrogen atom, methyl, ethyl, isopropyl, cyclohexyl, phenyl, 1-naphthyl, 2-naphthyl, biphenylyl, or terphenylyl.

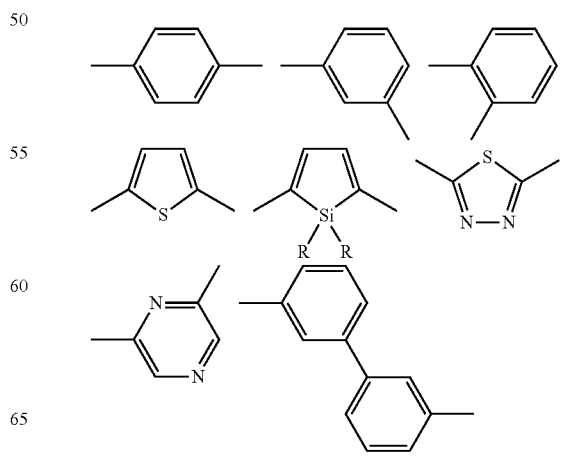

-continued

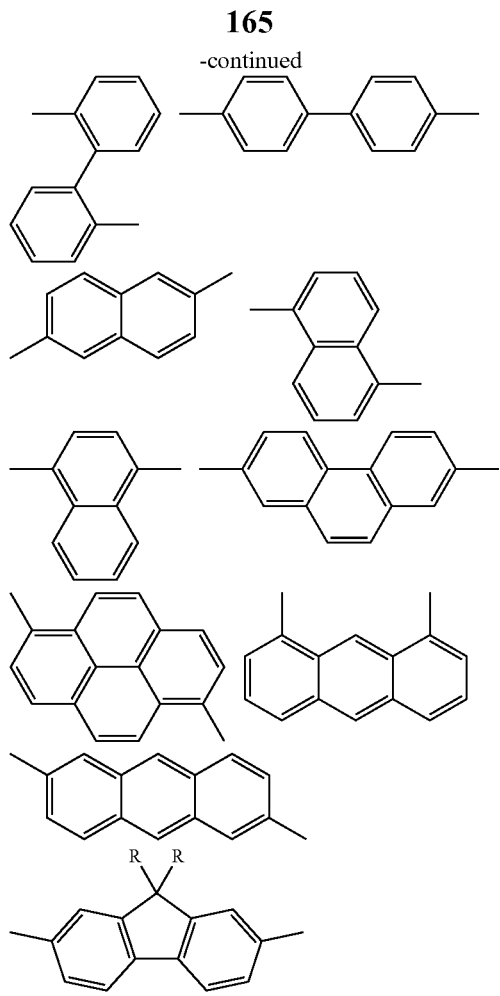

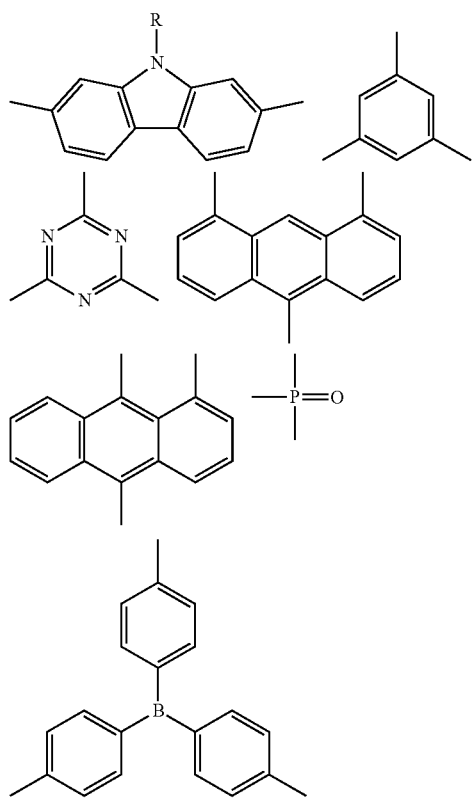

-continued

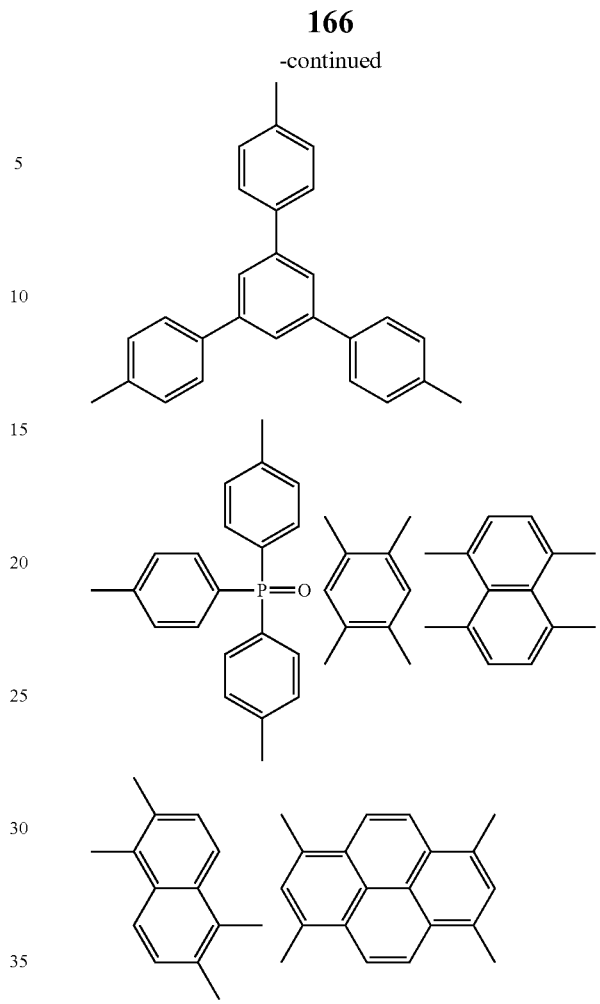

Specific examples of this phenanthroline derivative include 4,7-diphenyl-1,10-phenanthroline, 2,9-dimethyl-4,7-diphenyl-1,10-phenanthroline, 9,10-di(1,10-phenanthrolin-2-yl)anthracene, 2,6-di(1,10-phenanthrolin-5-yl)pyridine, 1,3,5-tri(1,10-phenanthrolin-5-yl)benzene, 9,9'-difluoro-bi(1,10-phenanthrolin-5-yl), bathocuproine, and 1,3-bis(2-phenyl-1,10-phenanthrolin-9-yl)benzene.

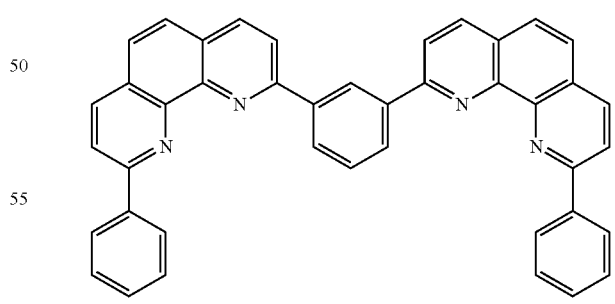

This phenanthroline derivative can be manufactured using known raw materials and known synthesis methods.

<Quinolinol-Based Metal Complex>

The quinolinol-based metal complex is, for example, a compound represented by the following general formula (ETM-13).

(ETM-13)

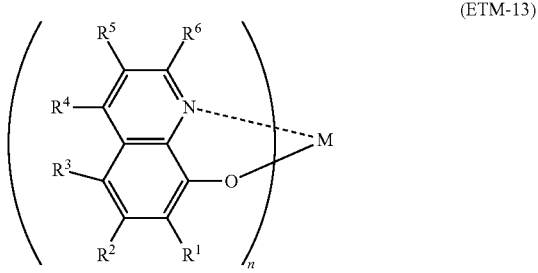

In the formula, $R^1$ to $R^6$ each independently represent a hydrogen atom, a fluorine atom, an alkyl, an aralkyl, an alkenyl, a cyano, an alkoxy, or an aryl, M represents Li, Al, Ga, Be, or Zn, and n represents an integer of 1 to 3.

Specific examples of the quinolinol-based metal complex include 8-quinolinol lithium, tris(8-quinolinolato) aluminum, tris(4-methyl-8-quinolinolato) aluminum, tris(5-methyl-8-quinolinolato) aluminum, tris(3,4-dimethyl-8-quinolinolato) aluminum, tris(4,5-dimethyl-8-quinolinolato) aluminum, tris(4,6-dimethyl-8-quinolinolato) aluminum, bis(2-methyl-8-quinolinolato) (phenolato) aluminum, bis(2-methyl-8-quinolinolato) (2-methylphenolato) aluminum, bis(2-methyl-8-quinolinolato) (3-methylphenolato) aluminum, bis(2-methyl-8-quinolinolato) (4-methylphenolato) aluminum, bis(2-methyl-8-quinolinolato) (2-phenylphenolato) aluminum, bis(2-methyl-8-quinolinolato) (3-phenylphenolato) aluminum, bis(2-methyl-8-quinolinolato) (4-phenylphenolato) aluminum, bis(2-methyl-8-quinolinolato) (2,3-dimethylphenolato) aluminum, bis(2-methyl-8-quinolinolato) (2,6-dimethylphenolato) aluminum, bis(2-methyl-8-quinolinolato) (3,4-dimethylphenolato) aluminum, bis(2-methyl-8-quinolinolato) (3,5-dimethylphenolato) aluminum, bis(2-methyl-8-quinolinolato) (3,5-di-t-butylphenolato) aluminum, bis(2-methyl-8-quinolinolato) (2,6-diphenylphenolato) aluminum, bis(2-methyl-8-quinolinolato) (2,4,6-triphenylphenolato) aluminum, bis(2-methyl-8-quinolinolato) (2,4,6-trimethylphenolato) aluminum, bis(2-methyl-8-quinolinolato) (2,4,5,6-tetramethylphenolato) aluminum, bis(2-methyl-8-quinolinolato) (1-naphtholato) aluminum, bis(2-methyl-8-quinolinolato) (2-naphtholato) aluminum, bis(2,4-dimethyl-8-quinolinolato) (2-phenylphenolato) aluminum, bis(2,4-dimethyl-8-quinolinolato) (3-phenylphenolato) aluminum, bis(2,4-dimethyl-8-quinolinolato) (4-phenylphenolato) aluminum, bis(2,4-dimethyl-8-quinolinolato) (3,5-dimethylphenolato) aluminum, bis(2,4-dimethyl-8-quinolinolato) (3,5-di-t-butylphenolato) aluminum, bis(2-methyl-8-quinolinolato) aluminum-μ-oxo-bis(2-methyl-8-quinolinolato) aluminum, bis(2,4-dimethyl-8-quinolinolato) aluminum-μ-oxo-bis(2,4-dimethyl-8-quinolinolato) aluminum, bis(2-methyl-4-ethyl-8-quinolinolato) aluminum-μ-oxo-bis(2-methyl-4-ethyl-8-quinolinolato) aluminum, bis(2-methyl-4-methoxy-8-quinolinolato) aluminum-μ-oxo-bis(2-methyl-4-methoxy-8-quinolinolato) aluminum, bis(2-methyl-5-cyano-8-quinolinolato) aluminum-μ-oxo-bis(2-methyl-5-cyano-8-quinolinolato) aluminum, bis(2-methyl-5-trifluoromethyl-8-quinolinolato) aluminum-μ-oxo-bis(2-methyl-5-trifluoromethyl-8-quinolinolato) aluminum, and bis(10-hydroxybenzo[h]quinoline) beryllium.

This quinolinol-based metal complex can be manufactured using known raw materials and known synthesis methods.

<Thiazole Derivative and Benzothiazole Derivative>

The thiazole derivative is, for example, a compound represented by the following formula (ETM-14-1).

φ-(Thiazole-based substituent)n          (ETM-14-1)

The benzothiazole derivative is, for example, a compound represented by the following formula (ETM-14-2).

φ-(Benzothiazole-based substituent)n          (ETM-14-2)

φ in each formula represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4. A "thiazole-based substituent" or a "benzothiazole-based substituent" is a substituent in which the pyridyl group in the "pyridine-based substituent" in the formulas (ETM-2), (ETM-2-1), and (ETM-2-2) is substituted by a thiazole group or a benzothiazole group, and at least one hydrogen atom in the thiazole derivative and the benzothiazole derivative may be substituted by a deuterium atom.

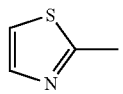 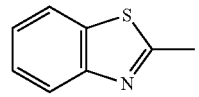

thiazole group          benzothiazole group

Furthermore, c is preferably an anthracene ring or a fluorene ring. For the structure in this case, the structure of the above formula (ETM-2-1) or (ETM-2-2) can be cited. For $R^{11}$ to $R^{18}$ in each formula, those described in the above formula (ETM-2-1) or (ETM-2-2) can be cited. In the above formula (ETM-2-1) or (ETM-2-2), a form in which two pyridine-based substituents are bonded has been described. However, when these substituents are substituted by thiazole-based substituents (or benzothiazole-based substituents), both the pyridine-based substituents may be substituted by thiazole-based substituents (or benzothiazole-based substituents) (that is, n=2), or one of the pyridine-based substituents may be substituted by a thiazole-based substituent (or benzothiazole-based substituent) and the other pyridine-based substituent may be substituted by any one of $R^{11}$ to $R^{18}$ (that is, n=1). Furthermore, for example, at least one of $R^{11}$ to $R^{18}$ in the above formula (ETM-2-1) may be substituted by a thiazole-based substituent (or benzothiazole-based substituent) and the "pyridine-based substituent" may be substituted by any one of $R^{11}$ to $R^{18}$.

These thiazole derivatives or benzothiazole derivatives can be manufactured using known raw materials and known synthesis methods.

An electron transport layer or an electron injection layer may further contain a substance that can reduce a material to form an electron transport layer or an electron injection layer. As this reducing substance, various substances are used as long as having reducibility to a certain extent. For example, at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal, can be suitably used.

Preferable examples of the reducing substance include an alkali metal such as Na (work function 2.36 eV), K (work function 2.28 eV), Rb (work function 2.16 eV), or Cs (work function 1.95 eV), and an alkaline earth metal such as Ca (work function 2.9 eV), Sr (work function 2.0 to 2.5 eV), or Ba (work function 2.52 eV). A reducing substance having a work function of 2.9 eV or less is particularly preferable. Among these substances, an alkali metal such as K, Rb, or Cs is a more preferable reducing substance, Rb or Cs is a still more preferable reducing substance, and Cs is the most preferable reducing substance. These alkali metals have particularly high reducing ability, and can enhance emission luminance of an organic EL element or can lengthen a lifetime thereof by adding the alkali metals in a relatively small amount to a material to form an electron transport layer or an electron injection layer. Furthermore, as the reducing substance having a work function of 2.9 eV or less, a combination of two or more kinds of these alkali metals is also preferable, and particularly, a combination including Cs, for example, a combination of Cs with Na, a combination of Cs with K, a combination of Cs with Rb, or a combination of Cs with Na and K, is preferable. By inclusion of Cs, reducing ability can be efficiently exhibited, and emission luminance of an organic EL element is enhanced or a lifetime thereof is lengthened by adding Cs to a material to form an electron transport layer or an electron injection layer.

<Negative Electrode in Organic Electroluminescent Element>

The negative electrode 108 plays a role of injecting an electron to the light emitting layer 105 through the electron injection layer 107 and the electron transport layer 106.

A material to form the negative electrode 108 is not particularly limited as long as being a substance capable of efficiently injecting an electron to an organic layer. However, a material similar to the materials to form the positive electrode 102 can be used. Among these materials, a metal such as tin, indium, calcium, aluminum, silver, copper, nickel, chromium, gold, platinum, iron, zinc, lithium, sodium, potassium, cesium, or magnesium, and alloys thereof (a magnesium-silver alloy, a magnesium-indium alloy, an aluminum-lithium alloy such as lithium fluoride/aluminum, and the like) are preferable. In order to enhance element characteristics by increasing electron injection efficiency, lithium, sodium, potassium, cesium, calcium, magnesium, or an alloy containing these low work function-metals is effective. However, many of these low work function-metals are generally unstable in air. In order to ameliorate this problem, for example, a method for using an electrode having high stability obtained by doping an organic layer with a trace amount of lithium, cesium, or magnesium is known. Other examples of a dopant that can be used include an inorganic salt such as lithium fluoride, cesium fluoride, lithium oxide, or cesium oxide. However, the dopant is not limited thereto.

Furthermore, in order to protect an electrode, a metal such as platinum, gold, silver, copper, iron, tin, aluminum, or indium, an alloy using these metals, an inorganic substance such as silica, titania, or silicon nitride, polyvinyl alcohol, vinyl chloride, a hydrocarbon-based polymer compound, or the like may be laminated as a preferable example. These method for manufacturing an electrode are not particularly limited as long as being capable of conduction, such as resistance heating, electron beam, sputtering, ion plating, or coating.

<Binder that May be Used in Each Layer>

The materials used in the above-described hole injection layer, hole transport layer, light emitting layer, electron transport layer, and electron injection layer can form each layer by being used singly. However, it is also possible to use the materials by dispersing the materials in a solvent-soluble resin such as polyvinyl chloride, polycarbonate, polystyrene, poly(N-vinylcarbazole), polymethyl methacrylate, polybutyl methacrylate, polyester, polysulfone, polyphenylene oxide, polybutadiene, a hydrocarbon resin, a ketone resin, a phenoxy resin, polyamide, ethyl cellulose, a vinyl acetate resin, an ABS resin, or a polyurethane resin; or a curable resin such as a phenolic resin, a xylene resin, a petroleum resin, a urea resin, a melamine resin, an unsaturated polyester resin, an alkyd resin, an epoxy resin, or a silicone resin.

<Method for Manufacturing Organic Electroluminescent Element>

Each layer constituting an organic EL element can be formed by forming thin films of the materials to constitute each layer by methods such as a vapor deposition method, resistance heating deposition, electron beam deposition, sputtering, a molecular lamination method, a printing method, a spin coating method, a casting method, and a coating method. The film thickness of each layer thus formed is not particularly limited, and can be appropriately set according to a property of a material, but is usually within a range of 2 nm to 5000 nm. The film thickness can be usually measured using a crystal oscillation type film thickness analyzer or the like. In a case of forming a thin film using a vapor deposition method, deposition conditions depend on the kind of a material, an intended crystal structure and association structure of the film, and the like. It is preferable to appropriately set the vapor deposition conditions generally in ranges of a boat heating temperature of +50 to +400° C., a degree of vacuum of $10^{-6}$ to $10^{-3}$ Pa, a rate of deposition of 0.01 to 50 nm/sec, a substrate temperature of −150 to +300° C., and a film thickness of 2 nm to 5 μm.

Next, as an example of a method for manufacturing an organic EL element, a method for manufacturing an organic EL element formed of positive electrode/hole injection layer/hole transport layer/light emitting layer including a host material and a dopant material/electron transport layer/electron injection layer/negative electrode will be described. A thin film of a positive electrode material is formed on an appropriate substrate by a vapor deposition method or the like to manufacture a positive electrode, and then thin films of a hole injection layer and a hole transport layer are formed on this positive electrode. A thin film is formed thereon by co-depositing a host material and a dopant material to obtain a light emitting layer. An electron transport layer and an electron injection layer are formed on this light emitting layer, and a thin film formed of a substance for a negative electrode is formed by a vapor deposition method or the like to obtain a negative electrode. An intended organic EL element is thereby obtained. Incidentally, in manufacturing the above organic EL element, it is also possible to manufacture the organic EL element by reversing the manufacturing order, that is, in order of a negative electrode, an electron injection layer, an electron transport layer, a light emitting layer, a hole transport layer, a hole injection layer, and a positive electrode.

In a case where a direct current voltage is applied to the organic EL element thus obtained, it is only required to apply the voltage by assuming a positive electrode as a positive polarity and assuming a negative electrode as a negative polarity. By applying a voltage of about 2 to 40 V, light emission can be observed from a transparent or semi-transparent electrode side (the positive electrode or the negative electrode, or both the electrodes). This organic EL element also emits light even in a case where a pulse current or an alternating current is applied. Note that a waveform of an alternating current applied may be any waveform.

<Application Examples of Organic Electroluminescent Element>

The present invention can also be applied to a display apparatus including an organic EL element, a lighting apparatus including an organic EL element, or the like.

The display apparatus or lighting apparatus including an organic EL element can be manufactured by a known method such as connecting the organic EL element according to the present embodiment to a known driving apparatus, and can be driven by appropriately using a known driving method such as direct driving, pulse driving, or alternating driving.

Examples of the display apparatus include panel displays such as color flat panel displays; and flexible displays such as flexible organic electroluminescent (EL) displays (see, for example, JP 10-335066 A, JP 2003-321546 A, JP 2004-281086 A, and the like). Examples of a display method of the display include a matrix method and/or a segment method. Note that the matrix display and the segment display may co-exist in the same panel.

The matrix refers to a system in which pixels for display are arranged two-dimensionally as in a lattice form or a mosaic form, and characters or images are displayed by an assembly of pixels. The shape or size of the pixel depends on intended use. For example, for display of images and characters of a personal computer, a monitor, or a television, square pixels each having a size of 300 μm or less on each side are usually used, and in a case of a large-sized display such as a display panel, pixels having a size in the order of millimeters on each side are used. In a case of monochromic display, it is only required to arrange pixels of the same color. However, in a case of color display, display is performed by arranging pixels of red, green and blue. In this case, typically, delta type display and stripe type display are available. For this matrix driving method, either a line sequential driving method or an active matrix method may be employed. The line sequential driving method has an advantage of having a simpler structure. However, in consideration of operation characteristics, the active matrix method may be superior. Therefore, it is necessary to use the line sequential driving method or the active matrix method properly according to intended use.

In the segment method (type), a pattern is formed so as to display predetermined information, and a determined region emits light. Examples of the segment method include display of time or temperature in a digital clock or a digital thermometer, display of a state of operation in an audio instrument or an electromagnetic cooker, and panel display in an automobile.

Examples of the lighting apparatus include a lighting apparatuses for indoor lighting or the like, and a backlight of a liquid crystal display apparatus (see, for example, JP 2003-257621 A, JP 2003-277741 A, and JP 2004-119211 A). The backlight is mainly used for enhancing visibility of a display apparatus that is not self-luminous, and is used in a liquid crystal display apparatus, a timepiece, an audio apparatus, an automotive panel, a display panel, a sign, and the like. Particularly, in a backlight for use in a liquid crystal display apparatus, among the liquid crystal display apparatuses, for use in a personal computer in which thickness reduction has been a problem to be solved, in consideration of difficulty in thickness reduction because a conventional type backlight is formed from a fluorescent lamp or a light guide plate, a backlight using the luminescent element according to the present embodiment is characterized by its thinness and lightweightness.

EXAMPLES

Hereinafter, the present invention will be described more specifically by way of Examples, but the present invention is not limited thereto. First, synthesis examples of a polycyclic aromatic compound and a multimer thereof will be described below.

Synthesis Example (1)

Synthesis of Compound (1-1152): 9-([1,1'-biphenyl]-4-yl)-5,12-diphenyl-5,9-dihydro-5,9-diaza-13b-boranaphtho[3,2,1-de]anthracene

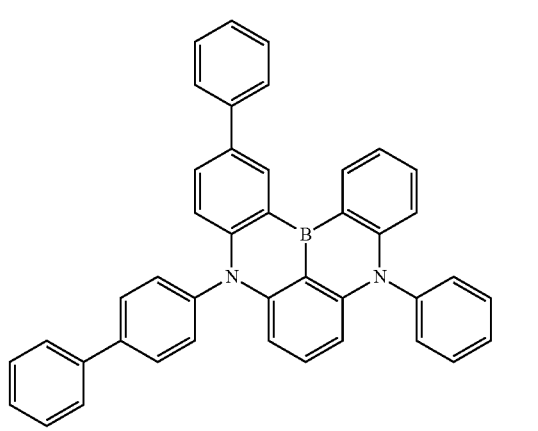

(1-1152)

In a nitrogen atmosphere, a flask containing diphenylamine (37.5 g), 1-bromo-2,3-dichlorobenzene (50.0 g), Pd-132 (Johnson Matthey) (0.8 g), NaOtBu (32.0 g) and xylene (500 ml) was heated and stirred for 4 hours at 80° C., subsequently the temperature of the mixture was increased to 120° C., and the mixture was heated and stirred for three hours. The reaction liquid was cooled to room temperature, subsequently water and ethyl acetate were added thereto, and the mixture was partitioned. Subsequently, purification was performed by silica gel column chromatography (developing liquid: toluene/heptane=1/20 (volume ratio)), and thus 2,3-dichloro-N,N-diphenylaniline (63.0 g) was obtained.

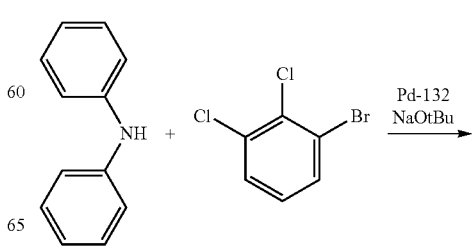

-continued

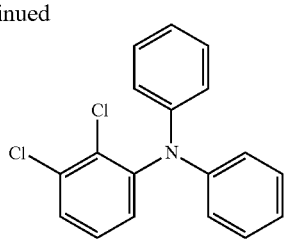

In a nitrogen atmosphere, a flask containing 2,3-dichloro-N,N-diphenylaniline (16.2 g), di([1,1'-biphenyl]-4-yl)amine (15.0 g), Pd-132 (Johnson Matthey) (0.3 g), NaOtBu (6.7 g) and xylene (150 ml) was heated and stirred for one hour at 120° C. The reaction liquid was cooled to room temperature, subsequently water and ethyl acetate were added thereto, and the mixture was partitioned. Subsequently, purification was performed using a silica gel short pass column (developing liquid: heated toluene) and was further washed with a heptane/ethyl acetate=1 (volume ratio) mixed solvent. Thus, $N^1,N^1$-di([1,1'-biphenyl]-4-yl)-2-chloro-$N^3,N^3$-diphenylbenzene-1,3-diamine (22.0 g) was obtained.

A 1.6 M tert-butyllithium pentane solution (37.5 ml) was put into a flask containing $N^1,N^1$-di([1,1'-biphenyl]-4-yl)-2-chloro-$N^3,N^3$-diphenylbenzene-1,3-diamine (22.0 g) and tert-butylbenzene (130 ml) at −30° C. in a nitrogen atmosphere. After completion of dropwise addition, the temperature of the mixture was increased to 60° C., the mixture was stirred for one hour, and then components having boiling points lower than that of tert-butylbenzene were distilled off under reduced pressure. The residue was cooled to −30° C., boron tribromide (6.2 ml) was added thereto, the temperature of the mixture was raised to room temperature, and the mixture was stirred for 0.5 hours. Thereafter, the mixture was cooled again to 0° C., N,N-diisopropylethylamine (12.8 ml) was added thereto, and the mixture was stirred at room temperature until heat generation was settled. Subsequently, the temperature of the mixture was raised to 120° C., and the mixture was heated and stirred for two hours. The reaction liquid was cooled to room temperature, an aqueous solution of sodium acetate that had been cooled in an ice bath and then ethyl acetate were added thereto, and the mixture was partitioned. Subsequently, purification was performed using a silica gel short pass column (developing liquid: heated chlorobenzene). The purification product was washed with refluxed heptane and refluxed ethyl acetate, and then was reprecipitated from chlorobenzene. Thus, a compound (5.1 g) represented by formula (1-1152) was obtained.

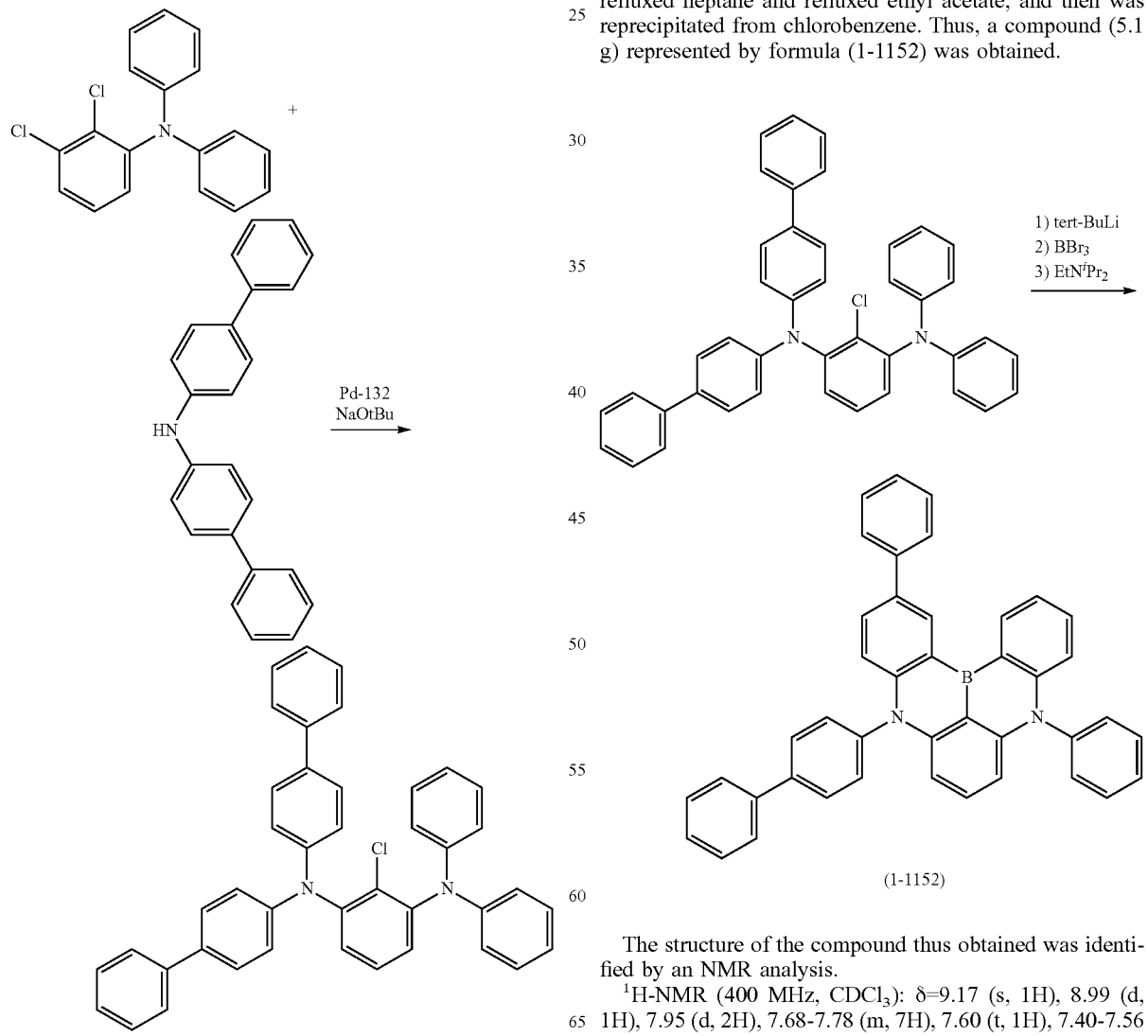

The structure of the compound thus obtained was identified by an NMR analysis.

$^1$H-NMR (400 MHz, CDCl$_3$): δ=9.17 (s, 1H), 8.99 (d, 1H), 7.95 (d, 2H), 7.68-7.78 (m, 7H), 7.60 (t, 1H), 7.40-7.56 (m, 10H), 7.36 (t, 1H), 7.30 (m, 2H), 6.95 (d, 1H), 6.79 (d, 1H), 6.27 (d, 1H), 6.18 (d, 1H).

Synthesis Example (2)

Synthesis of Compound (1-422): 5,9,11,15-tetraphenyl-5,9,11,15-tetrahydro-5,9,11,15-tetraaza-19b,20b-diboranaphtho[3,2,1-de:1',2',3'-jk]pentacene

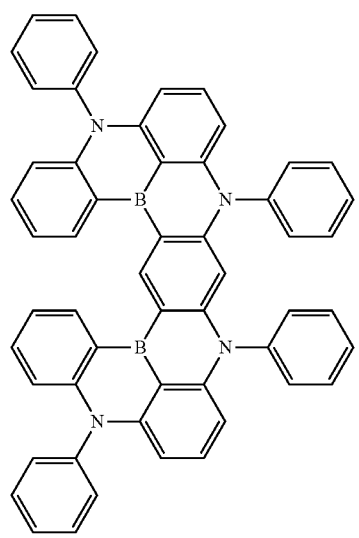

(1-422)

In a nitrogen atmosphere, a flask containing 2,3-dichloro-N,N-diphenylaniline (36.0 g), $N^1,N^3$-diphenylbenzene-1,3-diamine (12.0 g), Pd-132 (Johnson Matthey) (0.3 g), NaOtBu (11.0 g) and xylene (150 ml) was heated and stirred for three hours at 120° C. The reaction liquid was cooled to room temperature, subsequently water and ethyl acetate were added thereto, and the mixture was partitioned. Subsequently, purification was performed by silica gel column chromatography (developing liquid: toluene/heptane mixed solvent). At this time, the proportion of toluene in the developing liquid was gradually increased, and a desired product was thereby eluted. The intended substance was further purified by activated carbon column chromatography (developing liquid: toluene), and thus $N^1,N^{1'}$-(1,3-phenylene)bis(2-chloro-$N^1,N^3,N^3$-triphenylbenzene-1,3-diamine) (22.0 g) was obtained.

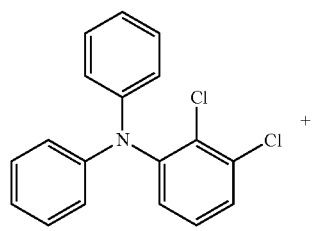

+

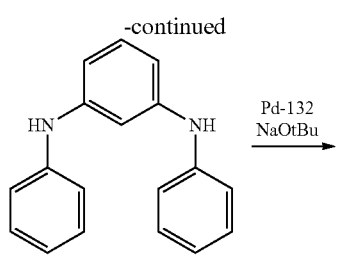

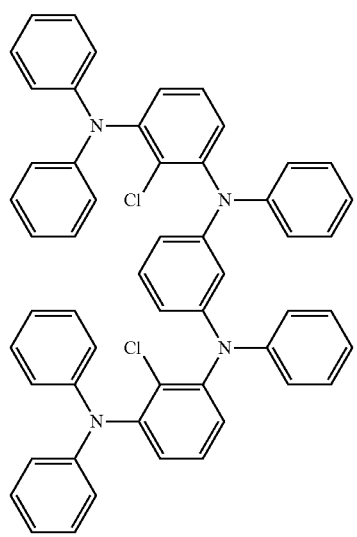

A 1.6 M tert-butyllithium pentane solution (42.0 ml) was put into a flask containing $N^1,N^{1'}$-(1,3-phenylene)bis(2-chloro-$N^1,N^3,N^3$-triphenylbenzene-1,3-diamine) (22.0 g) and tert-butylbenzene (150 ml) at −30° C. in a nitrogen atmosphere. After completion of dropwise addition, the temperature of the mixture was increased to 60° C., the mixture was stirred for 5 hours, and components having boiling points lower than that of tert-butylbenzene were distilled off under reduced pressure. The residue was cooled to −30° C., boron tribromide (7.6 ml) was added thereto, the temperature of the mixture was raised to room temperature, and the mixture was stirred for 0.5 hours. Thereafter, the mixture was cooled again to 0° C., N,N-diisopropylethylamine (18.9 ml) was added thereto, and the mixture was stirred at room temperature until heat generation was settled. Subsequently, the temperature of the mixture was raised to 120° C., and the mixture was heated and stirred for two hours. The reaction liquid was cooled to room temperature, an aqueous solution of sodium acetate that had been cooled in an ice bath was added thereto, and a solid thus precipitated was separated by filtration. A filtrate was partitioned, and the organic layer was purified by silica gel column chromatography (developing liquid: toluene/heptane=1 (volume ratio)). The solvent was distilled off under reduced pressure, a solid thus obtained was dissolved in chlorobenzene, and the solid was reprecipitated by adding ethyl acetate. Thus, a compound (0.6 g) represented by formula (1-422) was obtained.

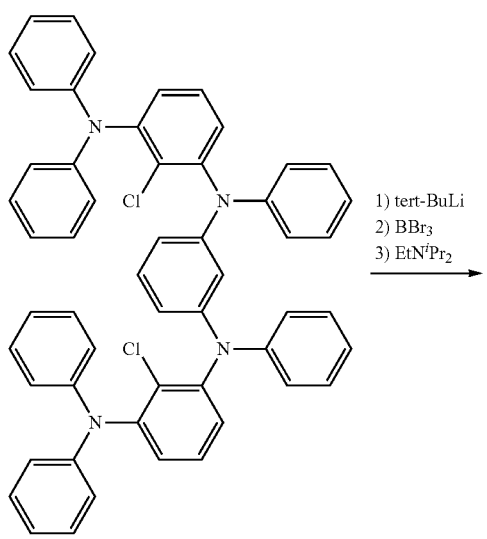

The structure of the compound thus obtained was identified by an NMR analysis.

¹H-NMR (400 MHz, DMSO-d6): δ=10.38 (s, 1H), 9.08 (d, 2H), 7.81 (t, 4H), 7.70 (t, 2H), 7.38-7.60 (m, 14H), 7.30 (t, 2H), 7.18 (d, 4H), 6.74 (d, 2H), 6.07 (d, 2H), 6.02 (d, 2H), 5.78 (s, 1H).

Synthesis Example (3)

Synthesis of Compound (1-2620)

The compound represented by formula (1-422) was precipitated in the purification step of Synthesis Example (2). Thereafter, the filtrate collected by suction filtration was purified by activated carbon column chromatography (developing solution: toluene). Thereafter, the eluate was concentrated, and the precipitated solid was washed with heptane to obtain a solid (0.3 g). It was confirmed by NMR analysis that the solid obtained by this operation was a compound represented by the following formula (1-2620) as a by-product in the above reaction step.

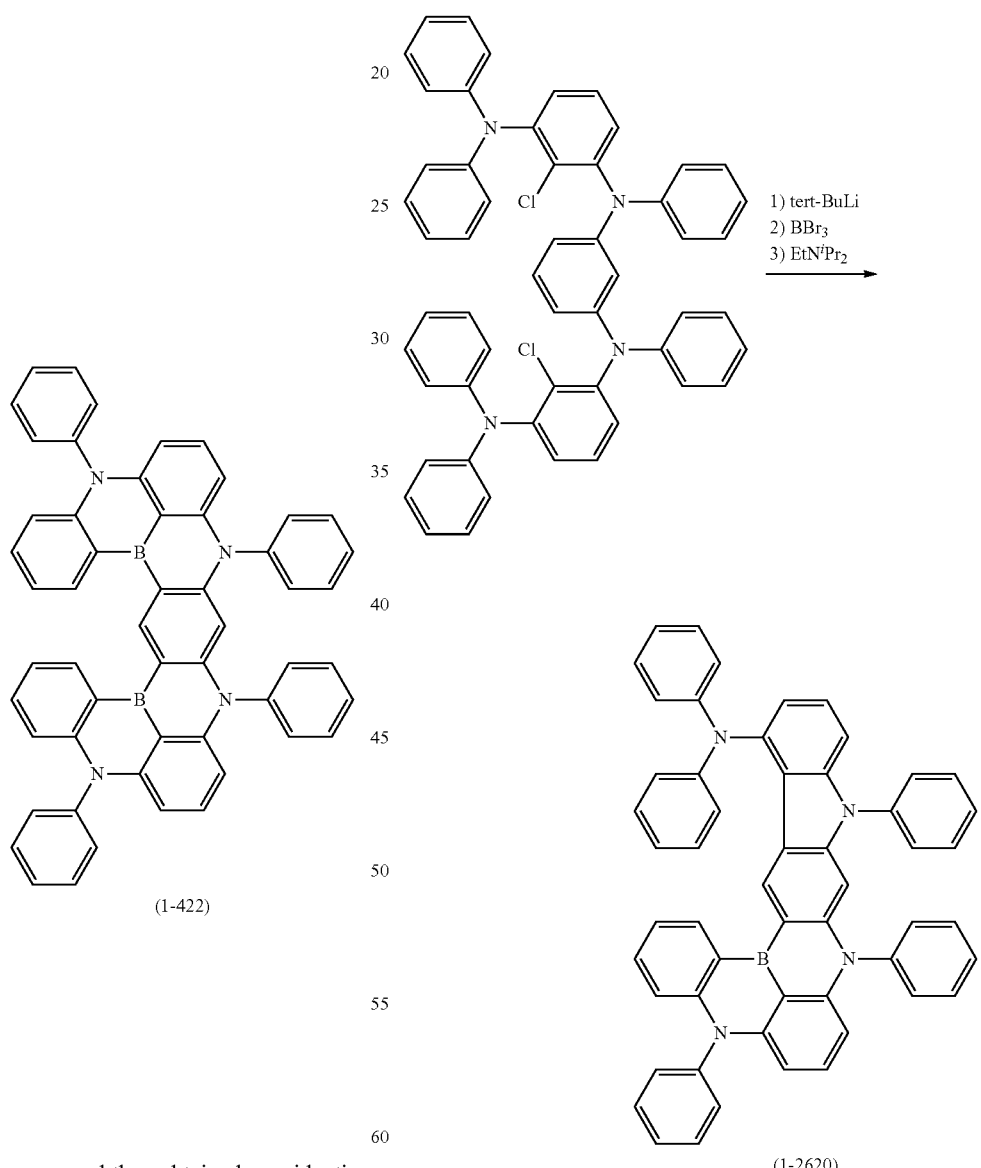

¹H-NMR (400 MHz, DMSO-d6): δ=9.39 (s, 1H), 8.35 (d, 1H), 7.77 (t, 2H), 7.69 (m, 3H), 7.35-7.62 (m, 12H), 7.28 (m, 4H), 7.20 (d, 6H), 7.09 (d, 1H), 7.03 (t, 1H), 6.96 (t, 2H), 6.62 (d, 1H), 6.55 (s, 1H), 6.00 (d, 2H).

Synthesis Example (4)

Synthesis of Compound (1-1159): N¹-(5,9-diphenyl-5,9-dihydro-5,9-diaza-13b-boranaphtho[3,2,1-de]anthracen-3-yl)-N¹,N³,N³-triphenylbenzene-1,3-diamine

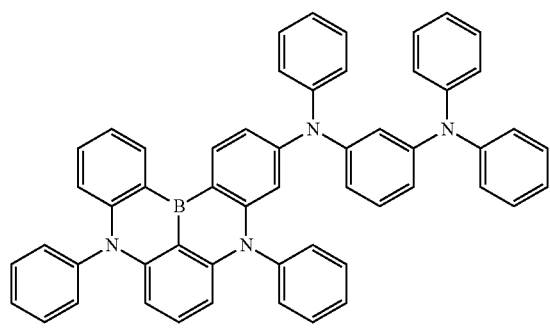

(1-1159)

During the silica gel column chromatographic purification of the compound (0.6 g) represented by formula (1-422), a fraction containing the relevant derivative was fractionated. The fraction was further washed with refluxed heptane, and then was reprecipitated from chlorobenzene/ethyl acetate. Thus, a compound (1.1 g) represented by formula (1-1159) was obtained.

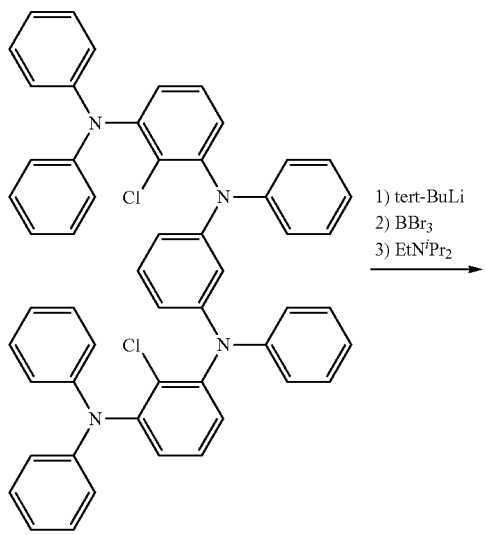

1) tert-BuLi
2) BBr₃
3) EtN$^i$Pr₂
→

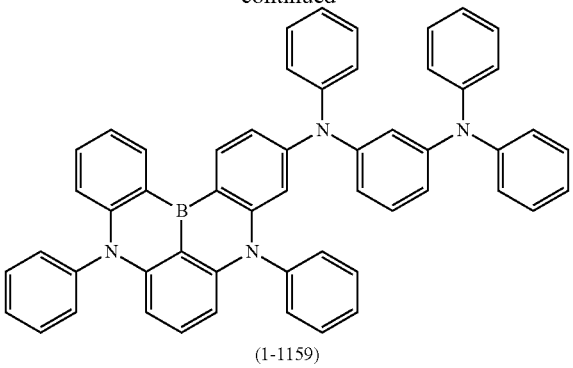

(1-1159)

The structure of the compound thus obtained was identified by an NMR analysis.

¹H-NMR (400 MHz, DMSO-d6): δ=8.78 (d, 1H), 8.66 (d, 1H), 7.69 (t, 2H), 7.59 (t, 1H), 7.59 (t, 2H), 7.49 (m, 2H), 7.40 (d, 2H), 7.22-7.32 (m, 10H), 7.18 (t, 1H), 6.97-7.07 (m, 9H), 6.89 (d, 1H), 6.60-6.70 (m, 4H), 6.11 (s, 1H), 5.96 (m, 2H).

Synthesis Example (5)

Synthesis of Compound (1-2679): 9-([1,1'-biphenyl]-4-yl)-N,N,5,12-tetraphenyl-5,9-dihydro-5,9-diaza-13b-boranaphtho[3,2,1-de]anthracene-3-amine

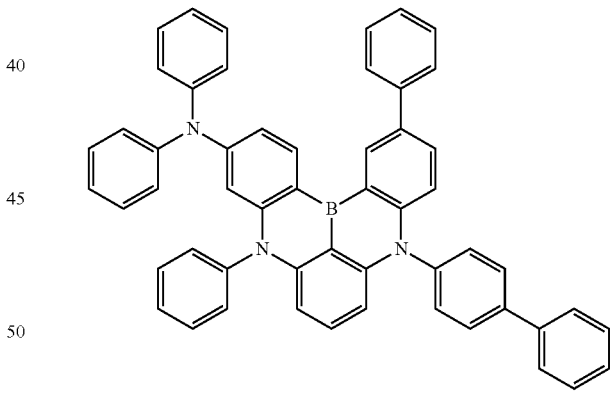

(1-2679)

In a nitrogen atmosphere, a flask containing N¹,N¹,N³-triphenylbenzene-1,3-diamine (51.7 g), 1-bromo-2,3-dichlorobenzene (35.0 g), Pd-132 (0.6 g), NaOtBu (22.4 g), and xylene (350 ml) was heated and stirred for two hours at 90° C. The reaction liquid was cooled to room temperature, subsequently water and ethyl acetate were added thereto, and the mixture was partitioned. Subsequently, purification was performed by silica gel column chromatography (developing liquid: toluene/heptane=5/5 (volume ratio)), and thus N¹-(2,3-dichlorophenyl)-N¹,N³,N³-triphenylbenzene-1,3-diamine (61.8 g) was obtained.

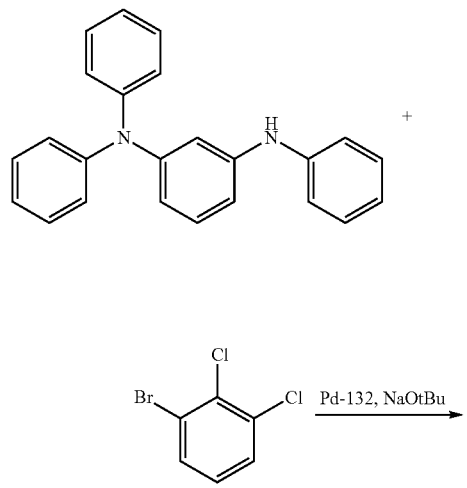

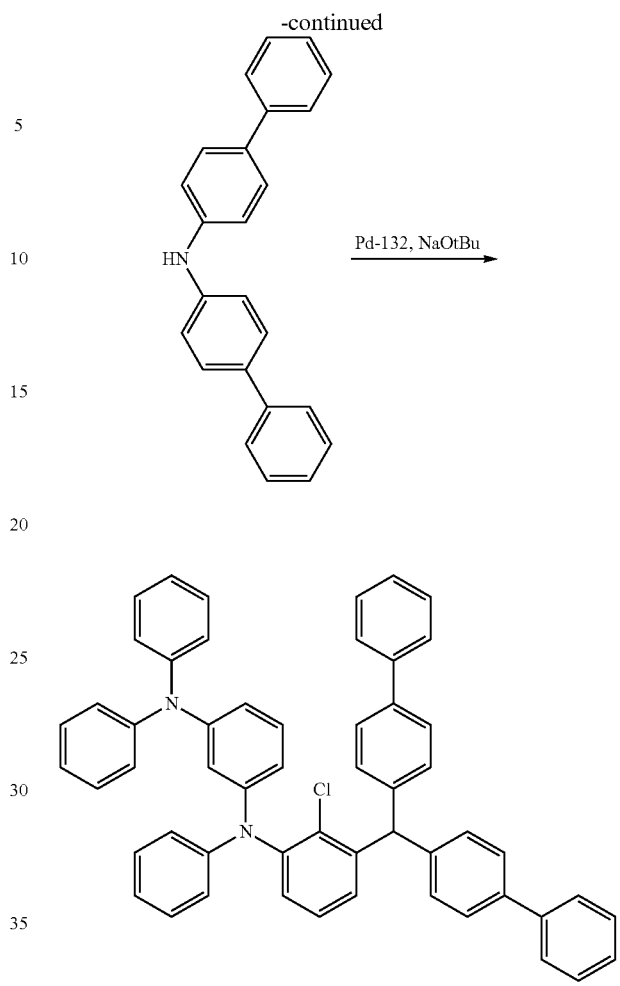

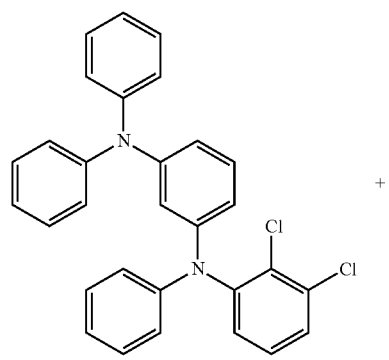

In a nitrogen atmosphere, a flask containing $N^1$-(2,3-dichlorophenyl)-$N^1,N^3,N^3$-triphenylbenzene-1,3-diamine (15.0 g), di([1,1'-biphenyl]-4-yl)amine (10.0 g), Pd-132 (0.2 g), NaOtBu (4.5 g), and xylene (70 ml) was heated and stirred for one hour at 120° C. The reaction liquid was cooled to room temperature, subsequently water and toluene were added thereto, and the mixture was partitioned. Subsequently, purification was performed using a silica gel short pass column (developing liquid: toluene). An oily material thus obtained was reprecipitated with an ethyl acetate/heptane mixed solvent, and thus $N^1,N^1$-di([1,1'-biphenyl]-4-yl)-2chloro-$N^3$-(3-(diphenylamino)phenyl)-$N^3$-phenylbenzene-1,3-diamine (18.5 g) was obtained.

A 1.7 M t-butyllithium pentane solution (27.6 ml) was put into a flask containing $N^1,N^1$-di([1,1'-biphenyl]-4-yl)-2-chloro-$N^3$-(3-(diphenylamino)phenyl)-$N^3$-phenylbenzene-1,3-diamine (18.0 g) and t-butylbenzene (130 ml) in a nitrogen atmosphere, while the flask was cooled in an ice bath. After completion of dropwise addition, the temperature was increased to 60° C., the mixture was stirred for three hours, and then components having boiling points that were lower than that of t-butylbenzene were distilled off under reduced pressure. The residue was cooled to −50° C., boron tribromide (4.5 ml) was added thereto, the temperature of the mixture was raised to room temperature, and the mixture was stirred for 0.5 hours. Thereafter, the mixture was cooled again in an ice bath, and N,N-diisopropylethylamine (8.2 ml) was added thereto. The mixture was stirred at room temperature until heat generation was settled, subsequently the temperature of the mixture was raised to 120° C., and the mixture was heated and stirred for one hour. The reaction liquid was cooled to room temperature, an aqueous solution of sodium acetate that had been cooled in an ice bath and then ethyl acetate were added thereto, and the mixture was partitioned. Subsequently, dissolution in hot chlorobenzene was performed, and purification was performed using a silica gel short pass column (developing liquid: hot toluene). The purification product was further recrystallized from chlorobenzene, and thus a compound (3.0 g) represented by formula (1-2679) was obtained.

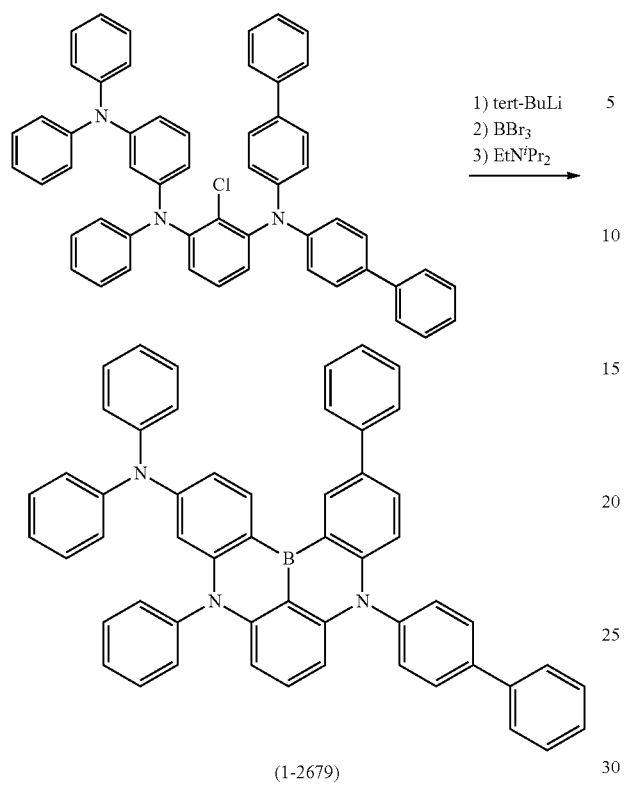

(1-2679)

The structure of the compound thus obtained was identified by an NMR analysis.

$^1$H-NMR (400 MHz, CDCl$_3$): δ=9.09 (m, 1H), 8.79 (d, 1H), 7.93 (d, 2H), 7.75 (d, 2H), 7.72 (d, 2H), 7.67 (m, 1H), 7.52 (t, 2H), 7.40-7.50 (m, 7H), 7.27-7.38 (m, 2H), 7.19-7.26 (m, 7H), 7.11 (m, 4H), 7.03 (t, 2H), 6.96 (dd, 1H), 6.90 (d, 1H), 6.21 (m, 2H), 6.12 (d, 1H).

Synthesis Example (6)

Synthesis of Compound (1-2676): 9-([1,1'-biphenyl]-3-yl)-N,N,5,11-tetraphenyl-5,9-dihydro-5,9-diaza-13b-boranaphtho[3,2,1-de]anthracene-3-amine (1-2676)

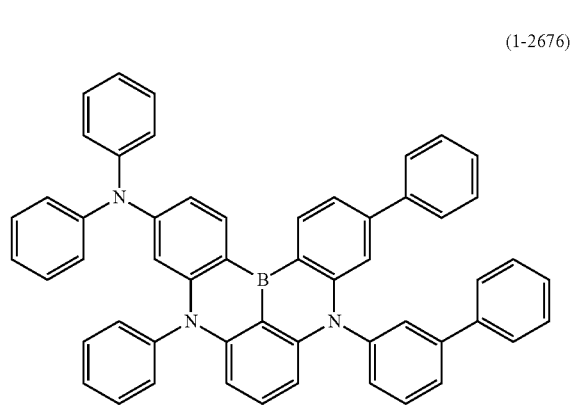 [SMILES: c1ccc(-c2cccc(N3c4cc(-c5ccccc5)ccc4B4c5ccc(N(c6ccccc6)c6ccccc6)cc5N(c5ccccc5)c5cccc3c54)c2)cc1]

In a nitrogen atmosphere, a flask containing [1,1'-biphenyl]-3-amine (19.0 g), 4-bromo-1,1'-biphenyl (25.0 g), Pd-132 (0.8 g), NaOtBu (15.5 g) and xylene (200 ml) was heated and stirred for six hours at 120° C. The reaction liquid was cooled to room temperature, subsequently water and ethyl acetate were added thereto, and the mixture was partitioned. Subsequently, purification was performed by silica gel column chromatography (developing liquid: toluene/heptane=5/5 (volume ratio)). A solid obtained by distilling off the solvent under reduced pressure was washed with heptane, and thus di([1,1'-biphenyl]-3-yl)amine (30.0 g) was obtained.

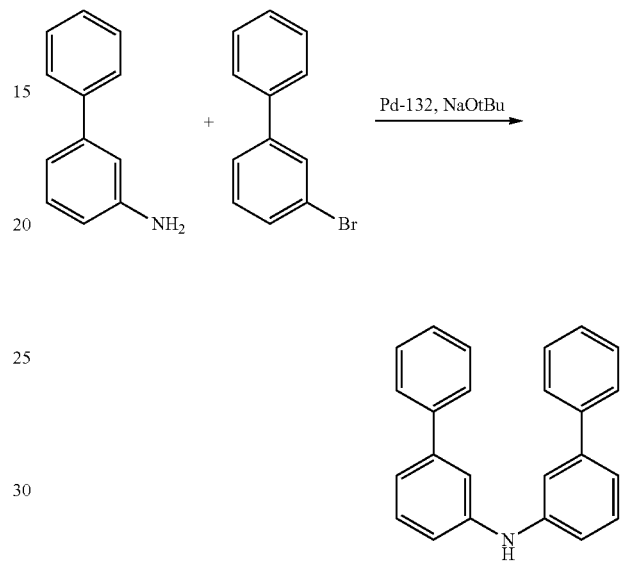

In a nitrogen atmosphere, a flask containing N$^1$-(2,3-dichlorophenyl)-N$^1$,N$^3$,N$^3$-triphenylbenzene-1,3-diamine (15.0 g), di([1,1'-biphenyl]-3-yl)amine (10.0 g), Pd-132 (0.2 g), NaOtBu (4.5 g), and xylene (70 ml) was heated and stirred for one hour at 120° C. The reaction liquid was cooled to room temperature, subsequently water and ethyl acetate were added thereto, and the mixture was partitioned. Subsequently, purification was performed by silica gel column chromatography (developing liquid: toluene/heptane=5/5 (volume ratio)). A fraction containing a desired product was reprecipitated by distilling off the solvent under reduced pressure, and thus N$^1$,N$^1$-di([1,1'-biphenyl]-3-yl)-2-chloro-N$^3$-(3-(diphenylamino)phenyl)-N$^3$-phenylbenzene-1,3-diamine (20.3 g) was obtained.

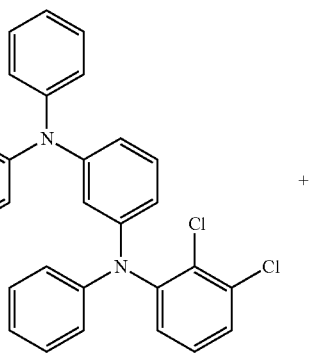

+

-continued

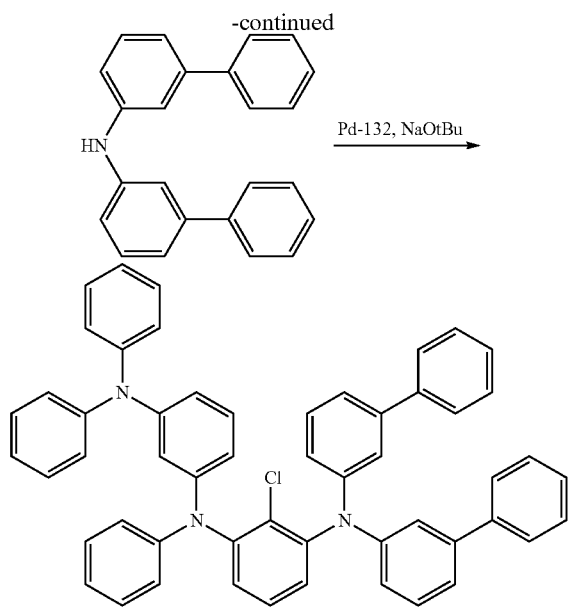

A 1.6 M t-butyllithium pentane solution (32.6 ml) was put into a flask containing $N^1,N^1$-di([1,1'-biphenyl]-3-yl)-2-chloro-$N^3$-(3-(diphenylamino)phenyl)-$N^3$-phenylbenzene-1,3-diamine (20.0 g) and t-butylbenzene (150 ml) in a nitrogen atmosphere, while the flask was cooled in an ice bath. After completion of dropwise addition, the temperature was increased to 60° C., the mixture was stirred for two hours, and then the components having boiling points that were lower than that of t-butylbenzene were distilled off under reduced pressure. The residue was cooled to −50° C., boron tribromide (5.0 ml) was added thereto, the temperature of the mixture was raised to room temperature, and the mixture was stirred for 0.5 hours. Thereafter, the mixture was cooled again in an ice bath, and N,N-diisopropylethylamine (9.0 ml) was added thereto. The mixture was stirred at room temperature until heat generation was settled, subsequently the temperature was raised to 120° C., and the mixture was heated and stirred for 1.5 hours. The reaction liquid was cooled to room temperature, an aqueous solution of sodium acetate that had been cooled in an ice bath and then ethyl acetate were added thereto, and the mixture was partitioned. Subsequently, purification was performed by silica gel column chromatography (developing liquid: toluene/heptane=5/5). Furthermore, the purification product was reprecipitated using a toluene/heptane mixed solvent and a chlorobenzene/ethyl acetate mixed solvent, and thus a compound (5.0 g) represented by formula (1-2676) was obtained.

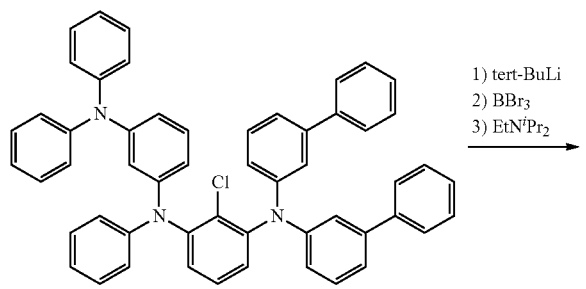

-continued

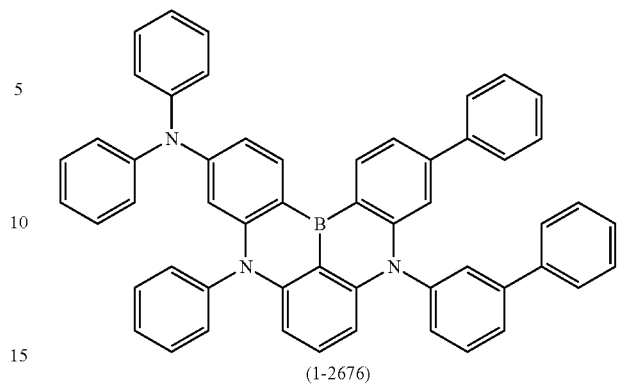

(1-2676)

The structure of the compound thus obtained was identified by an NMR analysis.

$^1$H-NMR (400 MHz, CDCl$_3$): δ=8.93 (d, 1H), 8.77 (d, 1H), 7.84 (m, 1H), 7.77 (t, 1H), 7.68 (m, 3H), 7.33-7.50 (m, 12H), 7.30 (t, 1H), 7.22 (m, 7H), 7.11 (m, 4H), 7.03 (m, 3H), 6.97 (dd, 1H), 6.20 (m, 2H), 6.11 (d, 1H)).

Synthesis Example (7)

Synthesis of Compound (1-411): 5,9-dimethyl-5,9-dihydro-5,9-diaza-13b-boranaphtho[3,2,1-de]anthracene (1-411)

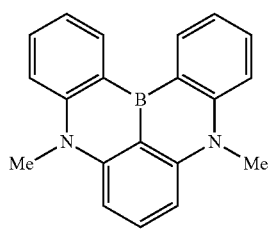

A 1.6 M n-butyllithium hexane solution (25.0 ml) was added to a t-butylbenzene (20 ml) solution of $N^1,N^3$-dimethyl-$N^1,N^3$-diphenylbenzene-1,3-diamine (2.9 g) at 0° C. in a nitrogen atmosphere. The temperature of the mixture was increased to 100° C., hexane was distilled off, and the residue was further heated and stirred for 21 hours. The mixture was cooled to −40° C., THF (10 ml) was added thereto, and then boron tribromide (1.9 ml) was added thereto. The temperature of the mixture was increased to room temperature over one hour, and then the mixture was cooled to 0° C. N,N-diisopropylamine (5.2 ml) was added thereto, and the mixture was filtered using a Florisil short pass column. The solvent was distilled off under reduced pressure, and then the residue was washed with acetonitrile. Thus, a compound (0.96 g) represented by formula (1-411) was obtained as a yellowish green solid.

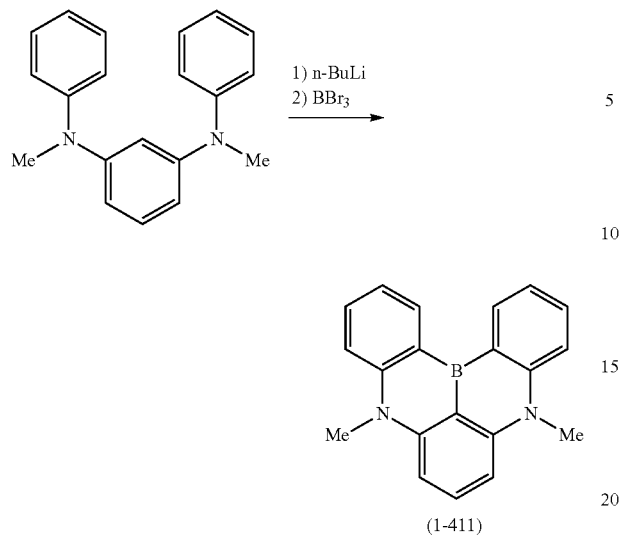

The structure of the compound thus obtained was identified by an NMR analysis.

$^1$H-NMR (400 MHz, CDCl$_3$): δ=8.73 (dd, 2H), 7.75 (t, 1H), 7.67 (m, 2H), 7.57 (dd, 2H), 7.29 (m, 2H), 7.00 (d, 2H), 3.91 (s, 6H).

Synthesis Example (8)

Synthesis of Compound (1-447): N,N,5,9-tetraphenyl-5,9-dihydro-5,9-diaza-13b-boranaphtho[3,2,1-de]anthracen-7-amine

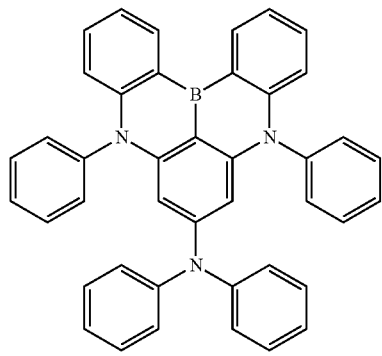
(1-447)

In a nitrogen atmosphere, boron tribromide (3.78 ml, 40 mmol) was introduced at room temperature into a flask containing N$^1$,N$^1$,N$^3$,N$^3$,N$^5$,N$^5$-hexaphenyl-1,3,5-benzenetriamine (11.6 g, 20 mmol) and o-dichlorobenzene (120 ml), and then the mixture was heated and stirred for 48 hours at 170° C. Subsequently, the reaction solution was distilled off at 60° C. under reduced pressure. The reaction solution was filtered using a Florisil short pass column, and the solvent was distilled off under reduced pressure. Thus, a crude product was obtained. The crude product was washed using hexane, and thus a compound (11.0 g) represented by formula (1-447) was obtained as a yellow solid.

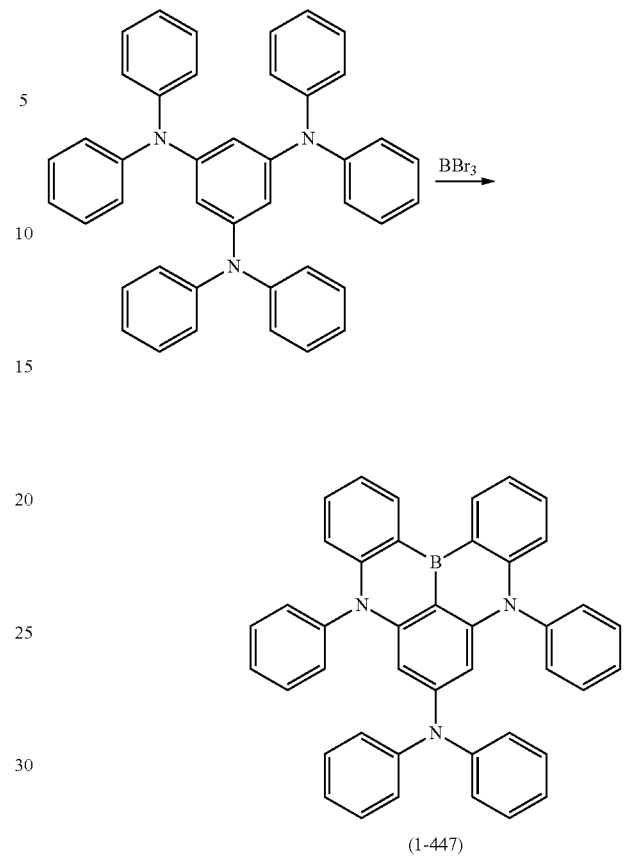

The structure of the compound thus obtained was identified by an NMR analysis.

$^1$H-NMR (400 MHz, CDCl$_3$): δ=8.89 (dd, 2H), 7.47 (t, 4H), 7.39 (m, 4H), 7.24 (m, 6H), 7.10 (m, 4H), 6.94 (m, 6H), 6.72 (d, 2H), 5.22 (m, 2H).

Furthermore, boron tribromide (3.78 mL, 40 mmol) was added to N$^1$,N$^1$,N$^3$,N$^3$,N$^5$,N$^5$-hexaphenylbenzene-1,3,5-triamine (11.6 g, 20 mmol) and ortho-dichlorobenzene (ODCB, 120 mL) at room temperature in a nitrogen atmosphere, and then the mixture was heated and stirred for 48 hours at 170° C. Subsequently, the reaction solution was distilled off at 60° C. under reduced pressure. The reaction solution was filtered using a Florisil short pass column, the solvent was distilled off under reduced pressure, and a crude product was obtained. The crude product was washed using hexane, and thus a compound represented by formula (1-447) was obtained as a yellow solid (11.0 g, yield 94%).

The structure of the compound thus obtained was identified by an NMR analysis.

$^1$H NMR (400 MHz, CDCl$_3$) δ 5.62 (brs, 2H), 6.71 (d, 2H), 6.90-6.93 (m, 6H), 7.05-7.09 (m, 4H), 7.20-7.27 (m, 6H), 7.33-7.38 (m, 4H), 7.44-7.48 (m, 4H), 8.90 (dd, 2H)

$^{13}$C NMR (101 MHz, CDCl$_3$) δ 98.4 (2C), 116.8 (2C), 119.7 (2C), 123.5 (2C), 125.6 (2C), 128.1 (2C), 128.8 (4C), 130.2 (4C), 130.4 (2C), 130.7 (4C), 134.8 (2C), 142.1 (2C), 146.6 (2C), 147.7 (2C), 147.8 (2C), 151.1

Synthesis Example (9)

Synthesis of Compound (1-401): 5,9-diphethyl-5,9-dihydro-5,9-diaza-13b-boranaphtho[3,2,1-de]anthracene

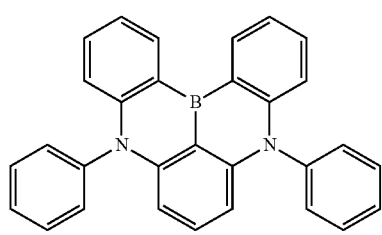

(1-401)

In a nitrogen atmosphere, a flask containing diphenylamine (66.0 g), 1-bromo-2,3-dichlorobenzene (40.0 g), Pd-132 (Johnson Matthey) (1.3 g), NaOtBu (43.0 g) and xylene (400 ml) was heated and stirred for 2 hours at 80° C. Subsequently, the temperature of the mixture was increased to 120° C., and the mixture was heated and stirred for three hours. The reaction liquid was cooled to room temperature, and then a solid precipitated by adding water and ethyl acetate was collected by suction filtration. Subsequently, the solid was purified using a silica gel short pass column (developing liquid: heated toluene). The solvent was distilled off under reduced pressure, and a solid thus obtained was washed with heptane. Thus, 2-chloro-$N^1,N^1,N^3,N^3$-tetraphenylbenzene-1,3-diamine (65.0 g) was obtained.

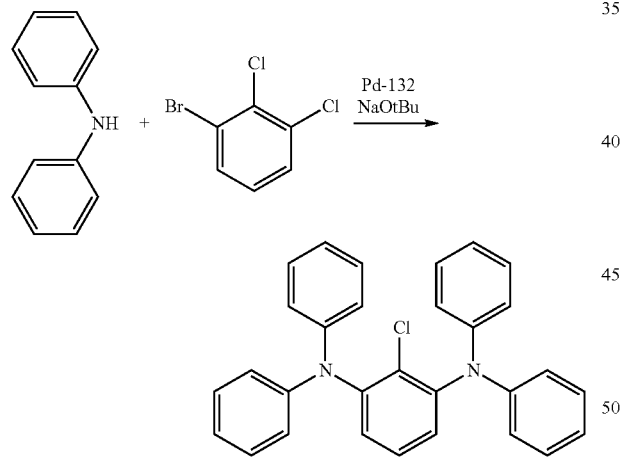

A 1.7 M tert-butyllithium pentane solution (27.6 ml) was introduced into a flask containing 2-chloro-$N^1,N^1,N^3,N^3$-tetraphenylbenzene-1,3-diamine (20.0 g) and tert-butylbenzene (150 ml), at −30° C. in a nitrogen atmosphere. After completion of dropwise addition, the temperature of the mixture was increased to 60° C., the mixture was stirred for 2 hours, and then components having boiling points lower than that of tert-butylbenzene were distilled off under reduced pressure. The mixture was cooled to −30° C., boron tribromide (5.1 ml) was added thereto, the temperature of the mixture was increased to room temperature, and the mixture was stirred for 0.5 hours. Thereafter, the mixture was cooled again to 0° C., N,N-diisopropylethylamine (15.6 ml) was added thereto, and the mixture was stirred at room temperature until heat generation was settled. Subsequently, the temperature of the mixture was increased to 120° C., and the mixture was heated and stirred for three hours. The reaction liquid was cooled to room temperature, an aqueous solution of sodium acetate that had been cooled in an ice bath and then heptane were added thereto, and the mixture was partitioned. Subsequently, purification was performed using a silica gel short pass column (additive liquid: toluene), and then a solid obtained by distilling off the solvent under reduced pressure was dissolved in toluene and reprecipitated by adding heptane thereto. Thus, a compound (6.0 g) represented by formula (1-401) was obtained.

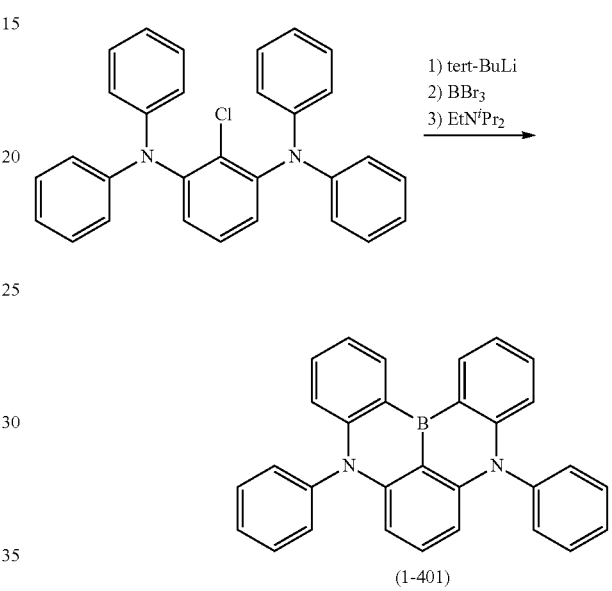

(1-401)

The structure of the compound thus obtained was identified by an NMR analysis.

$^1$H-NMR (400 MHz, CDCl$_3$): δ=8.94 (d, 2H), 7.70 (t, 4H), 7.60 (t, 2H), 7.42 (t, 2H), 7.38 (d, 4H), 7.26 (m, 3H), 6.76 (d, 2H), 6.14 (d, 2H).

Synthesis Examples (10) and (11)

Synthesis of Compound (1-2657): 3,7-diphenyl-3,7-dihydro-3,7-diaza-11b-boranaphtho[3,2,1-no]tetraphene

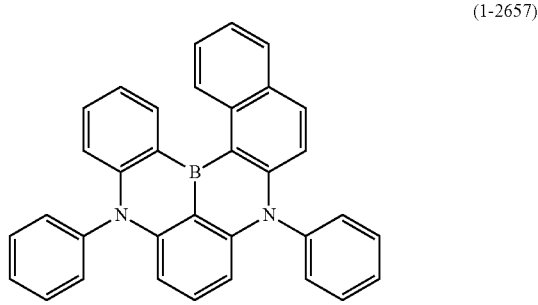 [SMILES: c1ccc(N2c3ccccc3B3c4c2cccc4N(c2ccccc2)c2ccc4ccccc4c23)cc1]

(1-2657)

Synthesis of Compound (1-2699): 9-(naphthalen-2-yl)-5-phenyl-5,9-dihydro-5,9-diaza-13b-boranaphtho[3,2,1-de]anthracene

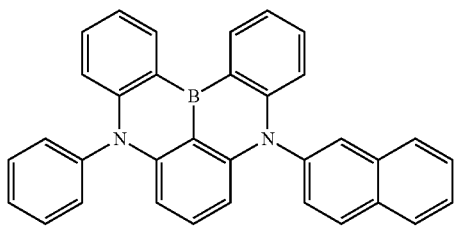

(1-2699)

In a nitrogen atmosphere, a flask containing 2,3-dichloro-N,N-diphenylaniline (15.0 g), N-phenylnaphthalene-1-amine (10.0 g), Pd-132 (0.3 g), NaOtBu (6.9 g) and xylene (100 ml) was heated and stirred for one hour at 120° C. The reaction liquid was cooled to room temperature, subsequently water and ethyl acetate were added thereto, and the mixture was partitioned. Subsequently, purification was performed using a silica gel short pass column (developing liquid: toluene/heptane=1/1 (volume ratio)), and was further reprecipitated with a heptane solvent. Thus, 2-chloro-N$^1$-(naphthalen-2-yl)-N$^1$,N$^3$,N$^3$-triphenylbenzene-1,3-diamine (18.0 g) was obtained.

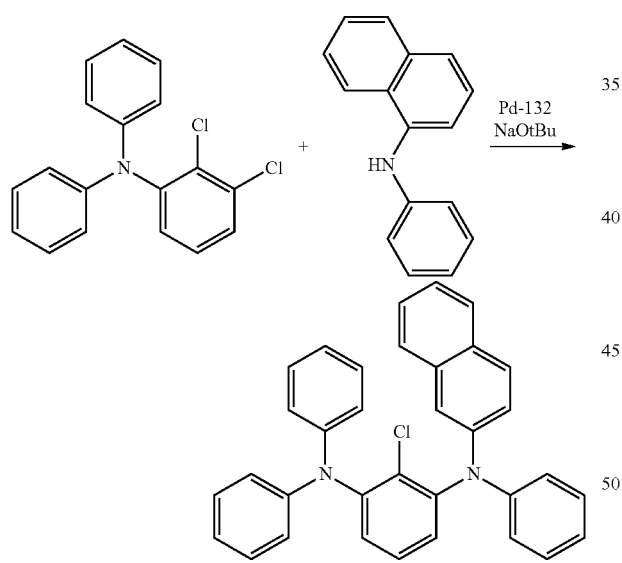

A 1.6 M t-butyllithium pentane solution (45.3 ml) was introduced into a flask containing 2-chloro-N$^1$-(naphthalen-2-yl)-N$^1$,N$^3$,N$^3$-triphenylbenzene-1,3-diamine (18.0 g) and t-butylbenzene (150 ml) in a nitrogen atmosphere, while the flask was cooled in an ice bath. After completion of dropwise addition, the temperature was increased to 60° C., the mixture was stirred for two hours, and then the components having boiling points that were lower than that of t-butylbenzene were distilled off under reduced pressure. The residue was cooled to −50° C., boron tribromide (6.8 ml) was added thereto, the temperature of the mixture was increased to room temperature, and the mixture was stirred for 0.5 hours. Thereafter, the mixture was cooled again in an ice bath, and N,N-diisopropylethylamine (12.5 ml) was added thereto. The mixture was stirred at room temperature until heat generation was settled, subsequently the temperature of the mixture was raised to 120° C., and the mixture was heated and stirred for one hour. The reaction liquid was cooled to room temperature, an aqueous solution of sodium acetate that had been cooled in an ice bath and then ethyl acetate were added thereto, and the mixture was partitioned. Subsequently, purification was performed by silica gel column chromatography (developing liquid: toluene/heptane=3/7). The purification product was further washed with hot heptane, and then was reprecipitated with a toluene/ethyl acetate mixed solution. Thus, a compound (3.2 g) represented by formula (1-2657) was obtained. Furthermore, this reprecipitated liquid was purified by activated carbon column chromatography (developing liquid: toluene/heptane=1/1), and then was reprecipitated with a heptane/ethyl acetate mixed solvent. Thus, a compound (0.1 g) represented by formula (1-2699) was obtained.

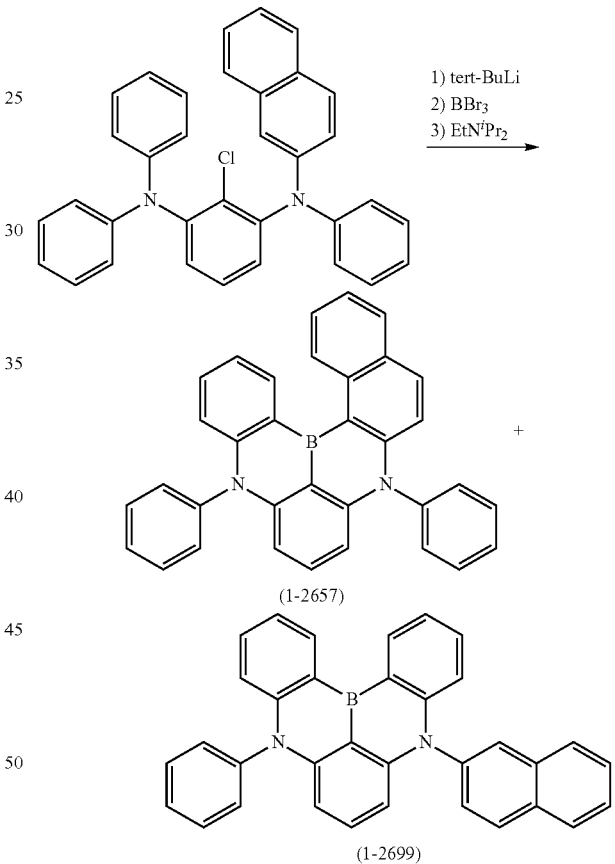

The structure of the compound (1-2657) thus obtained was identified by an NMR analysis.

$^1$H-NMR (400 MHz, CDCl$_3$): δ=8.94 (m, 1H), 8.50 (d, 1H), 7.80 (m, 1H), 7.77 (d, 1H), 7.70 (m, 4H), 7.61 (m, 2H), 7.46 (m, 2H), 7.35-7.44 (m, 5H), 7.25 (m, 1H), 7.03 (t, 1H), 6.95 (d, 1H), 6.77 (d, 1H), 6.23 (d, 1H), 6.18 (d, 1H).

The structure of the compound (1-2699) thus obtained was identified by an NMR analysis.

$^1$H-NMR (400 MHz, CDCl$_3$): δ=8.97 (m, 2H), 8.18 (d, 1H), 8.03 (d, 1H), 7.92 (m, 2H), 7.70 (t, 2H), 7.56-66 (m, 3H), 7.36-48 (m, 5H), 7.20-7.32 (m, 3H), 6.78 (t, 2H), 6.15 (m, 2H).

Synthesis Example (12)

Synthesis of Compound (1-2680): $N^3,N^3,N^{11},N^{11},5,9$-hexaphenyl-5,9-diaza-13b-boranaphtho[3,2,1-de]anthracene-3,11-diamine (1-2680)

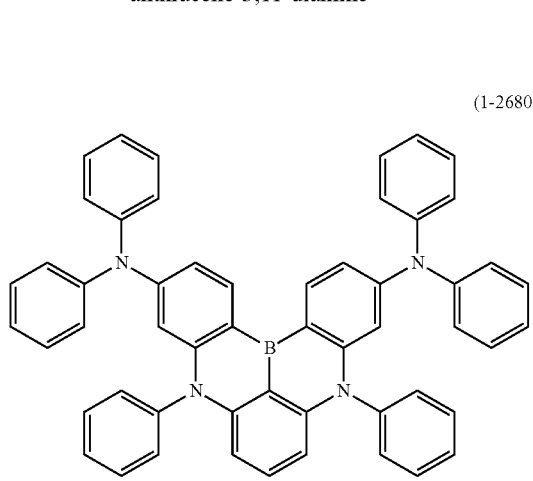

In a nitrogen atmosphere, a flask containing 3-nitroaniline (25.0 g), iodobenzene (81.0 g), copper iodide (3.5 g), potassium carbonate (100.0 g) and ortho-dichlorobenzene (250 ml) was heated and stirred for 14 hours at a reflux temperature. The reaction liquid was cooled to room temperature, subsequently aqueous ammonia was added thereto, and the mixture was partitioned. Subsequently, purification was performed by silica gel column chromatography (developing liquid: toluene/heptane=3/7 (volume ratio)), and thus 3-nitro-N,N-diphenylaniline (44.0 g) was obtained.

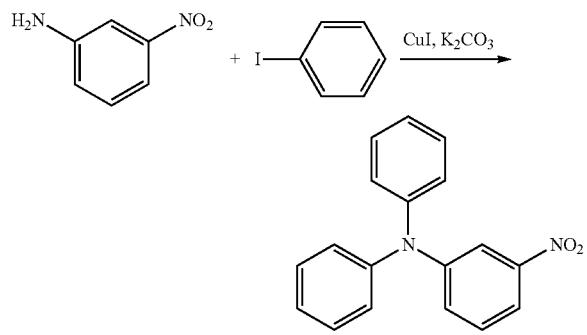

In a nitrogen atmosphere, acetic acid that had been cooled in an ice bath was added to the product, and the mixture was stirred. 3-Nitro-N,N-diphenylaniline (44.0 g) was added to this solution in divided portions such that the reaction temperature would not noticeably increase. After completion of the addition, the mixture was stirred for 30 minutes at room temperature, and any loss of the raw material was checked. After completion of the reaction, a supernatant was collected by decantation and was neutralized with sodium carbonate, and the resultant was extracted with ethyl acetate. Subsequently, the resultant was purified by silica gel column chromatography (developing liquid: toluene/heptane=9/1 (volume ratio)). A fraction containing an intended product was reprecipitated by distilling off the solvent under reduced pressure and adding heptane thereto. Thus, $N^1,N^1$-diphenylbenzene-1,3-diamine (36.0 g) was obtained.

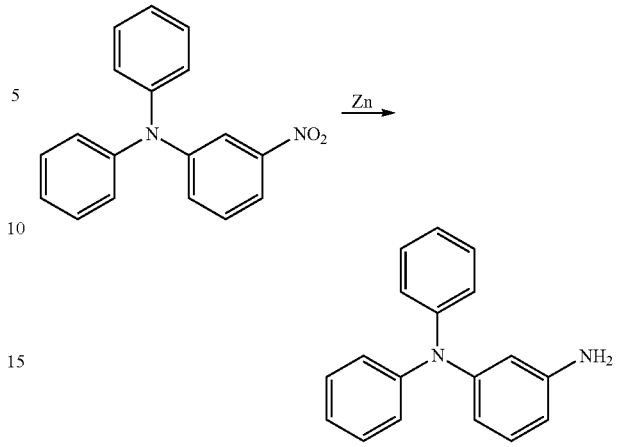

In a nitrogen atmosphere, a flask containing $N^1,N^1$-diphenylbenzene-1,3-diamine (60.0 g), Pd-132 (1.3 g), NaOtBu (33.5 g) and xylene (300 ml) was heated and stirred at 120° C. To this solution, a xylene (50 ml) solution of bromobenzene (36.2 g) was slowly added dropwise, and after completion of the dropwise addition, the mixture was heated and stirred for one hour. The reaction liquid was cooled to room temperature, subsequently water and ethyl acetate were added thereto, and the mixture was partitioned. Subsequently, purification was performed by silica gel column chromatography (developing liquid: toluene/heptane=5/5 (volume ratio)), and thus $N^1,N^1,N^3$-triphenylbenzene-1,3-diamine (73.0 g) was obtained.

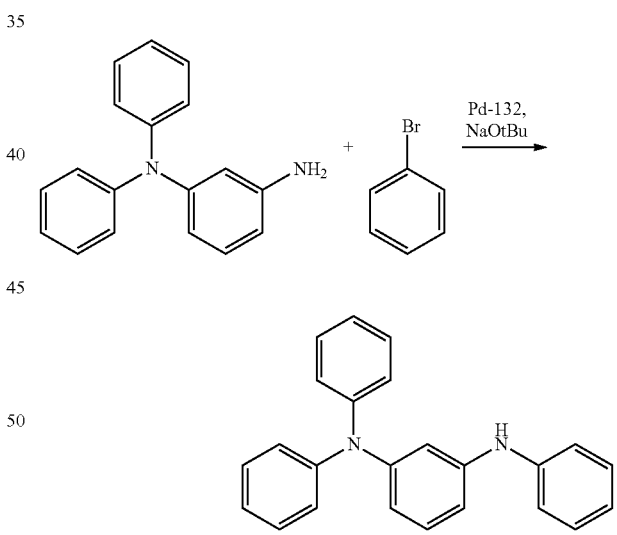

In a nitrogen atmosphere, a flask containing $N^1,N^1,N^3$-triphenylbenzene-1,3-diamine (20.0 g), 1-bromo-2,3-dichlorobenzene (6.4 g), Pd-132 (0.2 g), NaOtBu (6.8 g), and xylene (70 ml) was heated and stirred for two hours at 120° C. The reaction liquid was cooled to room temperature, subsequently water and ethyl acetate were added thereto, and the mixture was partitioned. Subsequently, purification was performed by silica gel column chromatography (developing liquid: toluene/heptane=4/6 (volume ratio)), and thus $N^1,N^{1'}$-(2-chloro-1,3-phenylene)bis($N^1,N^3,N^3$-triphenylbenzene-1,3-diamine) (15.0 g) was obtained.

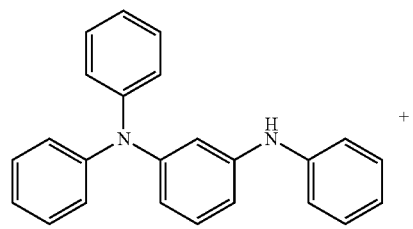

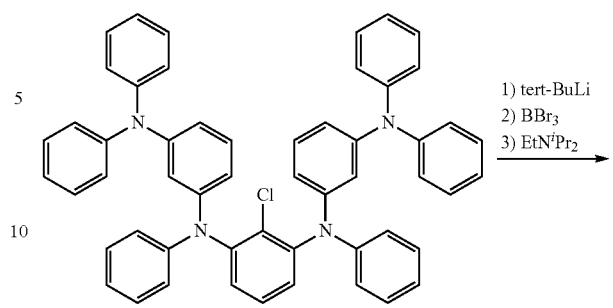

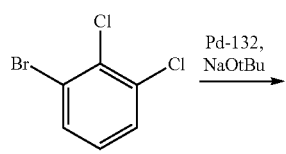

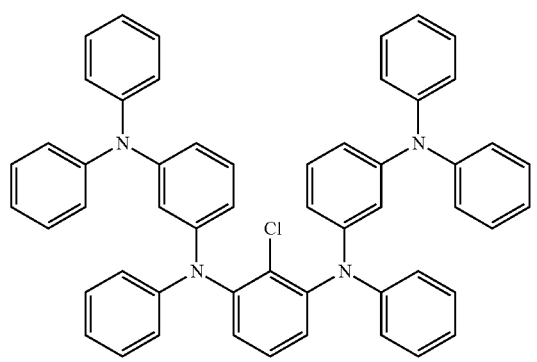

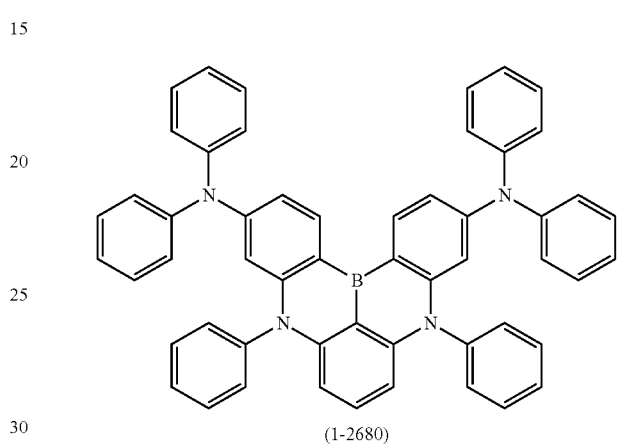

(1-2680)

A 1.7 M t-butyllithium pentane solution (18.1 ml) was introduced into a flask containing $N^1,N^{1'}$-(2-chloro-1,3-phenylene)bis($N^1,N^3,N^3$-triphenylbenzene-1,3-diamine) (12.0 g) and t-butylbenzene (100 ml) in a nitrogen atmosphere, while the flask was cooled in an ice bath. After completion of dropwise addition, the temperature was increased to 60° C., the mixture was stirred for two hours, and then the components having boiling points that were lower than that of t-butylbenzene were distilled off under reduced pressure. The residue was cooled to −50° C., boron tribromide (2.9 ml) was added thereto, the temperature of the mixture was increased to room temperature, and the mixture was stirred for 0.5 hours. Thereafter, the mixture was cooled again in an ice bath, and N,N-diisopropylethylamine (5.4 ml) was added thereto. The mixture was stirred at room temperature until heat generation was settled, subsequently the temperature of the mixture was increased to 120° C., and the mixture was heated and stirred for three hours. The reaction liquid was cooled to room temperature, and an aqueous solution of sodium acetate that had been cooled in an ice bath and then ethyl acetate were added to the reaction liquid. An insoluble solid was separated by filtration, and then the liquid was partitioned. Subsequently, purification was performed by silica gel column chromatography (developing liquid: toluene/heptane=5/5). The purification product was further washed with hot heptane and ethyl acetate, and then was reprecipitated with a toluene/ethyl acetate mixed solvent. Thus, a compound (2.0 g) represented by formula (1-2680) was obtained.

The structure of the compound thus obtained was identified by an NMR analysis.

$^1$H-NMR (400 MHz, CDCl$_3$): δ=8.65 (d, 2H), 7.44 (t, 4H), 7.33 (t, 2H), 7.20 (m, 12H), 7.13 (t, 1H), 7.08 (m, 8H), 7.00 (t, 4H), 6.89 (dd, 2H), 6.16 (m, 2H), 6.03 (d, 2H).

Synthesis Examples (13) and (14)

Synthesis of Compound (1-2681): N,N,5,9,11-pentaphenyl-9,11-dihydro-5H-5,9,1-triaza-16b-boraindeno[2,1-b]naphtho[1,2,3-fg]anthracene-3-amine (1-2681)

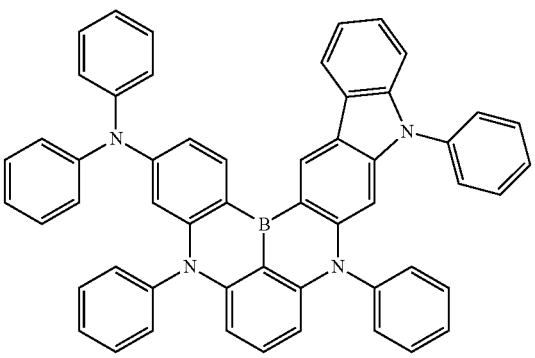

Synthesis of Compound (1-2682): N,N,5-triphenyl-9-(9-phenyl-9H-carbazol-2-yl)-5,9-dihydro-5H-5,9-diaza-13b-boranaphtho[3,2,1-de]anthracene-3-amine

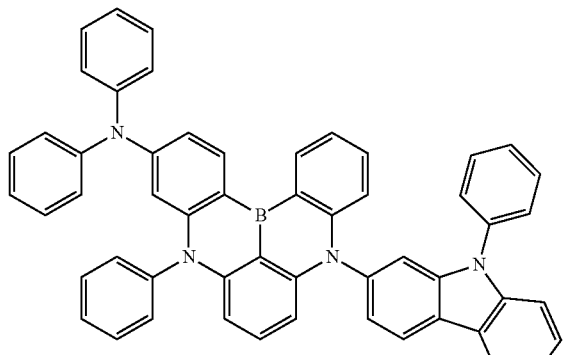

(1-2682)

In a nitrogen atmosphere, a flask containing 2-bromo-9-phenyl-9H-carbazole (10.0 g), aniline (3.5 g), Pd-132 (0.2 g), NaOtBu (4.5 g) and xylene (100 ml) was heated and stirred for four hours at 120° C. The reaction liquid was cooled to room temperature, subsequently water and ethyl acetate were added thereto, and the mixture was partitioned. The organic layer was further washed with dilute hydrochloric acid, and unreacted aniline was removed. Subsequently, the resultant was purified by silica gel column chromatography (developing liquid: toluene/heptane=4/6 (volume ratio)), and thus N,9-diphenyl-9H-carbazole-2-amine (10.4 g) was obtained.

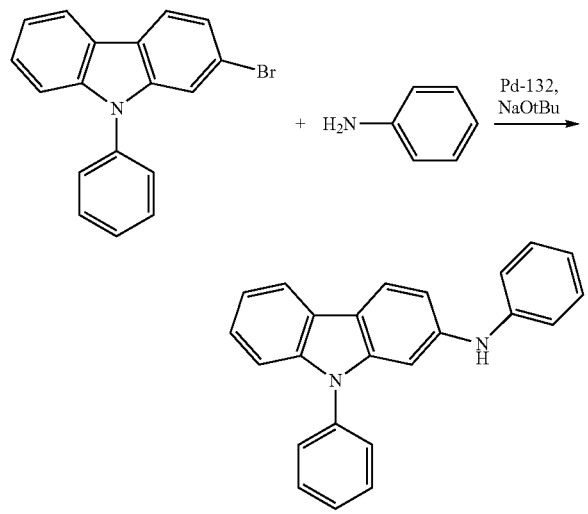

In a nitrogen atmosphere, a flask containing N-(2,3-dichlorophenyl)-$N^1,N^3,N^3$-triphenylbenzene-1,3-diamine (14.0 g), N,9-diphenyl-9H-carbazole-2-amine (10.4 g), Pd-132 (0.2 g), NaOtBu (4.1 g) and xylene (90 ml) was heated and stirred for one hour at 120° C. The reaction liquid was cooled to room temperature, subsequently water and toluene were added thereto, and the mixture was partitioned. Subsequently, purification was performed by silica gel column chromatography (developing liquid: toluene/heptane=4/6 (volume ratio)), and thus 2-chloro-$N^1$-(3-(diphenylamino)phenyl)-$N^1,N^3$-diphenyl-$N^3$-(9-phenyl-9H-carbazol-2-yl)benzene-1,3-diamine (18.5 g) was obtained.

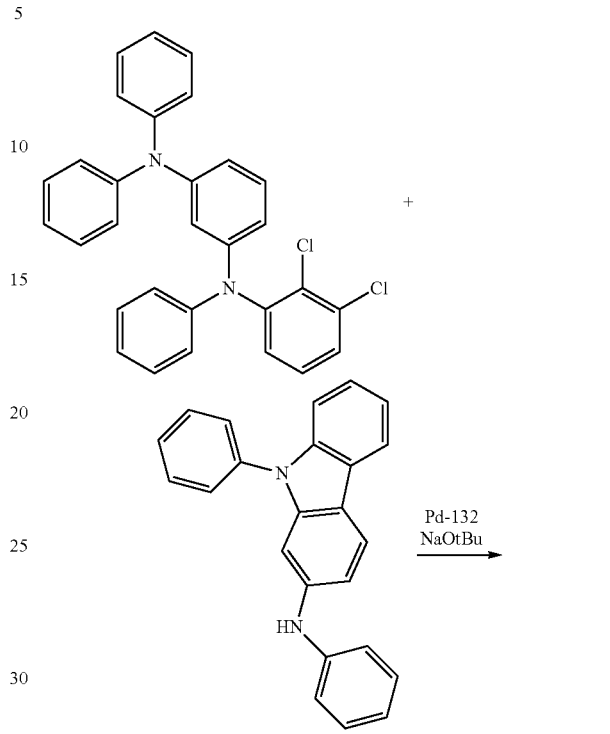

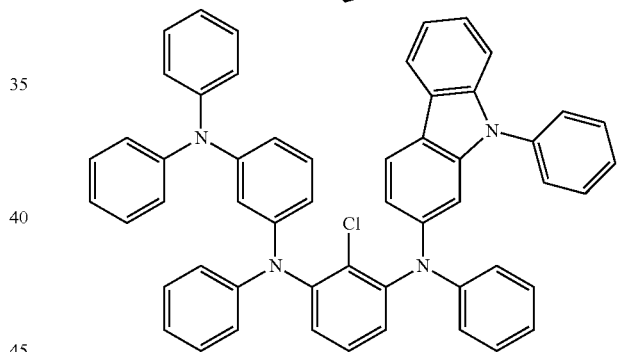

A 1.7 M t-butyllithium pentane solution (27.2 ml) was introduced into a flask containing 2-chloro-$N^1$-(3-(diphenylamino)phenyl)-$N^1,N^3$-diphenyl-$N^3$-(9-phenyl-9H-carbazol-2-yl)benzene-1,3-diamine (18.0 g) and t-butylbenzene (100 ml) in a nitrogen atmosphere, while the flask was cooled in an ice bath. After completion of dropwise addition, the temperature was increased to 60° C., the mixture was stirred for three hours, and then components having boiling points that were lower than that of t-butylbenzene were distilled off under reduced pressure. The residue was cooled to −50° C., boron tribromide (4.4 ml) was added thereto, the temperature of the mixture was raised to room temperature, and the mixture was stirred for 0.5 hours. Thereafter, the mixture was cooled again in an ice bath, and N,N-diisopropylethylamine (8.1 ml) was added thereto. The mixture was stirred at room temperature until heat generation was settled, subsequently the temperature of the mixture was raised to 120° C., and the mixture was heated and stirred for one hour. The reaction liquid was cooled to room temperature, and a precipitate generated by adding an aqueous solution of sodium acetate that had been cooled in an ice bath and ethyl acetate thereto was collected by suction filtration. Subsequently, dissolution in hot chlorobenzene was performed, and purification was performed using a silica gel short pass column (developing liquid: hot toluene). The purification product was washed with hot heptane, and then was reprecipitated using a chlorobenzene/ethyl acetate mixed solvent. Thus, a compound (3.0 g) represented by formula (1-2681) was obtained.

The reaction liquid was cooled to room temperature, and a filtrate obtained at the time of collecting a precipitated generated by adding an aqueous solution of sodium acetate that had been cooled in an ice bath and ethyl acetate thereto, was purified by activated carbon column chromatography (developing liquid: toluene/heptane=5/5 (volume ratio)) and then by silica gel column chromatography (toluene/heptane=4/6 (volume ratio)). The purification product was further reprecipitated using a heptane/ethyl acetate mixed solvent and then using a heptane/toluene mixed solvent, and thus a compound (0.6 g) represented by formula (1-2682) was obtained.

The structure of the compound (1-2681) thus obtained was identified by an NMR analysis.

$^1$H-NMR (400 MHz, CDCl$_3$): δ=9.57 (s, 1H), 8.93 (d, 1H), 8.26 (d, 1H), 7.61 (t, 2H), 7.10-7.50 (m, 25H), 7.04 (m, 3H), 6.59 (s, 1H), 6.25 (m, 1H), 6.10 (t, 2H).

The structure of the compound (1-2682) thus obtained was identified by an NMR analysis.

$^1$H-NMR (400 MHz, CDCl$_3$): δ=8.86 (d, 1H), 8.73 (d, 1H), 8.43 (d, 1H), 8.24 (d, 1H), 7.31-7.56 (m, 13H), 7.29 (dd, 1H), 7.12-24 (m, 8H), 7.10 (m, 4H), 7.02 (t, 2H), 6.94 (dd, 1H), 6.79 (d, 1H), 6.16 (m, 2H), 6.07 (d, 1H).

Synthesis Example (15)

Synthesis of Compound (1-2626): 12-methyl-N,N,5-triphenyl-9-(p-tolyl)-5,9-dihydro-5,9-diaza-13b-boranaphtho[3,2,1-de]anthracene-3-amine

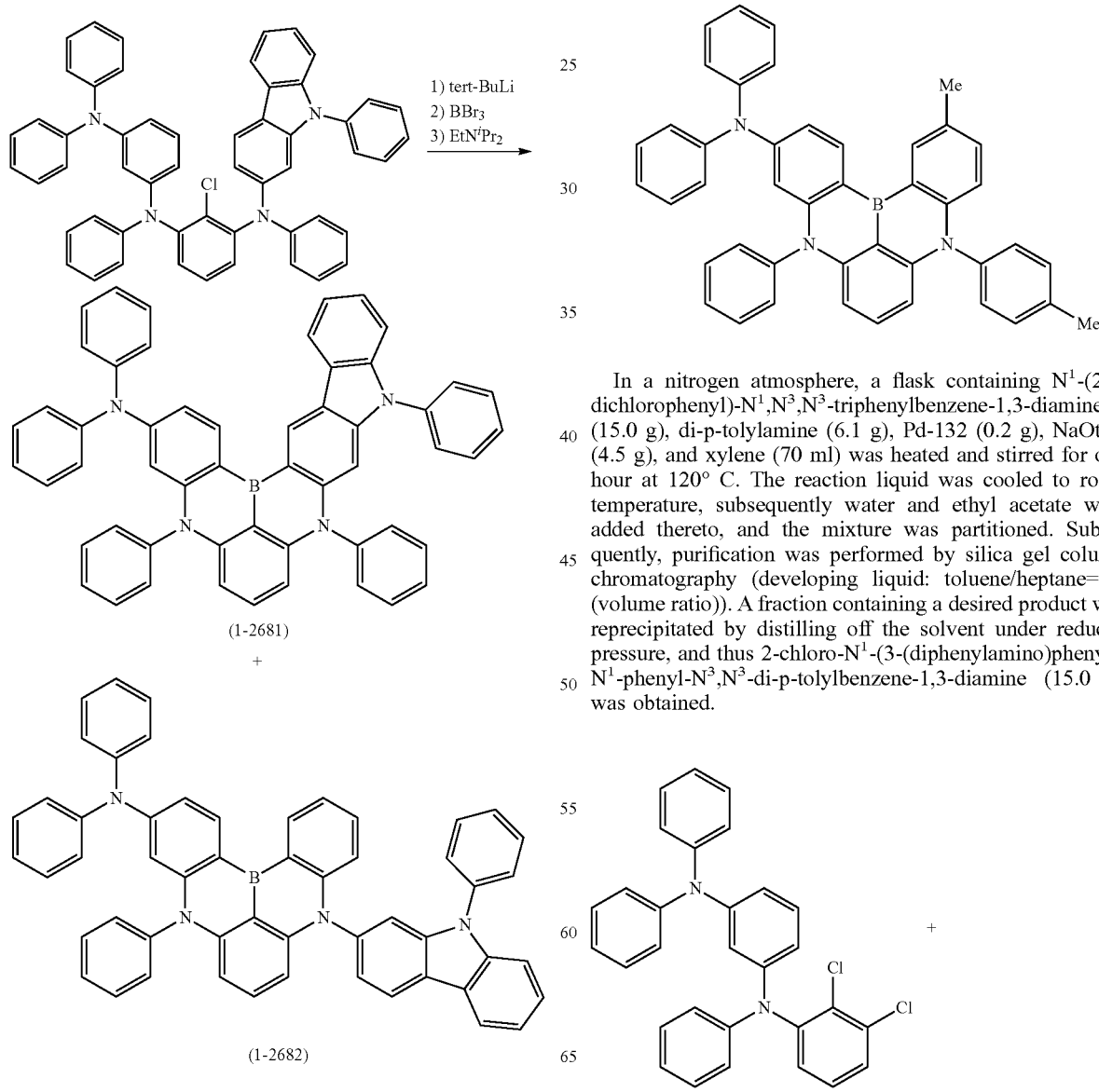

In a nitrogen atmosphere, a flask containing N$^1$-(2,3-dichlorophenyl)-N$^1$,N$^3$,N$^3$-triphenylbenzene-1,3-diamine (15.0 g), di-p-tolylamine (6.1 g), Pd-132 (0.2 g), NaOtBu (4.5 g), and xylene (70 ml) was heated and stirred for one hour at 120° C. The reaction liquid was cooled to room temperature, subsequently water and ethyl acetate were added thereto, and the mixture was partitioned. Subsequently, purification was performed by silica gel column chromatography (developing liquid: toluene/heptane=4/6 (volume ratio)). A fraction containing a desired product was reprecipitated by distilling off the solvent under reduced pressure, and thus 2-chloro-N$^1$-(3-(diphenylamino)phenyl)-N$^1$-phenyl-N$^3$,N$^3$-di-p-tolylbenzene-1,3-diamine (15.0 g) was obtained.

-continued

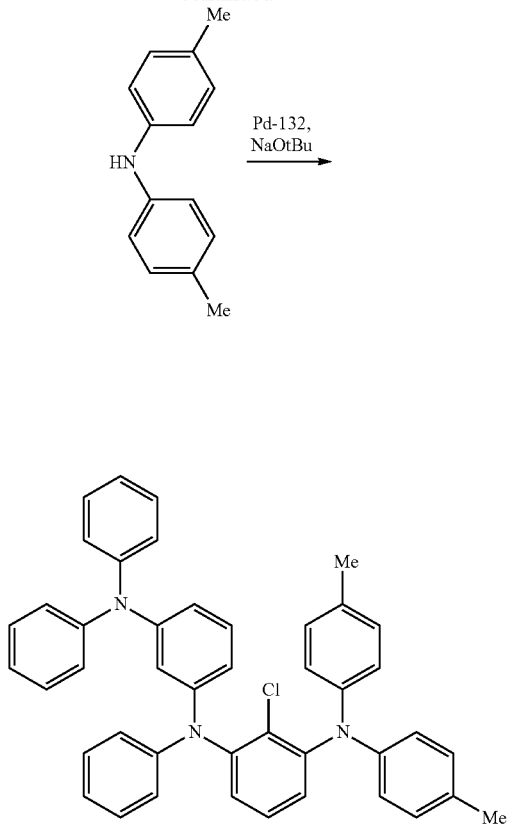

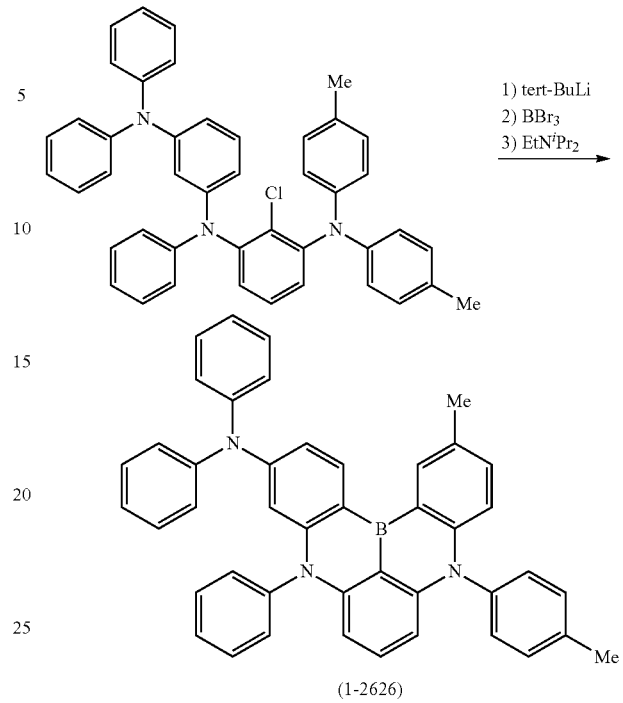

The structure of the compound thus obtained was identified by an NMR analysis.

$^1$H-NMR (400 MHz, CDCl$_3$): δ=8.74 (d, 1H), 8.64 (m, 1H), 7.42-7.50 (m, 4H), 7.35 (t, 1H), 7.15-7.25 (m, 10H), 7.10 (d, 4H), 7.02 (t, 2H), 7.94 (dd, 1H), 6.68 (d, 1H), 6.20 (m, 1H), 6.11 (d, 1H), 6.04 (d, 1H), 2.52 (s, 3H), 2.48 (s, 3H).

Synthesis Example (16)

Synthesis of Compound (1-2683): 5-([1,1'-biphenyl]-4-yl)-N,N,9-triphenyl-5,9-dihydro-5,9-diaza-13b-boranaphtho[3,2,1-de]anthracene-3-amine

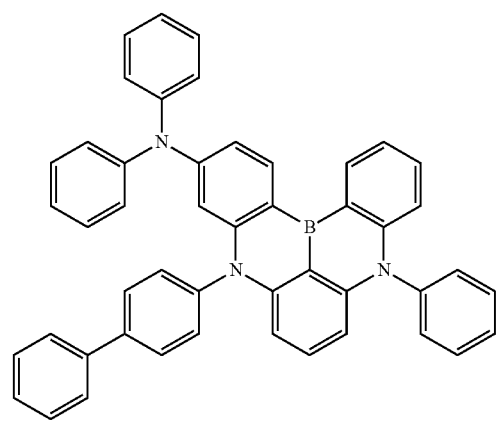

A 1.6 M t-butyllithium pentane solution (29.2 ml) was put into a flask containing 2-chloro-N$^1$-(3-(diphenylamino)phenyl)-N$^1$-phenyl-N$^3$,N$^3$-di-p-tolylbenzene-1,3-diamine (15.0 g) and t-butylbenzene (100 ml) in a nitrogen atmosphere, while the flask was cooled in an ice bath. After completion of dropwise addition, the temperature was increased to 60° C., the mixture was stirred for two hours, and then the components having boiling points that were lower than that of t-butylbenzene were distilled off under reduced pressure. The residue was cooled to −50° C., boron tribromide (4.4 ml) was added thereto, the temperature of the mixture was raised to room temperature, and the mixture was stirred for 0.5 hours. Thereafter, the mixture was cooled again in an ice bath, and N,N-diisopropylethylamine (8.1 ml) was added thereto. The mixture was stirred at room temperature until heat generation was settled, subsequently the temperature of the mixture was raised to 120° C., and the mixture was heated and stirred for two hours. The reaction liquid was cooled to room temperature, an aqueous solution of sodium acetate that had been cooled in an ice bath and then ethyl acetate were added thereto, and the mixture was partitioned. Subsequently, purification was performed by silica gel column chromatography (developing liquid: toluene/heptane=4/6). The purification product was further washed with hot heptane, and then was reprecipitated with a toluene/ethyl acetate mixed solvent. Thus, a compound (2.0 g) represented by formula (1-2626) was obtained.

In a nitrogen atmosphere, a flask containing N$^1$,N$^1$-diphenylbenzene-1,3-diamine (12.0 g), 4-bromo-1,1'-biphenyl (30.2 g), Pd-132 (0.3 g), NaOtBu (6.6 g) and xylene (100 ml) was heated and stirred for two hours at 100° C. The reaction liquid was cooled to room temperature, subsequently water and ethyl acetate were added thereto, and the mixture was partitioned. Subsequently, purification was performed by silica gel column chromatography (developing liquid: toluene/heptane=4/6 (volume ratio)). A solid obtained by distilling off the solvent under reduced pressure was washed with heptane, and thus $N^1$, ([1,1'-biphenyl]-4-yl)-$N^3$,$N^3$-diphenylbenzene-1,3-diamine (17.4 g) was obtained.

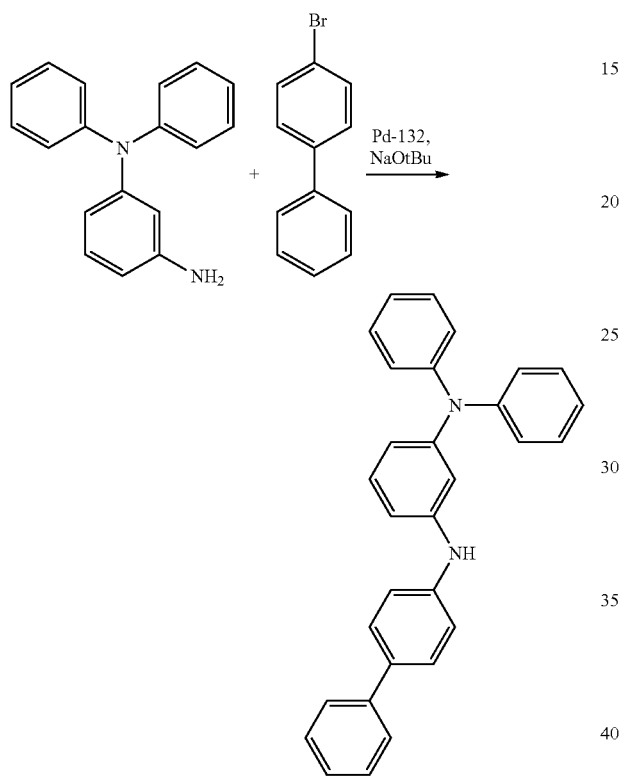

In a nitrogen atmosphere, a flask containing 2,3-dichloro-N,N-diphenylaniline (12.0 g), $N^1$, ([1,1'-biphenyl]-4-yl)-$N^3$, $N^3$-diphenylbenzene-1,3-diamine (15.0 g), Pd-132 (0.3 g), NaOtBu (5.5 g) and xylene (100 ml) was heated and stirred for one hour at 120° C. The reaction liquid was cooled to room temperature, subsequently water and ethyl acetate were added thereto, and the mixture was partitioned. Subsequently, purification was performed by silica gel column chromatography (developing liquid: toluene/heptane=4/6 (volume ratio)), and thus $N^1$-([1,1'-biphenyl]-4-yl)-2-chloro-$N^1$-(3-(diphenylamino)phenyl)-$N^3$,$N^3$-diphenylbenzene-1,3-diamine (20.2 g) was obtained.

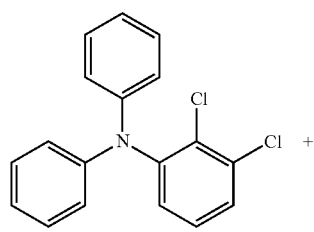

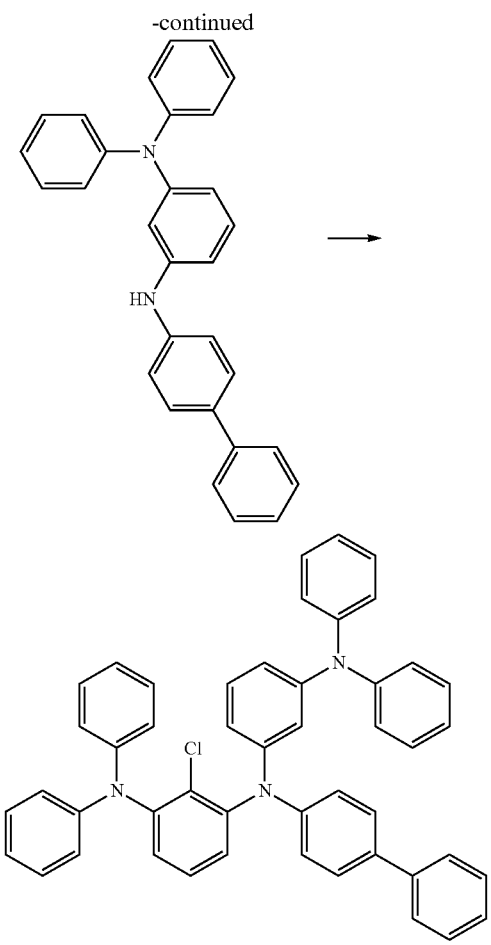

A 1.6 M t-butyllithium pentane solution (26.1 ml) was introduced into a flask containing $N^1$-([1,1'-biphenyl]-4-yl)-2-chloro-$N^1$-(3-(diphenylamino)phenyl)-$N^3$,$N^3$-diphenylbenzene-1,3-diamine (16.0 g) and t-butylbenzene (100 ml) in a nitrogen atmosphere, while the flask was cooled in an ice bath. After completion of dropwise addition, the temperature was increased to 60° C., the mixture was stirred for two hours, and then the components having boiling points that were lower than that of t-butylbenzene were distilled off under reduced pressure. The residue was cooled to –50° C., boron tribromide (4.0 ml) was added thereto, the temperature of the mixture was increased to room temperature, and the mixture was stirred for 0.5 hours. Thereafter, the mixture was cooled again in an ice bath, and N,N-diisopropylethylamine (8.1 ml) was added thereto. The mixture was stirred at room temperature until heat generation was settled, subsequently the temperature of the mixture was raised to 120° C., and the mixture was heated and stirred for two hours. The reaction liquid was cooled to room temperature, and a precipitate precipitated by adding an aqueous solution of sodium acetate that had been cooled in an ice bath and then ethyl acetate thereto was collected by suction filtration. Subsequently, purification was performed by silica gel column chromatography (developing liquid: toluene/heptane=4/6). The purification product was washed with hot heptane, and then was reprecipitated with a chlorobenzene/ethyl acetate mixed solvent. Thus, a compound (2.7 g) represented by formula (1-2683) was obtained.

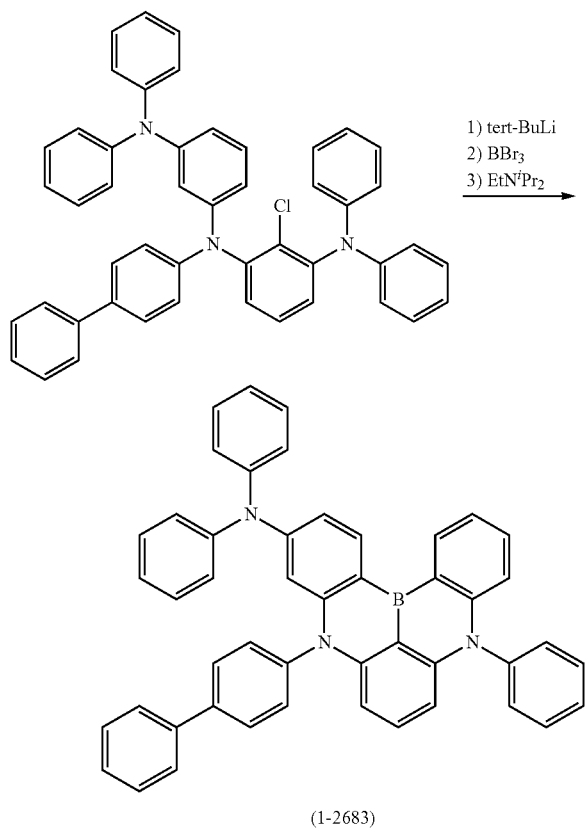

(1-2683)

The structure of the compound thus obtained was identified by an NMR analysis.

$^1$H-NMR (400 MHz, CDCl$_3$): δ=8.87 (d, 1H), 8.74 (d, 1H), 7.68 (t, 2H), 7.64 (d, 2H), 7.58 (m, 3H), 7.50 (t, 2H), 7.36-7.44 (m, 4H), 7.16-7.28 (m, 8H), 7.10 (m, 4H), 6.97 (m, 3H), 6.72 (d, 1H), 6.22 (m, 2H), 6.10 (d, 1H).

Synthesis Example (17)

Synthesis of Compound (1-2691): 16-phenyl-16H-8-oxa-12b,16-diaza-4b-boradibenzo[a,j]perylene (1-2691)

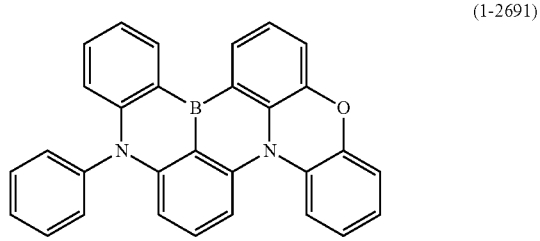 [SMILES: c1ccc(N2c3ccccc3B3c4cccc5c4N(c4ccccc4O5)c4cccc2c43)cc1]

In a nitrogen atmosphere, a flask containing 2,3-dichloro-N,N-diphenylaniline (18.0 g), 10H-phenoxazine (15.0 g), Pd-132 (0.4 g), NaOtBu (8.3 g) and xylene (100 ml) was heated and stirred for one hour at 120° C. The reaction liquid was cooled to room temperature, subsequently water and ethyl acetate were added thereto, and the mixture was partitioned. Subsequently, purification was performed by silica gel column chromatography (developing liquid: toluene). A fraction containing an intended product was precipitated by distilling off the solvent under reduced pressure and adding heptane thereto. Thus, 2-chloro-3-(10H-phenoxazin-10-yl)-N,N-diphenylaniline (23.0 g) was obtained.

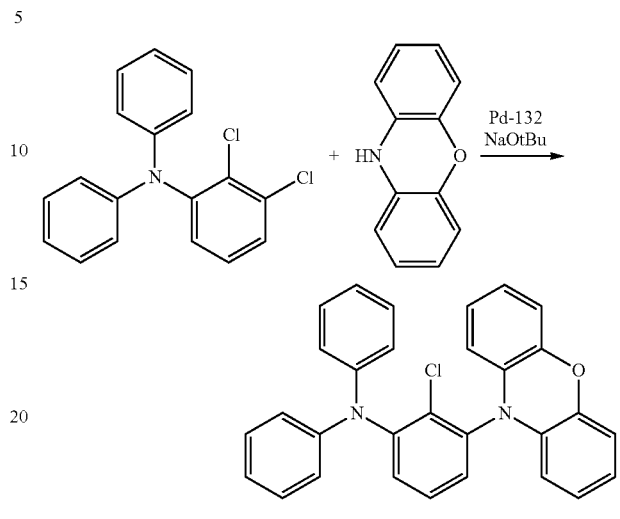

A 1.6 M t-butyllithium pentane solution (54.0 ml) was introduced into a flask containing 2-chloro-3-(10H-phenoxazin-10-yl)-N,N-diphenylaniline (20.0 g) and t-butylbenzene (150 ml) in a nitrogen atmosphere, while the flask was cooled in an ice bath. After completion of dropwise addition, the temperature was increased to 60° C., the mixture was stirred for three hours, and then components having boiling points that were lower than that of t-butylbenzene were distilled off under reduced pressure. The residue was cooled to −50° C., boron tribromide (8.2 ml) was added thereto, the temperature of the mixture was increased to room temperature, and the mixture was stirred for 0.5 hours. Thereafter, the mixture was cooled again in an ice bath, and N,N-diisopropylethylamine (15.1 ml) was added thereto. The mixture was stirred at room temperature until heat generation was settled, subsequently the temperature of the mixture was raised to 120° C., and the mixture was heated and stirred for two hours. The reaction liquid was cooled to room temperature, an aqueous solution of sodium acetate that had been cooled in an ice bath and then ethyl acetate were added thereto, and the mixture was partitioned. Subsequently, purification was performed by silica gel column chromatography (developing liquid: toluene/heptane=3/7), and was further purified by activated carbon chromatography (developing liquid: toluene/heptane=5/5 (volume ratio)). The purification product was reprecipitated using a chlorobenzene/ethyl acetate mixed solvent, and thus a compound (2.8 g) represented by formula (1-2691) was obtained.

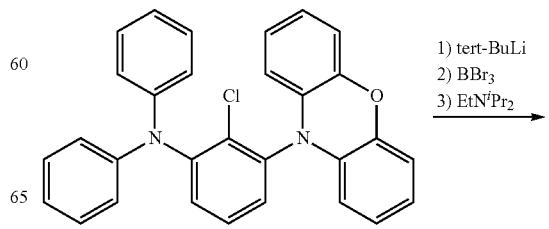

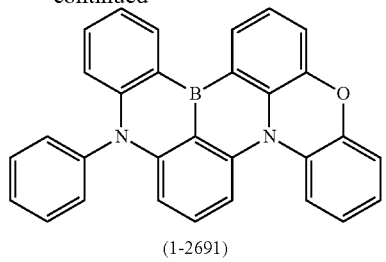

(1-2691)

The structure of the compound thus obtained was identified by an NMR analysis.

¹H-NMR (400 MHz, CDCl₃): δ=8.73 (d, 1H), 8.20 (d, 1H), 7.65-7.80 (m, 3H), 7.56-7.64 (d, 2H), 7.38-7.54 (m, 3H), 7.20-7.37 (m, 3H), 7.16 (m, 1H), 7.11 (m, 1H), 7.05 (t, 1H), 6.97 (t, 1H), 6.77 (d, 1H), 6.27 (d, 1H)).

Synthesis Example (18)

Synthesis of Compound (1-2662): 2,12-dimethyl-N,N,5,9-tetra-µ-tolyl-5,13-dihydro-5,9-diaza-13b-boranaphtho[3,2,1-de]anthracene-7-amine

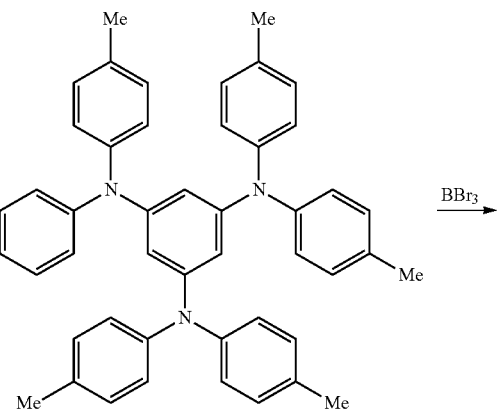

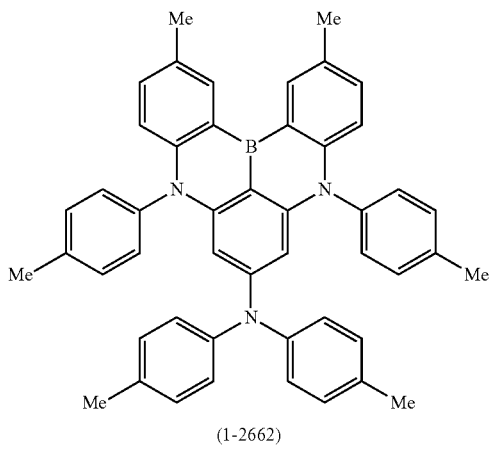

(1-2662)

First, boron tribromide (4.73 ml, 50 mmol) was added to N¹,N¹,N³,N³,N⁵,N⁵-hexakis (4-methylphenyl)-, 3,5-benzenetriamine (16.6 g, 25 mmol) and o-dichlorobenzene (150 ml) at room temperature in a nitrogen atmosphere, and then the mixture was heated and stirred for 20 hours at 170° C. Subsequently, the reaction solution was distilled off at 60° C. under reduced pressure. The reaction solution was filtered using a Florisil short pass column, the solvent was distilled off under reduced pressure, and a crude product was obtained. The crude product was washed using hexane, and the solid thus obtained was washed using toluene. Thus, a compound (8.08 g) represented by formula (1-2662) was obtained as a yellow solid.

The structure of the compound thus obtained was identified by an NMR analysis.

¹H-NMR (400 MHz, CDCl₃): δ=2.27 (s, 6H), 2.39 (s, 6H), 2.50 (s, 6H), 5.48 (brs, 2H), 6.68 (d, 2H), 6.83 (ddd, 4H), 6.89 (ddd, 4H), 7.07 (ddd, 4H), 7.17 (dd, 2H), 7.25 (ddd, 4H), 8.68 (sd, 2H).

¹³C-NMR (101 MHz, CDCl₃): δ=20.78 (2C), 21.06 (2C), 21.11 (2C), 96.5 (2C), 116.7 (2C), 126.0 (4C), 128.2 (2C), 129.3 (4C), 129.9 (4C), 131.1 (4C), 131.3 (2C), 133.0 (2C), 134.6 (2C), 137.6 (2C), 139.8 (2C), 143.9 (2C), 145.9 (2C), 148.0 (2C), 151.0.

Synthesis Example (19)

Synthesis of Compound (1-2665): 9,11-diphenyl-4b,11,15b,19b-tetrahydro-9H-9,11,19b-triaza-4b,15b-diborabenzo[3,4]phenanthro[2,1,10,9-fghi]pentacene

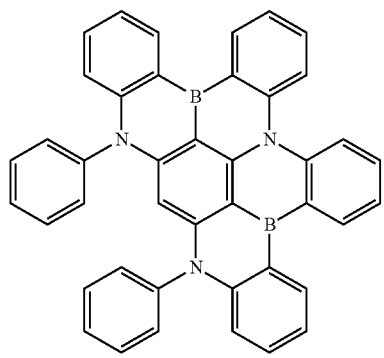

(1-2665)

First, boron tribromide (0.142 ml, 1.5 mmol) was added to N,N,5,9-tetraphenyl-5,13-dihydro-5,9-diaza-13b-boranaphtho[3,2,1-de]anthracene-7-amine (0.294 g, 0.5 mmol) and o-dichlorobenzene (3.0 ml) at room temperature in a nitrogen atmosphere in an autoclave, and then the mixture was heated and stirred for 48 hours at 260° C. Thereafter, N,N-diisopropylethylamine (0.775 ml, 4.5 mmol) was added thereto, and the mixture was filtered using a Florisil short pass column. The solvent was distilled off under reduced pressure, and thus a crude product was obtained. The crude product was washed using ethyl acetate, and thus a compound (0.118 g) represented by formula (1-2665) was obtained.

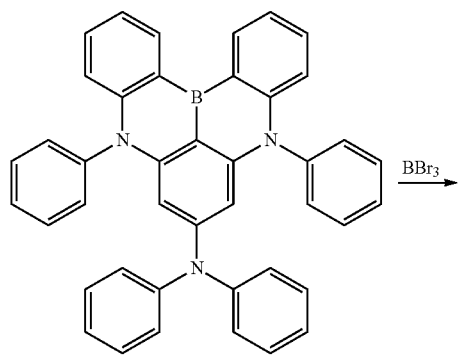

BBr₃ ⟶

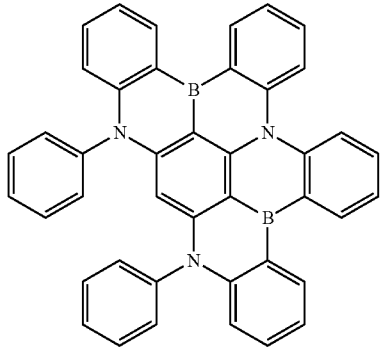

(1-2665)

The structure of the compound thus obtained was identified by an NMR analysis.

¹H-NMR (400 MHz, CDCl₃): δ=5.24 (s, 1H), 6.81 (d, 2H), 7.12-7.18 (m, 6H), 7.34 (td, 2H), 7.41-7.49 (m, 8H), 7.45 (ddd, 2H), 8.31 (dd, 2H), 8.81 (dd, 2H), 8.91 (dd, 2H).

HRMS (DART) m/z [M+H]⁺ Calcd for $C_{42}H_{28}B_2N_3$ 596.2483, observed 596.2499.

Synthesis Example (20)

Synthesis of Compound (1-2678): 3,6,14,17-tetramethyl-9,11-di-p-tolyl-4b,11,15b,19b-tetrahydro-9H-9,11,19b-triaza-4b,15b-diborabenzo[3,4]phenanthro[2,1,10,9-fghi]pentacene

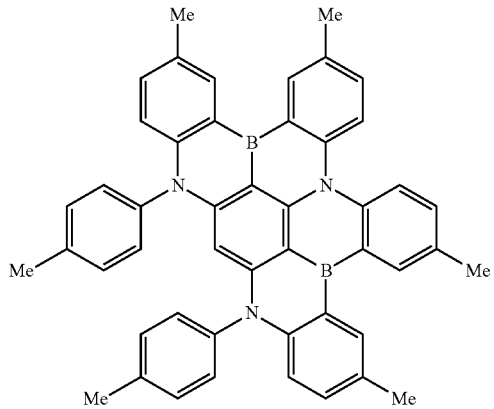

(1-2678)

First, triphenylborane (0.730 g, 3.0 mmol) and boron tribromide (0.284 ml, 3.0 mmol) were added to N¹,N¹,N³,N³,N⁵,N⁵-hexakis(4-methylphenyl)-1,3,5-benzenetriamine (0.322 g, 0.5 mmol) and o-dichlorobenzene (3.0 ml) at room temperature in a nitrogen atmosphere in an autoclave, and then the mixture was heated and stirred for 20 hours at 260° C. Thereafter, N,N-diisopropylethylamine (1.55 ml, 9.1 mmol) was added thereto, and the mixture was filtered using a Florisil short pass column. The solvent was distilled off under reduced pressure, and a crude product was obtained. The crude product was washed using hexane, and a solid thus obtained was washed using ethyl acetate. Thus, a compound (0.188 g) represented by formula (1-2678) was obtained as a yellow solid.

211

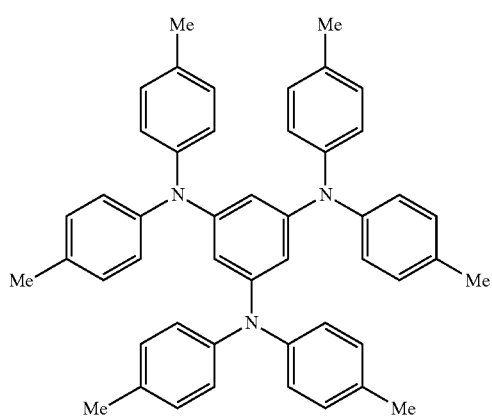

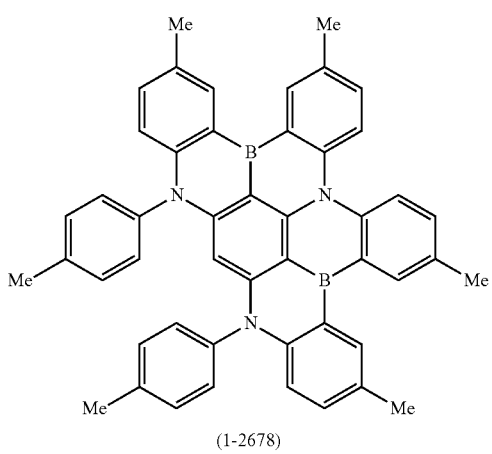

(1-2678)

The structure of the compound thus obtained was identified by an NMR analysis.

¹H-NMR (400 MHz, CDCl₃): δ=2.45 (s, 6H), 2.65 (s, 6H), 2.58 (s, 6H), 5.24 (brs, 1H), 6.74 (d, 2H), 6.97 (d, 4H), 7.15-7.27 (m, 6H), 7.34 (dd, 2H), 8.18 (d, 2H), 8.58 (d, 2H), 8.68 (d, 2H).

HRMS (DART) m/z [M+H]⁺ Calcd for $C_{48}H_{40}B_2N_3$ 680.3424, observed 680.3404.

Synthesis Example (21)

Synthesis of Compound (1-2621): 2,12-di-t-butyl-5,9-bis(4-(t-butyl)phenyl)-5,9-dihydro-5,9-diaza-13b-boranaphtho[3,2,1-de]anthracene

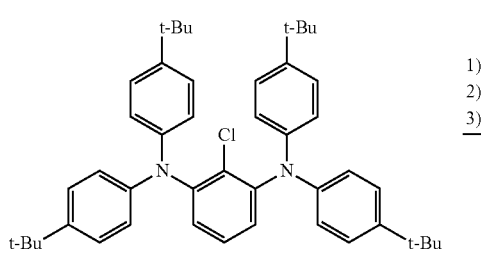

212

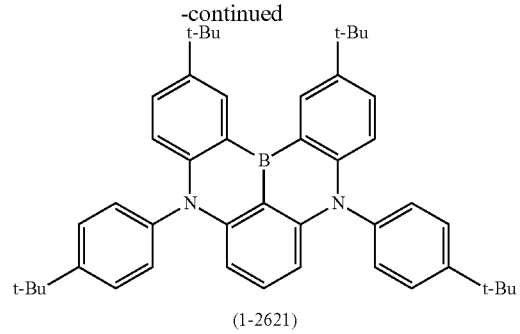

(1-2621)

The compound represented by formula (1-2621) was synthesized using a similar method to that in the Synthesis Example described above.

The structure of the compound thus obtained was identified by NMR measurement.

¹H-NMR (500 MHz, CDCl₃): δ=1.46 (s, 18H), 1.47 (s, 18H), 6.14 (d, 2H), 6.75 (d, 2H), 7.24 (t, 1H), 7.29 (d, 4H), 7.52 (dd, 2H), 7.67 (d, 4H), 8.99 (d, 2H).

Synthesis Example (22)

Synthesis of Compound (1-2619): 2,12-di-t-butyl-5,9-bis(4-(t-butyl)phenyl)-7-methyl-5,9-dihydro-5,9-diaza-13b-boranaphtho[3,2,1-de]anthracene

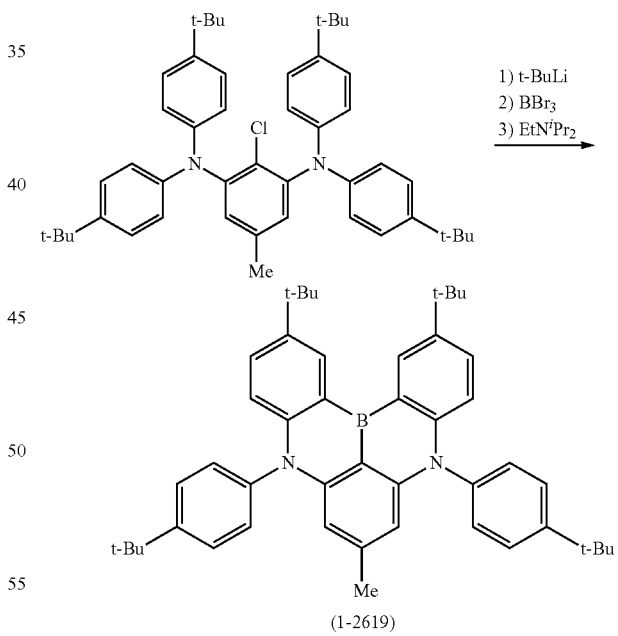

(1-2619)

The compound represented by formula (1-2619) was synthesized using a similar method to that in the Synthesis Example described above.

The structure of the compound thus obtained was identified by NMR measurement.

¹H-NMR (500 MHz, CDCl₃): δ=1.47 (s, 36H), 2.17 (s, 3H), 5.97 (s, 2H), 6.68 (d, 2H), 7.28 (d, 4H), 7.49 (dd, 2H), 7.67 (d, 4H), 8.97 (d, 2H).

Synthesis Example (23)

The compound (3-134-O) was synthesized by a method equivalent to the method described in paragraph [0106] of WO 2014/141725 A.

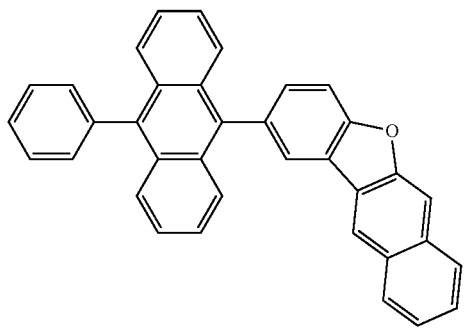

(3-134-O)

Synthesis Example (24)

Synthesis of Compound (1-447-1): 2,12-di-t-butyl-5,9-bis(4-(t-butyl)phenyl)-N,N-dipheny-5,9-dihydro-5,9-diaza-13b-boranaphtho[3,2,1-de]anthracene-7-amine

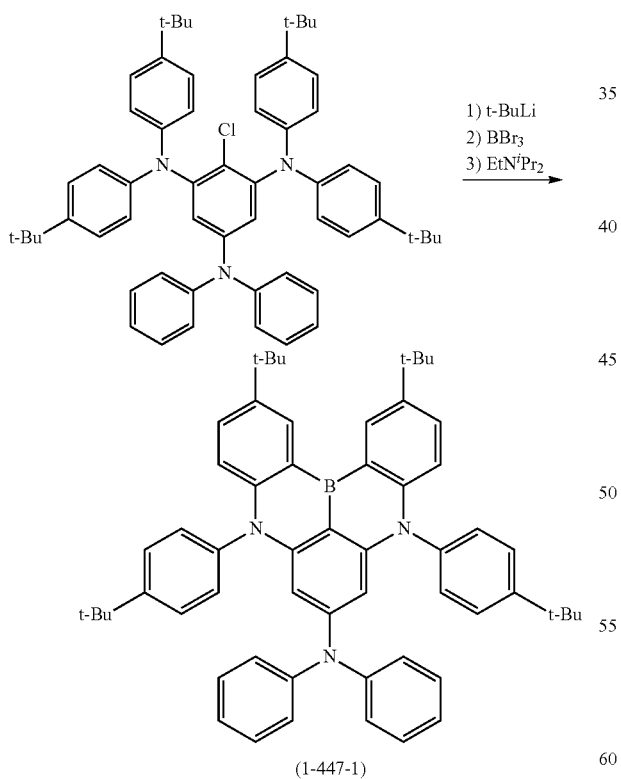

(1-447-1)

The compound represented by formula (1-447-1) was synthesized using a similar method to that in the Synthesis Example described above.

The structure of the compound thus obtained was identified by NMR measurement.

$^1$H-NMR (CDCl$_3$): δ=1.33 (s, 18H), 1.46 (s, 18H), 5.55 (s, 2H), 6.75 (d, 2H), 6.89 (t, 2H), 6.94 (d, 4H), 7.06 (t, 4H), 7.13 (d, 4H), 7.43-7.46 (m, 6H), 8.95 (d, 2H).

Synthesis Example (25)

Synthesis of Compound (1-448-1): 2,12-di-t-butyl-5,9-bis(4-(t-butyl)phenyl)-7-(9H-carbazol-9-yl)-5,9-dihydro-5,9-diaza-13b-boranaphtho[3,2,1-de]anthracene

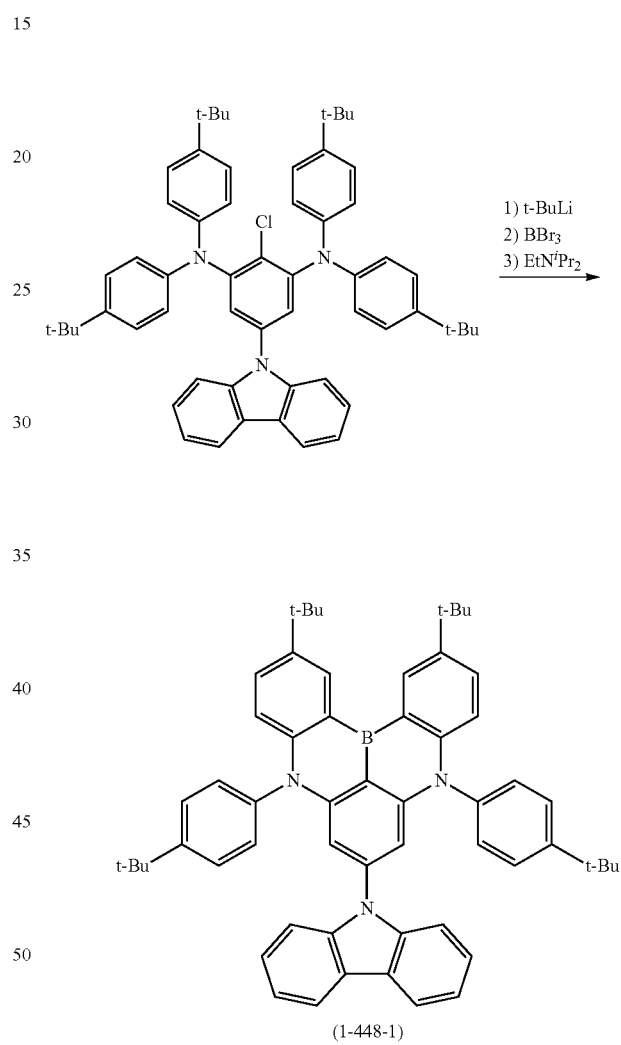

(1-448-1)

The compound represented by formula (1-448-1) was synthesized using a similar method to that in the Synthesis Example described above.

The structure of the compound thus obtained was identified by NMR measurement.

$^1$H-NMR (CDCl$_3$): δ=1.35 (s, 18H), 1.50 (s, 18H), 6.34 (s, 2H), 6.85 (d, 2H), 7.16 (t, 2H), 7.23 (t, 2H), 7.32-7.35 (m, 6H), 7.56 (dd, 2H), 7.63 (d, 4H), 7.99 (d, 2H), 9.05 (d, 2H).

Synthesis Example (26)

Synthesis of Compound (1-401-1): 12-(t-butyl)-9-(4-(t-butyl)phenyl)-5-(3,5-di-t-butylphenyl)-7-methyl-5,9-dihydro-5,9-diaza-13b-boranaphtho[3,2,1-de]anthracene

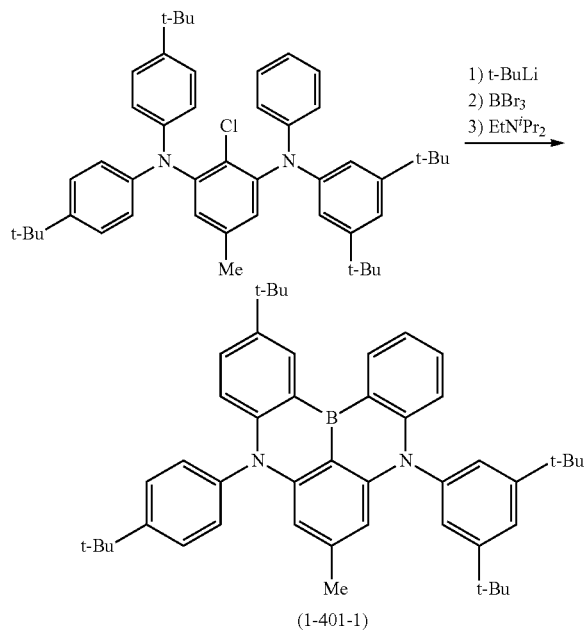

(1-401-1)

The compound represented by formula (1-401-1) was synthesized using a similar method to that in the Synthesis Example described above.

The structure of the compound thus obtained was identified by NMR measurement.

$^{1}$H-NMR (CDCl$_3$): δ=1.37 (s, 18H), 1.46 (s, 9H), 1.47 (s, 9H), 2.17 (s, 3H), 5.56 (s, 1H), 5.99 (s, 1H), 6.68 (d, 1H), 6.74 (d, 1H), 7.19 (d, 2H), 7.24-7.29 (m, 3H), 7.42 (t, 1H), 7.49 (dd, 1H), 7.61 (t, 1H), 7.68 (d, 2H), 8.91 (dd, 1H), 8.92 (d, 1H).

Synthesis Example (27)

Synthesis of Compound (1-401-2): 3,12-di-t-butyl-9-(4-(t-butyl)phenyl)-5-(3,5-di-t-butylphenyl)-5,9-dihydro-5,9-diaza-13b-boranaphtho[3,2,1-de]anthracene

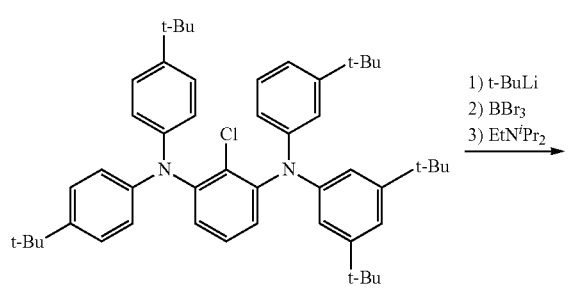

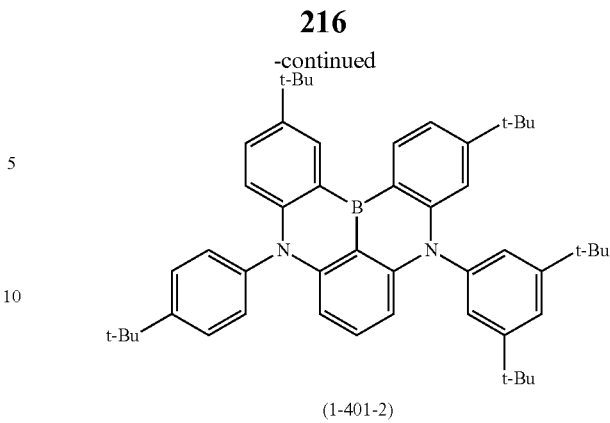

(1-401-2)

The compound represented by formula (1-401-2) was synthesized using a similar method to that in the Synthesis Example described above.

The structure of the compound thus obtained was identified by NMR measurement.

$^{1}$H-NMR (CDCl$_3$): δ=1.20 (s, 9H), 1.36 (s, 18H), 1.46 (s, 9H), 1.47 (s, 9H), 6.14 (d, 1H), 6.25 (d, 1H), 6.68 (d, 1H), 6.73 (d, 1H), 7.21 (d, 2H), 7.29 (d, 3H), 7.34 (dd, 1H), 7.51 (dd, 1H), 7.61 (t, 1H), 7.67 (d, 2H), 8.86 (d, 1H), 8.96 (d, 1H).

Synthesis Example (28)

Synthesis of Compound (1-401-3): 3,12-di-t-butyl-9-(4-(t-butyl)phenyl)-5-(3,5-di-t-butylphenyl)-7-methyl-5,9-dihydro-5,9-diaza-13b-boranaphtho[3,2,1-de]anthracene

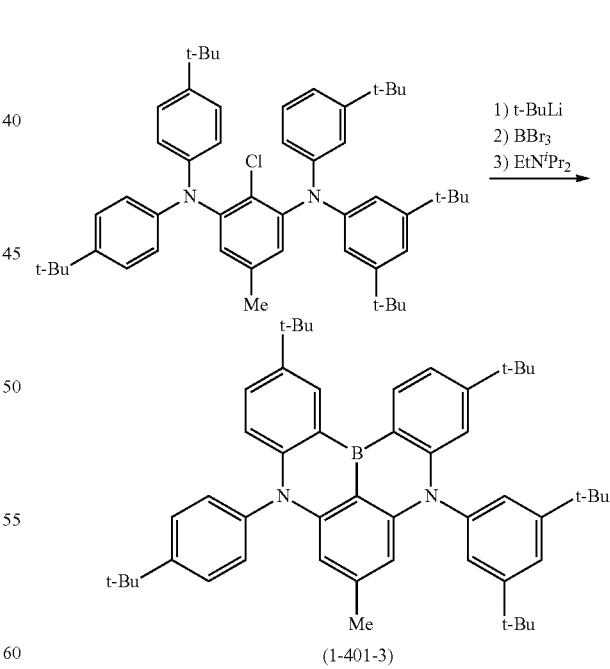

(1-401-3)

The compound represented by formula (1-401-3) was synthesized using a similar method to that in the Synthesis Example described above.

The structure of the compound thus obtained was identified by NMR measurement.

217

$^1$H-NMR (CDCl$_3$): δ=1.20 (s, 9H), 1.37 (s, 18H), 1.46 (s, 9H), 1.47 (s, 9H), 2.18 (s, 3H), 5.97 (s, 1H), 6.08 (d, 1H), 6.63 (d, 1H), 6.66 (d, 1H), 7.20 (d, 2H), 7.27 (d, 2H), 7.32 (dd, 1H), 7.48 (dd, 1H), 7.61 (t, 1H), 7.67 (d, 2H), 8.84 (d, 1H), 8.94 (d, 1H).

Synthesis Example (29)

Synthesis of Compound (1-449): 4-(5,9-diphenyl-5,9-dihydro-5,9-diaza-13b-boranaphtho[3,2,1-de]anthracene-7-yl)-N,N-diphenylaniline

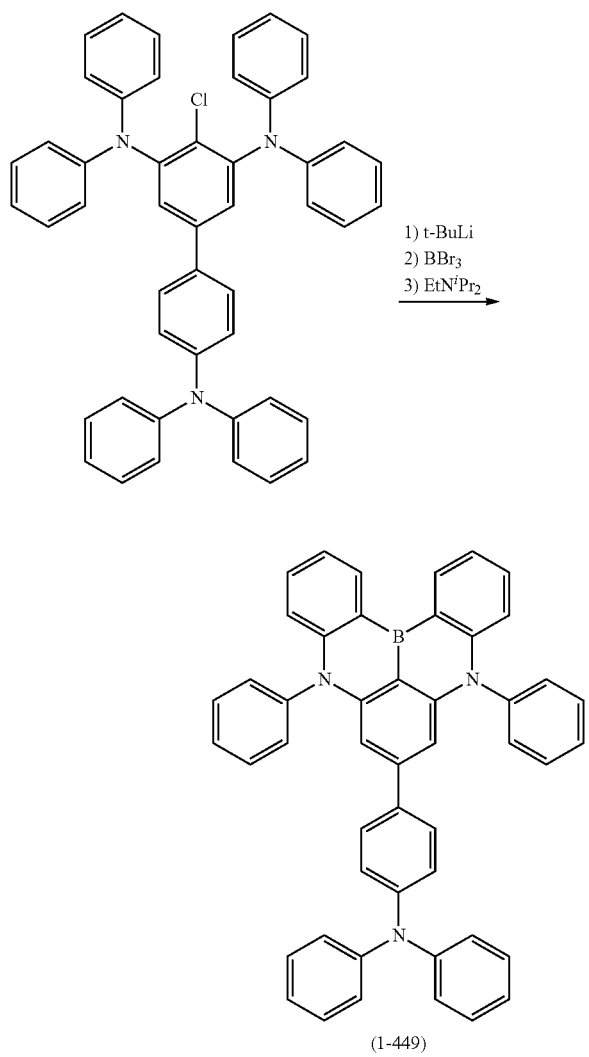

(1-449)

The compound represented by formula (1-449) was synthesized using a similar method to that in the Synthesis Example described above.

The structure of the compound thus obtained was identified by NMR measurement.

$^1$H-NMR (CDCl$_3$): δ=6.35 (s, 2H), 6.76 (d, 2H), 6.93 (d, 2H), 7.01 (t, 2H), 7.05 (d, 4H), 7.09 (d, 2H), 7.22 (t, 4H), 7.27 (t, 2H), 7.41-7.45 (m, 6H), 7.59 (t, 2H), 7.70 (d, 4H), 8.95 (dd, 2H).

218

Synthesis Example (30)

Synthesis of Compound (1-441-1): 5,9-diphethyl-7-(p-tolyl)-5,9-dihydro-5,9-diaza-13b-boranaphtho[3,2,1-de]anthracene

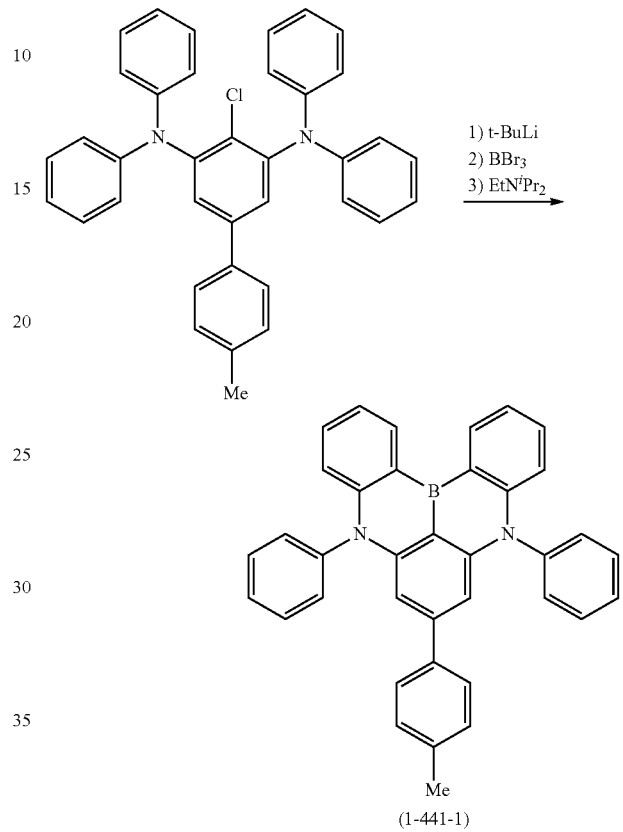

(1-441-1)

The compound represented by formula (1-441-1) was synthesized using a similar method to that in the Synthesis Example described above.

The structure of the compound thus obtained was identified by NMR measurement.

$^1$H-NMR (CDCl$_3$): δ=2.30 (s, 3H), 6.34 (s, 2H), 6.76 (s, 2H), 7.08 (d, 2H), 7.13 (d, 2H), 7.26-7.29 (m, 2H), 7.41-7.45 (m, 6H), 7.59 (t, 2H), 7.70 (t, 4H), 8.96 (dd, 2H).

Synthesis Example (31)

Synthesis of Compound (1-401-4): 3,12-di-t-butyl-5-(3-(t-butyl)phenyl)-9-(4-(t-butyl)phenyl)-5,9-dihydro-5,9-diaza-13b-boranaphtho[3,2,1-de]anthracene

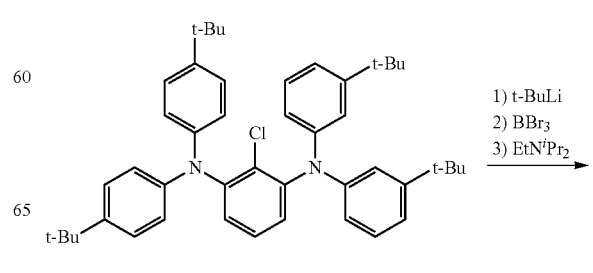

-continued

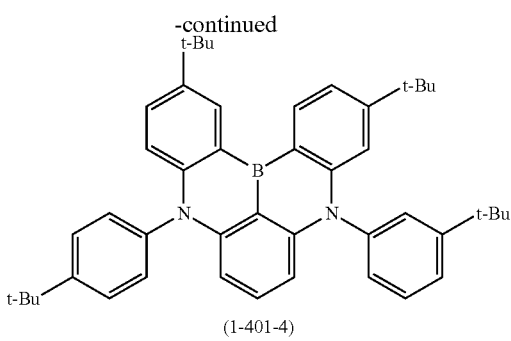

(1-401-4)

The compound represented by formula (1-401-4) was synthesized using a similar method to that in the Synthesis Example described above.

The structure of the compound thus obtained was identified by NMR measurement.

$^1$H-NMR (CDCl$_3$): δ=1.22 (s, 9H), 1.37 (s, 9H), 1.46 (s, 9H), 1.47 (s, 9H), 6.14 (d, 1H), 6.18 (d, 1H), 6.72 (d, 1H), 6.74 (d, 1H), 7.19 (ddd, 1H), 7.23-7.30 (m, 3H), 7.34 (dd, 1H), 7.41 (t, 1H), 7.51 (dd, 1H), 7.58-7.64 (m, 2H), 7.67 (d, 2H), 8.86 (d, 1H), 8.96 (d, 1H).

Synthesis Example (32)

Synthesis of Compound (1-401-5): 2,12-di-t-butyl-5,9-bis(4-(t-butyl)phenyl)-7-ethyl-5,9-dihydro-5,9-diaza-13b-boranaphtho[3,2,1-de]anthracene

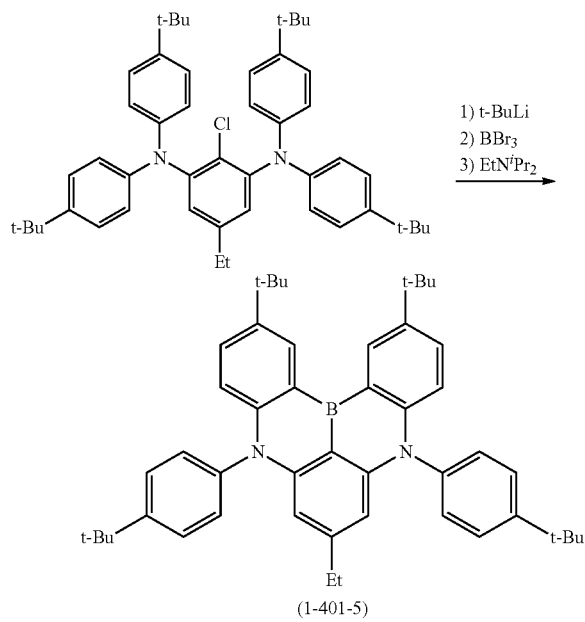

(1-401-5)

The compound represented by formula (1-401-5) was synthesized using a similar method to that in the Synthesis Example described above.

The structure of the compound thus obtained was identified by NMR measurement.

$^1$H-NMR (CDCl$_3$): δ=0.99 (t, 3H), 1.47 (s, 36H), 2.44 (q, 2H), 5.98 (s, 2H), 6.70 (d, 2H), 7.28 (d, 4H), 7.49 (dd, 2H), 7.67 (d, 4H), 8.97 (d, 2H).

Synthesis Example (33)

Synthesis of Compound (1-401-6): 3,11-di-t-butyl-5,9-bis(3,5-di-t-butylphenyl)-5,9-dihydro-5,9-diaza-13b-boranaphtho[3,2,1-de]anthracene

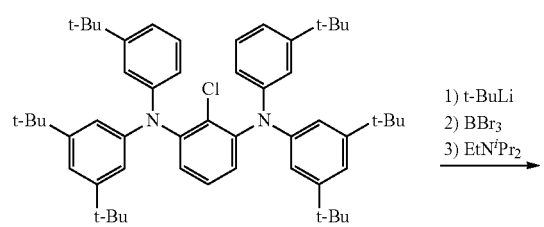

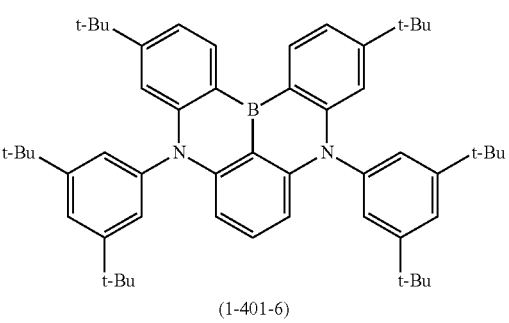

(1-401-6)

The compound represented by formula (1-401-6) was synthesized using a similar method to that in the Synthesis Example described above.

The structure of the compound thus obtained was identified by NMR measurement.

$^1$H-NMR (CDCl$_3$): δ=1.20 (s, 18H), 1.36 (s, 36H), 6.25 (d, 2H), 6.67 (d, 2H), 7.21 (d, 4H), 7.29-7.33 (m, 3H), 7.61 (t, 2H), 8.90 (d, 2H).

Synthesis Example (34)

Synthesis of Compound (1-447-2): N-([1,1'-biphenyl]-2-yl)-2,12-di-t-butyl-5,9-bis(4-(t-butyl)phenyl)-N-phenyl-5,9-dihydro-5,9-diaza-13b-boranaphtho[3,2,1-de]anthracene-7-amine

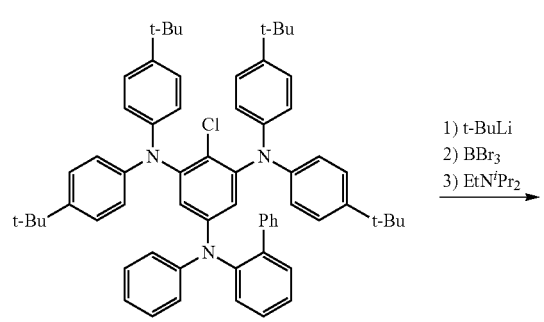

-continued

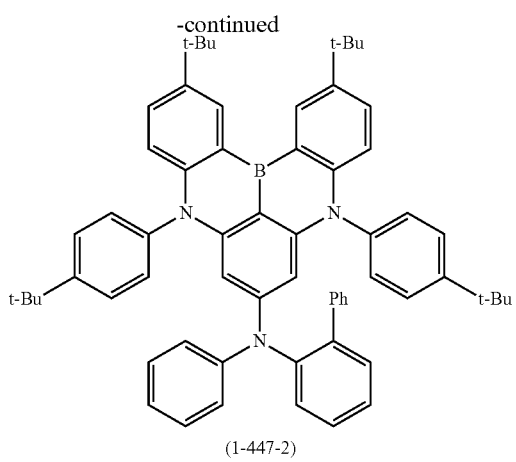

(1-447-2)

The compound represented by formula (1-447-2) was synthesized using a similar method to that in the Synthesis Example described above.

The structure of the compound thus obtained was identified by NMR measurement.

$^1$H-NMR (CDCl$_3$): δ=1.31 (s, 18H), 1.46 (s, 18H), 5.42 (s, 2H), 6.61 (d, 2H), 6.64 (t, 1H), 6.73 (d, 2H), 6.81 (t, 2H), 6.88 (d, 2H), 6.96-7.02 (m, 3H), 7.09-7.17 (m, 8H), 7.43-7.46 (m, 6H), 8.94 (d, 2H).

Synthesis Example (35)

Synthesis of Compound (1-447-3): 2,12-di-t-butyl-5,9-bis(4-(t-butyl)phenyl)-N,N-di-p-tolyl-5,9-dihydro-5,9-diaza-13b-boranaphtho[3,2,1-de]anthracene-7-amine

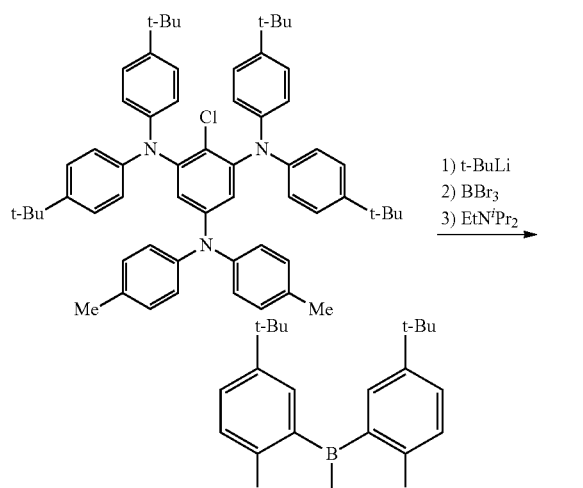

(1-447-3)

The compound represented by formula (1-447-3) was synthesized using a similar method to that in the Synthesis Example described above.

The structure of the compound thus obtained was identified by NMR measurement.

$^1$H-NMR (CDCl$_3$): δ=1.33 (s, 18H), 1.46 (s, 18H), 2.21 (s, 6H), 5.57 (s, 2H), 6.73 (d, 2H), 6.81 (d, 4H), 6.86 (d, 4H), 7.14 (d, 4H), 7.42-7.46 (m, 6H), 8.95 (d, 2H).

Synthesis Example (36)

Synthesis of Compound (1-401-7): 2,12-di-t-butyl-9-(4-(t-butyl) phenyl)-5-(3,5-di-t-butylphenyl)-5,9-dihydro-5,9-diaza-13b-boranaphtho[3,2,1-de]anthracene

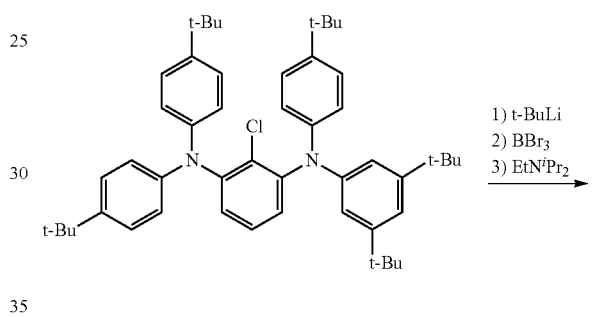

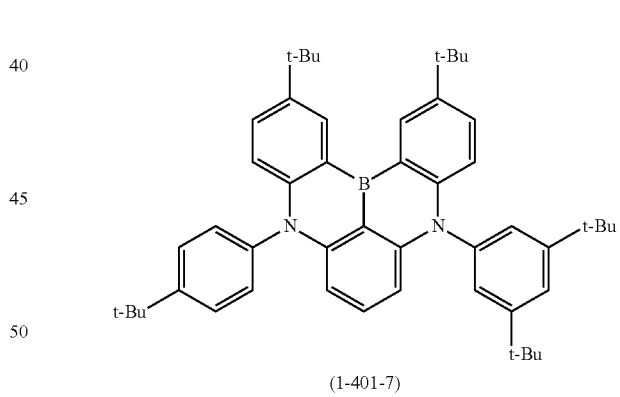

(1-401-7)

The compound represented by formula (1-401-7) was synthesized using a similar method to that in the Synthesis Example described above.

The structure of the compound thus obtained was identified by NMR measurement.

$^1$H-NMR (CDCl$_3$): δ=1.36 (s, 18H), 1.46 (s, 9H), 1.48 (s, 9H), 1.49 (s, 9H), 6.14 (dd, 2H), 6.74 (dd, 2H), 7.20 (d, 2H), 7.24-7.30 (m, 3H), 7.53 (m, 2H), 7.60 (t, 1H), 7.67 (d, 2H), 9.00 (d, 1H), 9.01 (d, 1H).

Synthesis Example (37)

Synthesis of Compound (3-180-O): 9-(10-phenylanthracen-9-yl) naphtho[1,2-b]benzofuran

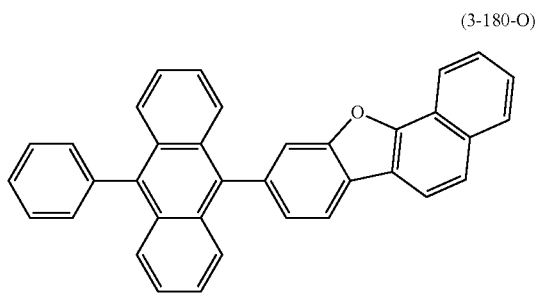 [SMILES: c1ccc(-c2c3ccccc3c(-c3ccc4c(c3)oc3c5ccccc5ccc43)c3ccccc23)cc1]

(3-180-O)

The compound (3-180-O) was synthesized by a method equivalent to the method described in paragraph [0150] of WO 2014/141725 A.

Synthesis Example (38)

Synthesis of Compound (3-141-O): 2-(4-(10-phenylanthracen-9-yl) phenyl) naphtho[2,3-b]benzofuran (3-141-O)

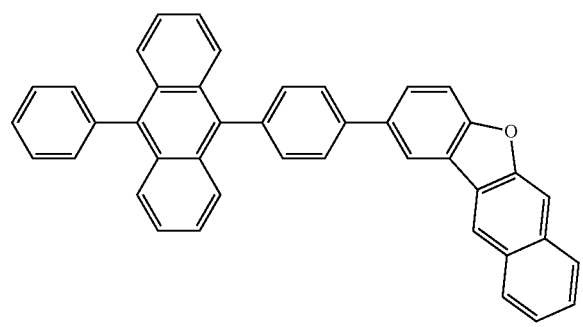

The compound (3-141-O) was synthesized by a method equivalent to the method described in paragraph [0117] of WO 2014/141725 A.

Synthesis Example (39)

Synthesis of Compound (3-181-O): 2-(10-phenylanthracen-9-yl) dibenzofuran

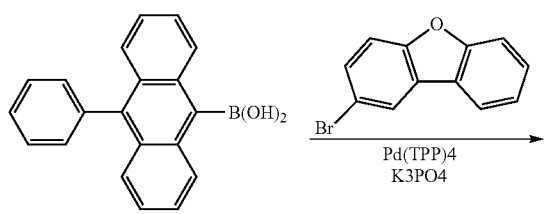

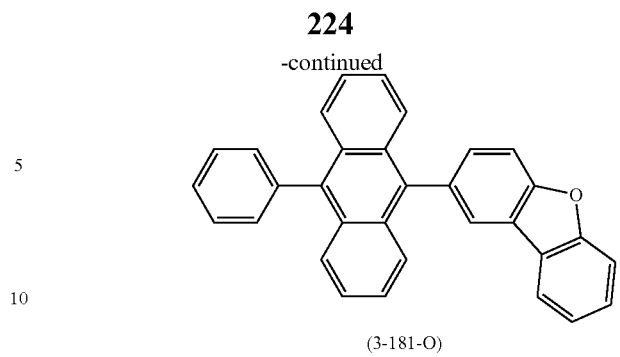

(3-181-O)

Under a nitrogen atmosphere, tetrakis(triphenylphosphine) palladium (0.1 g) was added to 10-phenyl-9-anthracene boronic acid (1.8 g), 2-bromodibenzofuran (1.0 g), potassium phosphate (1.7 g), xylene (10 mL), t-butanol (3 mL), and water (2 mL), and the resulting mixture was heated and stirred at 110° C. for 1.5 hours. The mixture was cooled to room temperature. Thereafter, water and heptane were added thereto and the resulting mixture was stirred for a while, and then the precipitate was filtered. The precipitate was purified with a silica gel short column (eluent: toluene) and then recrystallized from toluene to obtain 2-(10-phenylanthracen-9-yl) dibenzofuran (1.0 g).

The structure of the compound thus obtained was identified by NMR measurement.

$^{1}$H-NMR (CDCl$_3$): δ=7.31-7.39 (m, 5H), 7.50-7.64 (m, 7H), 7.68 (d, 1H), 7.73 (d, 4H), 7.81 (d, 1H), 7.93 (d, 1H), 8.08 (d, 1H).

Synthesis Example (40)

Synthesis of Compound (3-181-S): 2-(10-phenylanthracen-9-yl) dibenzothiophene

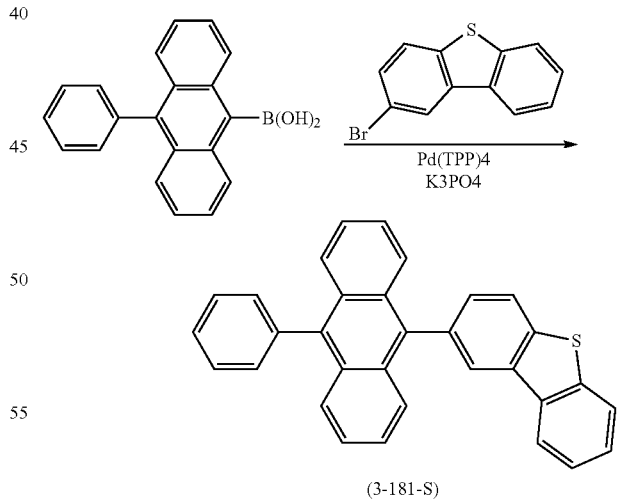

(3-181-S)

Synthesis was performed using 10-phenyl-9-anthraceneboronic acid (1.5 g) and 2-bromobenzothiophene (1.0 g) by a method equivalent to the method of the compound (3-181-O) to obtain 2-(10-phenylanthracen-9-yl) dibenzothiophene (1.5 g).

The structure of the compound thus obtained was identified by NMR measurement.

¹H-NMR (CDCl₃): δ=7.31-7.37 (m, 4H), 7.43-7.53 (m, 4H), 7.56-7.65 (m, 4H), 7.72-7.76 (m, 4H), 7.95 (d, 1H), 8.09-8.82 (m, 2H), 8.29 (d, 1H).

Synthesis Example (41)

Synthesis of Compound (3-182-N-1): 9-phenyl-2-(10-phenylanthracen-9-yl)-9H-carbazole

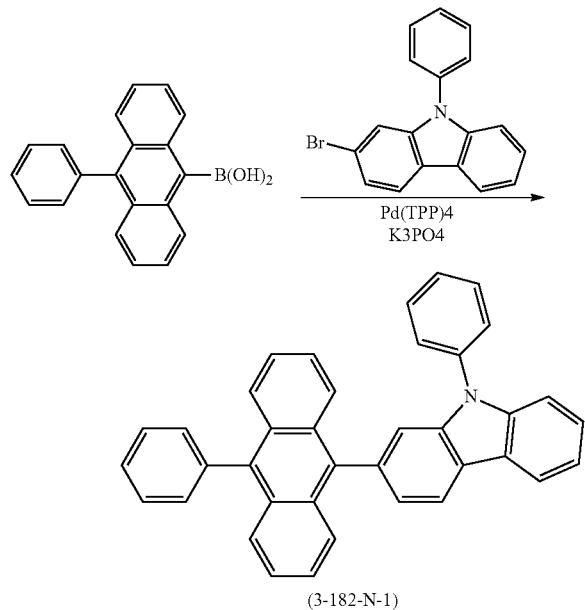

(3-182-N-1)

Synthesis was performed using 10-phenyl-9-anthraceneboronic acid (1.8 g) and 2-bromo-9-phenyl-9H-carbazole (1.5 g) by a method equivalent to the method of the compound (3-181-O) to obtain 9-phenyl-2-(10-phenylanthracen-9-yl)-9H-carbazole (2.1 g).

The structure of the compound thus obtained was identified by NMR measurement.

¹H-NMR (CDCl₃): δ=7.29-7.39 (m, 6H), 7.42-7.63 (m, 13H), 7.68-7.71 (m, 2H), 7.73-7.75 (m, 2H), 8.28 (d, 1H), 8.37 (d, 1H).

Synthesis Example (42)

Synthesis of Compound (3-183-N): 9-(4-(10-phenylanthracen-9-yl) phenyl)-9H-carbazole

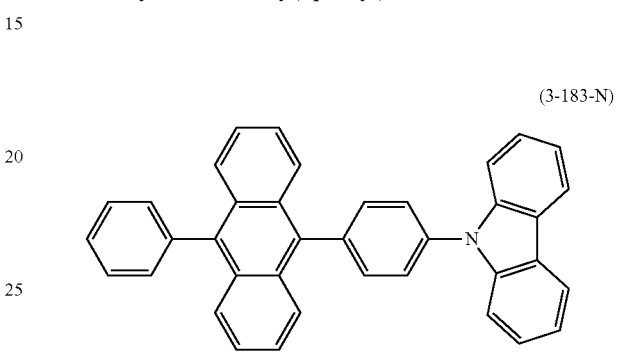

(3-183-N)

The compound (3-183-N) was synthesized by a method equivalent to the method described in paragraph [0225] of JP 2008-081497 A.

Synthesis Example (43)

Synthesis of Compound (3-131-N-1): 7,9-diphenyl-5-(10-phenylanthracen-9-yl)-7H-benzo[c]carbazole

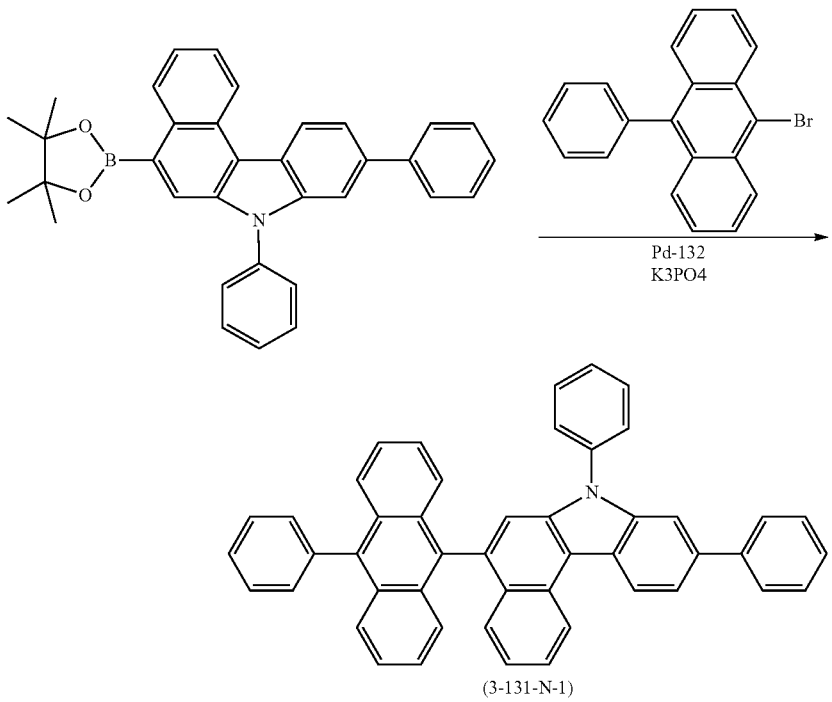 [SMILES: CC1(C)OB(c2cc3c(c4ccccc24)c2ccc(-c4ccccc4)cc2n3-c2ccccc2)OC1(C)C ; Brc1c2ccccc2c(-c2ccccc2)c2ccccc12 ; c1ccc(-c2ccc3c4c5ccccc5c(-c5c6ccccc6c(-c6ccccc6)c6ccccc56)cc4n(-c4ccccc4)c3c2)cc1]

(3-131-N-1)

Under a nitrogen atmosphere, Pd-132 (Johnson Massey) (49 mg) was added to 7,9-diphenyl-5-(4,4,5,5-tetramethyl-1,3,2-dioxaborolane-2-yl)-7H-benzo[c]carbazole (1.0 g) synthesized by a method equivalent to the method described in paragraphs [0289] and [0290] of WO 2012/073541 A, 10-phenyl-9-anthraceneboronic acid (0.77 g), potassium phosphate (1.0 g), xylene (10 mL), t-butanol (3 mL), and water (2 mL), and the resulting mixture was heated and stirred at 110° C. for two hours. The mixture was cooled to room temperature. Thereafter, water and heptane were added thereto and the resulting mixture was stirred for a while, and then the precipitate was filtered. The precipitate was purified by silica gel column chromatography (eluent: toluene/heptane=25/75 (volume ratio)) and then recrystallized from toluene to obtain 7,9-diphenyl-5-(10-phenylanthracen-9-yl)-7H-benzo[c]carbazole (1.1 g).

The structure of the compound thus obtained was identified by NMR measurement.

$^1$H-NMR (CDCl$_3$): δ=7.30-7.34 (m, 4H), 7.38 (t, 1H), 7.43-7.63 (m, 18H), 7.69-7.71 (m, 2H), 7.78-7.82 (m, 3H), 8.06 (d, 1H), 8.88 (d, 1H), 9.05 (d, 1H).

Hereinafter, Examples of an organic EL element using the compound of the present invention will be described in order to describe the present invention in more detail, but the present invention is not limited thereto.

Organic EL elements according to Examples 1, 2 and Comparative Example 1 were manufactured. Voltage (V), emission wavelength (nm), CIE chromaticity (x, y), and external quantum efficiency (%) thereof as characteristics at the time of emission of 1000 cd/m$^2$ were measured.

The quantum efficiency of a luminescent element includes an internal quantum efficiency and an external quantum efficiency. However, the internal quantum efficiency indicates a ratio at which external energy injected as electrons (or holes) into a light emitting layer of a luminescent element is purely converted into photons. Meanwhile, the external quantum efficiency is a value calculated based on the amount of photons emitted to an outside of the luminescent element. A part of the photons generated in the light emitting layer is absorbed or reflected continuously inside the luminescent element, and is not emitted to the outside of the luminescent element. Therefore, the external quantum efficiency is lower than the internal quantum efficiency.

A method for measuring the external quantum efficiency is as follows. Using a voltage/current generator R6144 manufactured by Advantest Corporation, a voltage at which luminance of an element was 1000 cd/m$^2$ was applied to cause the element to emit light. Using a spectral radiance meter SR-3AR manufactured by TOPCON Co., spectral radiance in a visible light region was measured from a direction perpendicular to a light emitting surface. Assuming that the light emitting surface is a perfectly diffusing surface, a numerical value obtained by dividing a spectral radiance value of each measured wavelength component by wavelength energy and multiplying the obtained value by n is the number of photons at each wavelength. Subsequently, the number of photons was integrated in the observed entire wavelength region, and this number was taken as the total number of photons emitted from the element. A numerical value obtained by dividing an applied current value by an elementary charge is taken as the number of carriers injected into the element. The external quantum efficiency is a numerical value obtained by dividing the total number of photons emitted from the element by the number of carriers injected into the element.

The following Table 1 indicates a material composition of each layer and EL characteristic data in organic EL elements manufactured according to Examples 1, 2 and Comparative Example 1.

TABLE 1A

| | Hole injection layer 1 | Hole injection layer 2 | Hole transport layer 1 | Hole transport layer 2 | Light emitting layer (25 nm) | | Electron transport layer | Negative electrode (1 nm/ |
|---|---|---|---|---|---|---|---|---|
| | (40 nm) | (5 nm) | (15 nm) | (10 nm) | Host | Dopant | (30 nm) | 100 nm) |
| Ex. 1 | HI | HAT-CN | HT-1 | HT-2 | compound 3-134-O | compound 1-2621 | ET + Liq | Liq/ MgAg |
| Ex. 2 | HI | HAT-CN | HT-1 | HT-2 | compound 3-134-O | compound 1-2619 | ET + Liq | Liq/ MgAg |
| Comp. Ex. 1 | HI | HAT-CN | HT-1 | HT-2 | Comparative compound (A) | compound 1-2621 | ET + Liq | Liq/ MgAg |

TABLE 1B

| | Wavelength (nm) | Chromaticity (x, y) | Voltage (V) | External quantum efficiency (%) |
|---|---|---|---|---|
| Ex. 1 | 464 | (0.126, 0.101) | 3.52 | 5.73 |
| Ex. 2 | 461 | (0.133, 0.080) | 3.66 | 5.68 |
| Comp. Ex. 1 | 464 | (0.126, 0.099) | 4.38 | 5.64 |

In Table 1, "HI" (hole injection layer material) is N$^4$,N$^{4'}$-diphenyl-N$^4$,N$^{4'}$-bis(9-phenyl-9H-carbazol-3-yl)-[1,1'-biphenyl]-4,4'-diamine, "HAT-CN" (hole injection layer material) is 1,4,5,8,9,12-hexaazatriphenylenehexacarbonitrile, "HT-1" (hole transport layer material) is N-([1,1'-biphenyl]-4-yl)-9,9-dimethyl-N-(4-(9-phenyl-9H-carbazol-3-yl)phenyl)-9H-fluorene-2-amine, "HT-2" (hole transport layer material) is N,N-bis(4-(dibenzo[b,d]furan-4-yl) phenyl)-[1,1': 4',1"-terphenyl]-4-amine," and "ET" (electron transport layer material) is 9-(4-(5,9-dioxa-13b-boranaphtho[3,2,1-de]anthracen-7-yl) phenyl)-9H-carbazole. Chemical structures thereof are indicated below together with "Liq".

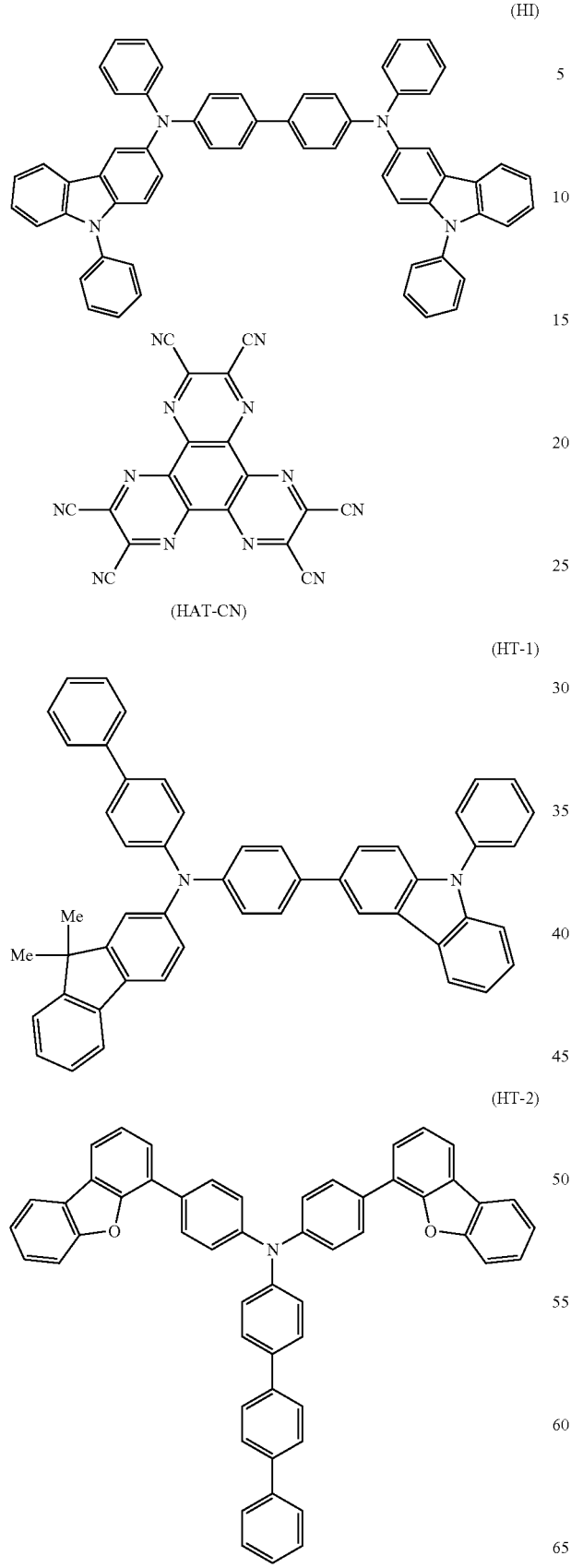

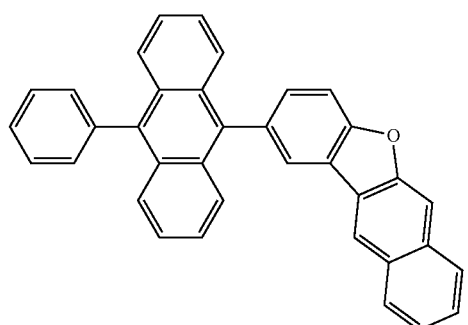

Comparative compound (A)

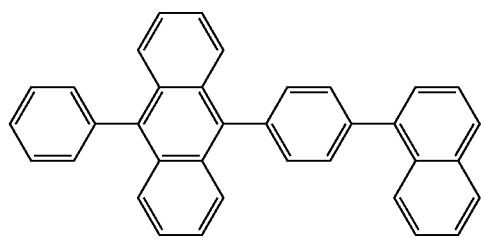

(ET)

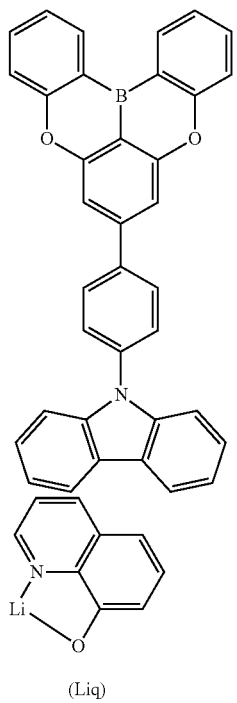

Example 1

<Host: Compound (3-134-O), Dopant: Element of Compound (1-2621)>

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition boat made of molybdenum and containing HI (hole injection layer material), a vapor deposition boat made of molybdenum and containing HAT-CN (hole injection layer material), a vapor deposition boat made of molybdenum and containing HT-1 (hole transport layer material), a vapor deposition boat made of molybdenum and containing HT-2 (hole transport layer material), a vapor deposition boat made of molybdenum and containing compound (3-134-O) (host material), a vapor deposition boat made of molybdenum and containing compound (1-2621) (dopant material), a vapor deposition boat made of molybdenum and containing ET (electron transport layer material), a vapor deposition boat made of molybdenum and containing Liq, a crucible made of SiC and containing magnesium, and a crucible made of SiC and containing silver were mounted in the apparatus.

Layers as described below were formed sequentially on the ITO film of the transparent supporting substrate. The pressure in a vacuum chamber was reduced to $1\times10^{-4}$ Pa. Thereafter, the vapor deposition boat containing HI was first heated, and vapor deposition was performed so as to obtain a film thickness of 40 nm to form a hole injection layer 1. Subsequently, the vapor deposition boat containing HAT-CN was heated, and vapor deposition was performed so as to obtain a film thickness of 5 nm to form a hole injection layer 2. Subsequently, the vapor deposition boat containing HT-1 was heated, and vapor deposition was performed so as to obtain a film thickness of 15 nm to form a hole transport layer 1. Subsequently, the vapor deposition boat containing HT-2 was heated, and vapor deposition was performed so as to obtain a film thickness of 10 nm to form a hole transport layer 2. Subsequently, the vapor deposition boat containing compound (3-134-O) and the vapor deposition boat containing compound (1-2621) were heated simultaneously, and vapor deposition was performed so as to obtain a film thickness of 25 nm to form a light emitting layer. The rate of deposition was regulated such that a weight ratio between compound (3-134-0) and compound (1-2621) was approximately 98:2. Subsequently, the vapor deposition boat containing compound ET and the vapor deposition boat containing Liq were heated simultaneously, and vapor deposition was performed so as to obtain a film thickness of 30 nm to form an electron transport layer. The rate of deposition was regulated such that the weight ratio between ET and Liq was approximately 50:50. The vapor deposition rate for each layer was 0.01 to 1 nm/sec.

Thereafter, the vapor deposition boat containing Liq was heated, and vapor deposition was performed at a rate of deposition of 0.01 to 0.1 nm/sec so as to obtain a film thickness of 1 nm. Subsequently, the crucible containing magnesium and the crucible containing silver were heated simultaneously, and vapor deposition was performed so as to obtain a film thickness of 100 nm to form a negative electrode, thereby obtaining an organic EL element. At this time, the vapor deposition rate was adjusted in a range between 0.1 nm to 10 nm/sec such that the ratio of the numbers of atoms between magnesium and silver was 10:1.

A direct current voltage was applied using an ITO electrode as a positive electrode and a magnesium/silver electrode as a negative electrode, and characteristics at the time of light emission at 1000 cd/m$^2$ were measured. As a result, blue light emission with a wavelength of 464 nm and CIE chromaticity (x, y)=(0.126, 0.101) was obtained. The driving voltage was 3.52 V, and the external quantum efficiency was 5.73%.

Example 2

<Host: Compound (3-134-O), Dopant: Element of Compound (1-2619)>

An organic EL element was obtained by a method equivalent to that of Example 1, except that the dopant material was changed to compound (1-2619). Characteristics at the time of light emission at 1000 cd/m$^2$ were measured, and blue light emission with a wavelength of 461 nm and CIE chromaticity (x, y)=(0.133, 0.080) was obtained. The driving voltage was 3.66 V, and the external quantum efficiency was 5.68%.

Comparative Example 1

<Host: Comparative Compound (A), Dopant: Element of Compound (1-2621)>

An organic EL element was obtained by a method equivalent to that of Example 1, except that the host material was changed to comparative compound (A). Characteristics at the time of light emission at 1000 cd/m$^2$ were measured, and blue light emission with a wavelength of 464 nm and CIE chromaticity (x, y)=(0.126, 0.099) was obtained. The driving voltage was 4.38 V, and the external quantum efficiency was 5.64%.

The following Table 2A indicates a material composition of each layer and the following Table 2B indicates EL characteristic data in organic EL elements manufactured according to Examples 3 to 27 and Comparative Example 2.

TABLE 2A

| | Hole injection layer 1 (40 nm) | Hole injection layer 2 (5 nm) | Hole transport layer 1 (15 nm) | Hole transport layer 2 (10 nm) | Light emitting layer (25 nm) Host | Light emitting layer (25 nm) Dopant | Electron transport layer 1 (5 nm) | Electron transport layer 2 (25 nm) | Negative electrode (1 nm/ 100 nm) |
|---|---|---|---|---|---|---|---|---|---|
| Ex. 3 | HI | HAT-CN | HT-1 | HT-2 | 3-134-O | 1-2621 | ET-1 | ET-2 + Liq | Liq/MgAg |
| Ex. 4 | HI | HAT-CN | HT-1 | HT-2 | 3-134-O | 1-2619 | ET-1 | ET-2 + Liq | Liq/MgAg |
| Ex. 5 | HI | HAT-CN | HT-1 | HT-2 | 3-134-O | 1-447-1 | ET-1 | ET-2 + Liq | Liq/MgAg |
| Ex. 6 | HI | HAT-CN | HT-1 | HT-2 | 3-134-O | 1-401-1 | ET-1 | ET-2 + Liq | Liq/MgAg |
| Ex. 7 | HI | HAT-CN | HT-1 | HT-2 | 3-134-O | 1-401-2 | ET-1 | ET-2 + Liq | Liq/MgAg |
| Ex. 8 | HI | HAT-CN | HT-1 | HT-2 | 3-134-O | 1-401-3 | ET-1 | ET-2 + Liq | Liq/MgAg |
| Ex. 9 | HI | HAT-CN | HT-1 | HT-2 | 3-134-O | 1-449 | ET-1 | ET-2 + Liq | Liq/MgAg |
| Ex. 10 | HI | HAT-CN | HT-1 | HT-2 | 3-134-O | 1-441-1 | ET-1 | ET-2 + Liq | Liq/MgAg |
| Ex. 11 | HI | HAT-CN | HT-1 | HT-2 | 3-134-O | 1-401-4 | ET-1 | ET-2 + Liq | Liq/MgAg |
| Ex. 12 | HI | HAT-CN | HT-1 | HT-2 | 3-134-O | 1-401-5 | ET-1 | ET-2 + Liq | Liq/MgAg |
| Ex. 13 | HI | HAT-CN | HT-1 | HT-2 | 3-134-O | 1-401-6 | ET-1 | ET-2 + Liq | Liq/MgAg |
| Ex. 14 | HI | HAT-CN | HT-1 | HT-2 | 3-134-O | 1-447-2 | ET-1 | ET-2 + Liq | Liq/MgAg |
| Ex. 15 | HI | HAT-CN | HT-1 | HT-2 | 3-134-O | 1-447-3 | ET-1 | ET-2 + Liq | Liq/MgAg |
| Ex. 16 | HI | HAT-CN | HT-1 | HT-2 | 3-134-O | 1-401-7 | ET-1 | ET-2 + Liq | Liq/MgAg |

TABLE 2A-continued

| | Hole injection layer 1 (40 nm) | Hole injection layer 2 (5 nm) | Hole transport layer 1 (15 nm) | Hole transport layer 2 (10 nm) | Light emitting layer (25 nm) Host | Light emitting layer (25 nm) Dopant | Electron transport layer 1 (5 nm) | Electron transport layer 2 (25 nm) | Negative electrode (1 nm/ 100 nm) |
|---|---|---|---|---|---|---|---|---|---|
| Ex. 17 | HI | HAT-CN | HT-1 | HT-2 | 3-180-O | 1-2619 | ET-1 | ET-2 + Liq | Liq/MgAg |
| Ex. 18 | HI | HAT-CN | HT-1 | HT-2 | 3-141-O | 1-2619 | ET-1 | ET-2 + Liq | Liq/MgAg |
| Ex. 19 | HI | HAT-CN | HT-1 | HT-2 | 3-141-O | 1-447-1 | ET-1 | ET-2 + Liq | Liq/MgAg |
| Ex. 20 | HI | HAT-CN | HT-1 | HT-2 | 3-141-O | 1-448-1 | ET-1 | ET-2 + Liq | Liq/MgAg |
| Ex. 21 | HI | HAT-CN | HT-1 | HT-2 | 3-181-O | 1-2619 | ET-1 | ET-2 + Liq | Liq/MgAg |
| Ex. 22 | HI | HAT-CN | HT-1 | HT-2 | 3-181-S | 1-2619 | ET-1 | ET-2 + Liq | Liq/MgAg |
| Ex. 23 | HI | HAT-CN | HT-1 | HT-2 | 3-181-S | 1-447-1 | ET-1 | ET-2 + Liq | Liq/MgAg |
| Ex. 24 | HI | HAT-CN | HT-1 | HT-2 | 3-181-S | 1-448-1 | ET-1 | ET-2 + Liq | Liq/MgAg |
| Ex. 25 | HI | HAT-CN | HT-1 | HT-2 | 3-182-N-1 | 1-2619 | ET-1 | ET-2 + Liq | Liq/MgAg |
| Ex. 26 | HI | HAT-CN | HT-1 | HT-2 | 3-183-N | 1-2619 | ET-1 | ET-2 + Liq | Liq/MgAg |
| Ex. 27 | HI | HAT-CN | HT-1 | HT-2 | 3-131-N-1 | 1-2619 | ET-1 | ET-2 + Liq | Liq/MgAg |
| Comp. Ex. 2 | HI | HAT-CN | HT-1 | HT-2 | Comparative compound (B) | 1-449 | ET-1 | ET-2 + Liq | Liq/MgAg |

TABLE 2B

| | Wavelength (nm) | Chromaticity (x, y) | Chromaticity (x, y) | External quantum efficiency (%) |
|---|---|---|---|---|
| Ex. 3 | 465 | (0.126, 0.099) | 3.54 | 6.98 |
| Ex. 4 | 461 | (0.133, 0.079) | 3.46 | 7.44 |
| Ex. 5 | 457 | (0.133, 0.067) | 3.56 | 6.93 |
| Ex. 6 | 460 | (0.135, 0.070) | 3.58 | 5.97 |
| Ex. 7 | 459 | (0.136, 0.070) | 3.47 | 5.94 |
| Ex. 8 | 457 | (0.139, 0.064) | 3.46 | 5.97 |
| Ex. 9 | 464 | (0.129, 0.091) | 3.72 | 5.66 |
| Ex. 10 | 465 | (0.126, 0.100) | 3.66 | 5.41 |
| Ex. 11 | 458 | (0.126, 0.067) | 3.66 | 5.86 |
| Ex. 12 | 461 | (0.133, 0.079) | 3.40 | 6.82 |
| Ex. 13 | 455 | (0.140, 0.062) | 3.61 | 5.45 |
| Ex. 14 | 457 | (0.139, 0.062) | 3.50 | 6.86 |
| Ex. 15 | 457 | (0.138, 0.066) | 3.66 | 6.54 |
| Ex. 16 | 463 | (0.129, 0.089) | 3.41 | 6.82 |
| Ex. 17 | 462 | (0.131, 0.084) | 3.94 | 7.19 |
| Ex. 18 | 463 | (0.128, 0.104) | 3.69 | 5.50 |
| Ex. 19 | 457 | (0.138, 0.066) | 3.61 | 5.93 |
| Ex. 20 | 454 | (0.143, 0.051) | 3.76 | 5.59 |
| Ex. 21 | 460 | (0.135, 0.072) | 3.89 | 6.70 |
| Ex. 22 | 461 | (0.132, 0.080) | 3.80 | 6.79 |
| Ex. 23 | 456 | (0.140, 0.059) | 3.90 | 6.58 |
| Ex. 24 | 453 | (0.144, 0.046) | 3.99 | 5.72 |
| Ex. 25 | 461 | (0.133, 0.079) | 3.82 | 7.05 |
| Ex. 26 | 462 | (0.131, 0.087) | 3.71 | 6.29 |
| Ex. 27 | 461 | (0.138, 0.083) | 3.51 | 5.65 |
| Comp. Ex. 2 | 464 | (0.129, 0.087) | 4.33 | 5.12 |

In Table 2, "HI", "HAT-CN", "HT-1", "HT-2", and "Liq" are the same as those in Table 1, "ET-1" (electron transport layer material) is 4,6,8,10-tetraphenyl[1,4]benzoxaborinino[2,3,4-kl]phenoxaborinine, and "ET-2" (electron transport layer material) is 3,3'-((2-phenylanthracene-9,10-diyl) bis(4,1-phenylene)) bis(4-methylpyridine). Chemical structures thereof are illustrated below.

(ET-1)

(ET-2)

Comparative compound (B)

Example 3

<Host: Compound (3-134-O), Dopant: Element of Compound (1-2621)>

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition boat made of molybdenum and containing HI (hole injection layer material), a vapor deposition boat made of molybdenum and containing HAT-CN (hole injection layer material), a vapor deposition boat made of molybdenum and containing HT-1 (hole transport layer material), a vapor deposition boat made of molybdenum and containing HT-2 (hole transport layer material), a vapor deposition boat made of molybdenum and containing compound (3-134-O) (host material), a vapor deposition boat made of molybdenum and containing compound (1-2621) (dopant material), a vapor deposition boat made of molybdenum and containing ET-1 (electron transport layer material), a vapor deposition boat made of molybdenum and containing ET-2 (electron transport layer material), a vapor deposition boat made of molybdenum and containing Liq, a crucible made of SiC and containing magnesium, and a crucible made of SiC and containing silver were mounted in the apparatus.

Layers as described below were formed sequentially on the ITO film of the transparent supporting substrate. The pressure in a vacuum chamber was reduced to $1\times10^{-4}$ Pa. Thereafter, the vapor deposition boat containing HI was first heated, and vapor deposition was performed so as to obtain a film thickness of 40 nm to form a hole injection layer 1. Subsequently, the vapor deposition boat containing HAT-CN was heated, and vapor deposition was performed so as to obtain a film thickness of 5 nm to form a hole injection layer 2. Subsequently, the vapor deposition boat containing HT-1 was heated, and vapor deposition was performed so as to obtain a film thickness of 15 nm to form a hole transport layer 1. Subsequently, the vapor deposition boat containing HT-2 was heated, and vapor deposition was performed so as to obtain a film thickness of 10 nm to form a hole transport layer 2. Subsequently, the vapor deposition boat containing compound (3-134-O) and the vapor deposition boat containing compound (1-2621) were heated simultaneously, and vapor deposition was performed so as to obtain a film thickness of 25 nm to form a light emitting layer. The rate of deposition was regulated such that a weight ratio between compound (3-134-0) and compound (1-2621) was approximately 98:2. Subsequently, the vapor deposition boat containing ET-1 was heated, and vapor deposition was performed so as to obtain a film thickness of 5 nm to form an electron transport layer 1. Subsequently, the vapor deposition boat containing ET-2 and the vapor deposition boat containing Liq were heated simultaneously, and vapor deposition was performed so as to obtain a film thickness of 25 nm to form an electron transport layer 2. The rate of deposition was regulated such that the weight ratio between ET-2 and Liq was approximately 50:50. The vapor deposition rate for each layer was 0.01 to 1 nm/sec.

Thereafter, the vapor deposition boat containing Liq was heated, and vapor deposition was performed at a rate of deposition of 0.01 to 0.1 nm/sec so as to obtain a film thickness of 1 nm. Subsequently, the crucible containing magnesium and the crucible containing silver were heated simultaneously, and vapor deposition was performed so as to obtain a film thickness of 100 nm to form a negative electrode, thereby obtaining an organic EL element. At this time, the vapor deposition rate was adjusted in a range between 0.1 nm to 10 nm/sec such that the ratio of the numbers of atoms between magnesium and silver was 10:1.

A direct current voltage was applied using an ITO electrode as a positive electrode and a magnesium/silver electrode as a negative electrode, and characteristics at the time of light emission at 1000 cd/m$^2$ were measured. As a result, blue light emission with a wavelength of 465 nm and CIE chromaticity (x, y)=(0.126, 0.099) was obtained. The driving voltage was 3.54 V, and the external quantum efficiency was 6.98%.

Examples 4 to 27

An organic EL element was manufactured with the material of each layer illustrated in Table 2A in a similar manner to Example 3, and an emission wavelength, CIE chromaticity (x, y), driving voltage, and external quantum efficiency were measured. Table 2B illustrates measurement results thereof.

Comparative Example 2

An organic EL element was manufactured with the material of each layer illustrated in Table 2A in a similar manner to Example 3, and an emission wavelength, CIE chromaticity (x, y), driving voltage, and external quantum efficiency were measured. Table 2B illustrates measurement results thereof.

INDUSTRIAL APPLICABILITY

According to a preferable embodiment of the present invention, it is possible to provide a novel polycyclic aromatic compound and an anthracene-based compound which can obtain optimum light emitting characteristics in combination with the polycyclic aromatic compound, and by manufacturing an organic EL element using a material for a light emitting layer obtained by combining these compounds, it is possible to provide an organic EL element having a low consumption power and an excellent quantum efficiency.

REFERENCE SIGNS LIST

100 Organic electroluminescent element
101 Substrate
102 Positive electrode
103 Hole injection layer
104 Hole transport layer
105 Light emitting layer
106 Electron transport layer
107 Electron injection layer
108 Negative electrode

The invention claimed is:

1. An organic electroluminescent element comprising a pair of electrodes composed of a positive electrode and a negative electrode and a light emitting layer disposed between the pair of electrodes, in which
the light emitting layer comprises at least one of a polycyclic aromatic compound represented by the following general formula (1) and a polycyclic aromatic compound multimer having a plurality of structures represented by the following general formula (1), and an anthracene-based compound represented by the following general formula (3)

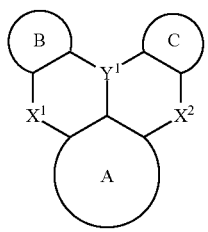
(1)

in the above formula (1),
ring A, ring B and ring C each independently represent an aryl ring or a heteroaryl ring, while at least one hydrogen atom in these rings may be substituted,
$Y^1$ represents B,
$X^1$ and $X^2$ each independently represent N—R, R of the N—R is an optionally substituted aryl, an optionally substituted heteroaryl or alkyl, R of the N—R may be bonded to the ring A, ring B, and/or ring C with a linking group or a single bond, and
at least one hydrogen atom in a compound or a structure represented by formula (1) may be substituted by a halogen atom or a deuterium atom

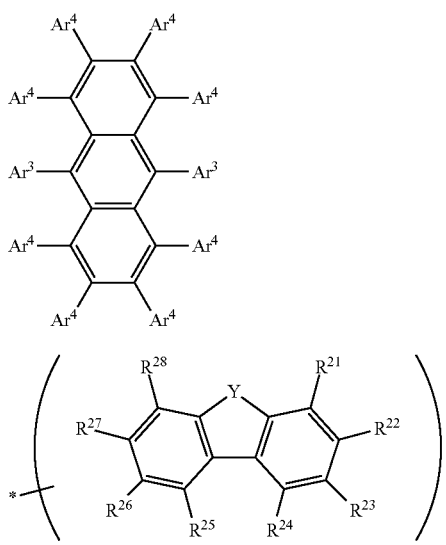
(3)

(4)

in the above formula (3),
$Ar^3$ and $Ar^4$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, provided that a naphthyl group and a naphthyl group fused with one benzene ring are excluded as $Ar^3$,
at least one hydrogen atom of a compound represented by formula (3) may be substituted by a deuterium atom,
at least one hydrogen atom of a compound represented by formula (3) is substituted by a group represented by the above formula (4),
Y represents —O—, —S— or >N—$R^{29}$ in the above formula (4), $R^{21}$ to $R^{28}$ each independently represent a hydrogen atom, an optionally substituted alkyl, an optionally substituted aryl, an optionally substituted heteroaryl, an optionally substituted alkoxy, an optionally substituted aryloxy, an optionally substituted arylthio, a trialkylsilyl, an optionally substituted amino, a halogen atom, a hydroxy, or a cyano, adjacent groups among $R^{21}$ to $R^{28}$ may be bonded to each other to form a hydrocarbon ring, an aryl ring, or a heteroaryl ring, $R^{29}$ is an optionally substituted aryl or a bonding position with a compound represented by formula (3), and a group represented by formula (4) is substituted by at least one hydrogen atom in a compound represented by formula (3) at *, and is bonded thereto at any position in a structure of formula (4).

2. The organic electroluminescent element described in claim 1, in which
in the above formula (1),
the ring A, ring B, and ring C each independently represent an aryl ring or a heteroaryl ring, while at least one hydrogen atom in these rings may be substituted by a substituted or unsubstituted aryl, a substituted or unsubstituted heteroaryl, a substituted or unsubstituted diarylamino, a substituted or unsubstituted diheteroarylamino, a substituted or unsubstituted arylheteroarylamino, a substituted or unsubstituted alkyl, a substituted or unsubstituted alkoxy, or a substituted or unsubstituted aryloxy, each of these rings has a 5-membered or 6-membered ring sharing a bond with a fused bicyclic structure at the center of the above formula constructed by $Y^1$, $X^1$, and $X^2$,
$Y^1$ represents B,
$X^1$ and $X^2$ each independently represent N—R, R of the N—R represents an aryl which may be substituted by an alkyl, a heteroaryl which may be substituted by an alkyl or alkyl, R of the N—R may be bonded to the ring A, ring B, and/or ring C with —O—, —S—, —C(—R)$_2$— or a single bond, R of the —C(—R)$_2$— represents a hydrogen atom or an alkyl,
at least one hydrogen atom in a compound or structure represented by formula (1) may be substituted by a halogen atom or a deuterium atom, and
in a case of a multimer, the multimer is a dimer or a trimer having two or three structures represented by formula (1).

3. The organic electroluminescent element described in claim 1, in which the light emitting layer comprises at least one of a polycyclic aromatic compound represented by the following general formula (2) and a polycyclic aromatic compound multimer having a plurality of structures represented by the following general formula (2), and the anthracene-based compound

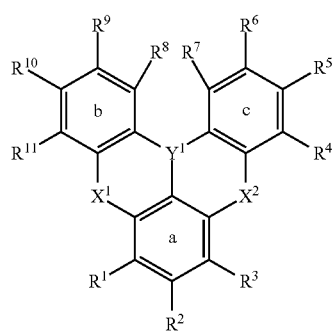
(2)

in the above formula (2), $R^1$, $R^2$, $R^3$, $R^4$, $R^5$, $R^6$, $R^7$, $R^8$, $R^9$, $R^{10}$, and $R^{11}$ each independently represent a hydrogen atom, an aryl, a heteroaryl, a diarylamino, a diheteroarylamino, an aryl-heteroarylamino, an alkyl, an alkoxy, or an aryloxy, while at least one hydrogen atom in these may be substituted by an aryl, a heteroaryl, or an alkyl, adjacent groups among $R^1$ to $R^{11}$ may be bonded to each other to form an aryl ring or a heteroaryl ring together with ring a, ring b, or ring c, at least one hydrogen atom in the ring thus formed may be substituted by an aryl, a heteroaryl, a diarylamino, a diheteroarylamino, an aryl-heteroarylamino, an alkyl, an alkoxy, or an aryloxy, at least one hydrogen atom in these may be substituted by an aryl, a heteroaryl or an alkyl, $Y^1$ represents B, $X^1$ and $X^2$ each independently represent N—R, R of the N—R represents an aryl having 6 to 12 carbon atoms, a heteroaryl having 2 to 15 carbon atoms, or an alkyl having 1 to 6 carbon atoms, R of the N—R may be bonded to the ring a, ring b and/or ring c with —O—, —S—, —C(—R)$_2$—, or a single bond, R of the —C(—R)$_2$— represents an alkyl having 1 to 6 carbon atoms, and at least one hydrogen atom in a compound represented by formula (2) may be substituted by a halogen atom or a deuterium atom;

wherein in the anthracene-based compound, $Ar^3$ each independently represent a hydrogen atom, an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, provided that a naphthyl group and a naphthyl group fused with one benzene ring are excluded as $Ar^3$ and at least one hydrogen atom in $Ar^3$ is substituted by a group represented by any one of formulas (4-1) to (4-11):

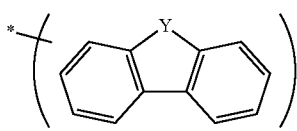

(4-1)

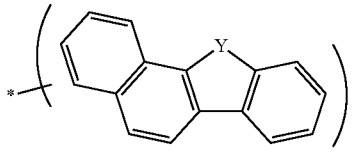

(4-2)

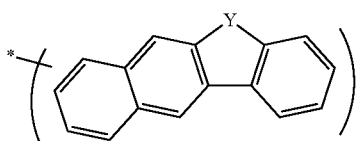

(4-3)

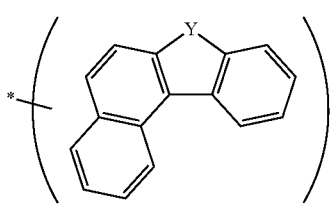

(4-4)

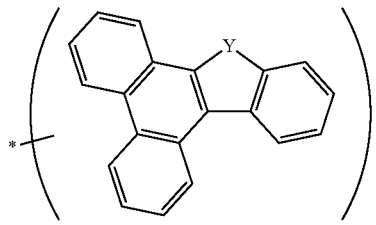

(4-5)

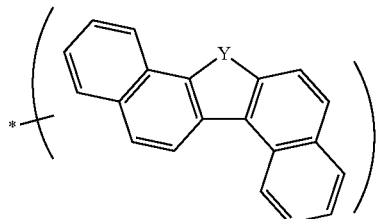

(4-6)

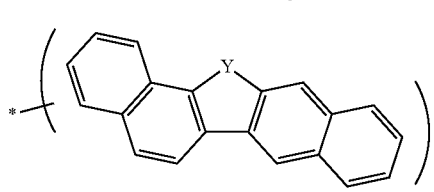

(4-7)

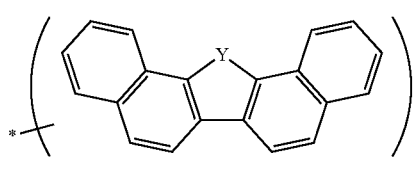

(4-8)

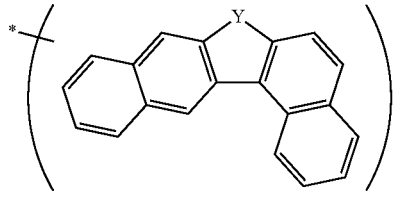

(4-9)

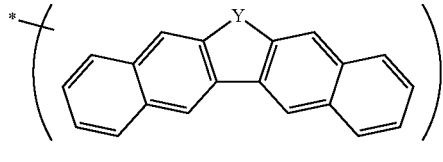

(4-10)

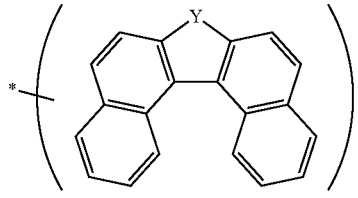

(4-11)

$Ar^4$ each independently represent a hydrogen atom, an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, and at least one hydrogen atom in a compound represented by formula (3) may be substituted by a deuterium atom, in the above formulas (4-1) to (4-11), Y represents —O—, —S— or >N—$R^{29}$, $R^{29}$ is an aryl or a bonding position with a compound represented by formula (3), at least one hydrogen atom in groups represented by formulas (4-1) to (4-11) may be substituted by an alkyl, an aryl, a heteroaryl, an alkoxy, an aryloxy, an arylthio, a trialkylsilyl, a diaryl substituted amino, a diheteroaryl substituted amino, an aryl heteroaryl substituted amino, a halogen atom, a hydroxy, or a cyano, and each of the groups represented by formulas (4-1) to (4-11) is substituted with at least one hydrogen atom in Ar³ at *, and is bonded thereto at any position in structures of formulas (4-1) to (4-11).

4. The organic electroluminescent element described in claim 3, in which in the above formula (2), $R^1$, $R^2$, $R^3$, $R^4$, $R^5$, $R^6$, $R^7$, $R^8$, $R^9$, $R^{10}$, and $R^{11}$ each independently represent a hydrogen atom, an aryl having 6 to 30 carbon atoms, a heteroaryl having 2 to 30 carbon atoms or a diarylamino (the aryl is an aryl having 6 to 12 carbon atoms), adjacent groups among $R^1$ to $R^{11}$ may be bonded to each other to form an aryl having 9 to 16 carbon atoms or a heteroaryl ring having 6 to 15 carbon atoms together with the ring a, ring b, or ring c, at least one hydrogen atom in the ring thus formed may be substituted by an aryl having 6 to 10 carbon atoms, $Y^1$ represents B, $X^1$ and $X^2$ each independently represent N—R, R of the N—R is an aryl having 6 to 10 carbon atoms, at least one hydrogen atom in a compound represented by formula (2) may be substituted by a halogen atom or a deuterium atom, in the above formula (3), Ar³ each independently represent a hydrogen atom, an aryl, a heteroaryl, a diaryl substituted amino, a diheteroaryl substituted amino, or an aryl heteroaryl substituted amino, provided that a naphthyl group and a naphthyl group fused with one benzene ring are excluded as Ar³ and at least one hydrogen atom in Ar³ is substituted by a group represented by formula any one of the above formulas (4-1) to (4-11), Ar⁴ each independently represent a hydrogen atom, an alkyl, an aryl, a heteroaryl, a trialkylsilyl, a diaryl substituted amino, a diheteroaryl substituted amino, or an aryl heteroaryl substituted amino, and at least one hydrogen atom in a compound represented by formula (3) may be substituted by a deuterium atom.

5. The organic electroluminescent element described in claim 1, in which the polycyclic aromatic compound represented by the general formula (1) and the polycyclic aromatic compound multimer having a plurality of structures represented by the general formula (1) are represented by any of the following formulas (1-401)

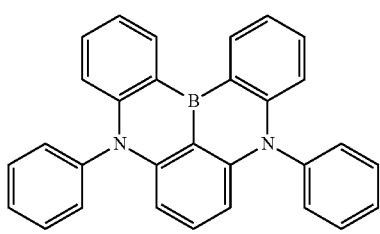

(1-411)

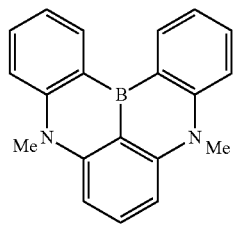

(1-422)

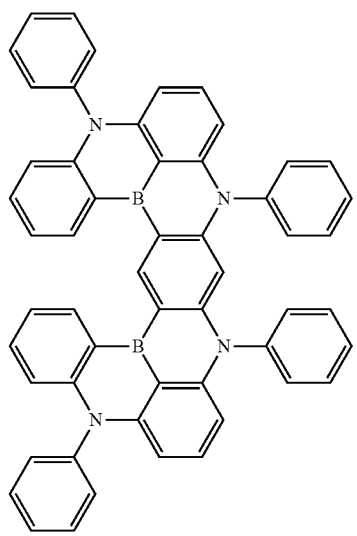

(1-447)

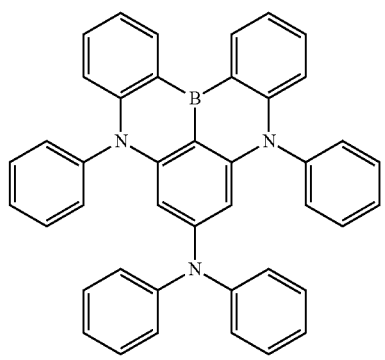

(1-1152)

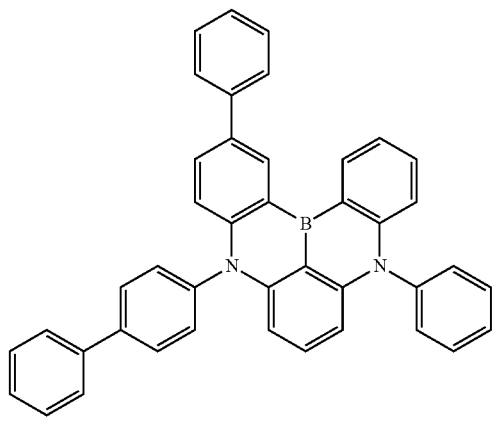

(1-1159)
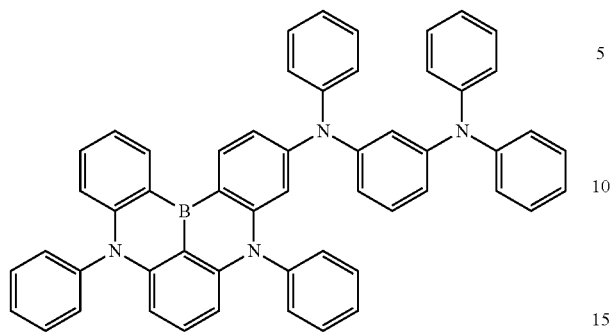
(1-2626)
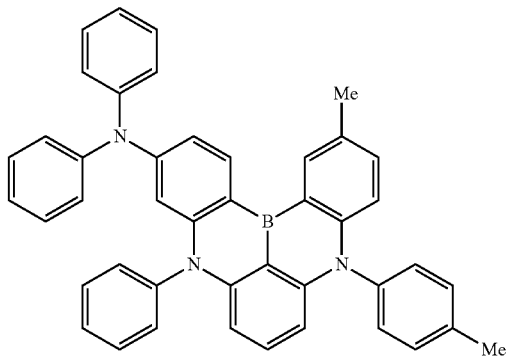
(1-2619)
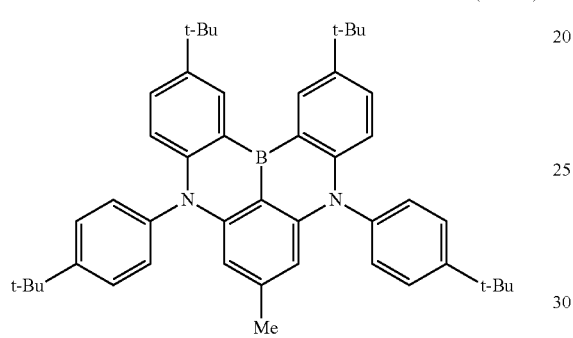
(1-2657)
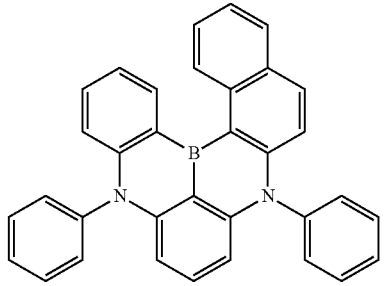
(1-2620)
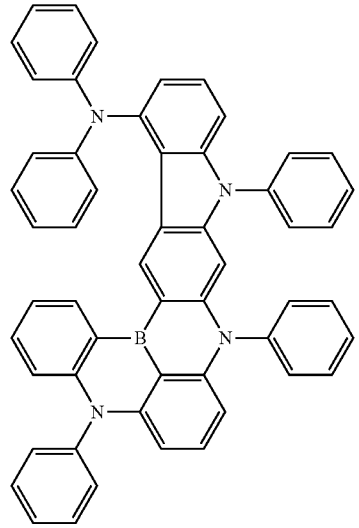
(1-2662)
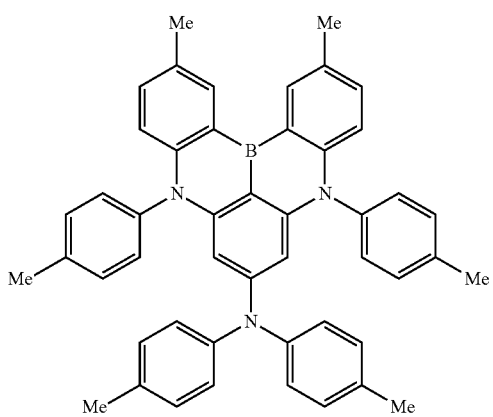
(1-2621)
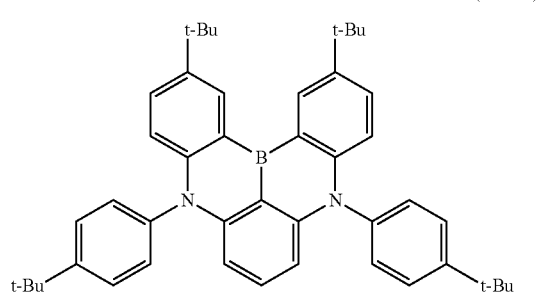
(1-2665)
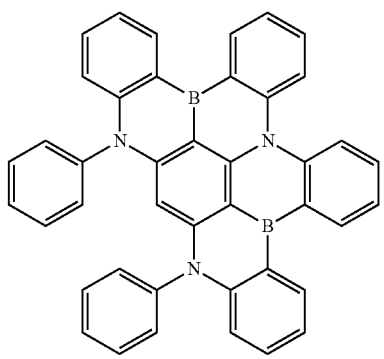

(1-2676)
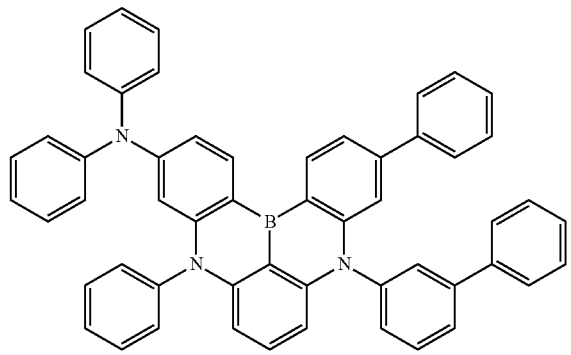
(1-2678)
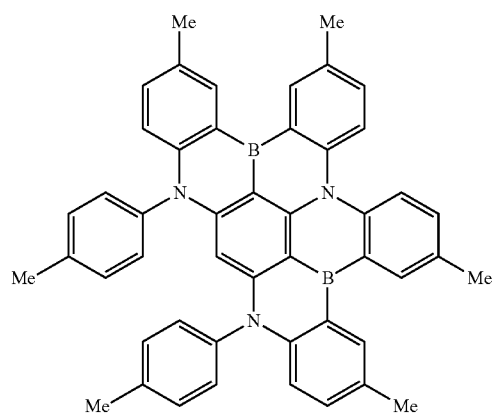
(1-2679)
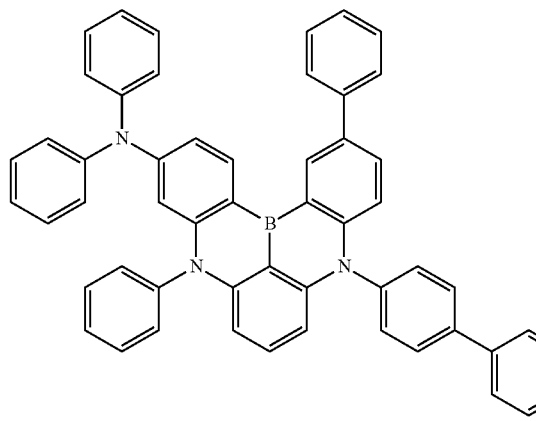
(1-2680)
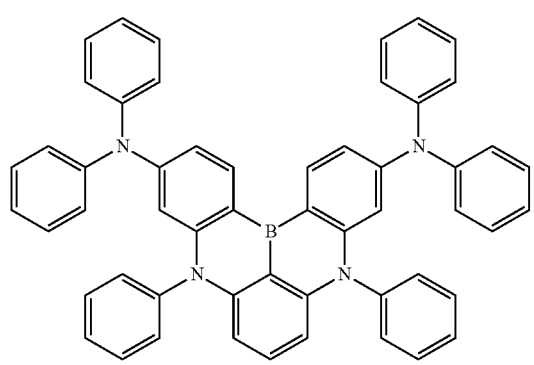
(1-2681)
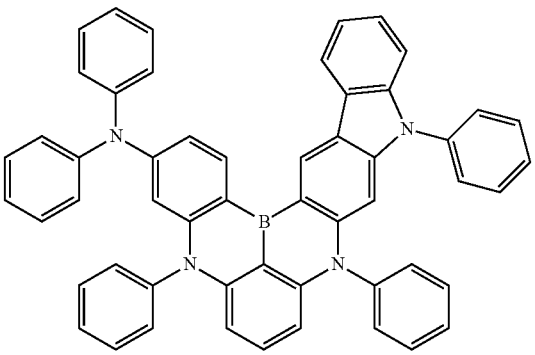
(1-2682)
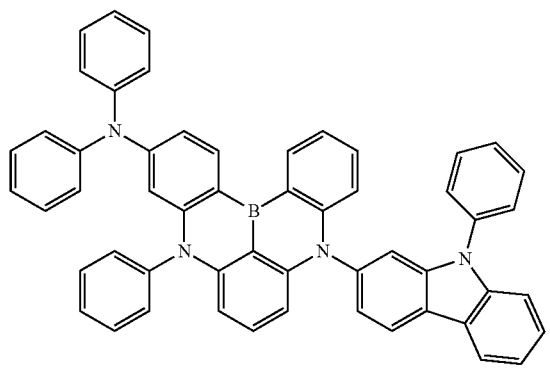
(1-2683)
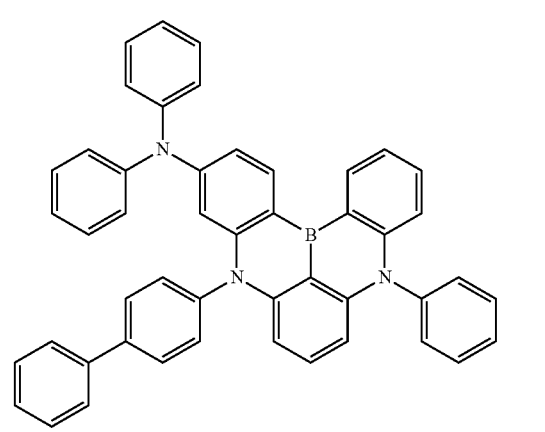

(1-2691)

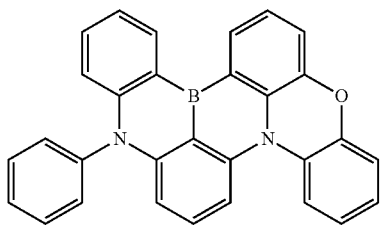

(1-2699)

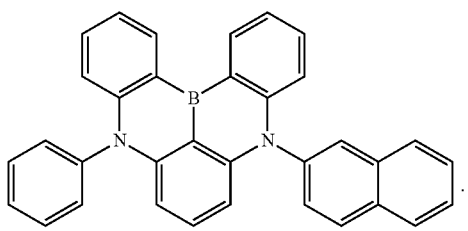

(ETM-4)

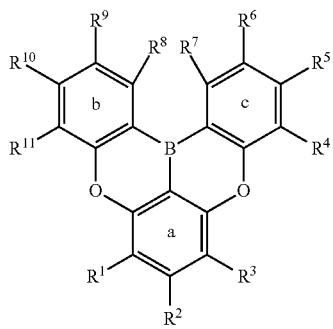

wherein $R^1$ to $R^{11}$ each independently represent a hydrogen atom, an aryl, a heteroaryl, a diarylamino, a diheteroarylamino, an arylheteroarylamino, an alkyl, an alkoxy, or an aryloxy, while at least one hydrogen atom in these may be substituted by an aryl, a heteroaryl, or an alkyl, wherein adjacent groups among $R^1$ to $R^{11}$ may be bonded to each other to form an aryl ring or a heteroaryl ring together with the ring a, ring b, or ring c, and at least one hydrogen atom in the ring thus formed may be substituted by an aryl, a heteroaryl, a diarylamino, a diheteroarylamino, an arylheteroarylamino, an alkyl, an alkoxy, or an aryloxy, while at least one hydrogen atom in these may be substituted by an aryl, a heteroaryl, or an alkyl.

6. The organic electroluminescent element described in claim 1, further comprising an electron transport layer and/or an electron injection layer disposed between the negative electrode and the light emitting layer, in which at least one of the electron transport layer and the electron injection layer comprises at least one selected from the group consisting of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, and a quinolinol-based metal complex, wherein the BO-based derivative is a polycyclic aromatic compound represented by the following formula (ETM-4) or a polycyclic aromatic compound multimer having a plurality of structures represented by the following formula (ETM-4):

7. The organic electroluminescent element described in claim 6, in which the electron transport layer and/or electron injection layer further comprise/comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

8. A display apparatus comprising the organic electroluminescent element described in claim 1.

9. A lighting apparatus comprising the organic electroluminescent element described in claim 1.

* * * * *